United States Patent
Tegzes

(10) Patent No.: US 10,058,318 B2
(45) Date of Patent: Aug. 28, 2018

(54) MEDICAL KIT FOR CONSTRICTING TISSUE OR A BODILY ORIFICE, FOR EXAMPLE, A MITRAL VALVE

(71) Applicant: Kardium Inc., Burnaby (CA)

(72) Inventor: Aleksandar Tegzes, Vancouver (CA)

(73) Assignee: KARDIUM INC., Burnaby (CA)

( * ) Notice: Subject to any disclaimer, the term of this patent is extended or adjusted under 35 U.S.C. 154(b) by 487 days.

(21) Appl. No.: 14/696,853

(22) Filed: Apr. 27, 2015

(65) Prior Publication Data

US 2015/0223802 A1 Aug. 13, 2015

Related U.S. Application Data

(62) Division of application No. 13/421,677, filed on Mar. 15, 2012, now Pat. No. 9,072,511.
(Continued)

(51) Int. Cl.
*A61F 2/24* (2006.01)
*A61B 17/04* (2006.01)
*A61B 17/06* (2006.01)

(52) U.S. Cl.
CPC ........ *A61B 17/0401* (2013.01); *A61F 2/2445* (2013.01); *A61F 2/2466* (2013.01);
(Continued)

(58) Field of Classification Search
CPC ..... A61F 2/2445; A61F 2/2466; A61F 2/2442
See application file for complete search history.

(56) References Cited

U.S. PATENT DOCUMENTS

| 566,521 A | 8/1896 | Leger |
|---|---|---|
| 3,132,438 A | 5/1964 | Ward et al. |

(Continued)

FOREIGN PATENT DOCUMENTS

| EP | 0723467 B1 | 4/2002 |
|---|---|---|
| EP | 2082690 A1 | 7/2009 |

(Continued)

OTHER PUBLICATIONS

Amendment filed in U.S. Appl. No. 12/899,407 on Jun. 14, 2016.
(Continued)

*Primary Examiner* — Gregory Anderson
(74) *Attorney, Agent, or Firm* — Rossi, Kimms & McDowell LLP

(57) ABSTRACT

A device, kit and method may include or employ an implantable device (e.g., annuloplasty implant) and a plurality of tissue anchors. The implantable device is positionable in a cavity of a bodily organ (e.g., a heart) and operable to constrict a bodily orifice (e.g., a mitral valve). Each of the tissue anchors may be guided into precise position by an intravascularly or percutaneously techniques. Constriction of the orifice may be accomplished via a variety of structures, for example an articulated annuloplasty ring, the ring attached to the tissue anchors. The annuloplasty ring may be delivered in an unanchored, generally elongated configuration, and implanted in an anchored generally arched, arcuate or annular configuration. Such may approximate the septal and lateral (clinically referred to as anterior and posterior) annulus of the mitral valve, to move the posterior leaflet anteriorly and the anterior leaflet posteriorly, thereby improving leaflet coaptation to reduce mitral regurgitation.

36 Claims, 66 Drawing Sheets

Related U.S. Application Data

(60) Provisional application No. 61/467,883, filed on Mar. 25, 2011.

(52) U.S. Cl.
CPC ... *A61B 17/0487* (2013.01); *A61B 2017/0409* (2013.01); *A61B 2017/0412* (2013.01); *A61B 2017/0414* (2013.01); *A61B 2017/0441* (2013.01); *A61B 2017/0472* (2013.01); *A61B 2017/0496* (2013.01); *A61B 2017/06052* (2013.01)

(56) References Cited

U.S. PATENT DOCUMENTS

| | | |
|---|---|---|
| 4,041,955 A | 8/1977 | Kelly et al. |
| 4,085,744 A | 4/1978 | Lewis et al. |
| 4,114,202 A | 9/1978 | Roy et al. |
| 4,164,046 A | 8/1979 | Cooley |
| 4,225,148 A | 9/1980 | Anderson |
| 4,240,441 A | 12/1980 | Khalil |
| 4,261,342 A | 4/1981 | Aranguren Duo |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,527,554 A | 7/1985 | Klein |
| 4,543,090 A | 9/1985 | McCoy |
| 4,699,147 A | 10/1987 | Chilson et al. |
| 4,770,187 A | 9/1988 | Lash et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,921,499 A | 5/1990 | Hoffman et al. |
| 4,942,788 A | 7/1990 | Farr et al. |
| 4,979,514 A | 12/1990 | Sekii et al. |
| 4,994,698 A | 2/1991 | Kliman et al. |
| 4,998,933 A | 3/1991 | Eggers et al. |
| 5,021,059 A | 6/1991 | Kensey et al. |
| 5,026,384 A | 6/1991 | Farr et al. |
| 5,039,894 A | 8/1991 | Teter et al. |
| 5,047,047 A | 9/1991 | Yoon |
| 5,100,418 A | 3/1992 | Yoon et al. |
| 5,104,399 A | 4/1992 | Lazarus |
| 5,122,137 A | 6/1992 | Lennox |
| 5,127,902 A | 7/1992 | Fischell |
| 5,156,151 A | 10/1992 | Imran |
| 5,156,609 A | 10/1992 | Nakao et al. |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,192,314 A | 3/1993 | Daskalakis |
| 5,201,316 A | 4/1993 | Pomeranz et al. |
| 5,228,442 A | 7/1993 | Imran |
| 5,242,386 A | 9/1993 | Holzer |
| 5,242,456 A | 9/1993 | Nash et al. |
| 5,245,987 A | 9/1993 | Redmond et al. |
| 5,258,000 A | 11/1993 | Gianturco |
| 5,279,299 A | 1/1994 | Imran |
| 5,293,869 A | 3/1994 | Edwards et al. |
| 5,312,435 A | 5/1994 | Nash et al. |
| 5,312,439 A | 5/1994 | Loeb |
| 5,317,952 A | 6/1994 | Immega |
| 5,320,632 A | 6/1994 | Heidmueller |
| 5,341,807 A | 8/1994 | Nardella |
| 5,345,936 A | 9/1994 | Pomeranz et al. |
| 5,364,408 A | 11/1994 | Gordon |
| 5,366,443 A | 11/1994 | Eggers et al. |
| 5,366,459 A | 11/1994 | Yoon |
| 5,368,601 A | 11/1994 | Sauer et al. |
| 5,374,275 A | 12/1994 | Bradley et al. |
| 5,375,612 A | 12/1994 | Cottenceau et al. |
| 5,379,773 A | 1/1995 | Hornsby |
| 5,383,887 A | 1/1995 | Nadal |
| RE34,866 E | 2/1995 | Kensey et al. |
| 5,390,664 A | 2/1995 | Redmond et al. |
| 5,417,698 A | 5/1995 | Green et al. |
| 5,419,767 A | 5/1995 | Eggers et al. |
| 5,423,859 A | 6/1995 | Koyfman et al. |
| 5,450,860 A | 9/1995 | O'Connor |
| 5,451,235 A | 9/1995 | Lock et al. |
| 5,454,834 A | 10/1995 | Boebel et al. |
| 5,462,561 A | 10/1995 | Voda |
| 5,478,353 A | 12/1995 | Yoon |
| 5,496,267 A | 3/1996 | Drasler et al. |
| 5,507,811 A | 4/1996 | Koike et al. |
| 5,531,760 A | 7/1996 | Alwafaie |
| 5,557,967 A | 9/1996 | Renger |
| 5,558,091 A | 9/1996 | Acker et al. |
| 5,575,810 A | 11/1996 | Swanson et al. |
| 5,593,424 A | 1/1997 | Northrup, III |
| 5,598,848 A | 2/1997 | Swanson et al. |
| 5,634,942 A | 6/1997 | Chevillon et al. |
| 5,645,566 A | 7/1997 | Brenneman et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,690,649 A | 11/1997 | Li |
| 5,697,285 A | 12/1997 | Nappi et al. |
| 5,713,896 A | 2/1998 | Nardella |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,752,965 A | 5/1998 | Francis et al. |
| 5,762,066 A | 6/1998 | Law et al. |
| 5,769,846 A | 6/1998 | Edwards et al. |
| 5,782,239 A | 7/1998 | Webster, Jr. |
| 5,782,861 A | 7/1998 | Cragg et al. |
| 5,782,879 A | 7/1998 | Rosborough et al. |
| 5,800,495 A | 9/1998 | Machek et al. |
| 5,824,066 A | 10/1998 | Gross |
| 5,830,222 A | 11/1998 | Makower |
| 5,836,990 A | 11/1998 | Li |
| 5,865,791 A | 2/1999 | Whayne et al. |
| 5,871,505 A | 2/1999 | Adams et al. |
| 5,876,343 A | 3/1999 | Teo |
| 5,881,727 A | 3/1999 | Edwards |
| 5,891,136 A | 4/1999 | McGee et al. |
| 5,904,711 A | 5/1999 | Flom et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,961,440 A | 10/1999 | Schweich, Jr. et al. |
| 5,964,782 A | 10/1999 | Lafontaine et al. |
| 5,971,994 A | 10/1999 | Fritzsch |
| 5,976,174 A | 11/1999 | Ruiz |
| 5,980,473 A | 11/1999 | Korakianitis et al. |
| 5,984,950 A | 11/1999 | Cragg et al. |
| 6,001,069 A | 12/1999 | Tachibana et al. |
| 6,024,096 A | 2/2000 | Buckberg |
| 6,045,497 A | 4/2000 | Schweich, Jr. et al. |
| 6,059,715 A | 5/2000 | Schweich, Jr. et al. |
| 6,063,082 A | 5/2000 | DeVore et al. |
| 6,074,417 A | 6/2000 | Peredo |
| 6,074,418 A | 6/2000 | Buchanan et al. |
| 6,077,214 A | 6/2000 | Mortier et al. |
| 6,104,944 A | 8/2000 | Martinelli |
| 6,113,610 A | 9/2000 | Poncet |
| 6,123,702 A | 9/2000 | Swanson et al. |
| 6,132,438 A | 10/2000 | Fleischman et al. |
| 6,138,043 A | 10/2000 | Avitall |
| 6,142,993 A | 11/2000 | Whayne et al. |
| 6,156,046 A | 12/2000 | Passafaro et al. |
| 6,183,496 B1 | 2/2001 | Urbanski |
| 6,203,554 B1 | 3/2001 | Roberts |

(56) References Cited

U.S. PATENT DOCUMENTS

| | | |
|---|---|---|
| 6,210,432 B1 | 4/2001 | Solem et al. |
| 6,214,032 B1 | 4/2001 | Loeb et al. |
| 6,217,573 B1 | 4/2001 | Webster |
| 6,221,103 B1 | 4/2001 | Melvin |
| 6,221,104 B1 | 4/2001 | Buchberg et al. |
| 6,231,561 B1 | 5/2001 | Frazier et al. |
| 6,241,747 B1 | 6/2001 | Ruff |
| 6,248,124 B1 | 6/2001 | Pedros et al. |
| 6,258,258 B1 | 7/2001 | Sartori et al. |
| 6,261,309 B1 | 7/2001 | Urbanski |
| 6,266,550 B1 | 7/2001 | Selmon et al. |
| 6,287,321 B1 | 9/2001 | Jang |
| 6,304,769 B1 | 10/2001 | Arenson et al. |
| 6,306,135 B1 | 10/2001 | Ellman et al. |
| 6,308,091 B1 | 10/2001 | Avitall |
| 6,332,864 B1 | 12/2001 | Schweich, Jr. et al. |
| 6,346,105 B1 | 2/2002 | Tu et al. |
| 6,358,258 B1 | 3/2002 | Arcia et al. |
| 6,358,277 B1 | 3/2002 | Duran |
| 6,360,749 B1 | 3/2002 | Jayaraman |
| 6,379,366 B1 | 4/2002 | Fleischman et al. |
| 6,383,151 B1 | 5/2002 | Diederich et al. |
| 6,389,311 B1 | 5/2002 | Whayne et al. |
| 6,391,048 B1 | 5/2002 | Ginn et al. |
| 6,391,054 B2 | 5/2002 | Carpentier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,409,760 B1 | 6/2002 | Melvin |
| 6,416,459 B1 | 7/2002 | Haindl |
| 6,432,115 B1 | 8/2002 | Mollenauer et al. |
| 6,436,052 B1 | 8/2002 | Nikolic et al. |
| 6,450,171 B1 | 9/2002 | Buckberg et al. |
| 6,475,223 B1 | 11/2002 | Werp et al. |
| 6,485,409 B1 | 11/2002 | Voloshin et al. |
| 6,485,489 B2 | 11/2002 | Teirstein et al. |
| 6,506,210 B1 | 1/2003 | Kanner |
| 6,514,194 B2 | 2/2003 | Schweich, Jr. et al. |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,582,447 B1 | 6/2003 | Patel et al. |
| 6,589,160 B2 | 7/2003 | Schweich, Jr. et al. |
| 6,589,208 B2 | 7/2003 | Ewers et al. |
| 6,626,930 B1 | 9/2003 | Allen et al. |
| 6,632,238 B2 | 10/2003 | Ginn et al. |
| 6,662,034 B2 | 12/2003 | Segner et al. |
| 6,676,685 B2 | 1/2004 | Pedros et al. |
| 6,681,773 B2 | 1/2004 | Murphy et al. |
| 6,704,590 B2 | 3/2004 | Haldeman |
| 6,723,038 B1 | 4/2004 | Schroeder et al. |
| 6,726,704 B1 | 4/2004 | Loshakove et al. |
| 6,726,716 B2 | 4/2004 | Marquez |
| 6,743,241 B2 | 6/2004 | Kerr |
| 6,746,471 B2 | 6/2004 | Mortier et al. |
| 6,749,622 B2 | 6/2004 | McGuckin, Jr. et al. |
| 6,752,810 B1 | 6/2004 | Gao et al. |
| 6,755,777 B2 | 6/2004 | Schweich, Jr. et al. |
| 6,760,616 B2 | 7/2004 | Hoey et al. |
| 6,780,197 B2 | 8/2004 | Roe et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,840,957 B2 | 1/2005 | Dimatteo et al. |
| 6,852,076 B2 | 2/2005 | Nikolic et al. |
| 6,855,143 B2 | 2/2005 | Davison et al. |
| 6,881,218 B2 | 4/2005 | Beyer et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,941,171 B2 | 9/2005 | Mann et al. |
| 6,942,657 B2 | 9/2005 | Sinofsky et al. |
| 6,949,122 B2 | 9/2005 | Adams et al. |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,991,649 B2 | 1/2006 | Sievers |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,101,395 B2 | 9/2006 | Tremulis et al. |
| 7,141,019 B2 | 11/2006 | Pearlman |
| 7,144,363 B2 | 12/2006 | Pai et al. |
| 7,160,322 B2 | 1/2007 | Gabbay |
| 7,166,127 B2 | 1/2007 | Spence et al. |
| 7,172,551 B2 | 2/2007 | Leasure |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,276,044 B2 | 10/2007 | Ferry et al. |
| 7,279,007 B2 | 10/2007 | Nikolic et al. |
| 7,280,863 B2 | 10/2007 | Shachar |
| 7,300,435 B2 | 11/2007 | Wham et al. |
| 7,303,526 B2 | 12/2007 | Sharkey et al. |
| 7,320,665 B2 | 1/2008 | Vijay |
| 7,335,196 B2 | 2/2008 | Swanson et al. |
| 7,374,530 B2 | 5/2008 | Schaller |
| 7,399,271 B2 | 7/2008 | Khairkhahan et al. |
| 7,413,568 B2 | 8/2008 | Swanson et al. |
| 7,431,726 B2 | 10/2008 | Spence et al. |
| 7,452,325 B2 | 11/2008 | Schaller |
| 7,452,375 B2 | 11/2008 | Mathis et al. |
| 7,507,252 B2 | 3/2009 | Lashinski et al. |
| 7,513,867 B2 | 4/2009 | Lichtenstein |
| 7,582,051 B2 | 9/2009 | Khairkhahan et al. |
| 7,611,534 B2 | 11/2009 | Kapadia et al. |
| 7,674,276 B2 | 3/2010 | Stone et al. |
| 7,704,277 B2 | 4/2010 | Zakay et al. |
| 7,736,388 B2 | 6/2010 | Goldfarb et al. |
| 7,738,967 B2 | 6/2010 | Salo |
| 7,749,249 B2 | 7/2010 | Gelbart et al. |
| 7,837,610 B2 | 11/2010 | Lichtenstein et al. |
| 7,869,854 B2 | 1/2011 | Shachar et al. |
| 7,873,402 B2 | 1/2011 | Shachar |
| 7,887,482 B2 | 2/2011 | Hamada |
| 8,027,714 B2 | 9/2011 | Shachar |
| 8,128,644 B2 | 3/2012 | Carley et al. |
| 8,150,499 B2 | 4/2012 | Gelbart et al. |
| 8,337,524 B2 | 12/2012 | Gelbart et al. |
| 8,449,605 B2 | 5/2013 | Lichtenstein et al. |
| 8,532,746 B2 | 9/2013 | Gelbart et al. |
| 8,672,998 B2 | 3/2014 | Lichtenstein et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0041915 A1 | 11/2001 | Roue et al. |
| 2001/0044568 A1 | 11/2001 | Langberg et al. |
| 2002/0002329 A1 | 1/2002 | Avitall |
| 2002/0013621 A1 | 1/2002 | Stobie et al. |
| 2002/0016628 A1 | 2/2002 | Langberg et al. |
| 2002/0026092 A1 | 2/2002 | Buckberg et al. |
| 2002/0055775 A1 | 5/2002 | Carpentier et al. |
| 2002/0082621 A1 | 6/2002 | Schurr et al. |
| 2002/0087156 A1 | 7/2002 | Maguire et al. |
| 2002/0087173 A1 | 7/2002 | Alferness et al. |

(56) References Cited

U.S. PATENT DOCUMENTS

| | | |
|---|---|---|
| 2002/0107478 A1 | 8/2002 | Wendlandt |
| 2002/0107511 A1 | 8/2002 | Collins et al. |
| 2002/0107530 A1 | 8/2002 | Sauer et al. |
| 2002/0111647 A1 | 8/2002 | Khairkhahan et al. |
| 2002/0115944 A1 | 8/2002 | Mendes et al. |
| 2002/0133143 A1 | 9/2002 | Murphy et al. |
| 2002/0161394 A1 | 10/2002 | MacOviak et al. |
| 2002/0161406 A1 | 10/2002 | Silvian |
| 2002/0169359 A1 | 11/2002 | McCarthy et al. |
| 2002/0169360 A1 | 11/2002 | Taylor et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2002/0198603 A1 | 12/2002 | Buckberg et al. |
| 2003/0018358 A1 | 1/2003 | Saadat |
| 2003/0023241 A1 | 1/2003 | Drewry et al. |
| 2003/0028202 A1 | 2/2003 | Sancoff et al. |
| 2003/0032979 A1 | 2/2003 | Mortier et al. |
| 2003/0036755 A1 | 2/2003 | Ginn |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0078465 A1 | 4/2003 | Pai et al. |
| 2003/0078652 A1 | 4/2003 | Sutherland |
| 2003/0078671 A1 | 4/2003 | Lesniak et al. |
| 2003/0083742 A1 | 5/2003 | Spence et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0124480 A1 | 7/2003 | Peacock |
| 2003/0149333 A1 | 8/2003 | Alferness |
| 2003/0158570 A1 | 8/2003 | Ferrazzi |
| 2003/0163191 A1 | 8/2003 | Nikolic et al. |
| 2003/0167055 A1 | 9/2003 | Kolata et al. |
| 2003/0181819 A1 | 9/2003 | Desai |
| 2003/0208210 A1 | 11/2003 | Dreyfuss et al. |
| 2003/0212453 A1 | 11/2003 | Mathis et al. |
| 2003/0220667 A1 | 11/2003 | Van Der Burg et al. |
| 2003/0229395 A1 | 12/2003 | Cox |
| 2004/0002626 A1 | 1/2004 | Feld et al. |
| 2004/0054279 A1 | 3/2004 | Hanley |
| 2004/0064014 A1 | 4/2004 | Melvin et al. |
| 2004/0122516 A1 | 6/2004 | Fogarty et al. |
| 2004/0127916 A1 | 7/2004 | Bolduc et al. |
| 2004/0133220 A1 | 7/2004 | Lashinski et al. |
| 2004/0133273 A1 | 7/2004 | Cox |
| 2004/0138529 A1 | 7/2004 | Wiltshire et al. |
| 2004/0138744 A1 | 7/2004 | Lashinski et al. |
| 2004/0138745 A1 | 7/2004 | MacOviak et al. |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0176797 A1 | 9/2004 | Opolski |
| 2004/0176800 A1 | 9/2004 | Paraschac et al. |
| 2004/0186566 A1 | 9/2004 | Hindrichs et al. |
| 2004/0193187 A1 | 9/2004 | Boehringer et al. |
| 2004/0215232 A1 | 10/2004 | Belhe et al. |
| 2004/0220593 A1 | 11/2004 | Greenhalgh |
| 2004/0236419 A1 | 11/2004 | Milo |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0260390 A1 | 12/2004 | Sarac et al. |
| 2004/0260393 A1 | 12/2004 | Rahdert et al. |
| 2004/0267191 A1 | 12/2004 | Gifford, III et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0038509 A1 | 2/2005 | Ashe |
| 2005/0054938 A1 | 3/2005 | Wehman et al. |
| 2005/0055089 A1 | 3/2005 | MacOviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0075727 A1 | 4/2005 | Wheatley |
| 2005/0080402 A1 | 4/2005 | Santamore et al. |
| 2005/0090840 A1 | 4/2005 | Gerbino et al. |
| 2005/0096047 A1 | 5/2005 | Haberman et al. |
| 2005/0096498 A1 | 5/2005 | Houser et al. |
| 2005/0096589 A1 | 5/2005 | Shachar |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0131441 A1 | 6/2005 | Iio et al. |
| 2005/0137659 A1 | 6/2005 | Garabedian et al. |
| 2005/0137689 A1 | 6/2005 | Salahieh et al. |
| 2005/0137695 A1 | 6/2005 | Salahieh et al. |
| 2005/0137700 A1 | 6/2005 | Spence et al. |
| 2005/0143809 A1 | 6/2005 | Salahieh et al. |
| 2005/0148892 A1 | 7/2005 | Desai |
| 2005/0149014 A1 | 7/2005 | Hauck et al. |
| 2005/0149114 A1 | 7/2005 | Cartledge et al. |
| 2005/0154252 A1 | 7/2005 | Sharkey et al. |
| 2005/0177180 A1 | 8/2005 | Kaganov et al. |
| 2005/0177227 A1 | 8/2005 | Heim et al. |
| 2005/0182365 A1 | 8/2005 | Hennemann et al. |
| 2005/0187620 A1 | 8/2005 | Pai et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0197716 A1 | 9/2005 | Sharkey et al. |
| 2005/0203558 A1 | 9/2005 | Maschke |
| 2005/0209636 A1 | 9/2005 | Widomski et al. |
| 2005/0216052 A1 | 9/2005 | Mazzocchi et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0267573 A9 | 12/2005 | MacOviak et al. |
| 2005/0267574 A1 | 12/2005 | Cohn et al. |
| 2005/0273138 A1 | 12/2005 | To et al. |
| 2006/0004424 A1 | 1/2006 | Loeb et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025784 A1 | 2/2006 | Starksen et al. |
| 2006/0025800 A1 | 2/2006 | Suresh |
| 2006/0030881 A1 | 2/2006 | Sharkey et al. |
| 2006/0052867 A1 | 3/2006 | Revuelta et al. |
| 2006/0058871 A1 | 3/2006 | Zakay et al. |
| 2006/0085049 A1 | 4/2006 | Cory et al. |
| 2006/0135968 A1 | 6/2006 | Schaller |
| 2006/0135970 A1 | 6/2006 | Schaller |
| 2006/0173536 A1 | 8/2006 | Mathis et al. |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0241334 A1 | 10/2006 | Dubi et al. |
| 2006/0241745 A1 | 10/2006 | Solem |
| 2006/0264980 A1 | 11/2006 | Khairkhahan |
| 2006/0276683 A1 | 12/2006 | Feld et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2006/0293739 A1 | 12/2006 | Vijay |
| 2007/0010817 A1 | 1/2007 | De Coninck |
| 2007/0016006 A1 | 1/2007 | Shachar |
| 2007/0016068 A1 | 1/2007 | Grunwald et al. |
| 2007/0016288 A1 | 1/2007 | Gurskis et al. |

(56) References Cited

U.S. PATENT DOCUMENTS

| | | |
|---|---|---|
| 2007/0027533 A1 | 2/2007 | Douk |
| 2007/0038208 A1 | 2/2007 | Kefer |
| 2007/0050019 A1 | 3/2007 | Hyde |
| 2007/0060895 A1 | 3/2007 | Sibbitt et al. |
| 2007/0083076 A1 | 4/2007 | Lichtenstein |
| 2007/0088362 A1 | 4/2007 | Bonutti et al. |
| 2007/0115390 A1 | 5/2007 | Makara et al. |
| 2007/0118151 A1 | 5/2007 | Davidson |
| 2007/0118215 A1 | 5/2007 | Moaddeb |
| 2007/0129717 A1 | 6/2007 | Brown, III et al. |
| 2007/0135826 A1 | 6/2007 | Zaver et al. |
| 2007/0135913 A1 | 6/2007 | Moaddeb et al. |
| 2007/0156233 A1 | 7/2007 | Kapadia et al. |
| 2007/0161846 A1 | 7/2007 | Nikolic et al. |
| 2007/0185571 A1 | 8/2007 | Kapadia et al. |
| 2007/0198057 A1 | 8/2007 | Gelbart et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0219460 A1 | 9/2007 | Goldenberg |
| 2007/0225736 A1 | 9/2007 | Zeiner et al. |
| 2007/0249999 A1 | 10/2007 | Sklar et al. |
| 2007/0250160 A1 | 10/2007 | Rafiee |
| 2007/0270681 A1 | 11/2007 | Phillips et al. |
| 2007/0270688 A1 | 11/2007 | Gelbart et al. |
| 2007/0270943 A1 | 11/2007 | Solem et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0033541 A1 | 2/2008 | Gelbart et al. |
| 2008/0045778 A1 | 2/2008 | Lichtenstein et al. |
| 2008/0051802 A1 | 2/2008 | Schostek et al. |
| 2008/0071298 A1 | 3/2008 | Khairkhahan et al. |
| 2008/0086164 A1 | 4/2008 | Rowe |
| 2008/0132915 A1 | 6/2008 | Buckman et al. |
| 2008/0133002 A1 | 6/2008 | Gelbart et al. |
| 2008/0140188 A1 | 6/2008 | Rahdert et al. |
| 2008/0177300 A1 | 7/2008 | Mas et al. |
| 2008/0228266 A1 | 9/2008 | McNamara et al. |
| 2008/0262609 A1 | 10/2008 | Gross et al. |
| 2008/0269785 A1 | 10/2008 | Lampropoulos et al. |
| 2008/0275477 A1 | 11/2008 | Sterrett et al. |
| 2008/0288060 A1 | 11/2008 | Kaye et al. |
| 2008/0312713 A1 | 12/2008 | Wilfley et al. |
| 2009/0076597 A1 | 3/2009 | Dahlgren et al. |
| 2009/0093890 A1 | 4/2009 | Gelbart |
| 2009/0131930 A1 | 5/2009 | Gelbart et al. |
| 2009/0157058 A1 | 6/2009 | Ferren et al. |
| 2009/0192441 A1 | 7/2009 | Gelbart et al. |
| 2009/0192527 A1 | 7/2009 | Messas |
| 2009/0192539 A1 | 7/2009 | Lichtenstein |
| 2009/0204180 A1 | 8/2009 | Gelbart |
| 2009/0287304 A1 | 11/2009 | Dahlgren et al. |
| 2010/0087836 A1 | 4/2010 | Jaramillo et al. |
| 2010/0087837 A1 | 4/2010 | Jaramillo et al. |
| 2010/0161047 A1 | 6/2010 | Cabiri |
| 2010/0179648 A1 | 7/2010 | Richter et al. |
| 2010/0222789 A1 | 9/2010 | Gelbart et al. |
| 2011/0022166 A1 | 1/2011 | Dahlgren et al. |
| 2011/0082538 A1 | 4/2011 | Dahlgren et al. |
| 2011/0087203 A1 | 4/2011 | Lichtenstein et al. |
| 2011/0087227 A1 | 4/2011 | Mazur et al. |
| 2011/0125172 A1 | 5/2011 | Gelbart et al. |
| 2011/0172658 A1 | 7/2011 | Gelbart et al. |
| 2011/0301618 A1 | 12/2011 | Lichtenstein |
| 2012/0083806 A1 | 4/2012 | Goertzen |
| 2012/0158016 A1 | 6/2012 | Gelbart et al. |
| 2012/0245604 A1 | 9/2012 | Tegzes |
| 2013/0041405 A1 | 2/2013 | Gelbart et al. |
| 2013/0238089 A1 | 9/2013 | Lichtenstein et al. |
| 2013/0345797 A1 | 12/2013 | Dahlgren et al. |
| 2014/0135913 A1 | 5/2014 | Lichtenstein et al. |

FOREIGN PATENT DOCUMENTS

| | | |
|---|---|---|
| WO | 90/15582 A1 | 12/1990 |
| WO | 95/10320 A1 | 4/1995 |
| WO | 01/78625 A1 | 10/2001 |
| WO | 03/015611 A2 | 2/2003 |
| WO | 03/077800 A1 | 9/2003 |
| WO | 2004/012629 A1 | 2/2004 |
| WO | 2004/07679 A1 | 6/2004 |
| WO | 2004/084746 A2 | 10/2004 |
| WO | 2004/100803 A1 | 11/2004 |
| WO | 2005/007031 A2 | 1/2005 |
| WO | 2005/046520 A2 | 5/2005 |
| WO | 2005/070330 A1 | 8/2005 |
| WO | 2005/102181 A1 | 11/2005 |
| WO | 2006/017809 A2 | 2/2006 |
| WO | 2006/105121 A2 | 10/2006 |
| WO | 2006/135747 A2 | 12/2006 |
| WO | 2006/135749 A2 | 12/2006 |
| WO | 2007/021647 A2 | 2/2007 |
| WO | 2007/115390 A1 | 10/2007 |
| WO | 2008/002606 A2 | 1/2008 |
| WO | 2009/065042 A2 | 5/2009 |

OTHER PUBLICATIONS

Office Action issued in U.S. Appl. No. 12/899,407 dated Sep. 1, 2016.
Amendment filed in co-pending U.S. Appl. No. 13/652,299 on Sep. 30, 2016.
Notice of Allowance issued in co-pending U.S. Appl. No. 13/652,299 dated Oct. 28, 2016.
Amendment filed in co-pending U.S. Appl. No. 12/904,885 on Nov. 17, 2016.
Amendment filed in co-pending U.S. Appl. No. 12/899,407 on Jan. 20, 2017.
Office Action issued in co-pending U.S. Appl. No. 14/955,544 dated Mar. 21, 2017.
Notice of Allowance issued in U.S. Appl. No. 12/899,407 dated May 5, 2017.
Intention to Grant issued in European Appln. No. 10821276.2 dated Jan. 3, 2017.
Intention to Grant issued in European Appln. No. 10821276.2 dated May 9, 2017.
Amendment filed in U.S. Appl. No. 12/899,407 on May 25, 2017.
Kuhn et al. "Hemodynamic Monitoring." Surgical Treatment: Evidence-Based and Problem-Oriented. In: Holzheimer RG, Mannick JA, editors. Munich: Zuckschwerdt. 2001.
Ratshin et al. "Determination of Left Ventricular Preload and Afterload by Quantitative Echocardiography in Man." Circulation Research. May 1974:711-718. vol. 34.
Office Action issued in U.S. Appl. No. 12/904,885 dated Jun. 28, 2017.
Amendment filed in U.S. Appl. No. 14/955,544 on Jun. 30, 2017.
Lichtenstein et al., "Method for Anchoring a Mitral Valve", Amendment filed Jun. 30, 2015 for U.S. Appl. No. 14/162,469, 7 pages.
Dahlgren et al., "Medical Device, Kit and Method for Constricting Tissue or a Bodily Orifice, for Example, a Mitral Valve", Amendment filed Jun. 4, 2015 for U.S. Appl. No. 13/917,469, 17 pgs.
Lichtenstein et al., "System for Improving Diastolic Dysfunction", Amendment filed Aug. 10, 2015 for U.S. Appl. No. 12/904,885, 18 pgs.
Gelbart et al., "Method and Device for Closing Holes in Tissue", Amendment filed Aug. 14, 2015 for U.S. Appl. No. 13/652,299, 16 pages.
Mack, Michael J., "New Techniques for Percutaneous Repair of the Mitral Valve", Heart Failure Review, 2006; 11:259-268.
Mazur et al., "Bone Fixation Device, Tools and Methods", U.S. Appl. No. 61/138,920, filed Dec. 18, 2008, 88 pgs.
Menicanti et al., "The Dor Procedure: What has Changed After Fifteen Years of Clinical Practice?", Journal of Thoracic and Cardiovascular Surgery 124(5):886-890, Nov. 2002.

(56) References Cited

OTHER PUBLICATIONS

Otasevic, et al., "First-in-Man Implantation of Left Ventricular Partitioning Device in a Patient With Chronic Heart Failure: Twelve-Month Follow-Up", Journal of Cardiac Failure, vol. 13, No. 7, 2007, pp. 517-520.
Rivera et al., "Ventricular Aneurysms and Akinesis", Cleveland Clinic Quarterly 45(1):133-135, 1978.
Sharkey, et al., "Left Ventricular Apex Occluder. Description of a Ventricular Partitioning Device", EuroIntervention, 2006, 2:125-127.
Tanaka, et al., "Artificial SMA Valve for Treatment of Urinary Incontinence: Upgrading of Valve and Introduction of Transcutaneous Transformer", Bio-Medical Materials and Engineering; vol. 9, 1999, pp. 97-112.
Timek, et al., "Septal-Lateral Annular Cinching (SLAC) Reduces Mitral Annular Size Without Perturbing Normal Annular Dynamics", Journal of Heart Valve Disease, vol. 11, No. 1, Jan. 2002; pp. 2-10.
Timek, et al., "Septal-Lateral Annular Cinching Abolishes Acute Ischemic Mitral Regurgitation", Journal of Thoracic and Cardiovascular Surgery, vol. 123, No. 5, May 2002, pp. 881-888.
Torrent-Guasp et al., "Spatial Orientation of the Ventricular Muscle Band and Approach to Partial Ventriculotomy in Heart Failure", Pathogenesis and Treatment, Ch. 36, pp. 685-693, 2002.
Valvano, et al., "Thermal Conductivity and Diffusivity of Biomaterials Measured with Self-Heated Thermistors", International Journal of Thermophysics, vol. 6, No. 3, 1985, pp. 301-311.
Written Opinion, dated Sep. 4, 2009 for PCT/US2009/043612, 6 pgs.
Written Opinion dated Jun. 16, 2011 for PCT/US2010/050945, 4 pgs.
Written Opinion, dated Jan. 8, 2007 for PCT/CA2006/001123, 6 pgs.
Dahlgren et al., "Medical Device, Kit and Method for Constricting Tissue or a Bodily Orifice, for Example, a Mitral Valve", Amendment filed Dec. 30, 2014 for U.S. Appl. No. 13/917,469, 18 pgs.
Gelbart et al., "Method and Device for Closing Holes in Tissue", Office Action dated Nov. 20, 2014 for U.S. Appl. No. 13/652,299, 9 pages.
Goertzen et al., "Tissue Anchor System", Notice of Allowance dated Dec. 3, 2014 for U.S. Appl. No. 13/247,380, 14 pgs.
Dahlgren et al., "Medical Device, Kit and Method for Constricting Tissue or a Bodily Orifice, for Example, a Mitral Valve", Office Action dated Mar. 5, 2015 for U.S. Appl. No. 13/917,469, 52 pgs.
Gelbart et al., "Method and Device for Closing Holes in Tissue", Amendment filed Feb. 5, 2015 for U.S. Appl. No. 13/652,299, 11 pages.
Lichtenstein et al., "System for Improving Diastolic Dysfunction", Office Action dated Apr. 10, 2015 for U.S. Appl. No. 12/904,885, 67 pages.
Lichtenstein et al., Method for Anchoring a Mitral Valve, Office Action dated Apr. 24, 2015 for U.S. Appl. No. 14/162,469, 61 pages.
Tegzes, "Medical Kit for Constricting Tissue or a Bodily Orifice, for Example, a Mitral Valve", Office Action dated Jul. 11, 2014 for U.S. Appl. No. 13/421,677, 9 pgs.
Tegzes, "Medical Kit for Constricting Tissue or a Bodily Orifice, for Example, a Mitral Valve", Amendment filed Dec. 3, 2014 for U.S. Appl. No. 13/421,677, 17 pgs.
Dahlgren et al., "Medical Device for Constricting Tissue or a Bodily Orifice, for Example a Mitral Valve", Office Action dated Dec. 23, 2015 for U.S. Appl. No. 12/899,407, 60 pages.
Extended European Search Report dated Sep. 18, 2014 for EP 10821276.2, 10 pages.
Gelbart et al., "Automatic Atherectomy System", Notice of Allowance dated May 10, 2013 and Certificate of Correction mailed May 6, 2014 for U.S. Appl. No. 13/404,834, 11 pgs.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance dated Aug. 20, 2010 for U.S. Appl. No. 11/436,584, 12 pgs.
Gelbart et al., "Automatic Atherectomy System", Notice of Allowance dated Nov. 25, 2011 and Certificate of Correction mailed Jul. 17, 2012 for U.S. Appl. No. 12/950,871, 24 pgs.
Gelbart et al., "Method and Device for Closing Holes in Tissue", Response to Quayle Action filed Jul. 14, 2014 for U.S. Appl. No. 13/652,299, 29 pages.
Gelbart et al., "Method and Device for Closing Holes in Tissue", Quayle Action dated May 20, 2014 for U.S. Appl. No. 13/652,299, 25 pages.
Gelbart et al., "Method and Device for Closing Holes in Tissue", Preliminary Amendment fiiled Feb. 21, 2013 for U.S. Appl. No. 13/652,299, 9 pages.
Gelbart et al., "Method and Device for Closing Holes in Tissue", Notice of Allowance dated Feb. 24, 2010, Supplemental Notice of Allowance dated Mar. 24, 2010 and Remarks filed after allowance on Apr. 9, 2010 for U.S. Appl. No. 11/436,585, 20 pgs.
Gelbart et al., "Method and Device for Closing Holes in Tissue", Notice of Allowance dated Aug. 22, 2012 for U.S. Appl. No. 12/777,883, 12 pgs.
Goertzen et al., "Tissue Anchor System", Notice of Allowance dated Jul. 7, 2014 for U.S. Appl. No. 13/247,380, 8 pgs.
Goertzen et al., "Tissue Anchor System", Notice of Allowance dated Oct. 16, 2014 for U.S. Appl. No. 13/247,380, 41 pgs.
Lichtenstein et al., "Method for Anchoring a Mitral Valve", Notices of Allowance dated Oct. 2, 2013 and Nov. 13, 2013 for U.S. Appl. No. 13/872,870, 35 pgs.
Lichtenstein et al., "Method for Anchoring a Mitral Valve", Notice of Allowance dated Jan. 28, 2013 for U.S. Appl. No. 11/475,978, 24 pgs.
Lichtenstein et al., "System for Improving Diastolic Dysfunction", Notice of Allowance dated Jul. 12, 2010 for U.S. Appl. No. 11/497,309, 8 pgs.
Lichtenstein et al., "System for Improving Diastolic Dysfunction", Office Action dated Jan. 29, 2014 for U.S. Appl. No. 12/904,885, 38 pgs.
Lichtenstein et al., "System for Improving Diastolic Dysfunction", Amendment filed Apr. 9, 2014 for U.S. Appl. No. 12/904,885, 24 pgs.
Lichtenstein et al., "System for Improving Diastolic Dysfunction", Amendment filed Dec. 18, 2012 for U.S. Appl. No. 12/904,885, 23 pgs.
Lichtenstein, "Closing Openings in Anatomical Tissue", Final Office Action dated Dec. 4, 2013 for U.S. Appl. No. 13/112,695, 31 pages.
Lichtenstein, "Methods and Devices for Altering Blood Flow Through the Left Ventricle", Office Action dated Jul. 9, 2010 for U.S. Appl. No. 10/571,165, 11 pages.
Lichtenstein, "Methods and Devices for Altering Blood Flow Through the Left Ventricle", Office Action dated Mar. 26, 2007 for U.S. Appl. No. 10/622,129, 17 pages.
Lichtenstein, "Methods and Devices for Altering Blood Flow Through the Left Ventricle", Office Action dated Nov. 14, 2007 for U.S. Appl. No. 10/622,129, 6 pages.
Lichtenstein, "Methods and Devices for Altering Blood Flow Through the Left Ventricle", Preliminary Amendment filed Feb. 14, 2008 for U.S. Appl. No. 10/622,129, 15 pages.
Lichtenstein, "Methods and Devices for Altering Blood Flow Through the Left Ventricle", Preliminary Amendment filed Mar. 6, 2006 for U.S. Appl. No. 10/571,165, 7 pages.
Lopes et al., "Enhanced Medical Device for Use in Bodily Cavities, for Example an Atrium", U.S. Appl. No. 61/435,213, filed Jan. 21, 2011, 320 pgs.
Lopes et al., "Enhanced Medical Device for Use in Bodily Cavities, for Example an Atrium", U.S. Appl. No. 61/485,987, filed May 13, 2011, 401 pgs.
Lopes et al., "Enhanced Medical Device for Use in Bodily Cavities, for Example an Atrium", U.S. Appl. No. 61/488,639, filed May 20, 2011, 434 pgs.
Lopes et al., "Enhanced Medical Device for Use in Bodily Cavities, for Example an Atrium", U.S. Appl. No. 61/515,141, filed Aug. 4, 2011, 508 pgs.

(56) References Cited

OTHER PUBLICATIONS

STAR Closure System Brochure, 2005, Abbott Vascular, pp. 1-4.
Stiles, et al., "Simulated Characterization of Atherosclerotic Lesions in the Coronary Arteries by Measurement of Bioimpedance", IEEE Transactions on Biomedical Engineering, vol. 50, No. 7, Jul. 2003, pp. 916-921.
Written Opinion, dated Dec. 5, 2007, for PCT/US2007/014902, 7 pages.
Written Opinion dated Dec. 6, 2004 for PCT/IB2004/002581, 8 pgs.
Written Opinion dated Sep. 10, 2010 for PCT/US2010/021835, 6 pgs.
Written Opinion, dated Dec. 2, 2009, for PCT/US2008/083644, 9 pages.
Dahlgren et al., "Medical Device, Kit and Method for Constricting Tissue or a Bodily Orifice, for Example, a Mitral Valve", Office Action dated Jul. 9, 2014 for U.S. Appl. No. 13/917,469, 37 pgs.
Dahlgren et al., "Medical Device for Constricting Tissue or a Bodily Orifice, for Example a Mitral Valve", Amendment filed Aug. 8, 2013 for U.S. Appl. No. 12/899,407, 65 pages.
Dahlgren et al., "Medical Device for Constricting Tissue or a Bodily Orifice, for Example a Mitral Valve", Amendment filed Dec. 13, 2012 for U.S. Appl. No. 12/899,407, 22 pages.
Dahlgren et al., "Medical Device for Constricting Tissue or a Bodily Orifice, for Example a Mitral Valve", Office Action dated Mar. 8, 2013 for U.S. Appl. No. 12/899,407, 23 pages.
Dahlgren et al., "Medical Device, Kit and Method for Constricting Tissue or a Bodily Orifice, for Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, for Example a Mitral Valve", Final Office Action dated Feb. 13, 2013 for U.S. Appl. No. 12/894,912, 35 pgs.
Dahlgren et al., "Medical Device, Kit and Method for Constricting Tissue or a Bodily Orifice, for Example a Mitral Valve", Office Action dated Aug. 30, 2012 for U.S. Appl. No. 12/894,912, 16 pgs.
Dahlgren et al., "Medical Device, Kit and Method for Constricting Tissue or a Bodily Orifice, for Example a Mitral Valve", Response filed Jun. 13, 2013 for U.S. Appl. No. 12/894,912, 3 pgs.
Gelbart et al., "Automatic Atherectomy System", Amendment filed Oct. 25, 2010 for U.S. Appl. No. 11/436,584, 9 pgs.
Gelbart et al., "Automatic Atherectomy System", Office Action dated Dec. 14, 2010 for U.S. Appl. No. 11/436,584, 12 pgs.
Gelbart et al., "Automatic Atherectomy System", Amendment filed Aug. 4, 2009 for U.S. Appl. No. 11/436,584, 35 pgs.
Goertzen et al., "Tissue Anchor System", Office Action dated Jan. 29, 2013 for U.S. Appl. No. 13/247,380, 10 pgs.
Goertzen et al., "Tissue Anchor System", Amendment filed Dec. 10, 2013 for U.S. Appl. No. 13/247,380, 11 pgs.
Goertzen et al., "Tissue Anchor System", Amendment filed Oct. 11, 2013 for U.S. Appl. No. 13/247,380, 10 pgs.
Goertzen et al., "Tissue Anchor System", Office Action dated Aug. 13, 2013 for U.S. Appl. No. 13/247,380, 15 pgs.
Gelbart et al., "Method and Device for Closing Holes in Tissue", Office Action dated Nov. 4, 2015 for U.S. Appl. No. 13/652,299, 12 pages.
Lichtenstein et al., "System for Improving Diastolic Dysfunction", Final Office Action dated Nov. 23, 2015 for U.S. Appl. No. 12/904,885, 43 pages.
Athanasuleas et al, "Surgical Anterior Ventricular Restoration for Ischemic Cardiomyopathy", Operative Techniques in Thoracic and Cardiovascular Surgery 7(2):66-75, May 2002.
Buchbinder, Maurice, "Dynamic Mitral Valve Annuloplasty: A Reshapable Ring for Residual and Recurring MR", Foundation for Cardiovascular Medicine, La Jolla, CA, May 24, 2007, 23 pgs.
Cardiac Implants, URL=http://nmtmedical.com/products/ci/index.htm, download date May 13, 2006, 1 pg.
Cooley, "Ventricular Aneurysms and Akinesis", Cleveland Clinic Quarterly 45(1):130-132, 1978.
Dahlgren et al, "Medical Device for Constricting Tissue or a Bodily Orifice, for Example a Mitral Valve", Office Action dated Sep. 13, 2012 for U.S. Appl. No. 12/899,407, 28 pgs.
Dahlgren et al., "Medical Device for Constricting Tissue or a Bodily Orifice, for Example a Mitral Valve", Amendment filed Apr. 13, 2010 for U.S. Appl. No. 12/120,195, 22 pgs.
Dahlgren et al., "Medical Device for Constricting Tissue or a Bodily Orifice, for Example a Mitral Valve", Office Action dated Dec. 18, 2009 for U.S. Appl. No. 12/120,195, 9 pgs.
Dahlgren et al., "Medical Device for Constricting Tissue or a Bodily Orifice, for Example a Mitral Valve", Office Action dated Jul. 7, 2010 for U.S. Appl. No. 12/120,195, 14 pgs.
Dahlgren et al., "Medical Device for Constricting Tissue or a Bodily Orifice, for Example a Mitral Valve", Preliminary Amendment filed Oct. 6, 2010 in U.S. Appl. No. 12/899,407, 8 pgs.
Dahlgren et al., "Medical Device, Kit and Method for Constricting Tissue or a Bodily Orifice, for Example a Mitral Valve", U.S. Appl. No. 61/278,232, filed Oct. 1, 2009, 215 pgs.
David et al., "Postinfarction Ventricular Septal Rupture:Repair by Endocardial Patch with Infarct Exclusion", Journal of Thoracic and Cardiovascular Surgery 110(5):1315-1322, 1995.
Dor et al., "Late Hemodynamic Results After Left Ventricular Patch Repair Associated with Coronary Grafting in Patients with Postinfarction Akinetic or Dyskinetic Aneurysm of the Left Ventricle", Journal of Thoracic Cardiovascular Surgery 110(5):1291-1301, 1995.
Dor et al., "Left Ventricular Aneurysm: A New Surgical Approach", Thoracic Cardiovascular Surgery 37:11-19, 1989.
Dor, "Left Ventricular Aneurysms: The Endoventricular Circular Patch Plasty", Seminars in Thoracic and Cardiovascular Surgery 9(2):123-130, Apr. 1997.
Gelbart et al., "Artificial Valve", Amendment filed Jan. 29, 2010 for U.S. Appl. No. 11/497,306, 22 pgs.
Gelbart et al., "Artificial Valve", Office Action dated May 7, 2010 for U.S. Appl. No. 11/497,306, 12 pgs.
Gelbart et al., "Automatic Atherectomy System", Amendment filed Mar. 30, 2010 for U.S. Appl. No. 11/436,584, 20 pgs.
Gelbart et al., "Automatic Atherectomy System", Office Action dated Dec. 1, 2009 for U.S. Appl. No. 11/436,584, 8 pgs.
Gelbart et al., "Automatic Atherectomy System", Office Action dated Mar. 4, 2009 for U.S. Appl. No. 11/436,584, 6 pgs.
Gelbart et al., "Method and Device for Closing Holes in Tissue", Amendment filed Jan. 30, 2009 for U.S. Appl. No. 11/436,585, 5 pgs.
Gelbart et al., "Method and Device for Closing Holes in Tissue", Amendment filed Jun. 2, 2009 for U.S. Appl. No. 11/436,585, 7 pgs.
Gelbart et al., "Method and Device for Closing Holes in Tissue", Amendment filed May 4, 2012 for U.S. Appl. No. 12/777,883, 12 pgs.
Gelbart et al., "Method and Device for Closing Holes in Tissue", Amendment filed Oct. 26, 2009 for U.S. Appl. No. 11/436,585, 13 pgs.
Gelbart et al., "Method and Device for Closing Holes in Tissue", Amendment filed Sep. 22, 2008 for U.S. Appl. No. 11/436,585, 3 pgs.
Gelbart et al., "Method and Device for Closing Holes in Tissue", Office Action dated Feb. 23, 2012 for U.S. Appl. No. 12/777,883, 23 pgs.
Gelbart et al., "Method and Device for Closing Holes in Tissue", Office Action dated Jan. 2, 2009 for U.S. Appl. No. 11/436,585, 11 pgs.
Gelbart et al., "Method and Device for Closing Holes in Tissue", Office Action dated Jul. 7, 2009 for U.S. Appl. No. 11/436,585, 9 pgs.
Gelbart et al., "Method and Device for Closing Holes in Tissue", Office Action dated Sep. 4, 2008 for U.S. Appl. No. 11/436,585, 8 pgs.
Goertzen et al., "Tissue Anchor System", Amendment filed Apr. 29, 2013 for U.S. Appl. No. 13/247,380, 22 pgs.
International Search Report dated Jan. 8, 2007 for PCT/CA2006/001123, 5 pgs.
International Search Report dated Jun. 16, 2011 for PCT/US2010/050945, 5 pgs.
International Search Report dated Sep. 4, 2009 for PCT/US2009/043612, 7 pgs.

(56) References Cited

OTHER PUBLICATIONS

Jatene, "Left Ventricular Aneurysmectomy", Journal of Thoracic and Cardiovascular Surgery 89(3):321-331, 1985.
Konings, et al., "Development of an Intravascular Impedance Catheter for Detection of Fatty Lesions in Arteries", IEEE Transactions on Medical Imaging, vol. 16, No. 4, Aug. 1997, pp. 439-446.
Lichtenstein "Closing Openings in Anatomical Tissue", Amendment filed Aug. 8, 2013 for U.S. Appl. No. 13/112,695, 23 pgs.
Lichtenstein "Closing Openings in Anatomical Tissue", Office Action dated May 8, 2013 for U.S. Appl. No. 13/112,695, 12 pgs.
Lichtenstein "Method and Apparatus for Percutaneous Reduction of Anterior-Posterior Diameter of Mitral Valve", Office Action dated Dec. 1, 2008 for U.S. Appl. No. 11/400,260, 10 pgs.
Lichtenstein "Method and Apparatus for Percutaneous Reduction of Anterior-Posterior Diameter of Mitral Valve", Office Action dated May 15, 2006 for U.S. Appl. No. 10/690,131, 9 pgs.
Lichtenstein "Method and Apparatus for Percutaneous Reduction of Anterior-Posterior Diameter of Mitral Valve", U.S. Appl. No. 10/690,131, filed Oct. 20, 2003, 31 pgs.
Lichtenstein et al., "Method for Anchoring a Mitral Valve", Amendment filed Aug. 31, 2009 for U.S. Appl. No. 11/475,978, 24 pgs.
Lichtenstein et al., "Method for Anchoring a Mitral Valve", Amendment filed Mar. 26, 2010 for U.S. Appl. No. 11/475,978, 26 pgs.
Lichtenstein et al., "Method for Anchoring a Mitral Valve", Office Action dated Dec. 29, 2009 for U.S. Appl. No. 11/475,978, 7 pgs.
Lichtenstein et al., "Method for Anchoring a Mitral Valve", Office Action dated May 1, 2009 for U.S. Appl. No. 11/475,978, 6 pgs.
Lichtenstein et al., "Method for Anchoring a Mitral Valve", Preliminary Amendment filed Jan. 24, 2014 for U.S. Appl. No. 14/162,469, 9 pgs.
Lichtenstein et al., "System for Improving Diastolic Dysfunction", Amendment filed Apr. 22, 2009 for U.S. Appl. No. 11/497,309, 23 pgs.
Lichtenstein et al., "System for Improving Diastolic Dysfunction", Amendment filed Apr. 7, 2010 for U.S. Appl. No. 11/497,309, 8 pgs.
Lichtenstein et al., "System for Improving Diastolic Dysfunction", Amendment filed Oct. 23, 2009 for U.S. Appl. No. 11/497,309, 9 pgs.
Lichtenstein et al., "System for Improving Diastolic Dysfunction", Office Action dated Aug. 5, 2009 for U.S. Appl. No. 11/497,309, 10 pgs.
Lichtenstein et al., "System for Improving Diastolic Dysfunction", Office Action dated Dec. 24, 2008 for U.S. Appl. No. 11/497,309, 8 pgs.
Lichtenstein et al., "System for Improving Diastolic Dysfunction", Office Action dated Jan. 20, 2010 for U.S. Appl. No. 11/497,309, 10 pgs.
Gelbart et al., "Method and Device for Closing Holes in Tissue", Office Action dated May 14, 2015 for U.S. Appl. No. 13/652,299, 67 pages.
"Constellation Mapping Catheters", Brochure, Boston Scientific Corp., 2 pgs, © 2007 Boston Scientific Corporation.
"Phased RF Catheter Ablation System", 2014 Medtronic Inc., 2 pgs, http://www.medtronic.eu/your-health/atrial-fibrillation/about-the-therapy/our-phased-rf-ablation-systern/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Becker, et al., "Ablation of Atrial Fibrillation: Energy Sources and Navigation Tools: A Review", Journal of Electrocardiology, vol. 37, Supplement 2004, pp. 55-62, 2004.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Calkins, Hugh, "Electrophysiology: Radiofrequency Catheter Ablation of Supraventricular Arrhythmias", Heart, 2001; 85; pp. 594-600.

Dahlgren et al., "Medical Device for Constricting Tissue or a Bodily Orifice, for Example a Mitral Valve", Amendment filed Jul. 23, 2013 for U.S. Appl. No. 12/899,407, 60 pages.
Dahlgren et al., "System for Mechanical Adjustment of Medical Implants", Amendment filed Apr. 2, 2010 for U.S. Appl. No. 11/902,099, 19 pgs.
Dahlgren et al., "System for Mechanical Adjustment of Medical Implants", Amendment filed Nov. 1, 2010 for U.S. Appl. No. 11/902,099, 12 pgs.
Dahlgren et al., "System for Mechanical Adjustment of Medical Implants", Office Action dated Jul. 8, 2010 for U.S. Appl. No. 11/902,099, 37 pgs.
Dahlgren et al., "System for Mechanical Adjustment of Medical Implants", Office Action dated Oct. 5, 2009 for U.S. Appl. No. 11/902,099, 13 pgs.
De Ponti, et al., "Non-Fluoroscopic Mapping Systems for Electrophysiology: the Tool or Toy Dilemma After 10 Years", European Heart Journal, 2006; 27, pp. 1134-1136.
European Search Report, dated Jun. 26, 2008 for EP 08100878.1, 11 pgs.
Gabriel, et al., "The Dielectric Properties of Biological Tissues: I. Literature Survey", Phys. Med. Biol.; 41, 1996, pp. 2231-2249.
Gelbart et al., "Automatic Atherectomy System", Amendment filed Sep. 15, 2011 for U.S. Appl. No. 12/950,871, 21 pgs.
Gelbart et al., "Automatic Atherectomy System", Office Action dated Jun. 15, 2011 for U.S. Appl. No. 12/950,871, 16 pgs.
Gelbart et al., "Automatic Atherectomy System", Office Action dated Sep. 25, 2012 for U.S. Appl. No. 13/404,834, 24 pgs.
Gelbart et al., "Intra-Cardiac Mapping and Ablation Method", Amendment filed Feb. 23, 2011 for U.S. Appl. No. 11/475,950, 28 pgs.
Gelbart et al., "Intra-Cardiac Mapping and Ablation Method", Amendment filed Mar. 5, 2008 for U.S. Appl. No. 11/475,950, 11 pgs.
Gelbart et al., "Intra-Cardiac Mapping and Ablation Method", Amendment filed Aug. 16, 2010 for U.S. Appl. No. 11/475,950, 22 pgs.
Gelbart et al., "Intra-Cardiac Mapping and Ablation Method", Office Action dated Nov. 23, 2010 for U.S. Appl. No. 11/475,950, 25 pgs.
Gelbart et al., "Intra-Cardiac Mapping and Ablation Method", Office Action dated Jun. 23, 2010 for U.S. Appl. No. 11/475,950, 18 pgs.
Gelbart et al., "Intra-Cardiac Mapping and Ablation Method", Pre Amend filed Aug. 29, 2007 for U.S. Appl. No. 11/475,950, 42 pgs.
Gelbart et al., "Liposuction System", Amendment filed Dec. 7, 2011 for U.S. Appl. No. 12/010,458, 15 pgs.
Gelbart et al., "Liposuction System", Amendment filed Jun. 10, 2011 for U.S. Appl. No. 12/010,458, 10 pgs.
Gelbart et al., "Liposuction System", Office Action dated Mar. 16, 2011 for U.S. Appl. No. 12/010,458, 12 pgs.
Gelbart et al., "Liposuction System", Office Action dated Sep. 14, 2011 for U.S. Appl. No. 12/010,458, 9 pgs.
Gelbart et al., "Medical Device for Use in Bodily Lumens, for Example an Atrium", Office Action dated Jul. 25, 2011 for U.S. Appl. No. 11/941,819, 9 pgs.
Gelbart, "System for Implanting a Microstimulator", Amendment filed Jan. 20, 2010 for U.S. Appl. No. 12/068,878, 26 pgs.
Gelbart, "System for Implanting a Microstimulator", Office Action dated Aug. 18, 2010 for U.S. Appl. No. 12/068,878, 11 pgs.
Gelbart, "System for Implanting a Microstimulator", Office Action dated Aug. 20, 2009 for U.S. Appl. No. 12/068,878, 12 pgs.
International Preliminary Report on Patentability, dated Jan. 6, 2009 for PCT/US2007/014902, 8 pages.
International Search Report dated Dec. 6, 2004 for PCT/IB2004/002581, 3 pgs.
International Search Report dated Sep. 10, 2010 for PCT/US2010/021835, 4 pgs.
International Search Report, dated Dec. 2, 2009 for PCT/US2008/083644, 4 pages.
International Search Report, dated Dec. 5, 2007 for PCT/US2007/014902, 4 pages.

(56) References Cited

OTHER PUBLICATIONS

Jaramillo et al, "Surgical Instrument and Method for Tensioning and Securing a Flexible Suture", Amendment filed Dec. 4, 2012 for U.S. Appl. No. 12/436,926, 19 pgs.

Jaramillo et al, "Surgical Instrument and Method for Tensioning and Securing a Flexible Suture", Amendment filed Feb. 27, 2012 for U.S. Appl. No. 12/436,926, 25 pgs.

Jaramillo et al, "Surgical Instrument and Method for Tensioning and Securing a Flexible Suture", Amendment filed Jul. 26, 2011 for U.S. Appl. No. 12/246,614, 41 pgs.

Jaramillo et al, "Surgical Instrument and Method for Tensioning and Securing a Flexible Suture", Amendment filed Mar. 14, 2011 for U.S. Appl. No. 12/246,614, 22 pgs.

Jaramillo et al, "Surgical Instrument and Method for Tensioning and Securing a Flexible Suture", Amendment filed Oct. 5, 2011 for U.S. Appl. No. 12/436,926, 77 pgs.

Jaramillo et al, "Surgical Instrument and Method for Tensioning and Securing a Flexible Suture", Office Action dated Dec. 13, 2010 for U.S. Appl. No. 12/246,614, 15 pgs.

Jaramillo et al, "Surgical Instrument and Method for Tensioning and Securing a Flexible Suture", Office Action dated Jan. 11, 2012 for U.S. Appl. No. 12/436,926, 26 pgs.

Jaramillo et al, "Surgical Instrument and Method for Tensioning and Securing a Flexible Suture", Office Action dated Jul. 8, 2011 for U.S. Appl. No. 12/436,926, 17 pgs.

Jaramillo et al, "Surgical Instrument and Method for Tensioning and Securing a Flexible Suture", Office Action dated May 27, 2011 for U.S. Appl. No. 12/246,614, 24 pgs.

Jaramillo et al, "Surgical Instrument and Method for Tensioning and Securing a Flexible Suture", Office Action dated Sep. 21, 2012 for U.S. Appl. No. 12/436,926, 14 pgs.

Lichtenstein et al., "System for Improving Diastolic Dysfunction", Office Action dated Sep. 18, 2012 for U.S. Appl. No. 12/904,885, 15 pgs.

Lichtenstein et al., "System for Improving Diastolic Dysfunction", Preliminary Amendment filed Oct. 14, 2010 for U.S. Appl. No. 12/904,885, 23 pgs.

Lichtenstein, "Methods and Devices for Altering Blood Flow Through the Left Ventricle", Amendment filed Jul. 26, 2007 U.S. Appl. No. 10/622,129, 17 pages.

Lichtenstein, "Methods and Devices for Altering Blood Flow Through the Left Ventricle", Examiner's Amendment dated Mar. 2, 2009 for U.S. Appl. No. 10/622,129, 5 pages.

Notice of Allowance issued in copending U.S. Appl. No. 14/955,544 dated Sep. 5, 2017.

Amendment filed in copending U.S. Appl. No. 12/904,885 on Nov. 28, 2017.

Office Action issued in copending U.S. Appl. No. 12/904,885 dated Mar. 22, 2018.

MEDICAL KIT FOR CONSTRICTING TISSUE OR A BODILY ORIFICE, FOR EXAMPLE, A MITRAL VALVE

CROSS REFERENCE TO RELATED APPLICATIONS

This application is a divisional application of U.S. patent application Ser. No. 13/421,677, filed on Mar. 15, 2012, which claims benefit under 35 U.S.C. 119(e) to U.S. Provisional Patent Application No. 61/467,883, filed on Mar. 25, 2011, the entire disclosure of both of such applications is hereby incorporated herein by reference.

BACKGROUND

Field

This disclosure is generally related to percutaneous or minimally invasive surgery, and more particularly to percutaneously deployed medical devices suitable for constricting tissue or a bodily orifice, such as a mitral valve.

Description of the Related Art

Cardiac surgery was initially undertaken by performing a sternotomy, a type of incision in the center of the chest, which separates the sternum (chest bone) to allow access to the heart. In the previous several decades, more and more cardiac operations are performed using a percutaneous technique, which is a medical procedure where access to inner organs or other tissue is gained via a catheter.

Percutaneous surgeries benefit patients by reducing surgery risk, complications, and recovery time. However, the use of percutaneous technologies also raises some particular challenges. Medical devices used in percutaneous surgery need to be deployed via narrow tubes called catheter sheaths which significantly increase the complexity of the device structure. As well, doctors do not have direct visual contact with the medical tools used once they are placed within the body, and positioning the tools correctly and operating the tools successfully can often be very challenging. Various catheters can be deployed through a catheter sheath in percutaneous surgical applications.

One example of where percutaneous medical techniques are starting to be used is in the treatment of a heart disorder called mitral regurgitation. Mitral regurgitation is a condition in which blood flows backward from the left ventricle into the left atrium. The mitral apparatus is made up of four major structural components and includes the annulus, the two leaflets, the chordae and the papillary muscles. Improper function of anyone of these structures, alone or in combination can lead to mitral regurgitation. Annular dilation is a major component in the pathology of mitral regurgitation regardless of cause and is manifested in mitral regurgitation related to dilated cardiomyopathy and in chronic mitral regurgitation due to ischemia.

The mitral valve is intended to prevent the undesired flow of blood from the left ventricle into the left atrium when the left ventricle contracts. In a normal mitral valve, the geometry of the mitral valve ensures the cusps overlay each other to preclude the regurgitation of blood during left ventricular contraction and thereby prevent elevation of pulmonary vascular pressures and resultant symptoms of shortness of breath. Studies of the natural history of mitral regurgitation have found that totally asymptomatic patients with severe mitral insufficiency usually progress to severe disability within 5 years.

At present, treatment consists of either mitral valve replacement or repair. Both methods require open heart surgery. Replacement can be performed with either mechanical or biological valves and is particularly suitable when one of the mitral cusps has been severely damaged or deformed. The mechanical valve carries the risk of thromboembolism and requires anticoagulation with all of its potential hazards, whereas the biological prosthesis suffers from limited durability. Another hazard with replacement is the risk of endocarditis. These risks and other valve related complications are greatly diminished with valve repair. Mitral valve repair is theoretically possible if the mitral valve leaflets are structurally normal but fail to appropriately coapt because of annular dilatation or papillary muscle dysfunction, or both. Various surgical procedures have been developed to improve coaptation of the leaflet and to correct the deformation of the mitral valve annulus and retain the intact natural heart valve function. These procedures generally involve reducing the circumference of the posterior mitral leaflet annulus (lateral annulus) where most of the dilatation occurs. The annulus of the anterior leaflet (septal annulus) does not generally dilate because it is anchored to the fibrous skeleton at the base of the heart. Such techniques, known as mitral annuloplasty, typically suture a prosthesis around the base of the valve leaflets shortening the lateral annulus to reshape the mitral valve annulus and minimize further dilation. Different types of mitral annuloplasty prostheses have been developed for use in such surgery. In general, such prostheses are annular or partially annular shaped and may be formed from rigid or flexible material.

Mitral valve surgery requires an extremely invasive approach that includes a chest wall incision, cardiopulmonary bypass, cardiac and pulmonary arrest, and an incision on the heart itself to gain access to the mitral valve. Such a procedure is expensive, requires considerable time, and is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction. Furthermore, the effectiveness of such procedures is difficult to assess during the procedure and may not be known until a much later time. Hence, the ability to make adjustments to or changes in the prosthesis function to obtain optimum effectiveness is extremely limited. Correction at a later date would require another open heart procedure.

In an attempt to treat mitral regurgitation without the need for cardiopulmonary bypass and without opening the chest, percutaneous approaches have been devised to repair the valve or place a correcting apparatus for correcting the annulus relaxation. Such approaches make use of devices which can be generally grouped into two types: 1) devices deforming (mainly shortening) the coronary sinus; and 2) devices pulling together two anchor points in order to affect the mitral valve, one of the anchor points can be the coronary sinus (typically using a wire that is pulled and secured).

Neither approach emulates the current "gold standard" in mitral valve repair—annuloplasty using an open or closed ring. Both approaches suffer from several problems as a result of attempting to reshape the mitral annulus using an alternative method. Devices that deform the coronary sinus, while suitable for percutaneous procedures, are not effective in controlling the leakage of the mitral valve as the forces are not applied from the correct opposite sides of the valve, which are the lateral annulus and the septal annulus. The devices of the second type are not easily adapted to a percutaneous procedure. In order to achieve shortening in the direction connecting the lateral annulus to the septal annulus the anchor points should be located along this direction, so pulling them together will affect the desired direction of shortening. Pulling applied along a different direction will distort the mitral valve but will not achieve the optimal approximation of the two leaflets.

Thus, there is a need for methods and apparatus that enable the ability to create a mitral annuloplasty that applies forces from various desired directions via a percutaneous or intravascular procedure.

BRIEF SUMMARY

The subject of the present application is a medical device with capabilities for percutaneous deployment and annulus shape modification and a superior method for constricting tissue or a bodily orifice, such as the mitral valve, tricuspid valve, or aortic valve via such device. The device may enable methods that enable an open (i.e., split) ring to be anchored to tissue in the vicinity of an orifice or annulus and may enable a change in the shape of said annulus by the anchored ring. Reference throughout this specification is made to cardiac surgery, but the methods and apparatus described herein may also be used in gastric surgery, bowel surgery, or other surgeries in which tissue may be drawn together. The methods and apparatus described herein may also be used to draw or hold tissue not part of an orifice or annulus together. The methods and apparatus described herein may be used in minimally invasive surgery as well as intravascular or percutaneous surgery. Other advantages will become apparent from the teaching herein to those of skill in the art.

An implant kit may be summarized as including an implant member and a plurality of tissue anchors. Each of the plurality of tissue anchors is at least partially embeddable into tissue at a respective location about an orifice within a body during an implant procedure. The implant member is reconfigurable between a delivery configuration in which the implant member is manipulable to a size and dimension to be delivered percutaneously to the tissue within the body, and a deployed configuration in which the implant member forms a structure sufficiently rigid to affect a shape of the orifice in the tissue. The implant member includes a plurality of segments, each of the segments physically coupled to another of the plurality of segments. The implant member includes a plurality of tissue anchor receivers, each of the tissue anchor receivers arranged to selectively receive a respective one of the plurality of tissue anchors. The implant member includes at least a first pivot joint comprising a first pivot pin and a first pivot axis. The first pivot pin of the first pivot joint is arranged to pivotally couple a first set of two or more of the segments together, each segment in the first set of two or more of the segments arranged to pivot about the first pivot axis when the implant member is moved between the delivery configuration and the deployed configuration, the first pivot joint arranged such that the first pivot axis intersects a minimum cylindrical volume containing a first one of the plurality of tissue anchors when the first one of the plurality of tissue anchors is secured to the implant member.

The first one of the plurality of tissue anchors may be received by a first tissue anchor receiver of the plurality of tissue anchor receivers when the first one of the plurality of tissue anchors is secured to the implant member. The first tissue anchor receiver may be arranged to impede a portion of the first one of the plurality of tissue anchors from moving along at least one direction when the first one of the plurality of tissue anchors is secured to the implant member, the at least one direction having a directional component parallel to a direction that the first pivot axis extends along. The first tissue anchor receiver may be arranged to impede the portion of the first one of the plurality of tissue anchors from moving perpendicularly to the first pivot axis when the first one of the plurality of tissue anchors is secured to the implant member.

The first one of the plurality of tissue anchors may be embedded in the tissue when the first one of the plurality of tissue anchors is received by a first tissue anchor receiver of the plurality of tissue anchor receivers. The first one of the plurality of tissue anchors may be embedded in the tissue when the first one of the plurality of tissue anchors is secured to the implant member. The implant kit may include at least one implant guide line physically coupled to the first one of the plurality of tissue anchors to provide a physical path for the implant member to the first one of the plurality of tissue anchors when the first one of the plurality of tissue anchors is embedded in the tissue, the implant member moveable along the physical path to a position where the implant member is secured to the first one of the plurality of tissue anchors. The implant member include at least one guide line receiver, the at least one guide line receiver sized and dimensioned to receive the at least one implant guide line.

The first pivot joint may be one of a plurality of pivot joints, each of the pivot joints including a respective pivot axis, and each of the pivot joints arranged to pivotally couple each of the segments together in a respective one of a plurality of sets of two or more of the segments. Each tissue anchor of at least one of the plurality of tissue anchors may positioned such that a minimum cylindrical volume containing a respective tissue anchor of the at least one of the plurality of tissue anchors is not intersected by each of the pivot axes when the plurality of tissue anchors are secured to the implant member. Each pivot axis may be parallel to another of the pivot axes. At least one of the pivot axes may not be parallel to another of the pivot axes.

Each of the plurality of tissue anchor receivers may include a respective at least one alignment surface arranged to guide a portion of a respective one of the plurality of tissue anchors to a position where the respective one of the plurality of tissue anchors is securable to the implant member. The respective at least one alignment surface of each of one or more of the plurality of tissue anchor receivers may include a curved surface portion. The respective at least one alignment surface of each of one or more of the plurality of tissue anchor receivers may include a tapered or conical surface portion. The at least one alignment surface of the respective one of the plurality of tissue anchor receivers associated with the first one of the plurality of tissue anchors may be circumferentially arranged about an axis that is substantially parallel to the first pivot axis of the first pivot joint. The at least one alignment surface of the respective one of the plurality of tissue anchor receivers associated with the first one of the plurality of tissue anchors may be circumferentially arranged about an axis that is collinear with the first pivot axis associated with the first pivot joint.

The implant kit may further include a biasing device, the biasing device applying force to the first one of the plurality of tissue anchors when the first one of the plurality of tissue anchors is secured to the implant member, the force applied along a direction having a directional component parallel to a direction that the first pivot axis associated with the first pivot joint extends along.

The implant kit may further include a coupler arranged to engage a portion of the first one of the plurality of tissue anchors to capture a portion of the implant member between the coupler and a second portion of the first one of the plurality of tissue anchors when the first one of the plurality of tissue anchors is secured to the implant member, the second portion of the first one of the plurality of tissue anchors embeddable into the tissue. The first one of the plurality of tissue anchors may be embedded in the tissue when the first one of the plurality of tissue anchors is secured to the implant member. The implant kit may further include at least one implant guide line physically coupled to the first one of the plurality of tissue anchors to provide a physical path for the coupler to the first one of the plurality of tissue anchors when embedded in the tissue, the coupler moveable along the physical path to a position where the coupler engages the portion of the first one of the plurality of tissue anchors when embedded in the tissue to capture the portion of the implant member between the coupler and the second portion of the first one of the plurality of tissue anchors. A portion of the coupler and the implant member may be provided in a unitary structure.

The implant may further include a holder activatable between a free configuration in which a first segment in the first set of two or more of the segments is arranged to pivot about the first pivot axis along each of a first rotational direction towards a second segment in the first set of two or more of the segments and along a second rotational direction away from the second segment in the first set of two or more of the segments, and a fixed configuration in which the first segment in the first set of two or more of the segments is impeded from pivoting about the first pivot axis along each of the first rotational direction and the second rotational direction with a greater resistance than when the holder is in the free configuration, wherein the first rotational direction and the second rotational direction are opposing rotational directions. A portion of the first segment in the first set of two or more of the segments may be spaced relatively farther apart from a portion of the second segment in the first set of two or more of the segments along an axis parallel to the first pivot axis when the holder is in the free configuration. The portion of the first segment in the first set of two or more of the segments may be spaced relatively closer to the portion of the second segment in the first set of two or more of the segments along the axis parallel to the first pivot axis when the holder is in the fixed configuration. The holder may include a plurality of interlockable elements which are brought into interlocked engagement when the implant member is moved into the deployed configuration. Each of the plurality of interlockable elements may include a trapezoidal shaped projection or a trapezoidal shaped recess.

The first segment in the first set of two or more of the segments may be impeded from pivoting about the first pivot axis along the first rotational direction towards the second segment in the first set of two or more of the segments with a first resistance when the holder is in the fixed configuration, and the first segment in the first set of two or more of the segments may be impeded from pivoting about the first pivot axis along the second rotational direction away from the second segment in the first set of two or more of the segments with a second resistance when the holder is in the fixed configuration. Each of the first resistance and the second resistance may be provided at least in part by the holder, and a magnitude of the second resistance may be less than a magnitude of the first resistance.

The first pivot joint may be arranged such that the first pivot axis intersects a surface of the first one of the plurality of tissue anchors when the first one of the plurality of tissue anchors is secured to the implant member.

Various systems and methods may include combinations and subsets of those summarized above.

An implant kit may be summarized as including an implant member and a plurality of tissue anchors. The plurality of tissue anchors is configured to be at least partially embedded into tissue at respective locations about an orifice within a body during an implant procedure. The implant member is reconfigurable between a delivery configuration in which the implant member is manipulable to a size and dimension to be delivered percutaneously to the tissue within the body, and a deployed configuration in which the implant member forms a structure sufficiently rigid to affect a shape of the orifice in the tissue. The implant member includes a plurality of segments and a number of pivot joints, each pivot joint including a respective pivot pin and a respective pivot axis. The pivot pin of each pivot joint is arranged to pivotally couple each of the segments together in a respective one of a number of sets of two or more of the segments, at least one segment in each respective one of the number of sets of two or more of the segments pivoting about the respective pivot axis of the pivot joint when the implant member is moved between the delivery configuration and the deployed configuration. The implant member includes a plurality of tissue anchor receivers, each tissue anchor receiver including at least one alignment surface arranged to contact a portion of a respective one of the plurality of tissue anchors and align the portion of the respective one of the plurality of tissue anchors with respect to an alignment axis of the tissue anchor receiver when the respective one of the plurality of tissue anchors is secured to the implant member. The portion of the respective one of the plurality of tissue anchors is impeded from moving along the alignment axis of the tissue anchor receiver to break contact with the at least one alignment surface of the tissue anchor receiver when the respective one of the plurality of tissue anchors is secured to the implant member. The respective alignment axis of at least a first one of the plurality of tissue anchor receivers is non-parallel with the respective pivot axis of at least one of the number of pivot joints. The respective alignment axis of at least a second one of the plurality of tissue anchor receivers is substantially parallel to the respective pivot axis of the at least one of the number of pivot joints.

The respective at least one alignment surface of each tissue anchor receiver may be arranged to restrain or impede the portion of the respective one of the plurality of tissue anchors from moving along a direction having a directional component perpendicular to the respective alignment axis of the tissue anchor receiver when the respective one of the plurality of tissue anchors is secured to the implant member.

At least one of the plurality of tissue anchors may be embedded in the tissue when the respective portion of the at least one of the plurality of tissue anchors is aligned by the at least one alignment surface of a respective one of the plurality of tissue anchor receivers. At least one of the plurality of tissue anchors may be embedded in the tissue when the at least one of the plurality of tissue anchors is secured to the implant member. The implant kit may further include a number of implant guide lines, each of the number of implant guide lines physically coupled to the at least one of the plurality of tissue anchors when the at least one of the plurality of tissue anchors is embedded in the tissue to provide a physical path for the implant member to the at least one of the plurality of tissue anchors. The implant member may be moveable along the physical path to a position where the implant member is secured to the at least one of the plurality of tissue anchors.

The number of pivot joints may include a plurality of pivot joints arranged such that the respective pivot axes of at least two of the plurality of pivot joints are parallel with respect to one another. The number of pivot joints may include a plurality of pivot joints arranged such that the respective pivot axes of at least two of the plurality of pivot joints are non-parallel with respect to one another.

The implant kit may further include a plurality of biasing devices, each of the biasing devices biasing the segments together in a respective one of the number of sets of two or more of the segments when the plurality of tissue anchors are secured to the implant member. The implant kit may further include a plurality of couplers, each coupler arranged to engage a respective first portion of a respective one of the plurality of tissue anchors to capture a portion of the implant member between the coupler and a respective second portion of the respective one of the plurality of tissue anchors when the respective one of the plurality of tissue anchors is secured to the implant member, the respective second portion of each of the plurality of tissue anchors may be embeddable into the tissue.

The implant kit may further include a number of holders, each holder activatable between a free configuration in which each segment in a respective one of the number of sets of two or more of the segments is arranged to pivot towards and away from another one of the segments in the respective one of the number of sets of two or more of the segments, and a fixed configuration in which the segment in the respective one of the number of sets of two or more of the segments is impeded from pivoting towards and away from the another one of the segments in the respective one of the number of sets of two or more of the segments with a greater resistance than when the holder is in the free configuration. Each holder may include a respective plurality of interlockable elements which are brought into interlocked engagement when the implant member is moved into the deployed configuration. Each of the plurality of interlockable elements may include a trapezoidal shaped projection or a trapezoidal shaped recess.

The respective alignment axis of at least the second one of the plurality of tissue anchor receivers may be collinear with the respective pivot axis of the at least one of the number of pivot joints.

Various systems and methods may include combinations and subsets of those summarized above.

An implant may be summarized as including an implant member and a plurality of tissue anchors. Each of the plurality of tissue anchors is at least partially embeddable in tissue at a respective location about an orifice within a body during an implant procedure. The implant member is reconfigurable between a delivery configuration in which the implant member is manipulable to a size and dimension to be delivered percutaneously to the tissue within the body, and a deployed configuration in which the implant member forms a structure sufficiently rigid to affect a shape of the orifice in the tissue. The implant member includes a plurality of segments and a pivot joint including a pivot axis. The pivot joint is arranged to pivotally couple two segments of the plurality of segments together. The implant member includes a holder activatable between a free configuration in which the two segments are arranged to pivot towards and away from each other about the pivot axis, and a fixed configuration in which the two segments are impeded from pivoting towards and away from each other about the pivot axis with a greater resistance than when the holder is in the free configuration. The holder includes a plurality of interlockable elements positioned in interlocked engagement when the holder is in the fixed configuration. A first one of the two segments is impeded with a first resistance from pivoting about the pivot axis along a first rotational direction towards a second one of the two segments when the holder is in the fixed configuration, and the first one of the two segments is impeded with a second resistance from pivoting about the pivot axis along a second rotational direction away from the second one of the two segments when the holder is in the fixed configuration. The second rotational direction is opposite to the first rotational direction. Each of the first resistance and the second resistance is provided at least in part by the holder, and a magnitude of the second resistance is less than a magnitude of the first resistance.

The plurality of interlockable elements comprise a first set of the interlockable elements having a plurality of projections and a plurality of recesses, and a second set of the interlockable elements having a plurality of projections and a plurality of recesses. Each of the projections in each of the first and the second sets of the interlockable elements may be sized and dimensioned to be received by a respective one of the recesses in the other of the first and the second sets of the interlockable elements when the first set of the interlockable elements is moved relatively closer to the second set of the interlockable elements along a direction having a directional component parallel to a direction that the pivot axis extends along.

Each of the projections and recesses in the first set of the interlockable elements and the first one of the two segments may be provided in a first unitary structure. Each of the projections and recesses in the second set of the interlockable elements and the second one of the two segments may be provided in a second unitary structure.

Each of the projections in each of the first and the second sets of the interlockable elements may be sized and dimensioned to be received by a respective one of the recesses in the other of the first and the second sets of the interlockable elements when the plurality of interlockable elements are moved into interlocked engagement. Each of the projections and recesses in each of the first and the second sets of the interlockable elements may be radially arranged about the pivot axis. The plurality of interlockable elements may be moved into interlocked engagement when a portion of the first one of the two segments is moved relatively with respect to a portion of the second one of two segments along an axis that is substantially parallel to the pivot axis. The pivot joint may include a pivot pin, and the plurality of interlockable elements may be moved into interlocked engagement when at least one of the two segments is moved axially along the pivot pin to reduce a distance between the two segments. The first one of the two segments may be axially positioned along the pivot pin relatively closer to the second one of the two segments on the pivot pin when the implant member is in the deployed configuration, and the first one of the two segments may be axially positioned along the pivot pin relatively farther from the second one of two segments when the implant member is in the delivery configuration.

The implant may further include a biasing device arranged to apply a force to bias the two segments together when the implant member is in the deployed configuration, the force applied along a direction having a directional component parallel to a direction that the pivot axis extends along. The implant may further include a coupler arranged to secure the first one of the plurality of tissue anchors to the implant member, at least the coupler and the biasing device provided in a unitary structure.

At least some of the projections in at least one of the first and the second sets of the interlockable elements may be shaped and sized for wedged engagement with at least some of the recesses in the other of the first and the second sets of the interlockable elements when the at least one of the first and the second sets of the interlockable elements is moved relatively closer to the other of the first and the second sets of the interlockable elements along a direction having a first directional component parallel to a direction that the pivot axis extends along. At least one projection in the at least one of the first and the second sets of the interlockable elements may include a respective pair of non-parallel opposing surfaces positioned to be wedged between two opposing surfaces of a respective one of the recesses in the other of the first and the second sets of the interlockable elements when the at least one of the first and the second sets of the interlockable elements is moved relatively closer to the other of the first and the second sets of the interlockable elements along the direction having the first directional component. A first surface of the respective pair of non-parallel opposing surfaces may be oriented with respect to the first directional component by a greater angular amount than a second surface of the respective pair of non-parallel opposing surfaces. The second surface of the respective pair of non-parallel opposing surfaces may be oriented substantially parallel to the first directional component.

The plurality of interlockable elements may be brought into wedged engagement when a portion of the first one of the two segments is moved relatively closer to a portion of the second one of two segments along an axis that is substantially parallel to the pivot axis. The portion of the first one of the two segments may be positioned relatively closer to the portion of the second one of the two segments along the axis that is substantially parallel to the pivot axis when the implant member is in the deployed configuration than when the implant member is in the delivery configuration.

The plurality of interlockable elements may be arranged within the holder to interlock with one another when the implant member is moved into the deployed configuration. At least one recess in the at least one of the first and the second sets of the interlockable elements may include a respective pair of nonparallel opposing surfaces positioned to be wedged against two opposing surfaces of a respective one of the projections in the other of the first and the second sets of the interlockable elements when the at least one of the first and the second sets of the interlockable elements is moved relatively closer to the other of the first and the second sets of the interlockable elements along the direction having the first directional component. A first surface of the respective pair of non-parallel opposing surfaces may be oriented with respect to the first directional component by a greater angular amount than a second surface of the respective pair of nonparallel opposing surfaces.

Various systems and methods may include combinations and subsets of those summarized above.

An implant kit may be summarized as including an implant member and a plurality of tissue anchors. Each of the plurality of tissue anchors is at least partially embeddable into tissue at a respective location about an orifice within a body during an implant procedure. The implant member is reconfigurable between a delivery configuration in which the implant member is manipulable to a size and dimension to be delivered percutaneously to the tissue within the body, and a deployed configuration in which the implant member forms a structure sufficiently rigid to affect a shape of the orifice in the tissue. The implant member includes a plurality of segments and a plurality of tissue anchor receivers. Each tissue anchor receiver includes at least one alignment surface arranged to contact a portion of a respective one of the plurality of tissue anchors and position the portion of the respective one of the plurality of tissue anchors at a location where the one of the plurality of tissue anchors is securable to the implant member. The implant member includes at least a first pivot joint comprising a first pivot member. The first pivot joint is arranged to pivotally couple a first set of two or more of the segments together, at least some of the segments in the first set of two or more of the segments arranged to turn about the first pivot member when the implant member is moved between the delivery configuration and the deployed configuration. The first pivot member and a first one of the tissue anchor receivers are provided in a unitary structure.

The first pivot member may be fixedly coupled to one of the segments in the first set of two or more of the segments. At least one segment in the first set of two or more of the segments may be slidably and pivotably coupled to the first pivot member. The at least one segment in the first set of two or more of the segments may be arranged to translate along, and turn about, the first pivot member when the implant member is moved between the delivery configuration and the deployed configuration. The first pivot member may include at least one obstruction positioned to capture the at least one segment in the first set of two or more of the segments on the first pivot member.

The respective at least one alignment surface of the first one of the tissue anchor receivers may be radially spaced apart from a pivot axis of the first pivot joint by a different radial distance than a surface of the first pivot member contacted by the at least some of the segments in the first set of two or more of the segments. The respective at least one alignment surface of the first one of the tissue anchor receivers may include a tapered surface portion.

The implant member may include a plurality of interlockable elements arranged about a pivot axis of the first pivot joint, a first set of the interlockable elements arranged to interlock with a second set of interlockable elements when the implant member is in the deployed configuration.

Various systems and methods may include combinations and subsets of those summarized above.

An implant kit may be summarized as including an implant member and a plurality of tissue anchors. Each of the plurality of tissue anchors is at least partially embeddable into tissue at a respective location about an orifice within a body during an implant procedure. The implant member is reconfigurable between a delivery configuration in which the implant member is manipulable to a size and dimension to be delivered percutaneously to the tissue within the body, and a deployed configuration in which the implant member forms a structure sufficiently rigid to affect a shape of the orifice in the tissue. The implant member includes a plurality of rigid portions and at least one bendable portion arranged to pivotally couple at least one of the rigid portions with at least another of the rigid portions. The implant member includes a plurality of tissue anchor receivers. Each tissue anchor receiver includes at least one alignment surface arranged to contact a portion of a respective one of the plurality of tissue anchors and position the portion of the respective one of the plurality of tissue anchors at a location where the one of the plurality of tissue anchors is securable to the implant member. At least a first one of the plurality of tissue anchor receivers is located in one of the plurality of rigid portions and at least a second one of the plurality of tissue anchor receivers located in the at least one bendable portion.

Various systems and methods may include combinations and subsets of all those summarized above.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the embodiments of the invention.

Reference throughout this specification to "one embodiment" or "an embodiment" or "an example embodiment" or "an illustrated embodiment" means that a particular feature, structure or characteristic described in connection with the embodiment is included in at least one embodiment of the present invention. Thus, the appearances of the phrases such as "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the claimed invention.

Overview of Device and Orifice Constriction Methods

Various embodiments of medical apparatus which are percutaneously or intravascularly deployed and may be used for constricting a bodily orifice are described herein.

Figure 1:
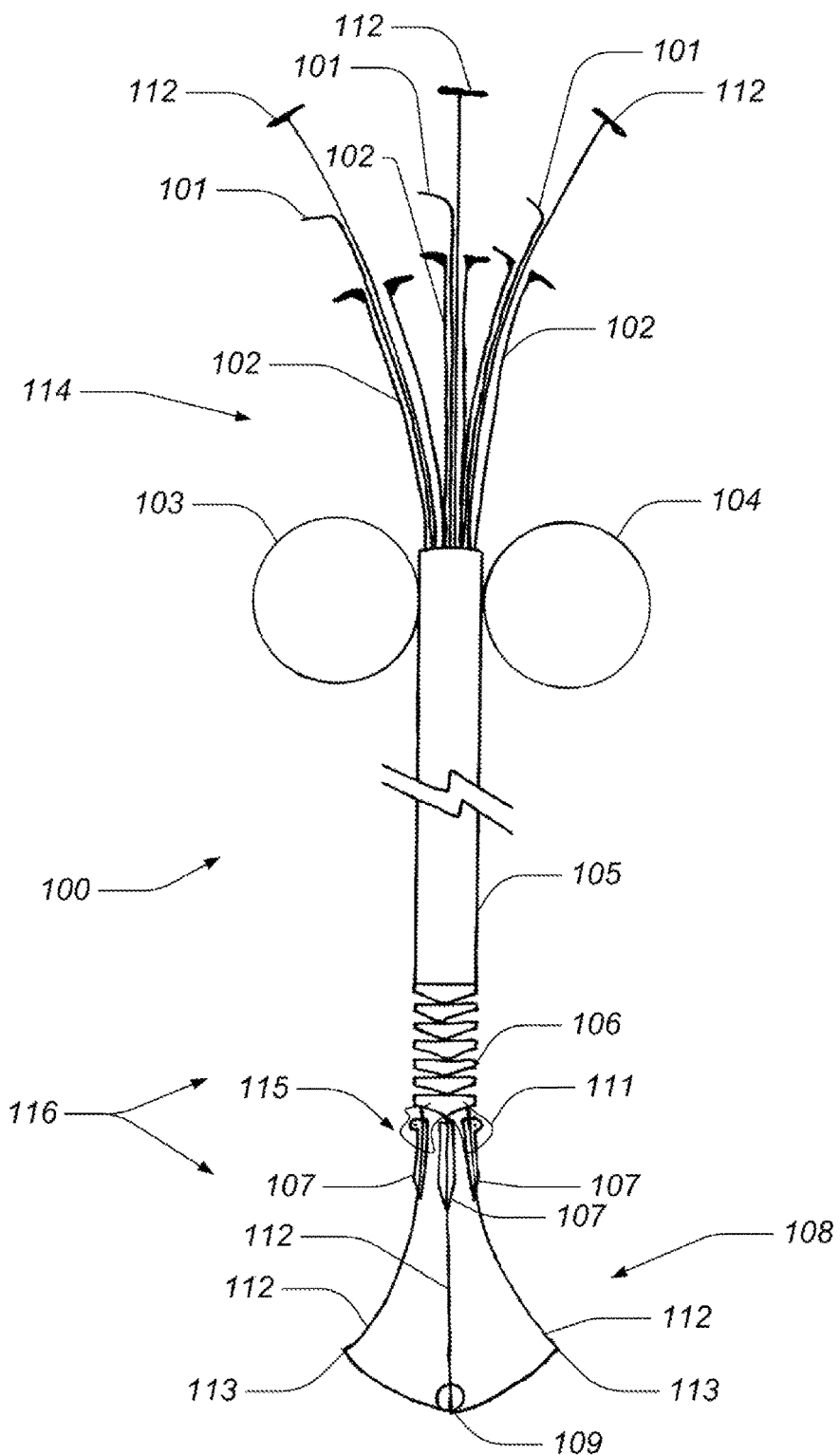
FIG. 1 is a schematic diagram of a medical device system according to one illustrated embodiment, including an implantable device and a tool with a control handle, tissue anchors, and anchor guide mechanism that is operable to implant the implantable device.

FIG. 1 shows a medical device system 100 including an implantable device 115 and tool 116 to implant the implantable device 115, according to one illustrated embodiment.

The tool 116 of the medical device system 100 may be used to deploy the implantable device 115 having tissue anchors 107 and a flexible cable 111. The tissue anchors 107 may be secured to the annulus of an orifice and the flexible cable 111 may be used to constrict the orifice by pulling the tissue anchors 107 inward. The tool 116 of the medical device system 100 includes a flexible anchor guide frame 108 that may be used to guide tissue anchors 107 of the implantable device 115 to target positions on the orifice annulus. The anchor guide frame 108 may be made of a material such as Nitinol. The anchor guide frame 108 shown in FIG. 1 includes three guide members, for instance guide wires 112—one guide member for each of the tissue anchors 107 shown. The guide frame 108 may include a different number of guide members or arms (e.g., guide wires or guide rails) 112 if more tissue anchors are desired. The guide members 112 shown preferably have hinges 113 and may be connected with small loops 109. The hinges 113 and loops 109 enable the anchor guide frame 108 to fold up to fit inside a catheter and to expand to extend across an orifice. Both the hinges 113 and loops 109 may be replaced by other mechanisms or structures that enable bending or compression. The tool 116 of the medical device system 100 typically has an articulation mechanism 106 (e.g., a plurality of articulation joints) that enables correctly orienting the anchor guide frame 108 during deployment of tissue anchors 107. The articulation mechanism 106 is preferably able to bend in various directions. The tool 116 of the medical device system 100 may include control knobs 103 and 104 which may be used to control the bending of the articulation mechanism 106 via cables that are carried in long flexible tube 105.

Long flexible tube 105 extends from the articulation mechanism 106 to a medical device control mechanism 114 located at a proximal end of the catheter. Control mechanism 114 may include control knobs 103 and 104, elongated release members (e.g., rods or wires) 101, push tubes 102, and guide wires 112. Additional controls may be included in other embodiments. The flexible tube 105 may have multiple lumens. Multi-lumen push tubes 102, guide members (e.g., guide wires) 112, release members 101, cable 111, and other mechanisms may be carried in flexible tube 105. In the illustrated embodiment, each push tube 102 has two lumens. A guide wire 112 is carried in a first lumen and a release member 101 is carried in a second lumen. Tissue anchors 107 are attached at distal tips of release members 101. The tissue anchor 107 may be inserted into the annulus of an orifice by advancing the push tube 102 along the guide member 112 and advancing or rotating the release member 101 carried in the push tube 102 at the same rate. The tissue anchor 107 may advance past the hinge 113 and embed into the annulus of the orifice to be constricted while in an unretracted configuration. Once the tissue anchor 107 is embedded, the release member 101 attached to the anchor may be retracted while the push tube 102 is held in place in a retracted configuration. Retraction of the release member 101 causes the tissue anchor 107 to detach from the distal tip of the release member 101 and remain embedded in the tissue at least proximate a desired location. Other embodiments may use different methods or structures, or both to release the tissue anchors 107.

Figure 2:
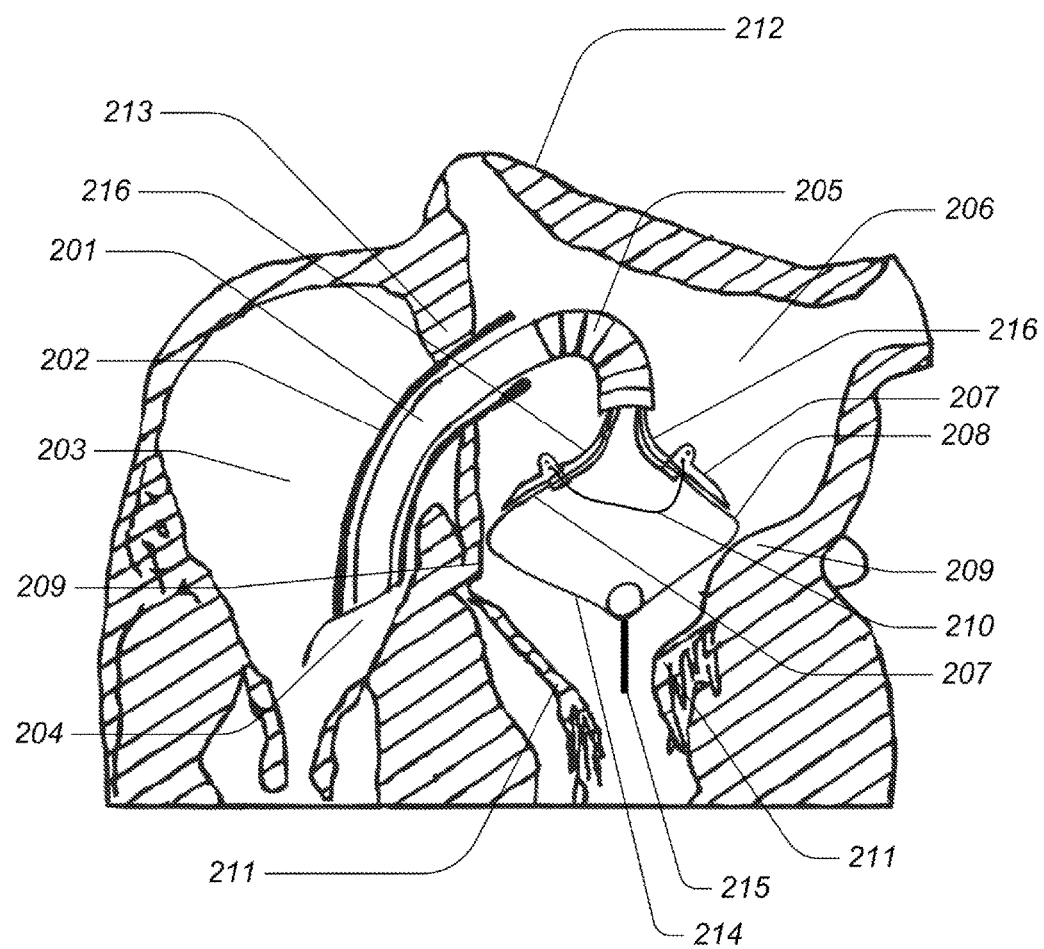
FIG. 2 is a cutaway diagram of a heart showing an implantable medical device implanted in tissue therein according to one illustrated embodiment, the implantable device percutaneously placed in a left atrium of the heart.

FIG. 2 shows an implantable device 207, 210 implantable in a portion of a heart to constrict a bodily orifice, for example a mitral valve of the heart, according to one illustrated embodiment.

A portion of the medical device 207, 210 may be percutaneously and/or intravascularly inserted into a portion of a heart 212, for example in a left atrium 206 of the heart 212. In this example embodiment, a flexible anchor guide frame 214 and implantable device are delivered via a catheter 202 inserted via the inferior vena cava 204 and penetrating the transatrial septum 213 from a right atrium 203. The catheter 202 is preferably less than 8 mm in diameter.

The flexible anchor guide frame 214 expands after being delivered via the catheter 202 into a shape that preferably enables the tissue anchors 207 of the implantable device to be delivered to the desired respective positions on the mitral annulus 209 (called out twice). The flexible anchor guide frame 214 may be moved into the correct orientation by adjusting a shape of an articulation mechanism 205, advancing or retracting flexible tube 201, or rotating flexible tube 201. The flexible anchor guide frame 214 preferably has an overall shape that enables the frame to take on a desired orientation within a cavity by conforming to the shape or being affected by the movement of anatomical features. Such a property is known as "self-locating". Minimal insertion force and operator guidance is typically needed to properly position the anchor guide frame 214. The flexible anchor guide frame 214 may also have specific features which cause the flexible anchor guide frame 214 to orient correctly based on the position of an anatomical feature, such as the mitral valve cusps or leaflets 211. An example of such a feature is alignment fin 215. Alignment fin 215 is attached rigidly to flexible anchor guide frame 214 and shaped so that it may be deflected to a particular orientation by an anatomical feature, such as mitral valve leaflets 211. As the flexible anchor guide frame 214 is advanced toward an anatomical feature, such as the mitral valve annulus 209, the shape or motion of an anatomical feature, such as the mitral valve leaflets 211, may cause alignment fin 215, and thus attached flexible anchor guide frame 214, to rotate or translate to a desired orientation or location.

The tissue anchors 207 may be inserted into the mitral annulus 209 by advancing the push tubes 216 along various guide members (e.g., guide wires or rails) 112. The tissue anchors 207 may advance past the bend 208 and embed into the mitral annulus 209. The embedded tissue anchors 207 may then be released from the push tubes 216. The flexible cable 210 connecting the tissue anchors 207 may then be tightened and secured to constrict the mitral annulus 209.

Figures 3, 4A:
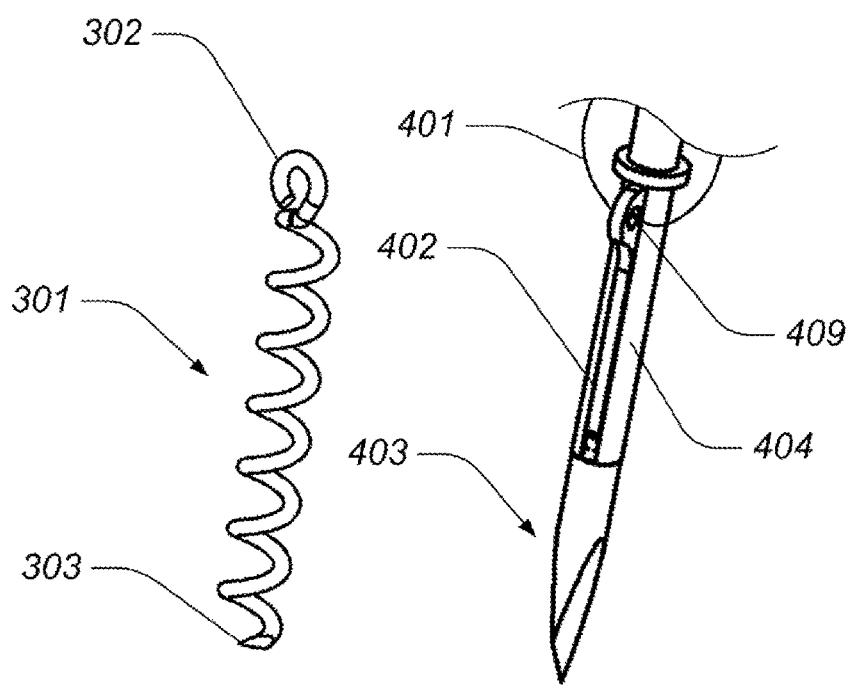
FIG. 3 is a diagram showing an example of a helical tissue anchor according to one illustrated embodiment.
FIG. 4A is an isometric partial view showing an example of a multi-barbed tissue anchor with resilient barbs retained by a constriction tube according to one illustrated embodiment.

FIG. 3 shows an example of a tissue anchor according to one illustrated embodiment.

The tissue anchor 301 has a helical structure with sharp tip 303, and hence is denominated as a helical tissue anchor 301. Loop 302 may be used to connect to a structure to hold the tissue anchor 301 to a release rod. Loop 302 may also be used to attach tissue anchor 301 to a cable used for cinching the annulus of a bodily orifice.

Figures 4B, 5A:
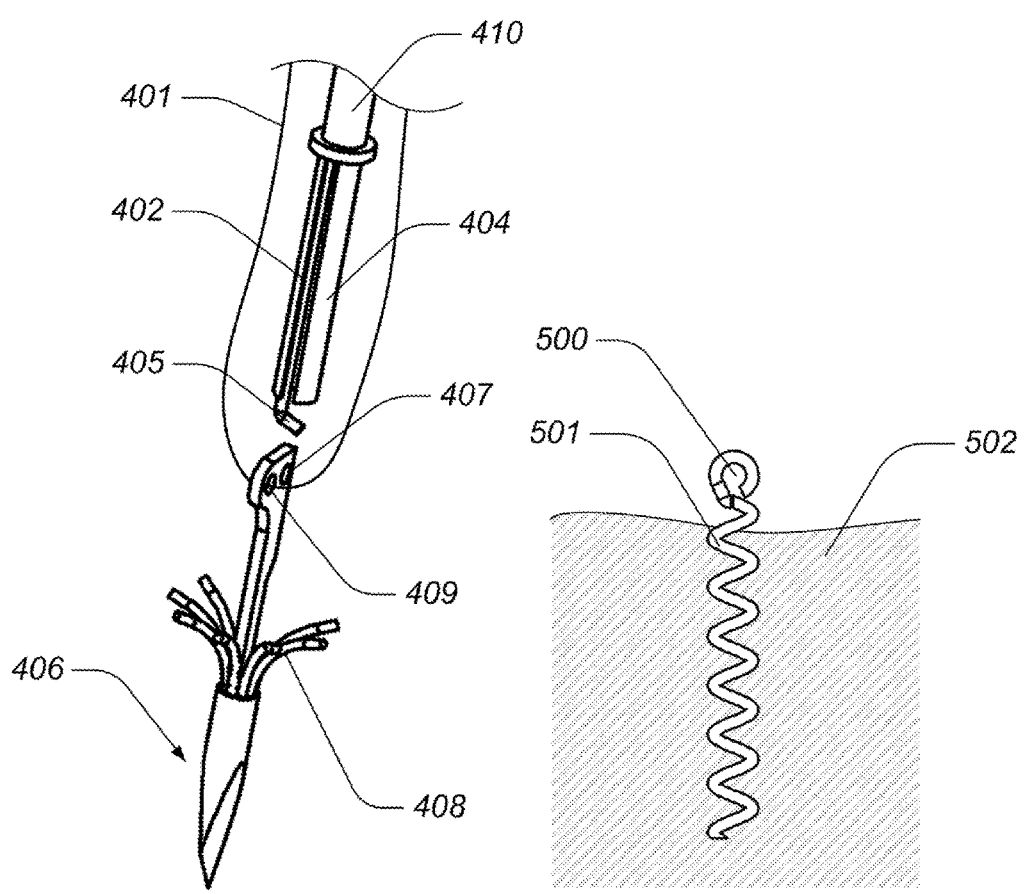
FIG. 4B is an isometric partial view showing an example of a multi-barbed anchor with the resilient barbs free of the constriction tube and exposed.
FIG. 5A is a front elevational view showing a helical tissue anchor embedded in tissue according to one illustrated embodiment.

FIGS. 4A and 4B show an example of a tissue anchor according to one illustrated embodiment.

In particular, FIG. 4A shows the tissue anchor 403 in a compressed configuration, while FIG. 4B shows the tissue anchor 406 in an expanded configuration. The tissue anchors 403, 406 include multiple barbs 408 (not shown in FIG. 4A), which may be resilient. The multiple barbs 408 may be compressed into constriction tube 404 as shown for tissue anchor 403. Compression of barbs 408 into constriction tube 404 enables the anchor to move more readily through a catheter and also to be inserted more readily into tissue without causing damage to the tissue.

Tissue anchor 403 may include a hole 409 that may be used to attach the anchor to a cable 401 used for cinching the annulus of a bodily orifice. Constriction tube 404 may include a slot 402 to allow tissue anchor 403 to be ejected from constriction tube 404 in the case where hole 409 is mounted on a protruding flange.

Tissue anchor 406 may include a hole 407 that may be used to connect the anchor to release rod 405. Release rod 405 may be carried in a lumen of push tube 410. If constriction tube 404 is extended over hole 407 as shown for tissue anchor 406, release rod 405 is held captive in hole 407 by the wall of constriction tube 404. If constriction tube 404 is retracted so as to not cover hole 407, as shown for tissue anchor 406, release rod 405 is not held captive in hole 407 and the tissue anchor may become disconnected from constriction tube 404 and release rod 405.

Tissue anchor 406 may be disconnected from release rod 405 and barbs 408 may be uncompressed by retracting constriction tube 404 relative to the release rod 405 and tissue anchor 406. Retracting constriction tube 404 past the tips of barbs 408 causes said barbs to be released and resiliently expand. Retracting constriction tube 404 past hole 407 may release tissue anchor 406.

FIGS. 5A-5E show examples of five types of tissue anchors embedded in tissue.

Figure 5B:
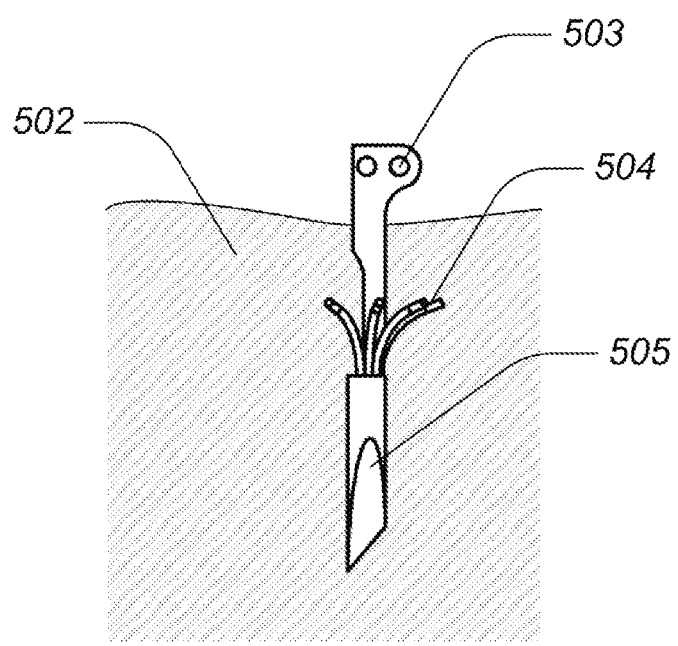
FIG. 5B is a front elevational view showing a barbed tissue anchor embedded in tissue according to one illustrated embodiment.
Figure 5C:
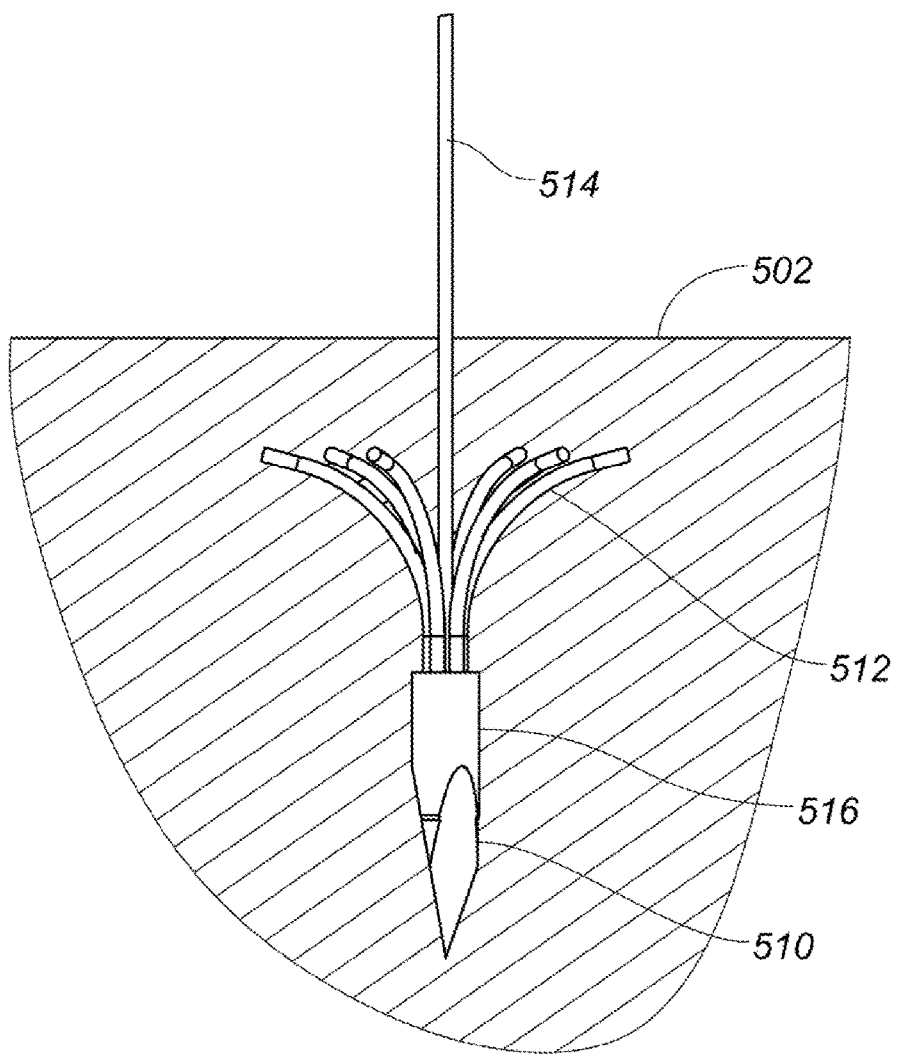
FIG. 5C is a front elevational view showing a barbed tissue anchor with an integral guide line such as a guide wire according to another illustrated embodiment, the tissue anchor embedded in tissue.
Figure 5D:
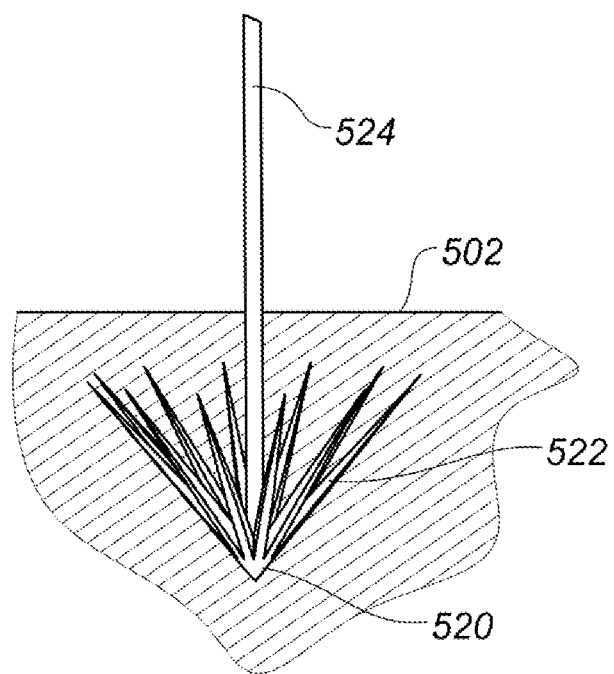
FIG. 5D is a front elevational view showing a barbed tissue anchor with a unitary guide line such as a guide wire according to a further illustrated embodiment, the tissue anchor embedded in tissue.

In particular, FIG. 5A shows a helical tissue anchor 500 embedded in tissue 502. The helical tissue anchor 500 includes a helical portion 501 that is embedded in tissue 502 by rotating the helical tissue anchor 500 about a longitudinal axis of helical portion 501. FIG. 5B shows a multi-barbed anchor 505 embedded in tissue 502. The multi-barbed tissue anchor 505 is embedded in tissue 502 by pushing the anchor into the tissue. Barbs 504 provide resistance to restrict the tissue anchor 505 from being extracted. In this embodiment, multi-barbed tissue anchor 505 includes an opening 503 sized to receive a guide member (not shown) or coupling (not shown). FIG. 5C shows a tissue anchor 510 with multiple barbs 512 (only one called out in FIG. 5C) and an integral guide line or guide wire 514 embedded in tissue 502. The barbs 512 and guide line or guide wire 514 may be secured in a shell 516 of the tissue anchor 510. For example, the barbs 512 and guide line or guide wire 514 may be secured via swaging. The guide line or guide wire 514 may take a variety of forms, for example a metal wire such as Nitinol. FIG. 5D shows a tissue anchor 520 with multiple barbs 522 (only one called out in FIG. 5D) and a unitary guide line or guide wire 524 embedded in tissue 502. In contrast to the embodiment of FIG. 5C, the embodiment of FIG. 5D forms the tissue anchor 520 and guide line or guide wire 524 from a single piece of material, for instance a thin flexible metal wire, which is selected from metals that are biocompatible (e.g., stainless steel, Nitinol).

Figure 5E:
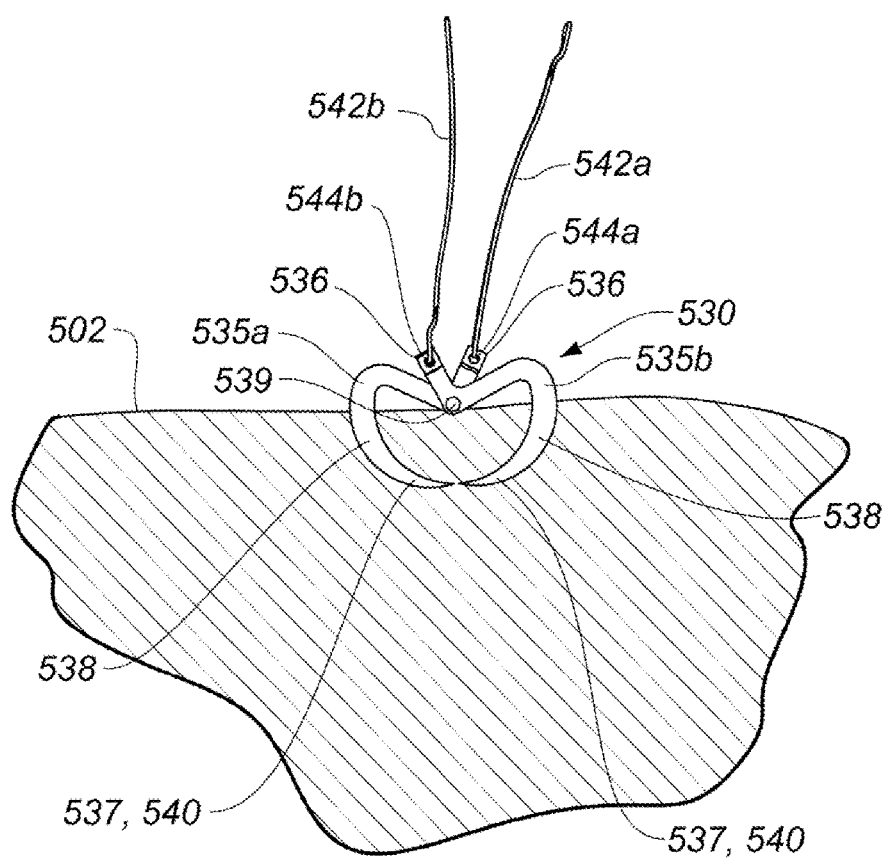
FIG. 5E is a front elevational view showing a grapple tissue anchor embedded in tissue according to one illustrated embodiment.

FIG. 5E shows a grapple tissue anchor 530 implanted into tissue 502. Grapple tissue anchor 530 includes a plurality of elongated members 535. At least two of the elongated members (i.e., first elongated member 535a and second elongated member 535b in this example embodiment) are pivotably coupled together by pivot member 539. Each of the elongated members 535 includes a first end 536, a second end 537, an intermediate portion 538 and a respective length along the elongated member 535 extending between the first end 536 and the second end 537. Each second end 537 includes a tip 540 shaped to penetrate tissue 502. In some example embodiments, each second end 537 includes a barb. In this example embodiment, each of the elongated members 535 is an arcuate elongated member. In this example embodiment, each of the elongated members 535 forms a prong. Pivot member 539 allows the elongated members 535 to pivot with respect to one another to space tips 540 apart from one another into a configuration advantageous for penetrating tissue 502. Upon further deployment of grapple tissue anchor 530 into tissue 502, the elongated members 535 are pivoted to draw tips 540 towards each other which causes tips 540 to travel along a path through tissue 502 such that tips 540 are positioned relatively closer to one another than during their initial deployment into tissue 502. This allows grapple tissue anchor 530 to firmly anchor itself into tissue 502. In this example embodiment, the plurality of elongated members 535 is physically coupled to a plurality of flexible lines 542a and 542b (collectively 542). Specifically, flexible line 542a is coupled to elongated member 535a and flexible line 542b is physically coupled to elongated member 535b. In this example embodiment, elongated member 535a includes an opening 544a sized to receive flexible line 542a and elongated member 535b includes an opening 544b sized to receive flexible line 542b. In some example embodiments, a single flexible line 542 is received in an opening provided in each of the elongate members 535. In this example embodiment, the flexible lines 542 are guide lines. In some example embodiments, the flexible lines 542 and respective ones of the elongate members 535 are provided as a unitary structure.

Figure 6A:
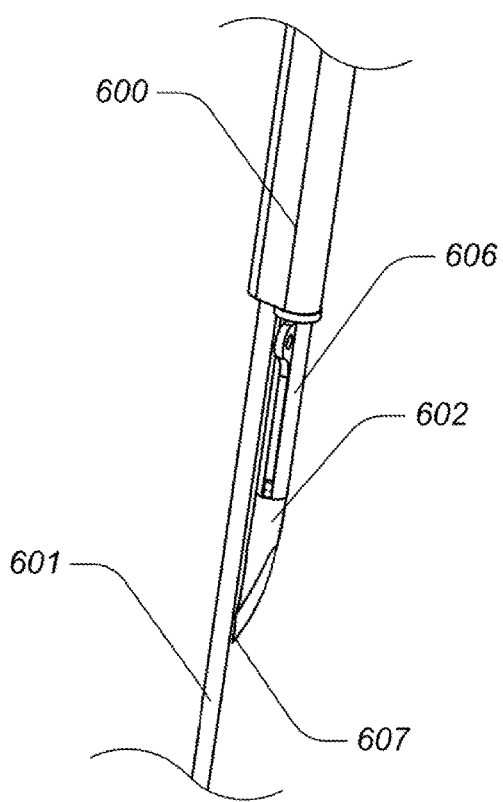
FIG. 6A is an elevational view showing a tissue anchor movably received on a guided member according to one illustrated embodiment.
Figure 6B:
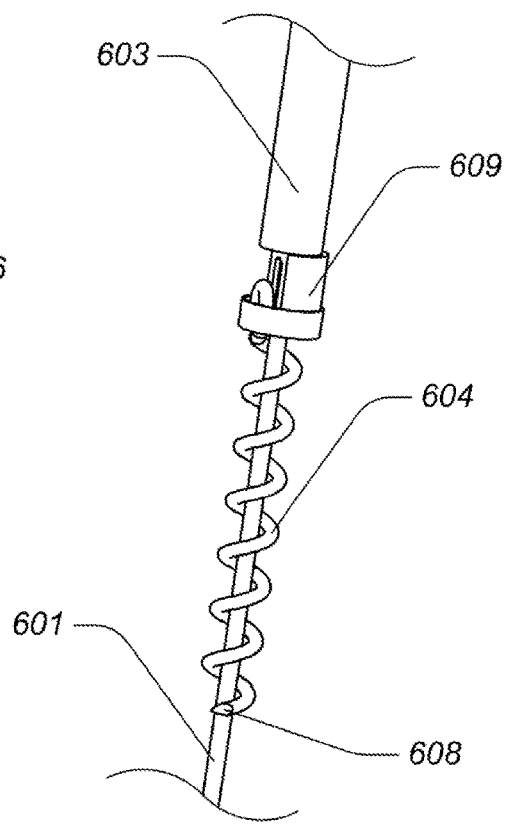
FIG. 6B is an elevational view showing a tissue anchor movably received on a guided rail according to another illustrated embodiment.

FIGS. 6A and 6B show examples of tissue anchors guided by a guide member in the form of a guide rail.

In particular, FIG. 6A shows a multi-lumen push tube 600 that may slide over a guide rail 601. Tissue anchor 602 may be temporarily attached to multi-lumen push tube 600 by constriction tube 606 and a release rod (not shown). Sliding push tube 600 along guide rail 601 enables tissue anchor 602 to be controllably delivered to a location proximate to guide rail 601. Tissue anchor 602 may be constructed or oriented in such a way that tissue anchor tip 607 slides along or very near to guide rail 601. Such orientation or construction enables the tip 607 to be protected from obstructions in the catheter or body that may dull the tip 607. Also, such orientation or construction protects areas of tissue proximate the guide rail 601 from inadvertent, damaging contact with the sharp tip 607 of tissue anchor 602.

FIG. 6B shows a single-lumen push tube 603 that may slide over guide rail 601. Helical tissue anchor 604 also may slide over guide rail 601 and may be temporarily attached to single-lumen push tube 603 by latch mechanism 609. Latch mechanism 609 may be fastened to tissue anchor 604 by a friction fitting that is released under sufficient axial force. This assembly enables tissue anchor 604 to be controllably delivered to a location proximate to guide rail 601. Tissue anchor 604 may be constructed or oriented in such a way that tissue anchor tip 608 slides along or very near to guide rail 601. Such orientation or construction enables the tip 608 of the tissue anchor 604 to be protected from obstructions in the catheter or body that may dull tip 608. Also, such orientation or construction protects areas of tissue proximate the guide rail 601 from inadvertent, damaging contact with the sharp tip 608 of tissue anchor 608.

While FIGS. 6A and 6B show examples of two particular types of tissue anchors being guided by a rail, it will be apparent to those skilled in the art that many other types of tissue anchors could also be deployed with the aid of a guide rail.

Figures 7A, 7B:
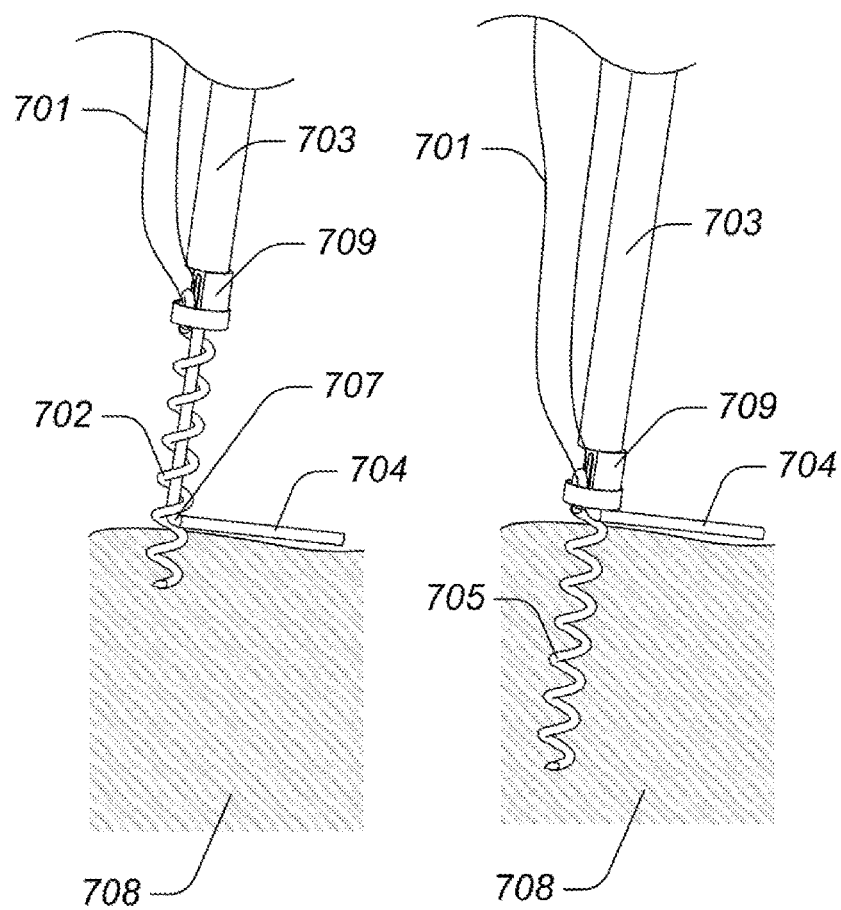
FIGS. 7A-7C are sequential elevational views showing a helical tissue anchor movably received on a guided member penetrating tissue at three successive intervals of time according to one illustrated embodiment.
Figure 7C:
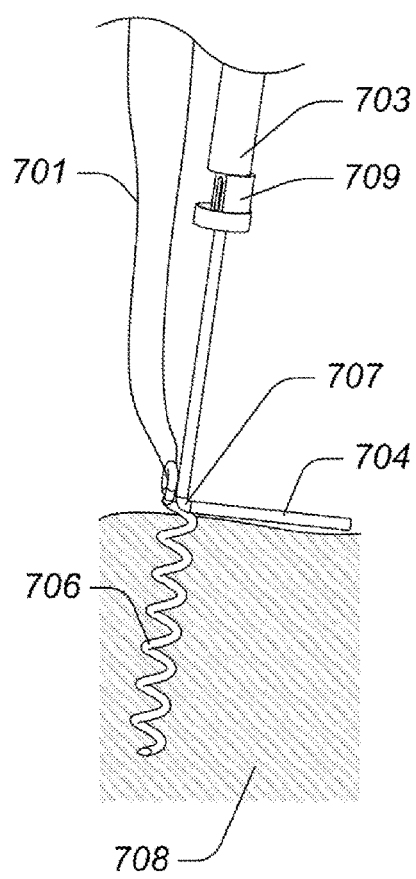

FIGS. 7A-7C illustrate a structure 701 used in a deployment of helical tissue anchors implanted or embedded in tissue according to one illustrated embodiment.

In particular, FIG. 7A shows a helical tissue anchor 702 partially deployed into tissue 708. The location where tissue anchor 702 enters tissue 708 may be determined by the position of a guide member, for instance guide rail 704. Bend 707 in guide rail 704 may be positioned at the approximate location where the tissue anchor 702 is to be deployed into the tissue. Bend 707 in guide rail 704 may comprise a hinge, a flexure, or one of many other joints. Tissue anchor 702 is deployed by rotating push tube 703. The rotation of tissue anchor 702 at the position of the bend 707 causes tissue anchor 702 to spiral off guide rail 704 and into tissue 708.

FIG. 7B shows a helical tissue anchor 705 fully deployed into tissue 708, but still connected to latch mechanism 709. In the fully deployed position, helical tissue anchor 705 may no longer wrap around guide rail 704. When still connected to latch mechanism 709, the helical tissue anchor 705 may be readily retracted by counter-rotating push tube 703.

FIG. 7C shows a helical tissue anchor 706 fully deployed into tissue 708 and disconnected from to latch mechanism 709. Latch mechanism 709 may become disconnected from tissue anchor 706 by retracting push tube 703 or releasing latch mechanism 709 with the addition of another cable to trigger a release mechanism.

Figure 8A:
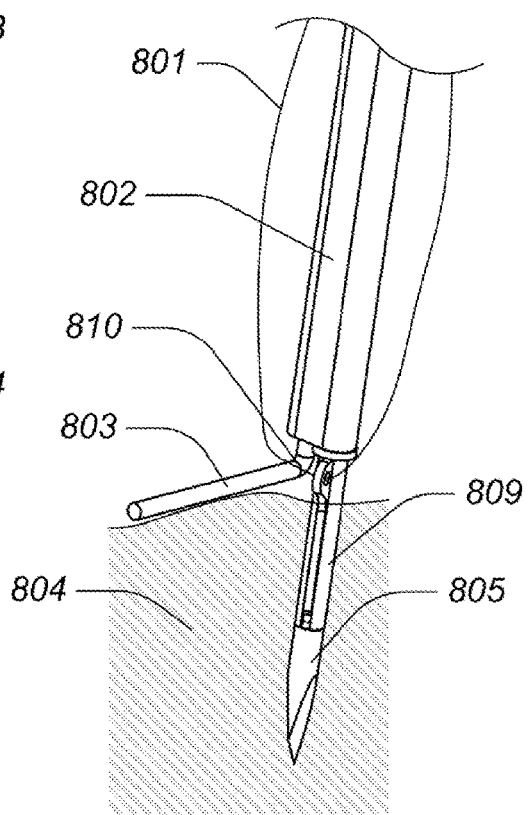
FIGS. 8A and 8B are sequential elevational views showing a multi-barbed tissue anchor movably received on a guided member penetrating tissue at two successive intervals of time according to one illustrated embodiment.
Figure 8B:
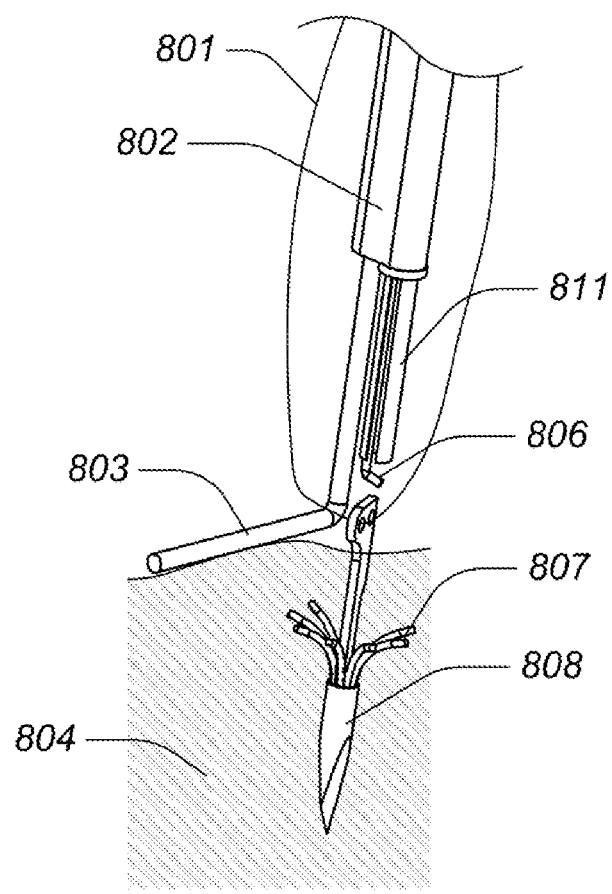

FIGS. 8A and 8B show a structure 801 employed in a deployment of multi-barbed tissue anchors in tissue according to one illustrated embodiment.

In particular, FIG. 8A shows a multi-barbed tissue anchor 805 fully inserted into tissue 804, but still encapsulated or retained by constriction tube 809. A location where the multi-barbed tissue anchor 805 enters the tissue may be determined by the position of a guide member, for instance guide rail 803. A bend 810 in guide rail 803 may be positioned at the approximate location where the multi-barbed tissue anchor 805 is to be deployed into the tissue 804. The bend 810 in guide rail 803 may be constructed using a hinge, a flexure, or one of many other methods. The multi-barbed tissue anchor 805 is deployed by advancing push tube 802 over guide rail 803. If encapsulated or retained by constriction tube 809, multi-barbed tissue anchor 805 may be readily retracted by retracting push tube 802.

FIG. 8B shows a multi-barbed tissue anchor 808 fully inserted into tissue 804, but disconnected from constriction tube 811 and release member 806. The multi-barbed tissue anchor 808 is preferably retracted slightly before release member 806 is disconnected in order to cause barbs 807 to expand. The multi-barbed tissue anchor 808 may be disconnected from release member 806 and barbs 807 may be expanded by retracting constriction tube 811 relative to the release member 806 and multi-barbed tissue anchor 808. Retracting constriction tube 811 past the tips of barbs 807 causes the resilient barbs to be released and expand.

FIGS. 8C through 8F show a tissue anchor 820 movably guided to tissue 824 and penetrating the tissue 824 at four successive intervals of time, according to one illustrated embodiment.

Figure 8C:
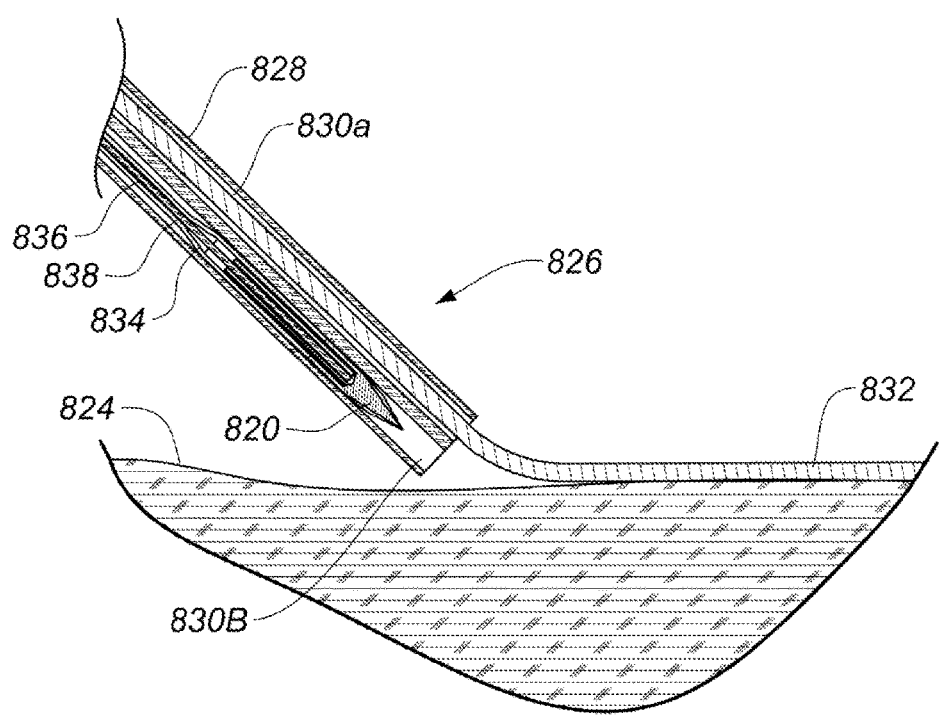
FIGS. 8C through 8F are sequential elevational views showing a multi-barbed tissue anchor movably guided via a guided member penetrating tissue at four successive intervals of time according to one illustrated embodiment.

In particular, FIG. 8C shows a guide member portion of an anchor guide frame 826 of a tool initially contacting the tissue 824.

The guide member portion of the anchor guide frame 826 includes an outer tube 828 having two lumens 830a, 830b. The guide member portion includes an engagement or locating member 832. The engagement or locating member 832 is used to physically engage the tissue 824 such that the anchor guide frame 826 is at a desired location and orientation in a bodily organ. The engagement or locating member 832 is movingly carried in one lumen 830a of the outer tube 828. The anchor guide frame 826 includes an inner or guide tube 834 movingly received in the other lumen 830b of the outer tube 828. The guide tube 834 functions to guide the tissue anchor 820 to a desired location on the tissue 824. A lumen 836 of the guide tube 834 carries a guide wire 838. The guide wire 838 is a thin flexible wire, for example a thin Nitinol wire. The guide wire 838 may include a lubricous coating or layer, such as polytetrafluoroethylene. The guide tube 834 provides lateral support for the guide wire 838 and retains barbs 840 (not called out in FIG. 8C) if the tissue anchor 820 is in a protected, contracted configuration. A butt end of the guide tube 834 may physically engage or bear against an end or lip of the tissue anchor 820. Thus, when the guide tube 834 and guide wire are pushed, the motion is effectively delivered to the tissue anchor 820, which will advance out of the outer tube 828 along with the inner or guide tube 834. The guide tube 834 may optionally be reinforced with one or more wires, for instance Nitinol wires. The guide wire 838 is attached to the tissue anchor 820 and functions as a guide line for an implant member (not shown in FIGS. 8C-F), as described in detail further below.

Figure 8D:
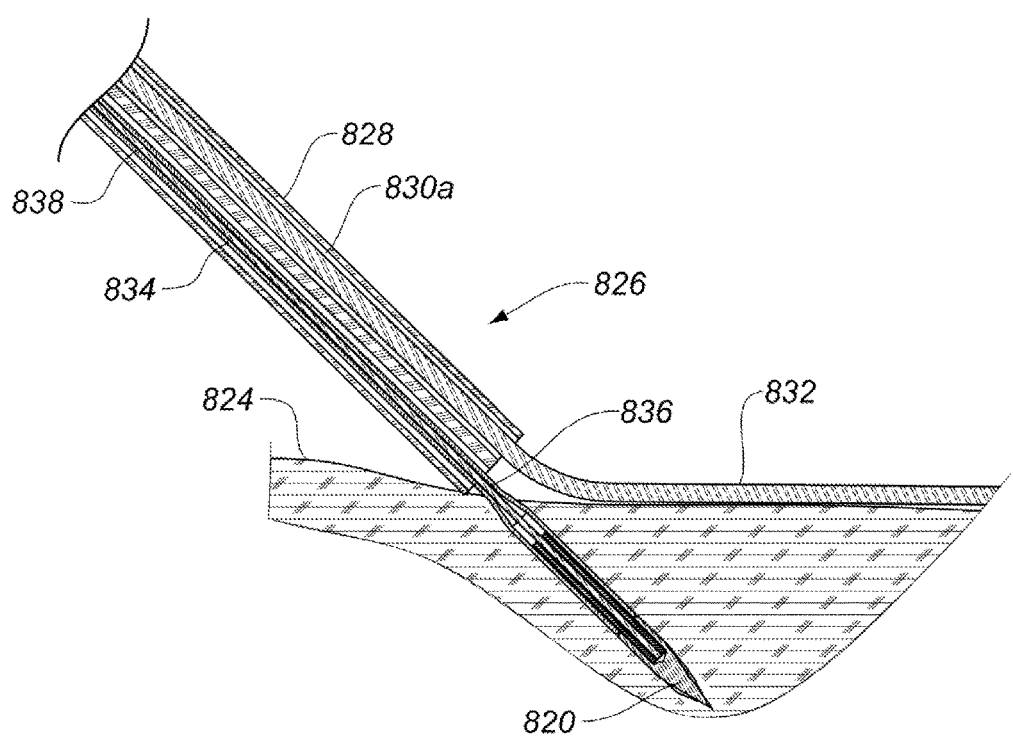
Figure 8E:
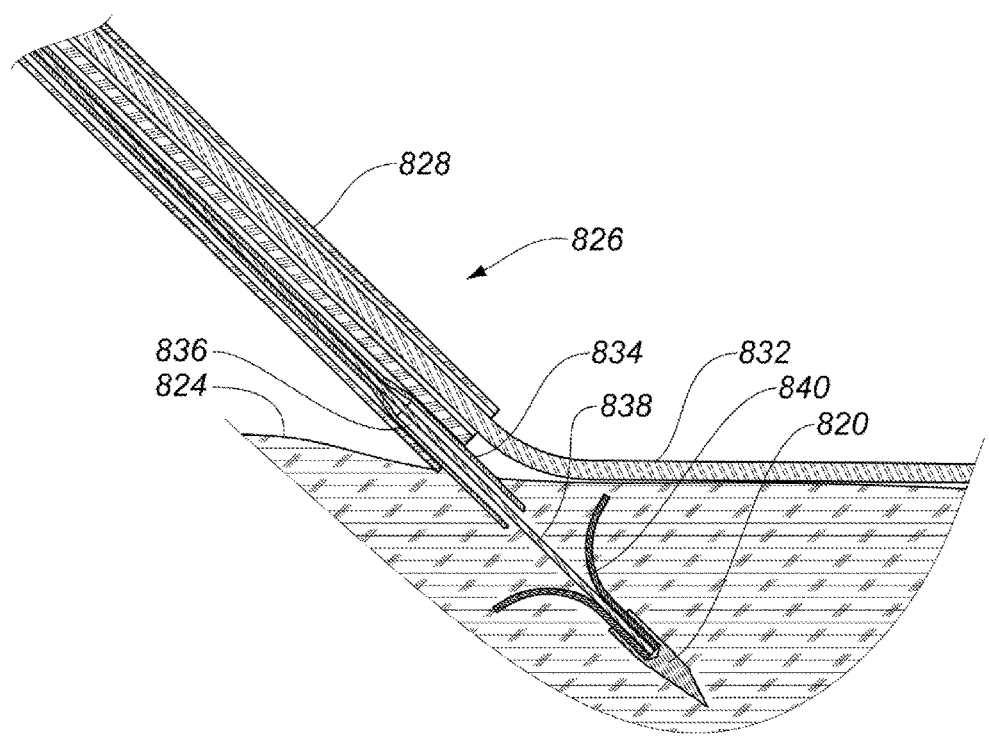

In particular, FIG. 8D shows the tissue anchor 820 being embedded in the tissue 824, along with a portion of the guide tube 834 and guide wire 838. FIG. 8E shows the guide tube 834 partially withdrawn from around the tissue anchor 820, exposing the barbs 840 of the tissue anchor 820. In going from FIG. 8D to FIG. 8E, the guide wire 838 is pushed relatively toward the tissue 824 while the guide tube 834 is pulled or drawn away from the tissue 824. Pushing the guide wire 838 supplies enough force to retain the tissue anchor 820 in the tissue 824 against any force exerted by way of withdrawal of the guide tube 834. As the guide tube 834 clears the barbs 840, the barbs 840 expand due to the resiliency of the material from which the barbs 840 are fashioned. The tissue anchor 820 is thus secured within the tissue 824.

Figure 8F:
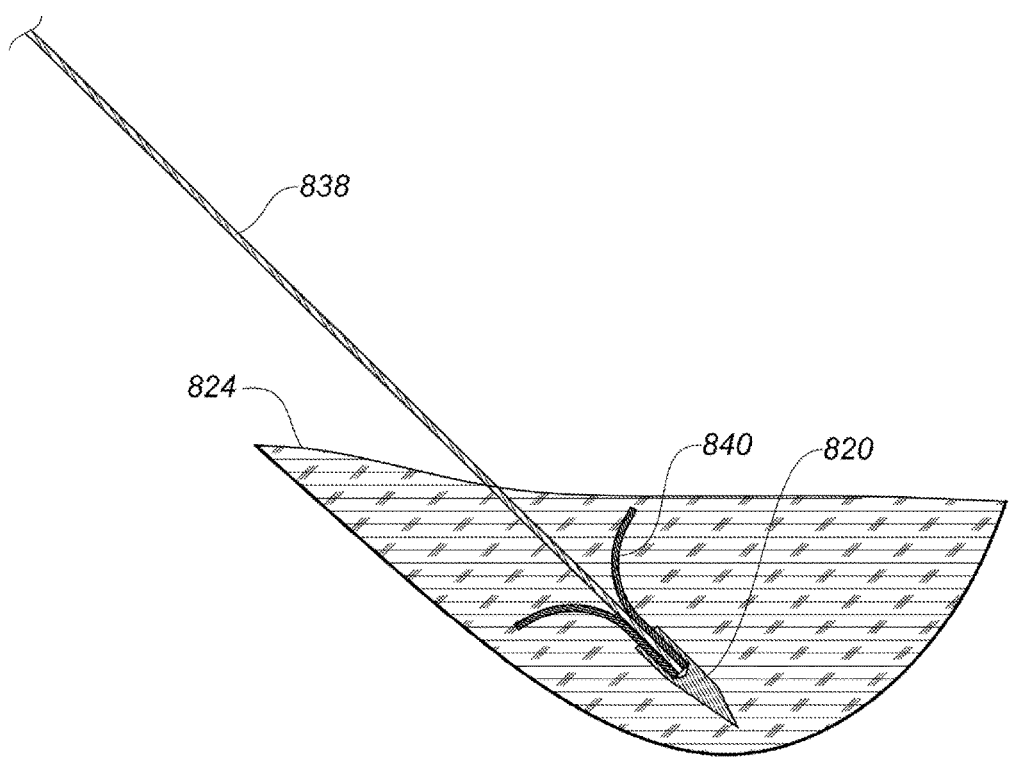

FIG. 8F shows the tissue anchor 820 and guide wire 838 which remain after the portion of the anchor guide frame 826 is withdrawn. The guide tube 834 may be fully retracted into the lumen 830b of the outer tube or catheter 828 prior to withdrawal of the anchor guide frame 826 from the bodily organ. As explained in detail below, the guide wire 838 may be used to guide an implant member (e.g., annuloplasty ring) to the tissue 824, and/or to secure the implant member to the tissue 824 at a desired position and orientation.

While illustrated with two tubes per anchoring location, some embodiments may employ three tubes per anchoring location or more. Using only two tubes per anchoring location advantageously increases the flexibility of the catheter(s) relative to embodiments employing more than two tubes per anchor location. Such eases the movement of the catheter through the bodily lumen (e.g., artery). Such may also allow the use of catheters with smaller diameters than would otherwise be necessary to accommodate one or more additional tubes per anchoring location.

Figure 9:
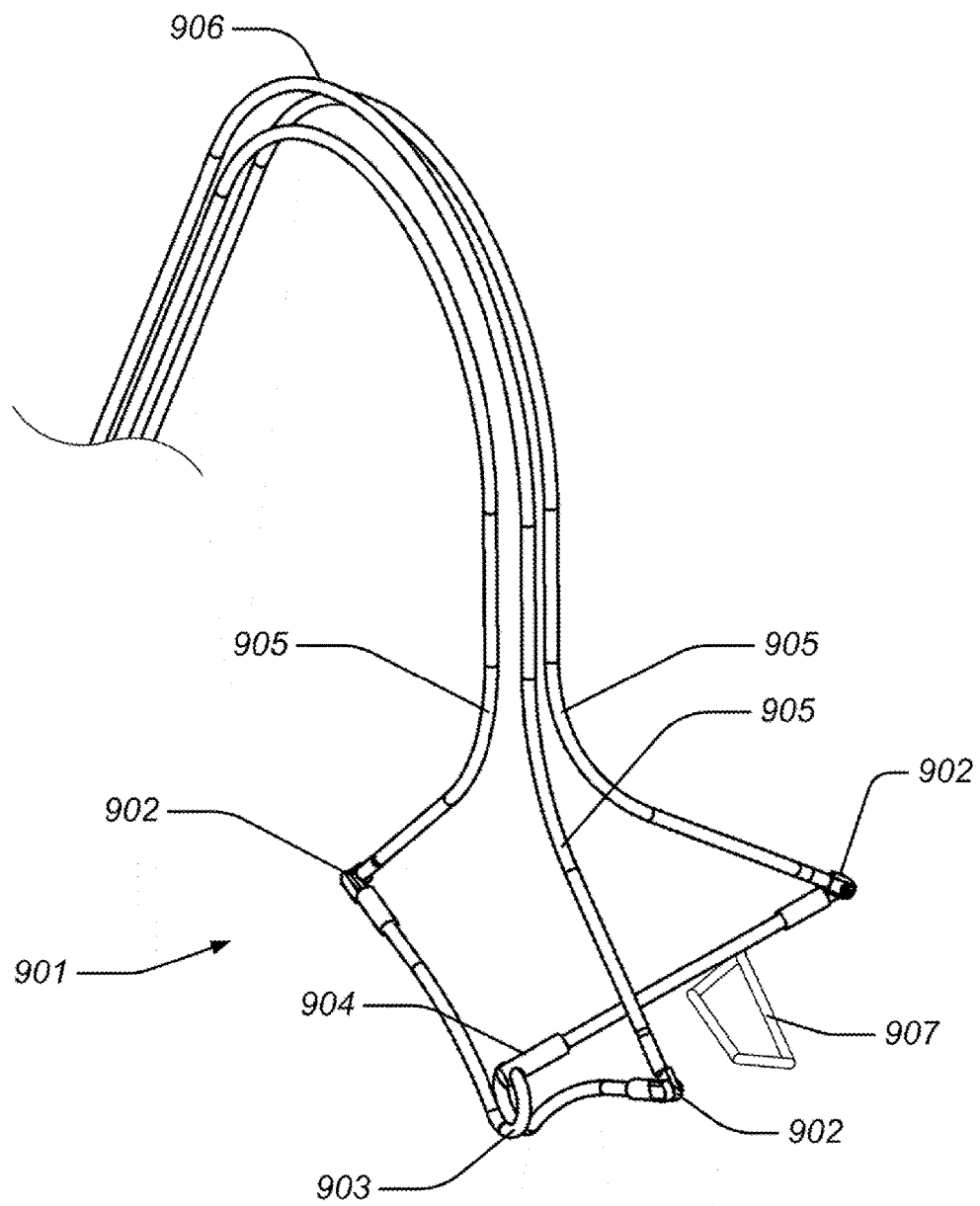
FIG. 9 is an isometric view of an anchor guide frame according to one illustrated embodiment.

FIG. 9 shows an example of an anchor guide frame of a tool according to one illustrated embodiment.

An anchor guide frame 901 is used to guide tissue anchors of the implant device to correct insertion or anchor points or locations. The anchor guide frame 901 shown includes three guide members, for instance rails 905, but said guide frame may comprise more or fewer guide members. The anchor guide frame 901 embodiment illustrated shows all guide rails 905 connected at the bottom of the guide frame 901. An anchor guide frame is not required to have all guide members connected together, although it is often preferable to do so to create a guide frame that enables tissue anchors to be positioned relative to each other and to anatomical features. Thus, an anchor guide frame may have multiple disconnected groups of connected guide wires.

The anchor guide frame 901 preferably is capable of folding to enable delivery via a catheter. Guide members (e.g., guide wires or rails) 905 may be hinged at bends 902 and guide connection point 904 to enable folding. Loop 903 facilitates folding and also acts as a spring to enable unfolding of the anchor guide frame 901.

Guide members 905 may be formed to have respective bends 906 when no external forces are being applied. When guide members 905 are carried in a catheter with an articulation mechanism shaped into a curve as shown in FIG. 2, the forces exerted on the guide member by the catheter and articulation mechanism will cause bend 906 to align with the curve in the articulation mechanism. Such alignment causes anchor guide frame 901 to rotate to a desired position relative to the catheter orientation. Bend 906 may also be formed to assist in curving the articulation mechanism in a particular way.

An anchor guide frame may also contain additional features which use anatomical features or movement to assist in orientation of said anchor guide mechanism or guide frame 901. An example of such a feature is an alignment fin 907. Alignment fin 907 is attached rigidly to flexible anchor guide frame 901 and shaped so that the alignment fin 907 may be deflected by an anatomical feature, such as mitral valve leaflets, to a particular orientation. As the flexible anchor guide frame 901 is advanced toward an anatomical feature, such as the mitral valve annulus, the shape or motion of an anatomical feature, such as the mitral valve leaflets, may cause alignment fin 907, and thus flexible anchor guide frame 901, to rotate to a desired orientation.

Figure 10:
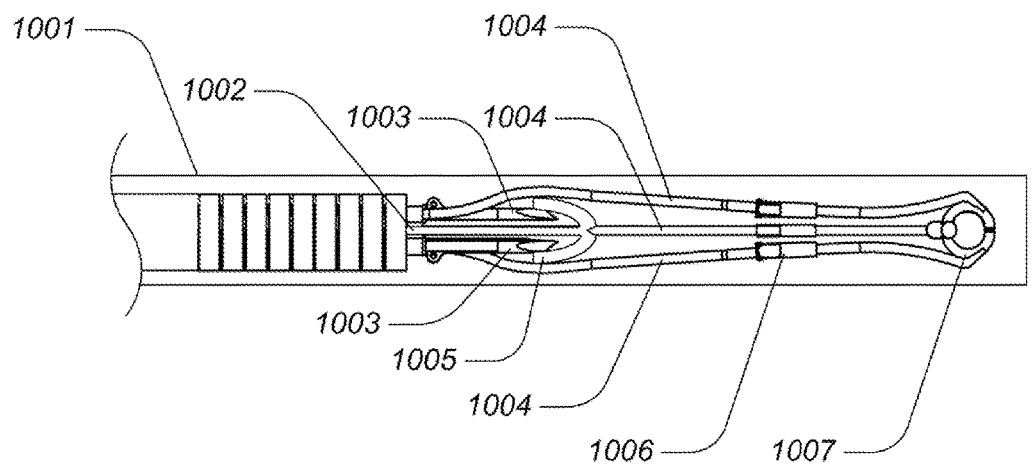
FIG. 10 is a side elevational view of an anchor guide frame compressed into a sheath according to one illustrated embodiment.

FIG. 10 shows an anchor guide frame folded for delivery inside a catheter according to one illustrated embodiment.

An anchor guide frame including guide members (e.g., guide wires or rails) 1004 may be folded inside a catheter sheath 1001. Hinges 1006 and loop 1007 enhance folding of the anchor guide mechanism. In the embodiment illustrated, tissue anchors 1003 fit between the guide members 1004 in the folded configuration. Protective anchor cap 1005 holds and covers the sharp tips of tissue anchors 1003 and may ensure that the tips do not catch or embed on the sides of catheter sheath 1001. Protective anchor cap 1005 may be held in place by control wire 1002.

Figure 11:
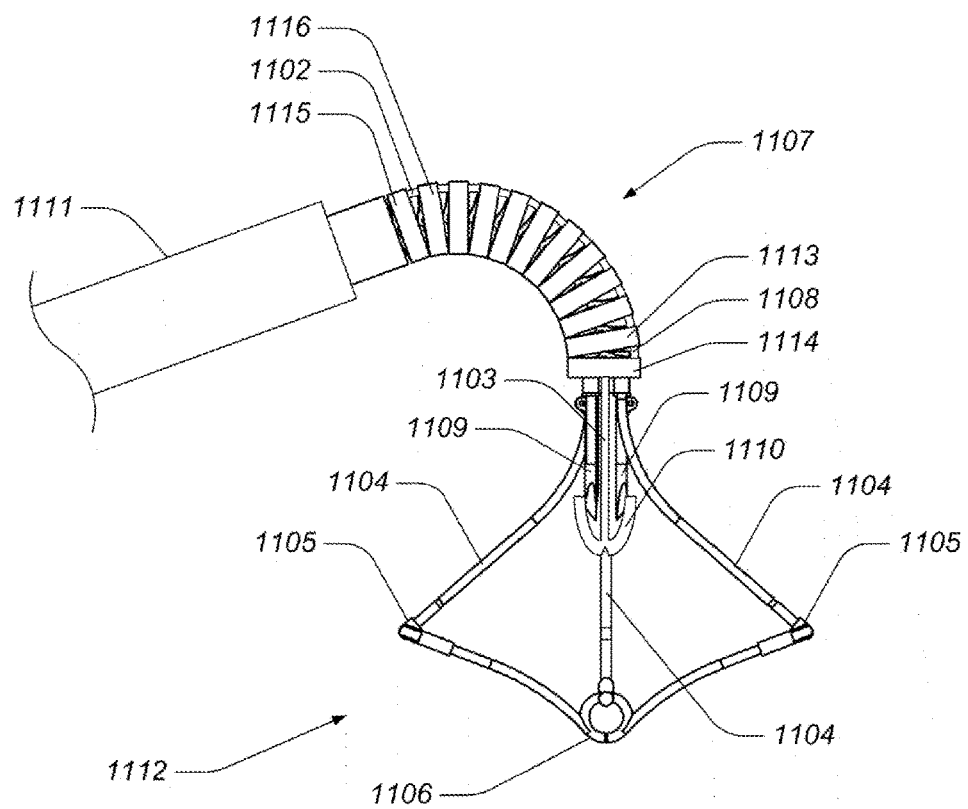
FIG. 11 is an isometric view of an expanded anchor guide frame according to one illustrated embodiment.

FIG. 11 shows an anchor guide frame in an expanded configuration according to one illustrated embodiment.

An anchor guide frame 1112 may self expand after exiting catheter sheath 1111. In particular, the anchor guide frame 1112 may be formed of a resilient material or a shape memory material such as Nitinol. Loop 1106 may be formed to cause the anchor guide frame 1112 to expand. Hinges 1105 facilitate separation of guide members 1104 by about 20 mm to 45 mm. In the illustrated embodiment, tissue anchors 1109 are held within the volume encompassed by anchor guide frame 1112 which ensures the tissue anchors 1109 do not accidentally impinge tissue. Also, the tips of the tissue anchors are held captive within protective anchor cap 1110. The tips of the tissue anchors may be released by advancing control wire 1103 and thereby also advancing anchor cap 1110. The tips of the tissue anchors are no longer held captive if anchor cap 1110 is advanced sufficiently to a point past the tips of the tissue anchors. As guide members 1104 curve away from anchor cap 1110, advancing tissue anchors 1109 causes the tips of the tissue anchors to move away from and avoid anchor cap 1110.

Articulation mechanism 1107 (e.g., articulation joints) of the tool is shown in a curved configuration or state. Articulation mechanism 1107 may be curved using wires (not shown) that are carried on opposing sides relative to a longitudinal axis of the articulation mechanism and fixed to the distal end of the articulation mechanism 1107. Tensioning one wire causes the articulation mechanism 1107 to arc in the direction of the side of the articulation mechanism on which the tensioned wire is carried in. For some situations, it is desirable to cause gaps between articulation links or articulation joints to open at different rates. For example, when inserting articulation mechanism 1107 into the left atrium, it may be preferable to cause the distal links, such as articulation link or joint 1113 and articulation link or joint 1114, to separate or bend prior to or more than the proximal articulation links or joints, such as articulation link or joint 1115 and articulation link or joint 1116. One embodiment to enable such an attribute is to insert springs, as indicated by 1108 and 1102, with varying spring constant k between the links or articulation joints. To cause the distal end of articulation mechanism 1107 to bend first, the distal links should be forced apart by springs with a higher spring constant than the springs between the proximal links. Another embodiment for enabling unequal separation of articulation links or joints is to control the shape of the guide members 1104 that are routed through the articulation mechanism 1107. The guide members should have a preformed bend with a decreasing radius of curvature in the area from proximal articulation link or joint 1115 to distal articulation link or joint 1114.

Figure 12:
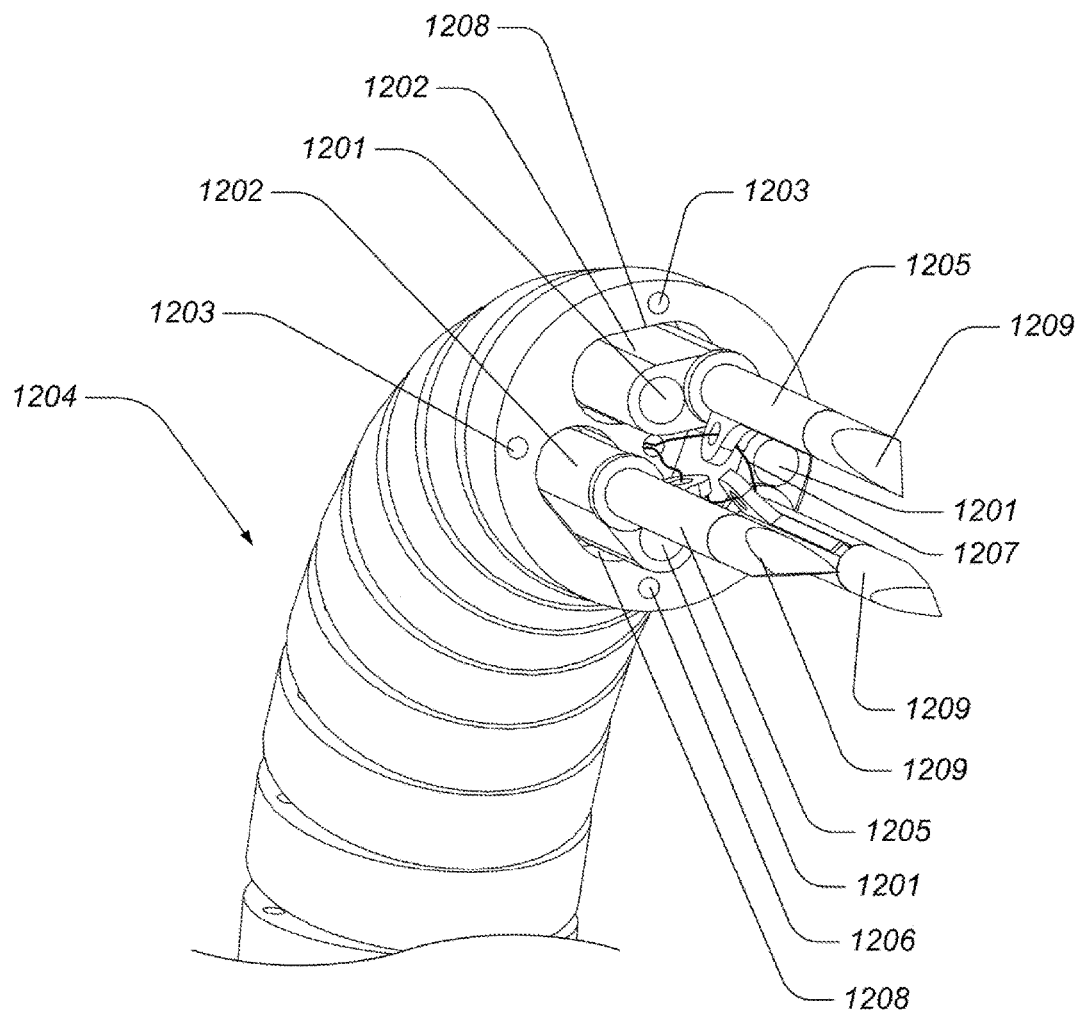
FIG. 12 is an isometric view showing a distal end of a medical device system according to one illustrated embodiment

FIG. 12 shows a configuration of tissue anchors and push tubes at a distal tip of a medical device system according to one illustrated embodiment. For clarity, FIG. 12 omits guide members and anchor guide frame that would typically be located at the distal tip of the medical device system.

An articulation mechanism 1204 may include multiple lumens 1208 through which push tubes 1202 are carried. In this particular embodiment, three lumens 1208 (two called out) are employed, but other embodiments may comprise more or less. Push tubes 1202 may also include multiple lumens. In this particular embodiment, each push tube 1202 has a lumen 1201 in which a guide member (e.g., guide wire or rail) (not shown) may be carried and a second lumen that carries a release member (e.g., rod or wire) (not shown) which is connected to the tissue anchors 1209. Constriction tubes 1205 may be mated into or onto the distal end of the second lumen. All tissue anchors may be connected by a flexible cable 1207. The flexible cable 1207 may also be carried within a separate lumen within the articulation mechanism 1204. Lumens 1203 are used to carry lines 1206 that control the curvature of the articulation mechanism 1204.

Figure 13:
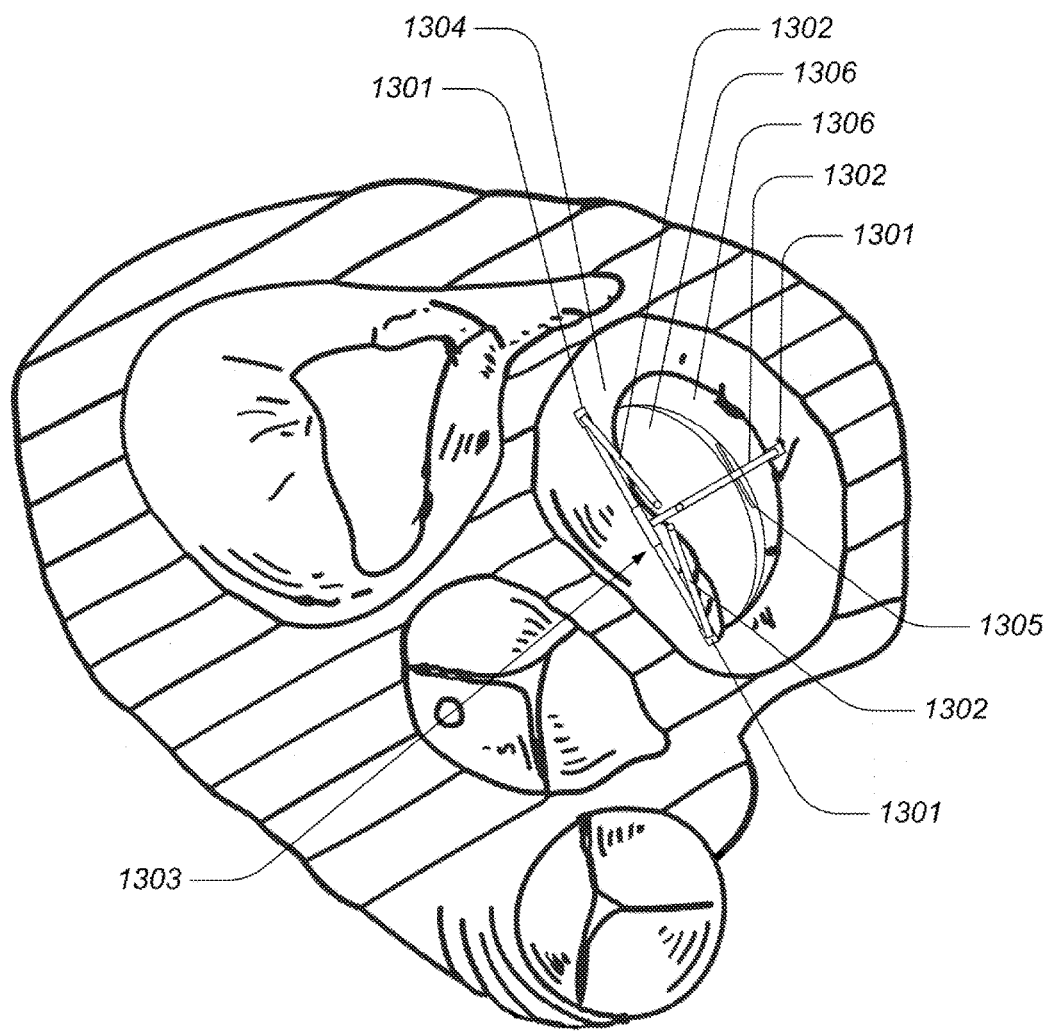
FIG. 13 is a cutaway diagram of a heart showing an example of tissue anchors secured in a mitral valve annulus according to one illustrated embodiment.

FIG. 13 shows a cross section of a heart with an anchor guide frame according to one illustrated embodiment positioned within a left atrium of the heart.

An anchor guide frame 1303 is shown self-located on a mitral annulus 1304 within the left atrium. The tissue anchor deployment sites 1301 are preferably located on the mitral annulus and coincident with bends in the guide members (e.g., guide wires or rails) 1302. While FIG. 13 shows three guide members 1302 and tissue deployment sites 1301 for simplicity, in many cases more deployment sites and guide members are desirable. In such cases, it is a simple matter to add additional guide members and anchor deployment sites to the illustrated embodiment.

An alignment fin 1305 may fit between mitral valve leaflets 1306. The movement and anatomical structure of the mitral valve leaflets 1306 exert force on alignment fin 1305 and assist in orienting the anchor guide frame 1303 correctly.

Figure 14:
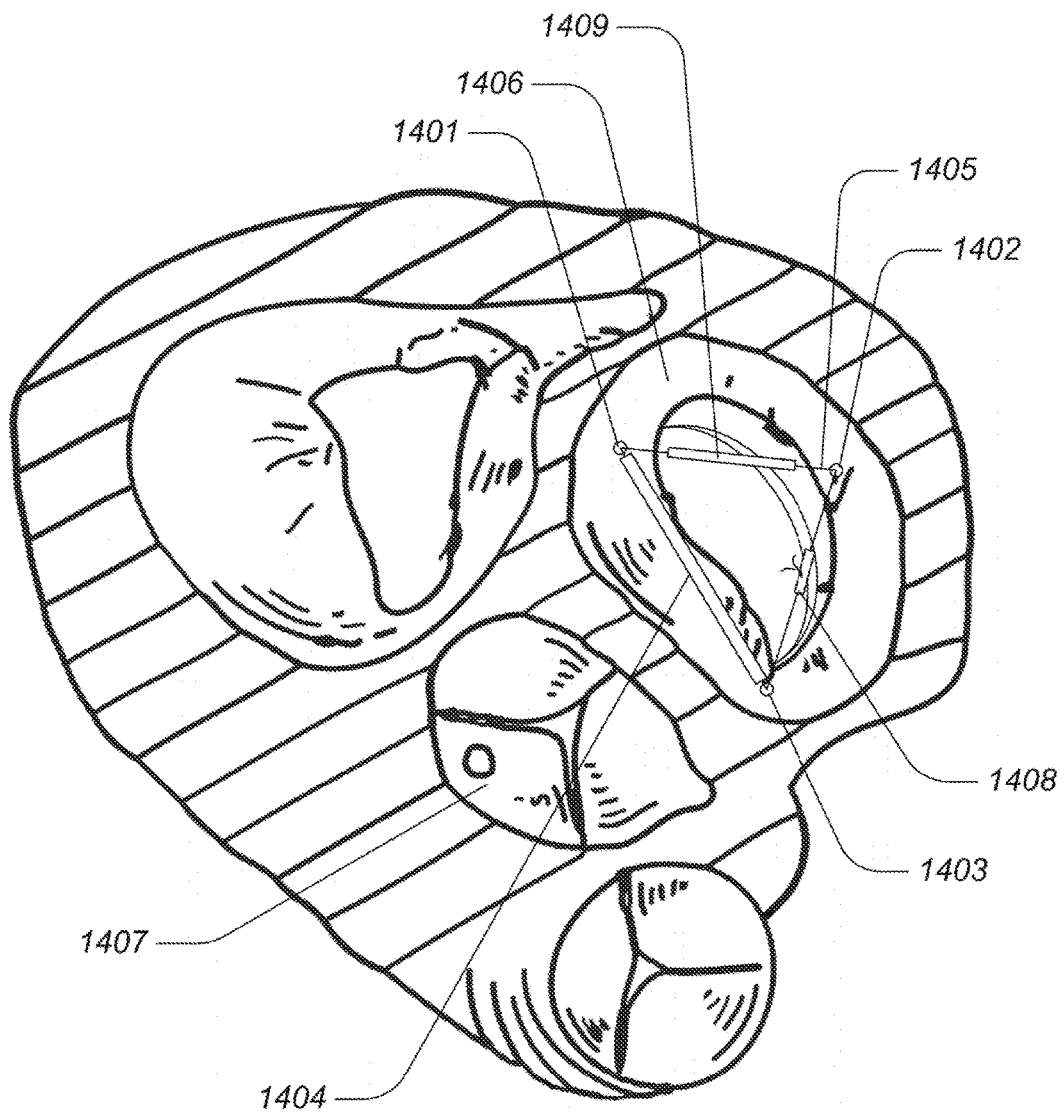
FIG. 14 is a cutaway diagram of a heart showing an example of tissue anchors and a cable used to constrict a mitral valve annulus according to one illustrated embodiment.

FIG. 14 shows a cross section of a heart with an installed assembly capable of constricting a mitral valve annulus according to one illustrated embodiment.

Tissue anchors 1401, 1402, and 1403 are shown fully deployed on the mitral annulus 1406. Tissue anchors 1401-1403 may be connected by a flexible cable 1405. Other mechanisms for connecting tissue anchors 1401, 1402, 1403 are possible. For example, rigid members, preferably with adjustable length (e.g., turn-buckles), may be used to connect the tissue anchors 1401-1403. Flexible cable 1405 may slide through holes on the tissue anchors 1401, 1402, 1403.

Flexible cable 1405 may pass through a hollow spreader bar 1404. Hollow spreader bar 1404 provides support to keep tissue anchors 1401 and 1403 from moving closer together when flexible cable 1405 is shortened. Such support reduces undesired forces being applied to an aortic valve 1407 of the heart.

Reducing a distance between pairs of the tissue anchors 1401, 1402 and 1402, 1403 causes an anterior-posterior (A-P) annular dimension of the mitral valve to reduce and improves leaflet coaptation. Several methods may be used to reduce the distance between two or more pairs of tissue anchors 1401, 1402 and 1402, 1403. A first method is to shorten the cable during the installation procedure by routing the flexible cable 1405 through fastener 1408, pulling the cable manually to be as tight as desired and crimping fastener 1408. Fastener 1408 may also be constructed using a one way clutch so that the flexible cable 1405 can only be pulled through in one direction, in which case crimping is not required. A second method of reducing tissue anchor separation (i.e., distance between two successive tissue anchors) is to include shortening actuator 1409 between two tissue anchors. In the case where shortening actuator 1409 is included, flexible cable 1405 is split and attached to either end of the shortening actuator. One embodiment of shortening actuator 1409 contains an element that is capable of changing length in response to a stimulus such as changes in an external magnetic field or heating induced by a changing magnetic field. The element capable of changing lengths may be made of a highly magnetostrictive alloy such as Terfenol-D or from a Shape Memory Alloy (SMA) such as specially treated Nitinol. Embodiments of such actuators are described in U.S. patent application Ser. No. 11/902,199.

The element capable of changing lengths may be made of a spring under tension (e.g., in an extended configuration) encapsulated in a retainer material that changes state in response to a stimulus (e.g., melts under low heat and solidifies at body temperature—such as a thermoplastic polymer). Current induced in a loop by an external magnetic field may be channeled through the spring. The current may heat the spring which will cause the polymer to soften and the spring length to contract to an unextended configuration. The contraction of the spring can be used to reduce the separation of the tissue anchors. Embodiments of such actuators are described in U.S. patent application Ser. No. 11/905,771.

A closed, electrically conducting loop is required if shortening actuator 1409 is to be responsive to heating or energy induced by a changing magnetic field. Such a loop may be achieved by using an electrically conductive material for flexible cable 1405 and ensuring an electrical contact between both ends of flexible cable 1405 that are connected to shortening actuator 1409.

Figure 15A:
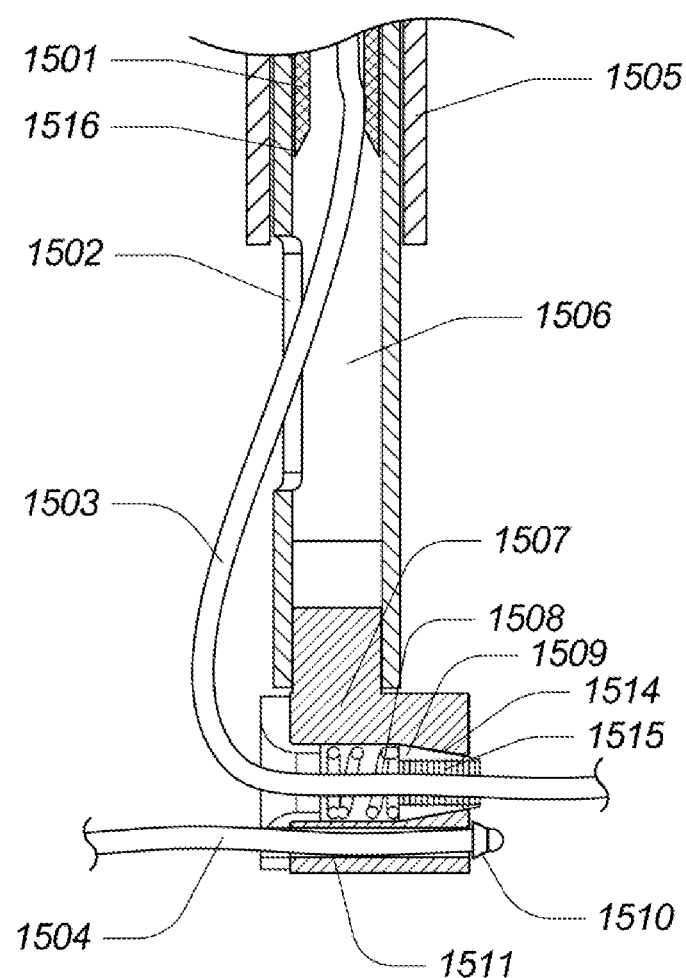
FIGS. 15A and 15B are cross-sectional views of a tool to secure a cable of an implantable device that constricts a bodily orifice at two successive intervals of time illustrating a time prior to cutting the cable and a time when the cable is being cut according to one illustrated embodiment.
Figure 15B:
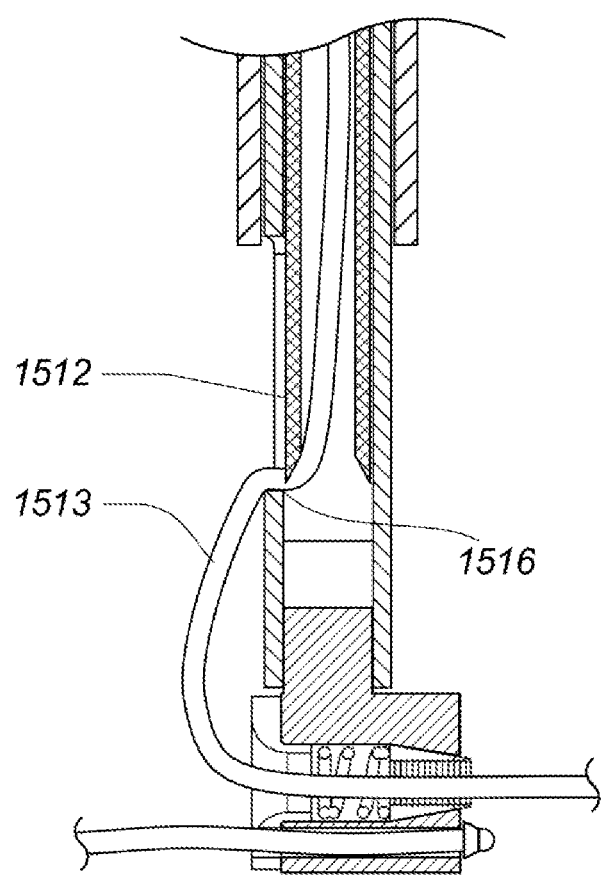

FIGS. 15A and 15B show a tool and fastener used to tighten and secure a cable according to one illustrated embodiment.

Fastener 1507 may be used to tighten or secure cables being used to constrict a bodily orifice. Typically prior to attachment of fastener 1507, tissue anchors have been implanted or placed in the tissue, and a flexible cable has been connected to the tissue anchors. Cable end 1504 and cable end 1503 are typically carried in catheter sheath 1505 and routed outside the body. Cable end 1504 and cable end 1503 may be the two ends of one flexible cable. The portion of the cable not shown loops around the orifice to be constricted and is attached to the implanted tissue anchors used to secure the cable to the orifice.

Cable end 1504 may be fed into hole 1511 and locked by ferrule 1510 while fastener 1507 is still outside the body. Cable end 1503 may be routed through taper lock 1509 while fastener 1507 is still outside the body.

Fastener 1507 may be attached to fastener positioning tube 1506. Cable end 1503 may be inserted through slot 1502 and into fastener positioning tube 1506. Fastener 1507 and fastener positioning tube 1506 may be inserted into catheter sheath 1505 and advanced until fastener 1507 is proximate an annulus of the orifice to be constricted. Cable end 1503 may be pulled in a direction away from fastener 1507, causing the cable to pull through taper lock 1509 and constrict the orifice. While the cable is being tightened and secured, fastener 1507 may be held by fastener positioning tube 1506. Taper lock 1509 restricts cable end 1503 from being pulled out the right side (as illustrated in FIGS. 15A, 15B) of fastener 1507. Taper lock 1509 may have teeth 1515 to grip cable end 1503. Taper lock 1509 may have a longitudinal slot to enable compression of taper lock 1509 and constriction around cable end 1503. Spring 1508 may force taper lock 1509 into a conical hole 1514, causing the taper lock 1509 to tighten around cable end 1503.

When the orifice has been sufficiently constricted, cable end 1503 may be severed using cable cutting tube 1501. Cable cutting tube 1501 includes a sharpened end 1516. In particular, FIG. 15A shows cable cutting tube 1501 in a retracted position. The cable cutting tube may slide inside of fastener positioning tube 1506. FIG. 15B shows cable cutting tube 1512 in the cable cutting position, physically engaging the cable 1513. Cable cutting tube 1512 may sever cable end 1513 by forcing cable end 1513 against the end of slot 1516. The cable end may be severed in other ways, including using a hot tip to melt through the cable.

Figure 16A:
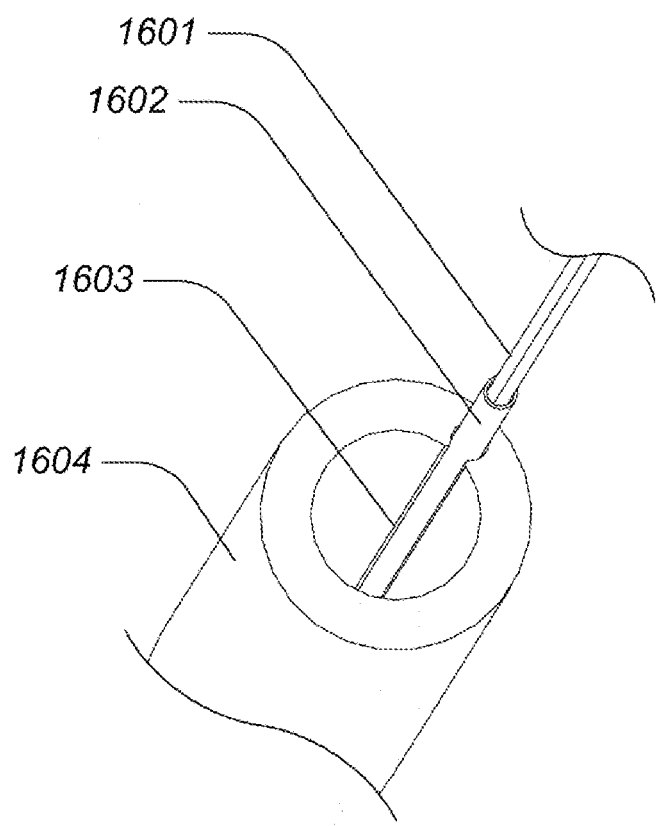
FIGS. 16A and 16B are sequential isometric views showing a portion of a catheter with side slots according to one illustrated embodiment.
Figure 16B:
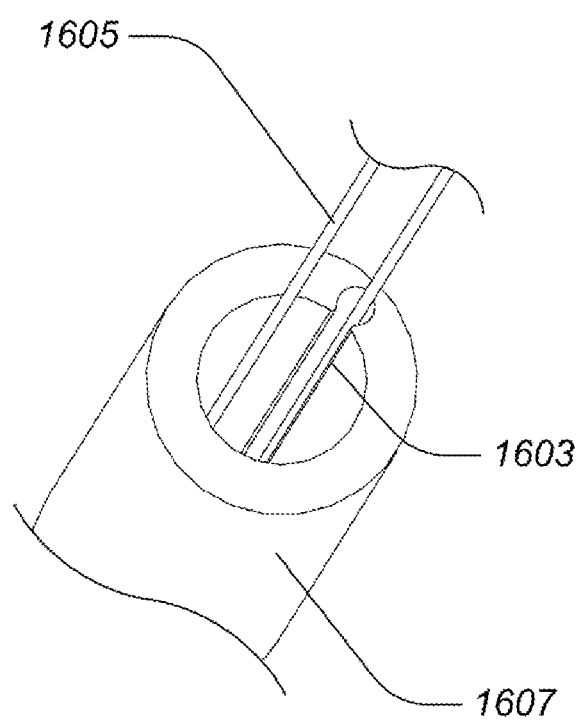

FIGS. 16A and 16B show a catheter with grooves, or side slots, and a mechanism for securing cables or wires in said side slots according to one illustrated embodiment.

In particular, FIG. 16A shows catheter 1604 with cables 1601 held within longitudinal groove 1603 on the inner surface of the tube wall by tube 1602. The longitudinal groove 1603 has a cross sectional shape that enables tube 1602 to be held captive. FIG. 16A shows a circular groove (i.e., arcuate cross-section), but other shapes may be used. Tube 1602 carries cables 1601. Tube 1602 could also carry wires or tubes. When tube 1602 is removed by pulling it out the end, as shown in FIG. 16B by catheter 1607, cables 1605 are free to move into the central area of the tube. Tube 1602 can be reinserted over cables 1605 to again constrain them in groove 1603.

Although FIGS. 16A and 16B show catheter 1604 and catheter 1607 with only one groove 1603, it is possible to have many such grooves in a catheter and to secure a plurality of wires and tubes in said grooves. One of the reasons for securing cables or wires in grooves, or side slots, is to eliminate tangling of cables or wires during medical procedures.

Figure 17:
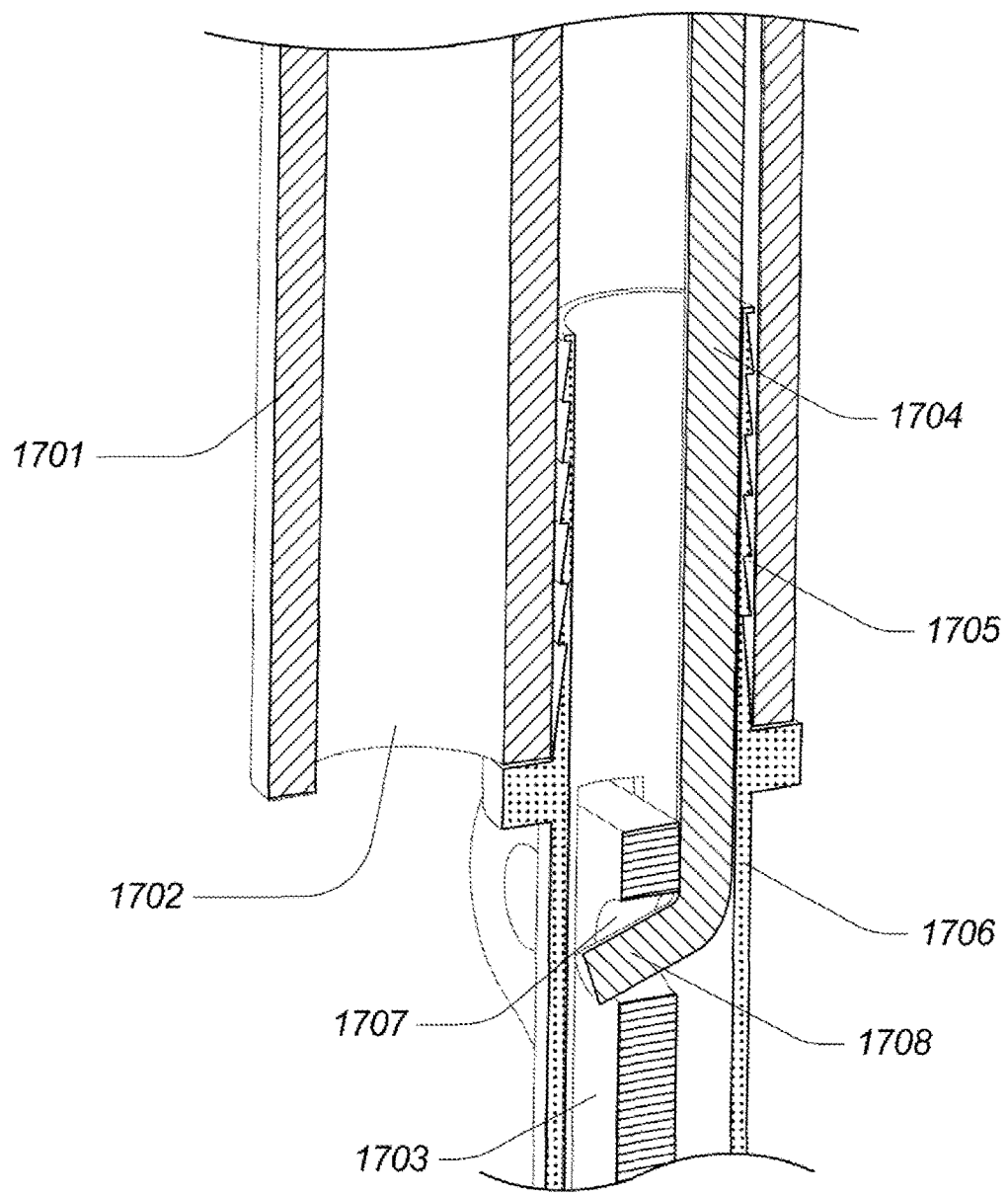
FIG. 17 is a cross-sectional partial view of a mechanism according to one illustrated embodiment for holding a tissue anchor captive.

FIG. 17 shows a mechanism for holding a tissue anchor captive according to one illustrated embodiment.

Tissue anchor 1703 may be held captive in constriction tube 1706 of the tool by release member 1704. Constriction tube 1706 may be inserted and secured to a distal end of one lumen of push tube 1701. Constriction tube 1706 may be held captive in the lumen by one or more ribs 1705.

Tissue anchor 1703 may be released from constriction tube 1706 by retracting push tube 1701 and constriction tube 1706 relative to release member 1704. As the distal end of constriction tube 1706 clears hole 1707, tip of release member 1708 will pop out of hole 1707 and tissue anchor 1703 will no longer be held captive.

Lumen 1702 of push tube 1701 may be used to slide over a guide member.

Figure 18A:
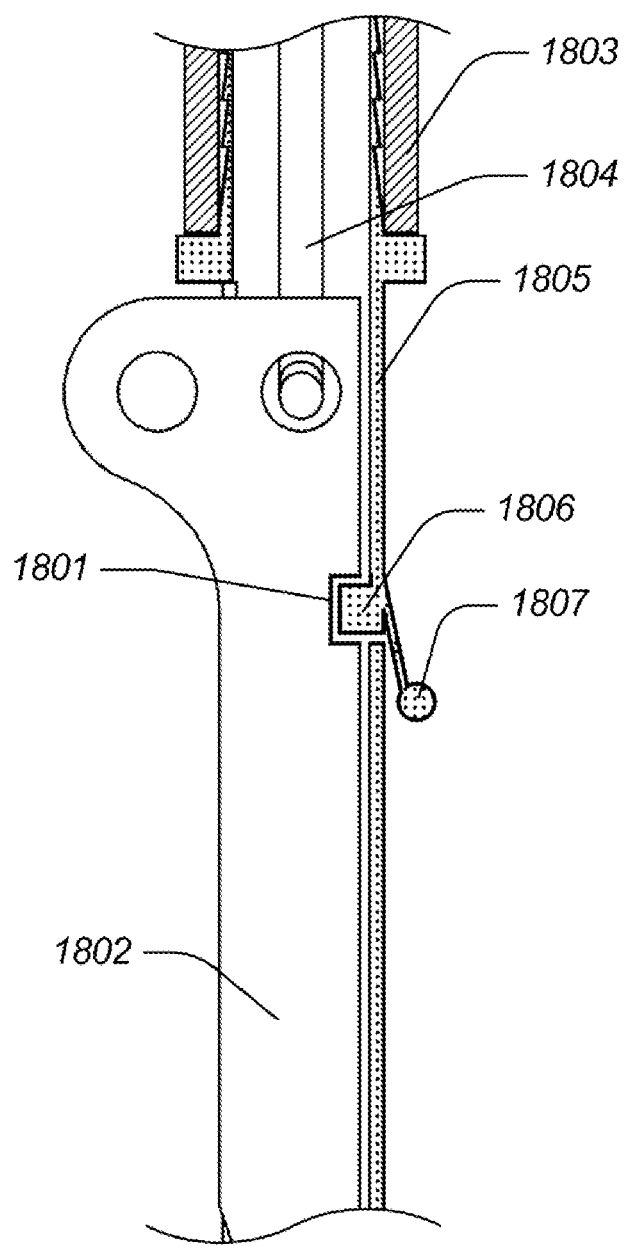
FIGS. 18A and 18B are successive side elevational views of a mechanism according to one illustrated embodiment for restricting a tissue anchor from release until the tissue anchor is fully embedded in tissue.
Figure 18B:
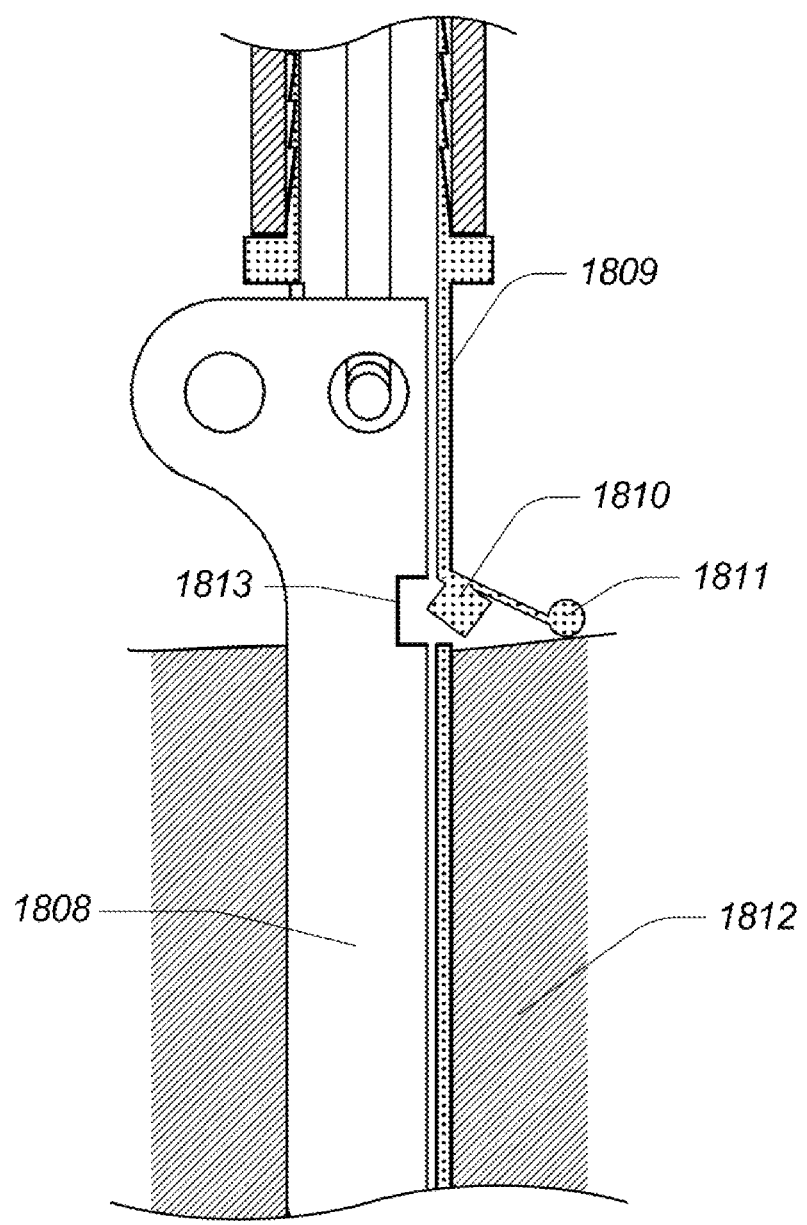

FIGS. 18A and 18B show mechanisms for restricting a tissue anchor from release until the anchor is fully embedded in tissue according to one illustrated embodiment An additional benefit is provided if the tool to implant the implantable device for constricting a bodily orifice does not release tissue anchors of the implantable device until the tissue anchors are fully embedded in the tissue. It is possible to achieve this benefit by adding an additional latch 1806, 1810 to the tool.

In particular, FIG. 18A shows a tissue anchor 1802 prior to deployment. The tissue anchor 1802 may not be released from constriction tube 1805 by retracting push tube 1803 and constriction tube 1805 relative to release member 1804 because latch 1806 in an engaged or locked position extends into a notch 1801. Latch 1806 is coupled to lever 1807 in this illustrated embodiment.

FIG. 18B shows the tissue anchor 1808 fully deployed into tissue 1812. As tissue anchor 1808 was deployed into tissue 1812, the surface of tissue 1812 causes lever 1811 to bend. When lever 1811 is bent, latch 1810 clears notch 1813. Once latch 1810 clears notch 1813, tissue anchor 1808 may be released from constriction tube 1809.

Figure 19A:
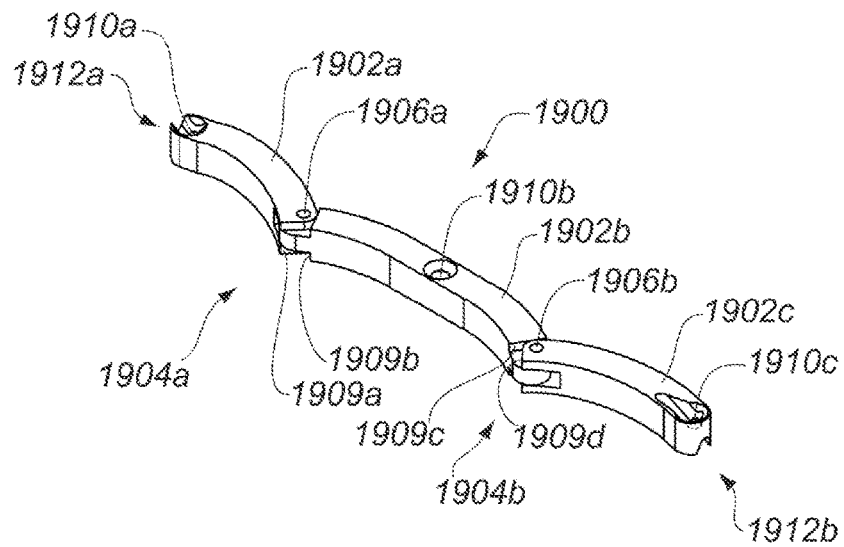
FIG. 19A is an isometric view of an implant member according to one illustrated embodiment, the implant member shown in a delivery configuration.
Figure 19B:
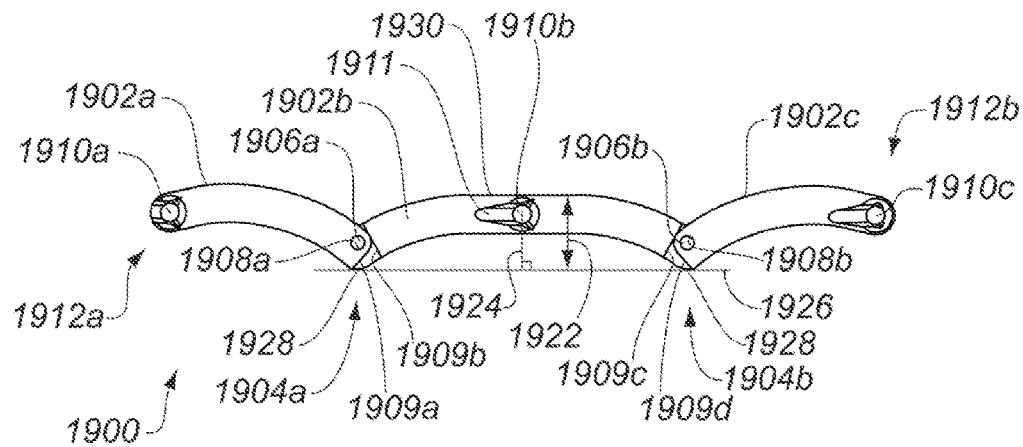
FIG. 19B is a top plan view of the implant member of FIG. 19A shown in the delivery configuration.
Figure 19C:
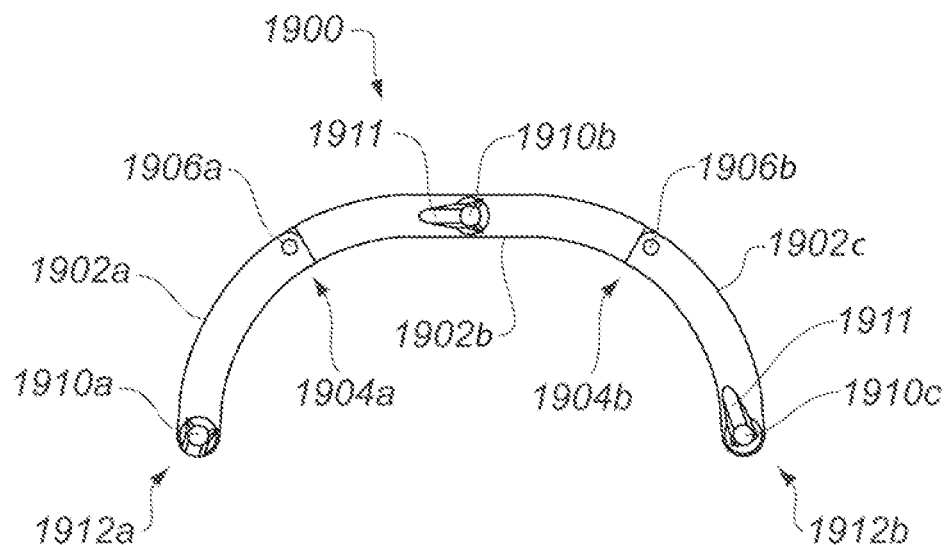
FIG. 19C is an isometric view of the implant member of FIGS. 19A and 19B, the implant member shown in an implantable or deployed configuration.
Figure 19D:
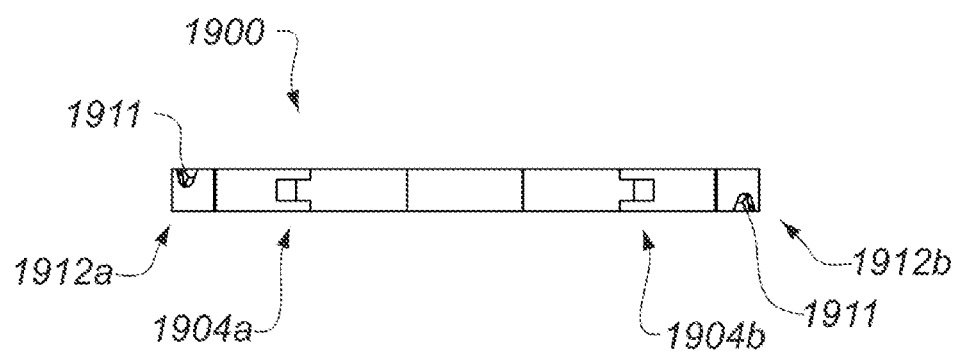
FIG. 19D is a front elevational view of the implant member of FIGS. 19A-19C, shown in the implantable or deployed configuration.

FIGS. 19A-19D show an implant member 1900, according to one illustrated embodiment. In particular, FIGS. 19A and 19B show the implant member in a first configuration that is representative of one of a delivery configuration, an unanchored configuration or an untensioned configuration, while FIGS. 19C and 19D show the implant member in a second configuration that is representative of one of an implantable configuration, a deployed configuration, an anchored configuration or a tensioned configuration. This implant member 1900 may be particularly suitable for use with the tissue anchors, anchoring guiding frame and techniques of FIGS. 5C, 5D, and FIGS. 8C-8F.

The implant member 1900 may be used to reshape, reconfigure and/or reinforce an orifice in bodily tissue. For example, the implant member 1900 may be used to reshape, reconfigure and/or reinforce a valve, for instance a natural valve or an artificial valve. The valve may, for example, take the form of a mitral, tricuspid, pulmonary and/or aortic valve of the heart. Alternatively, the valve may take the form of another valve in another organ of the body.

The implant member 1900 has a plurality of arcuate segments 1902a-1902c (collectively 1902). While three segments 1902 are illustrated, the implant member 1900 may include additional segments. The total number of segments 1902 may be based on the size of the valve that the implant member 1900 will be used with. The total number of segments 1902 may additionally or alternatively be based on a largest lateral dimension that may be accommodated by a given or desired catheter (i.e., diameter of catheter lumen). For instance, employing a greater number of segments 1902 means that each segment may have a smaller height 1922, while still achieving a desired lateral dimension or height of the overall implant member 1900 when in the implanted configuration.

The segments 1902 are physically coupled to one another, and in at least some configurations are articulated for movement with respect to one another, for example pivotal movement. The implant member 1900 includes a number of hinges 1904a, 1904b (collectively 1904 pivotally coupling neighboring ones of the segments 1902. Each hinge 1904 may include a hinge pin 1906a, 1906b (collectively 1906) received via through holes 1908a, 1908b (collectively 1908) (not called out in FIG. 19A) in the segments 1902. The hinge pin 1906 should be fixedly received in the throughhole 1908 to ensure that the hinge pin 1906 does not become dislodged after implantation. The hinge pin 1906 may be swaged in the throughhole 1908, and may additionally or alternatively be fixed using other mechanisms. The locations of the hinge pins 1906 of the hinges 1904 may be offset from a longitudinal centerline (i.e., the arc that passes longitudinally through the geometric center between the longitudinal arcuate edges) of the respective one of the arcuate segments 1902. Such may avoid having to remove material on an outside edge to allow the segments 1902 to pivot. Alternatively, the hinge pins 1906 may lie along the longitudinal centerline.

The segments 1902 include stops 1909a-1909d (collectively 1909) proximate the hinges 1904. The stops 1909 on neighboring ones of the segments 1902 cooperatively interact by engaging one another to prevent the segments 1902 from being pivoted past a defined angle with respect to one another. The stops thus serve to lock the segments 1902 from further articulation in one direction, from the delivery configuration to the implanted configuration. While illustrated as simple complementary engagement surfaces, the stops may take other forms. For example, stops may take the form a detent or other lock structure. Stops 1909 may lock the segments 1902 from movement in two, opposed directions. Stops 1909 may also provide torsional stiffness to the hinges 1904.

In some example embodiments, a portion of an implant member having a variable bending stiffness in at least one dimensional plane is employed. In this illustrated embodiment, implant member 1900 is configured to be bendable between a first configuration in which implant member 1900 has a generally elongated shape and a second configuration in which implant member 1900 has an arcuate shape. Stops 1909 allow portions of the implant member 1900 coupled by hinges 1904 to have a variable bending stiffness in at least one dimensional plane. Hinges 1904 allow implant member 1900 to bend via the articulation of segments 1902 in a plane when implant member 1900 is in its first configuration. Stops 1909 restrain further articulation between segments 1902 when implant member 1900 is in the second configuration and any further bending is dependent on any additional flexing of segments 1902. In this regard, the implant member 1900 has a reduced bending stiffness in the at least one dimensional plane when the implant member 1900 is in the first configuration and an increased bending stiffness in the one dimensional plane when the implant member 1900 is in the second configuration. Variable bending stiffness characteristics can be achieved in other ways by other example embodiments. The implant member 1900 includes a number of guide line receivers 1910a-1910c (collectively 1910). The guide line receivers 1910 may be formed as holes or apertures and are sized to receive a guide line such as a guide wire (not shown in FIGS. 19A-19D) to allow the implant member 1900 to ride on or otherwise be guided or advanced along the guide line. The guide line may, for example, take the form of the guide wire of FIGS. 5C, 5D and FIGS. 8C-8F. In various embodiments, the guide line receivers 1910 allow implant member 1900 to ride on, or otherwise be guided or advanced along a guide line that is received or coupled to a tissue anchor that is embedded into tissue. The guide line receivers 1910a, 1910c are located proximate a first end 1912a, a second end 1912b, respectively. The guide line receiver 1910b is between the first and second ends 1912a, 1912b. In particular, each of the segments 1902 may have at least one of the guide line receivers 1910. While illustrated as being approximately midway between the first and second ends 1912a, 1912b, the guide line receiver 1910b between the first and second ends 1912a, 1912b may be offset to one side or the other of a center line (perpendicular bisector 1924) of the implant member 1900, along a longitudinal axis thereof. The implant member 1900 may include additional guide line receivers (not shown). For instance, all or some of one or more additional segments (not shown) may have guide line receivers. Additionally, or alternatively, one segment 1902 may have more than one guide line receiver 1910. One or more of the segments 1902 may include relief 1911 (only one called out in FIG. 19B) proximate the guide line receiver 1910. The relief 1911 may accommodate a guide line such as a wire or suture.

As illustrated in FIGS. 19A and 19B, the segments 1902 of the implant member 1900 may be moved with respect to one another, into a first configuration, which in this illustrated embodiment is representative of a delivery configuration or unanchored configuration. In the delivery or unanchored configuration, the implant member 1900 is sized and dimensioned to be deliverable via a catheter. In the delivery configuration, the implant member 1900 may have an elongated, scallop or serpentine profile, as best illustrated in FIG. 19B. A maximum longitudinal dimension in the delivery or unanchored configuration is relatively long as compared to the maximum longitudinal dimension in the implanted or anchored configuration. Thus, a maximum lateral dimension of the implant member 1900 (i.e., maximum dimension measured perpendicularly to a longitudinal axis extending between the first and second ends 1912a, 1912b), is minimized. The maximum lateral dimension in the delivery or unanchored configurations is relatively short or small as compared to the maximum lateral dimension in a second configuration, which in this illustrated embodiment is representative of an implantable or deployed or anchored configuration. As illustrated in FIG. 19B, the maximum lateral dimension may, for example, be approximately equal to a height 1922 of the arch formed by the one of the arcuate segments 1902 (i.e., 1902b in this illustrated embodiment), as measured by a perpendicular bisector 1924 that extends from a chord line 1926 passing tangent to portions of an inner surface 1928 (called out twice in FIG. 19B) of one or more of the arcuate segments 1902, to where the perpendicular bisector 1924 intersects an outer surface 1930 of the arcuate segment 1902 when the plurality of arcuate segments are positioned in the delivery or unanchored configuration. Thus, the implant member 1900 may be accommodated by a catheter. Catheters are typically long, but have relatively narrow diameters. Thus, catheters have relatively unlimited longitudinal capacity as compared to lateral or radial capacity.

As illustrated in FIGS. 19C and 19D, the segments 1902 of the implant member 1900 may be moved with respect to one another into the second configuration representative of an implantable or deployed or anchored configuration. In the second configuration, the implant member 1900 has an arcuate or annular shape or profile. The arcuate or annular shape is sized and dimensioned to encompass at least part of an orifice. For example, the arcuate or annular shape may be sized and dimensioned to overlie part of an annulus of a mitral valve of a heart. In the second configuration, the dimensions of the implant member 1900 are too large to be accommodated by a typical catheter. In particular, a lateral dimension or height of the implant member is too large to be received by a lumen of the catheter.

As described in detail below, forces or tension may be applied to the implant member 1900 at the guide line receivers 1910, for instance via embedded tissue anchors and/or wires and/or sutures. Such may tension the implant member 1900 into the second configuration (FIGS. 19C and 19D), while the stops 1909 prevent the segments 1902 of implant member 1900 from articulating past the implanted configuration. Such results in the implant member 1900 having a generally rigid structure in the second configuration.

Figure 20A:
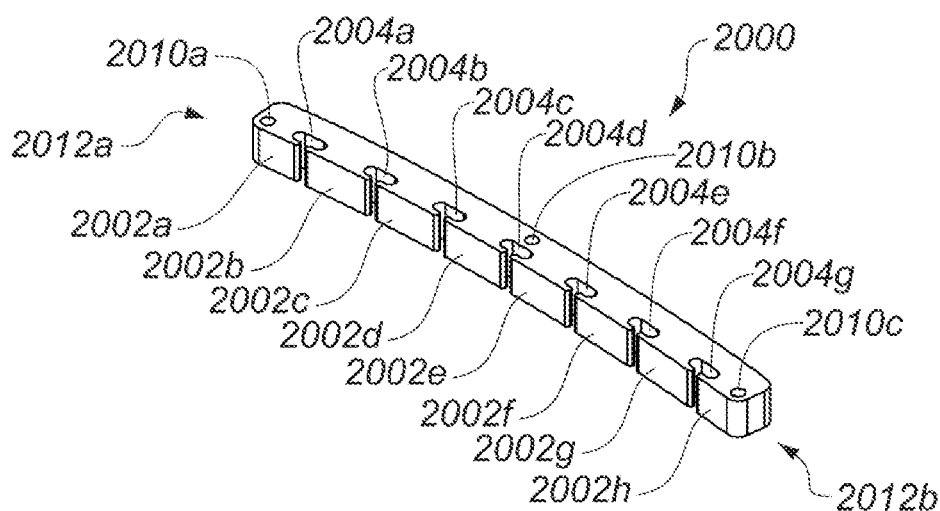
FIG. 20A is an isometric view of an implant member according to another illustrated embodiment, the implant member shown in a delivery configuration.
Figure 20B:
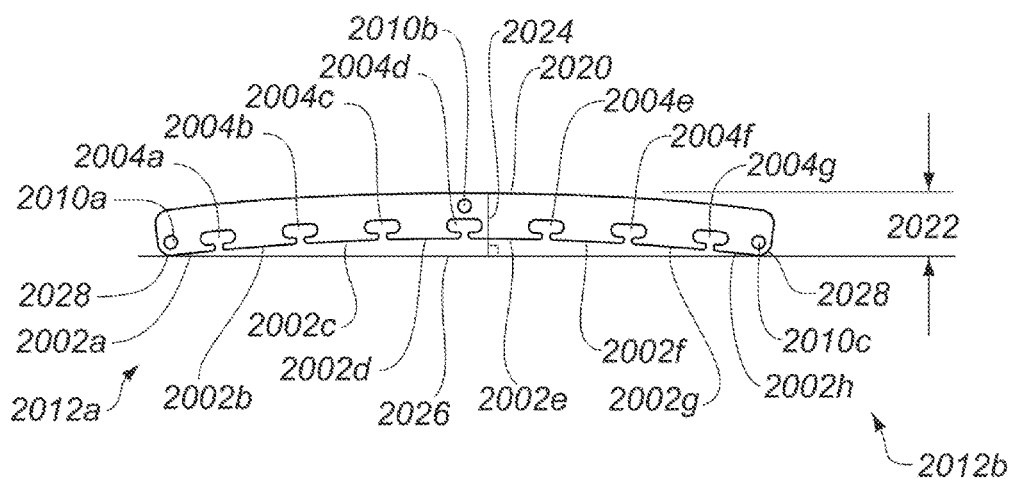
FIG. 20B is a top plan view of the implant member of FIG. 20A shown in the delivery configuration.
Figure 20C:
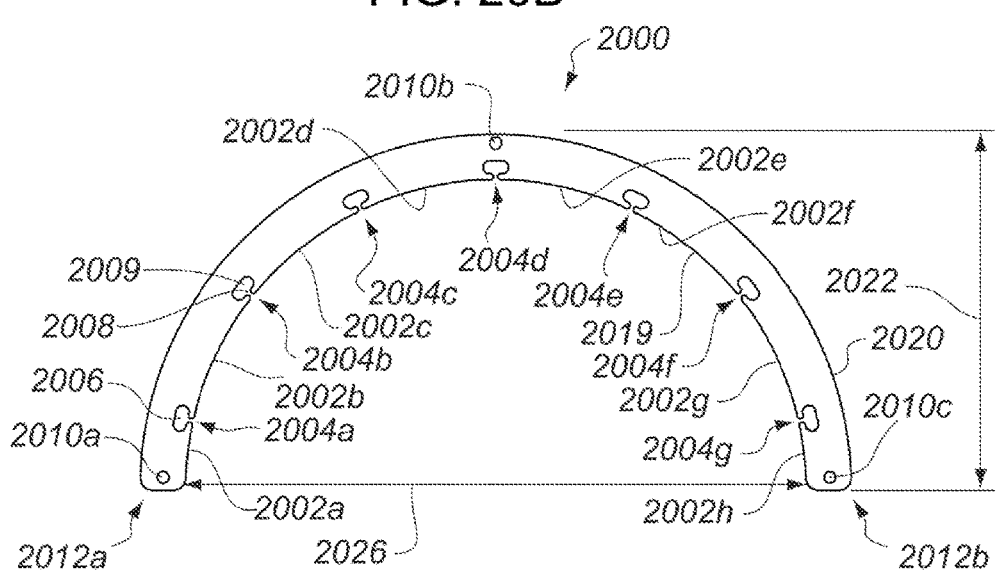
FIG. 20C is an isometric view of the implant member of FIGS. 20A and 20B, the implant member shown in an implantable configuration.
Figure 20D:
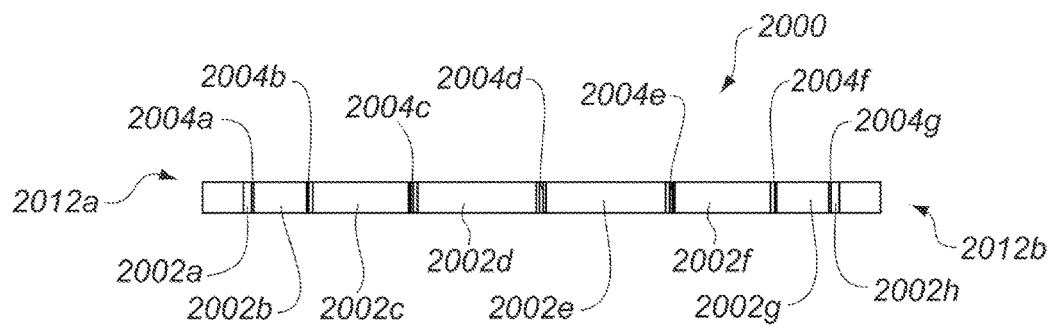
FIG. 20D is a front elevational view of the implant member of FIGS. 20A-20C, shown in the implantable configuration.

FIG. 20A-20D show an implant member 2000, according to one illustrated embodiment. In particular, FIGS. 20A and 20B show the implant member 2000 in a first configuration representative of a delivery configuration or an unanchored configuration, while FIGS. 20C and 20D show the implant member 2000 in a second configuration representative of a deployed configuration or an implantable configuration or an anchored configuration. This implant member 2000 may be particularly suitable for use with the tissue anchors, anchoring guiding frame and techniques of FIGS. 5C, 5D, and FIGS. 8C-8F, by way of non-limiting example.

The implant member 2000 may be used to reshape, reconfigure and/or reinforce an orifice in bodily tissue. For example, the implant member 2000 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 2000 has a plurality of arcuate segments 2002a-2002h (collectively 2002). While eight segments 2002 are illustrated, the implant member 2000 may include fewer or a greater number of segments. The total number of segments 2002 may be based on the size of the valve that the implant member 2000 will be used with. The total number of segments 2002 may additionally or alternatively be based on a largest lateral dimension that may be accommodated by a given or desired catheter (i.e., diameter of catheter lumen). For instance, employing a greater number of segments 2002 means that the implant member 2000 may have a smaller height in the first configuration, while still achieving a desired lateral dimension or height of the overall implant member 2000 when in the second configuration.

The segments 2002 are physically coupled to one another, and in at least some configurations are articulated for movement with respect to one another, for example pivotal movement. The implant member 2000 includes a number of flexure joints 2004a-2004g (collectively 2004) pivotally coupling neighboring ones of the segments 2002. Each flexure joint 2004 may be defined by a recess 2006 (only one called out in FIG. 20C) defined in the implant member 2000. Thus, in contrast to the implant member 1900 (FIGS. 19A-19D), the implant member 2000 may be a unitary structure formed from a single piece of material. The recesses 2006 are illustrated as being on an inner radius, diameter or surface 2019 of the implant member 2000. Alternatively, recesses may be formed on an outer radius, diameter or outer peripheral surface 2020 of the implant member, diametrically opposed to the recesses 2006 illustrated in FIGS. 20A-20D.

The recesses 2006 may be defined or formed via machining operations, for instance drilling, milling, laser cutting, water jetting, etc. In particular the recesses 2006 may have an entrance 2008 (only one called out in FIG. 20C) at an inner peripheral surface 2019 of the implant member 2000, and may have an enlarged portion 2009 (only one called out in FIG. 20C) spaced inwardly of the entrance 2008. The recesses 2006 may have rounded corners which may alleviate stress and/or possible crack formation. Such may also prevent snagging or tearing of bodily tissue.

The implant member 2000 may employ the resiliency of the material from which the implant member 2000 is formed to limit the bending or travel of the segments 2002. Alternatively, the implant member 2000 may include stops proximate the flexure joints 2004. The stops on neighboring ones of the segment 2002 would cooperatively interact by engaging one another to prevent the segments 2002 from being pivoted past a defined angle with respect to one another. Accordingly, in various example embodiments, a portion of implant member 2000 has a variable stiffness in at least one dimensional plane. In a manner similar to other described embodiments, the use of stops can allow implant member 2000 to have a reduced bending stiffness when implant member 2000 is in its first configuration and an increased bending stiffness when implant member 2000 is in its second configuration. In this example embodiment, a portion of implant member 2000 has a substantially equal bending stiffness in each of a plurality of directions in at least one dimensional plane when implant member 2000 is in its first configuration while the portion of implant member 2000 has a substantially unequal bending stiffness in each of the plurality of directions in the at least one dimensional plane when implant member 2000 is in its second configuration. In this example embodiment, the stops provide the unequal bending stiffness in each of the plurality of directions in the at least one dimensional plane when implant member 2000 is in its second configuration.

The implant member 2000 includes a number of guide line receivers 2010a-2010c (collectively 2010). The guide line receivers 2010 are formed as holes or apertures and are sized to receive a guide line or wire (not shown in FIGS.

20A-20D) to allow the implant member 2000 to ride on or otherwise be guided or advanced along the guide line. The guide line receivers 2010 are located proximate a first end 2012a, a second end 2012b and a location between the first and second ends 2012a, 2012b. In particular, only some of the segments 2002 may have one of the guide line receivers 2010. While illustrated as being approximately midway between the first and second ends 2012a, 2012b, the guide line receiver 2010b between the first and second ends 2012a, 2012b may be offset to one side or the other of a center line (perpendicular bisector 2024) of the implant member 2000, along a longitudinal axis thereof. The implant member 2000 may include additional guide line receivers (not shown). For instance, all or some of one or more additional segments (not shown) may have guide line receivers. Additionally, or alternatively, one segment 2002 may have more than one guide receiver 2010. Similar to previously described embodiments, each of one or more of the segments 2002 may include a relief (not shown) proximate the guide receiver 2010. Each of these reliefs may accommodate a guide line such as a guide wire or suture.

As illustrated in FIGS. 20A and 20B, the segments 2002 of the implant member 2000 may be moved with respect to one another, into a first configuration representative of a delivery or unanchored configuration. In the first configuration, the implant member 2000 is sized and dimensioned to be deliverable via a catheter. In the first configuration, the implant member 2000 may have an elongated crenulated profile, as best illustrated in FIG. 20B. A maximum longitudinal dimension in the first configuration is relatively long as compared to the maximum longitudinal dimension in a second configuration that is representative of an implantable, deployed or anchored configuration. Thus, a maximum lateral dimension of the implant member 2000 (i.e., maximum dimension measured perpendicularly to a longitudinal axis extending between the first and second ends 2012a, 2012b), is reduced. The maximum lateral dimension in the first configuration is relatively short or small as compared to the maximum lateral dimension in the second configuration. As illustrated in FIG. 20B, the maximum lateral dimension may, for example, be approximately equal to a height 2022 of the arch formed by the implant member 2000, as measured by a perpendicular bisector 2024 that extends from a chord line 2026 passing tangent to portions 2028 of an inner surface located at the first and second ends 2012a, 2012b, to where the perpendicular bisector 2024 intersects an outer surface 2020 of the implant member 2000. Thus, the implant member 2000 may be accommodated by a catheter, which catheters are typically long but which have relatively narrow diameters.

As illustrated in FIGS. 20C and 20D, the segments 2002 of the implant member 2000 may be moved with respect to one another into a second configuration representative of an implantable, deployed or anchored configuration. In the second configuration, the implant member 2000 has an arcuate, annular or C-shape or profile. The arcuate, annular or C-shape is sized and dimension to encompass at least part of an orifice. In the second configuration, the dimensions of the implant member 2000 are too large to be accommodated by a typical catheter sheath. In particular, a lateral dimension or height of the implant member is too large to be received by a lumen of the catheter.

As described in detail below, forces or tension may be applied to the implant member 2000 at the guide line receivers 2010, for instance via tissue anchors and/or guide lines, guide wires and/or sutures. Such may tension the implant member 2000 into the second configuration (FIGS. 20C and 20D).

Figure 20E:
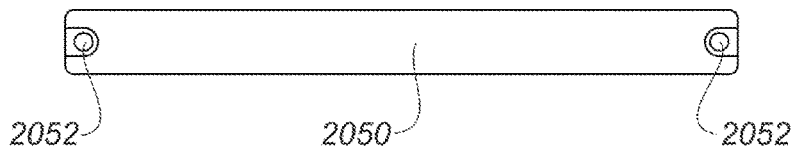
FIG. 20E is a top plan view showing an implant cross member, according to one illustrated embodiment.

FIG. 20E shows an implant cross member 2050, according to one illustrated embodiment. The implant cross member 2050 may have two or more guide line receivers 2052, to receive guide lines such as guide wires (not shown in FIG. 20E). The guide line receivers 2052 may be proximate opposite ends of the implant cross member 2050. Thus, the implant cross member 2050 may ride or otherwise advance along the guide lines or guide wires toward tissue anchors embedded in tissue. The implant cross member 2050 can be anchored across the ends of arms of an implant member such as implant member 1900 (FIGS. 19A-19D), or implant member 2000 (FIGS. 20A-20D) to form a generally D-shape profile with the implant member. The implant cross member 2050 may take the form of an elongated generally rigid structure or an elongated cable or wire, which is generally rigid once anchored. Such may result in a more rigid structure than the structures having generally C-shaped profiles. The implant cross member 2050 may optionally include couplers (not shown) to couple to complementary couplers on the implant member 1900, 2000.

In contrast to other valve reformation structures, at least some of the implant members described herein such as implant members 1900 (FIGS. 19A-19D), 2000 (FIGS. 20A-20D), do not need to have a cable passing through all of the segments as the sole means of coupling the various segments together. In contrast to other valve reformation structures, implant members such as implant members 1900 (FIGS. 19A-19D), 2000 (FIGS. 20A-20D) do not need to be positioned on tissue surrounding a valve, and then secured to the surrounding tissue and finally cinched together to alter the shape of the valve. Rather, in various embodiments, implant members such as implant members 1900, 2000 are secured to tissue anchors (i.e., FIG. 3, FIGS. 4A-4B, FIGS. 5A-5D, FIGS. 6A-6B, FIGS. 7A-7C and FIGS. 8A-8D, by way of non-limiting example) that have been previously embedded or previously anchored into the tissue surrounding the orifice proximate at least three locations. It is noted that in some example embodiments, each tissue anchor is individually embedded into tissue, while in other example embodiments, the tissue anchors are embedded into the tissue as a group. In the previously described example embodiments, guide lines that are received or coupled to the embedded tissue are received by guide line receivers 1910, 2010 provided by respective ones of implant members 1900, 2000 to provide a physical path for implant member 1900, 2000 to travel to the embedded tissue anchors. As the implant member 1900, 2000 travels towards the embedded tissue anchors, each of the guidelines is configured to receive a tensile force sufficient to apply force to bend or position implant member 1900, 2000 into its deployed or implantable configuration (i.e., the second configuration). In various example embodiments, at least some of the guide lines impart force to the implant member 1900, 2000 as it moves along the physical path to the embedded tissue anchors.

In various example embodiments, the implant member 1900, 2000 is appropriately sized and dimensioned so that the tensile force applied to each of the guide lines is sufficient to cause a portion of the tissue into which a respective tissue anchor is embedded to move towards the implant member 1900, 2000 as the implant member 1900, 2000 is positioned into its second configuration. In various example embodiments, the segments 1902, 2002 of respective ones of the implant member 1900, 2000 in the second configuration enclose at least partially an area that is smaller than an area of an annulus of an orifice (e.g., a mitral valve) prior to a physical coupling between the implant member 1900, 2000 and the tissue. In various example embodiments, a circumference defined by a circle passing through at least three locations of the guide line receivers 1910, 2010 on a respective one of the implant member 1900, 2000 in the second configuration is smaller than a circumference of an annulus of the tissue orifice or valve prior to a physical coupling between the implant member 1900, 2000 and the embedded tissue anchors. In various example embodiments, a circumference defined by a circle passing through at least three locations of the guide line receivers 1910, 2010 on a respective one of the implant member 1900, 2000 in the second configuration is smaller than a circumference defined by a circle passing through at least three locations of the embedded tissue anchors prior to a physical coupling between the implant member 1900, 2000 and the embedded tissue anchors.

It is noted that the force applied by the anchoring maintains the implant member 1900, 2000 under tension in the desired implantable configuration when the implant member 1900, 2000 is finally secured to the tissue. Advantageously, implant member 1900, 2000 is positionable between a first configuration in which respective ones of segments 1902, 2002 are articulable with respect to one another such that the implant member 1900, 2000 is manipulable to a size and dimension to be delivered via a catheter and a second configuration in which the segments 1902, 2002 form a structure sufficiently rigid to affect a shape of a tissue valve or orifice in a desired manner. In this regard, each of the implant member 1900, 2000 has a reduced bending stiffness in at least one dimensional plane in the first configuration to allow it to be deliverable via a catheter and an increased bending stiffness in the at least one dimensional plane sufficient to form a structure sufficiently rigid to affect the shape of a tissue orifice or valve in a desired manner. In various example embodiments, the guide lines and embedded tissue anchors apply tension to the implant member 1900, 2000 in the second configuration that is sufficient to restrain disengagement of a respective one of a coupled segment 1902, 2002 with a stop associated with the coupled segment. In various example embodiments, the guide lines and embedded tissue anchors apply tension to the implant member 1900, 2000 in the second configuration that is sufficient to flex at least one of a respective segment 1902, 2002 while the segment engages with an associated stop. The applied tension provided to the implanted implant member 1900 in these example embodiments may reduce wear on the components of the associated hinges 1904 as the implanted implant member 1900 is subsequently repeatedly stressed by the recipient's cardiac cycle which can be in the millions of cycles. The applied tension provided to the implanted implant member 2000 in these example embodiments may reduce fatigue effects as the implanted implant member 2000 is subsequently repeatedly stressed by the recipient's cardiac cycle. While some of the described embodiments may employ a cable between end segments of the articulated structure as an implant cross member, adjacent pairs of the segments are coupled together via respective hinges rather than a cable.

The implant member 1900, 2000 may, for example, have a length (e.g., measured from guide receiver 1910a to 1910b) of from approximately 24 mm to approximately 38 mm, inclusive. Implant members 1900, 2000 may be available in a variety of lengths, for instance in 2 mm increments, to accommodate various valve sizes. The implant members 1900, 2000 may have a thickness of approximate 2 mm, although other thickness may be employed. The width of the segments of the implant members 1900, 2000 may, for example, be approximately 2 mm, although other widths may be employed. The implant members 1900, 2000 may, for example, have a height that is between approximately 30% and approximately 50% of the longitudinal length. The implant members 1900, 2000 may, for example, have a height that is between approximately 60% and approximately 65% of the longitudinal length, for example 63% of the longitudinal length. Such ratio may provide sufficient force to approximate the anterior-posterior dimension of a mitral valve.

In some embodiments, the implant member 1900, 2000 may, for example, have an arcuate, annular or C-shape. The implant member 1900, 2000 may be sized and dimension to encompass over a third or over half (i.e., substantially) of the orifice. For example, the arcuate, annular or C-shape may be sized and dimensioned to overlie part of an annulus of a mitral valve of a heart, surrounding approximately half the mitral valve. Such may advantageously allow the anterior-posterior dimension of the mitral valve to be modified (e.g., reduced). Implant members such as implant members 1900, 2000 may be formed from or comprise a variety of materials. The materials may include a biocompatible material which does not react in or with the tissue or bodily fluids. For example, the implant members 1900, 2000 and/or implant cross member 2050 may be formed of metals such as Nitinol, stainless steel, platinum, iridium, titanium, or polymers such as polytetrafluoroethylene (PTFE) or silicone. Also for example, the implant members 1900, 2000 and/or implant cross member 2050 may be formed tissue (e.g., allograft, autograft).

The implant members 1900, 2000 and/or implant cross member 2050 may have a textured exterior. Alternatively, implant members 1900, 2000 and/or implant cross member 2050 may take the form of a tissue scaffold, for instance a scaffold constructed using 3-D printing techniques. Such textured surface or scaffold may encourage biological overgrowth. The implant members 1900, 2000 and/or implant cross member 2050 may carry one or more functional coatings or layers. Such may either encourage or inhibit formation of scarring, may deliver (e.g., elute) a therapeutic agent to the organ or blood. Such may include gold, heparin, carbon nanocomposite, silicon carbide, titanium-nitride-oxide, phosphorylcholine, etc.

Figures 21A, 21B:
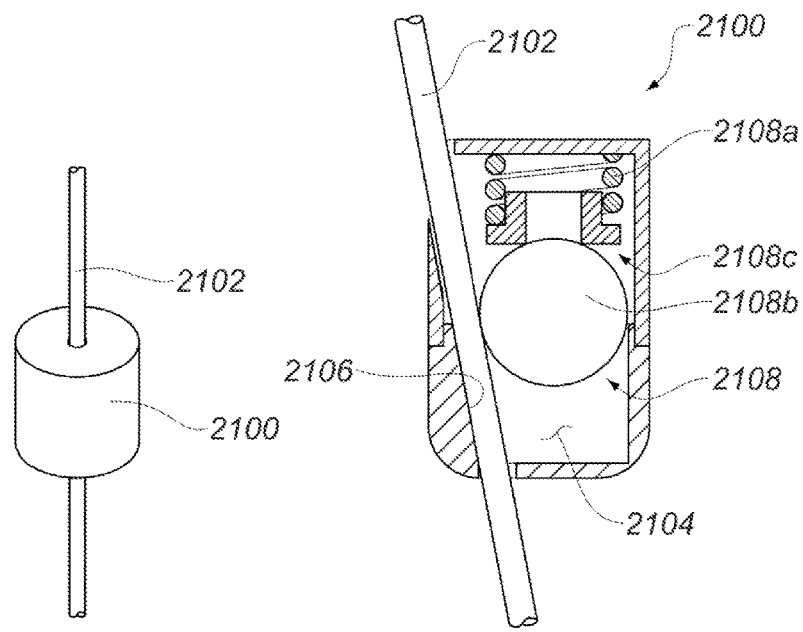
FIG. 21A is an isometric view of a fastener that fastens to a guide line, according to one illustrated embodiment.
FIG. 21B is a cross-sectional view of the fastener and guide line of FIG. 21A.

FIGS. 21A and 21B show a fastener 2100 that fastens to a guide line such as a guide wire 2102, according to one illustrated embodiment.

The fastener 2100 has a cavity 2104 which provides a passage through the fastener 2100 for the guide line (e.g., Nitinol wire). The cavity 2104 may include openings in two opposed surfaces of the fastener 2100 to provide a passage for the guide line or guide wire 2102. The cavity 2104 may have a sloped wall 2106. The cavity 2104 may contain one or more cams or clutches 2108, for instance a spring 2108a and ball 2108b. The ball 2108b is biased toward the sloped wall 2106 by the spring 2108a. While illustrated as a coil spring, other types of springs may be employed. The cam or clutch 2108 may include a seat 2108c which has a stem to retain the spring 2108a and an aperture or concavity to retain the ball 2108b. The ball 2108b frictionally engages the guide line or guide wire 2102 against the sloped wall 2106 in response to movement of the fastener 2100 along the guide line 2102 toward an embedded tissue anchor (not shown in FIG. 21A or 21B). The fastener 2100 may be a unidirectional or a one way fastener or clutch, allowing the fastener 2100 to ride or move along the guide line or guide wire 2102 in one direction, but resisting movement in the opposite direction. Such may be employed to secure the fastener 2100 against the implant member (not shown in FIG. 21A or 21B) percutaneously, to secure the implant member to the tissue anchors which are embedded in the tissue. Other cams or clutches may be employed. For instance, an arcuate section pivotally mounted and biased, for example by a leaf spring, to engage the guide line or guide wire, may be used. The fastener 2100 may be comprised of a biocompatible material, for example a metal that does not react with bodily tissues or fluids. The fastener 2100 may include a tubular housing, which may be cylindrical. An end cap may be secured to the housing, for example via spot welding. The fastener 2100 may, for example, have a total volume of 8 cubic millimeters. The ball 2108*b* may, for example, have a diameter of approximately 0.5 mm.

Figures 22A, 22B:
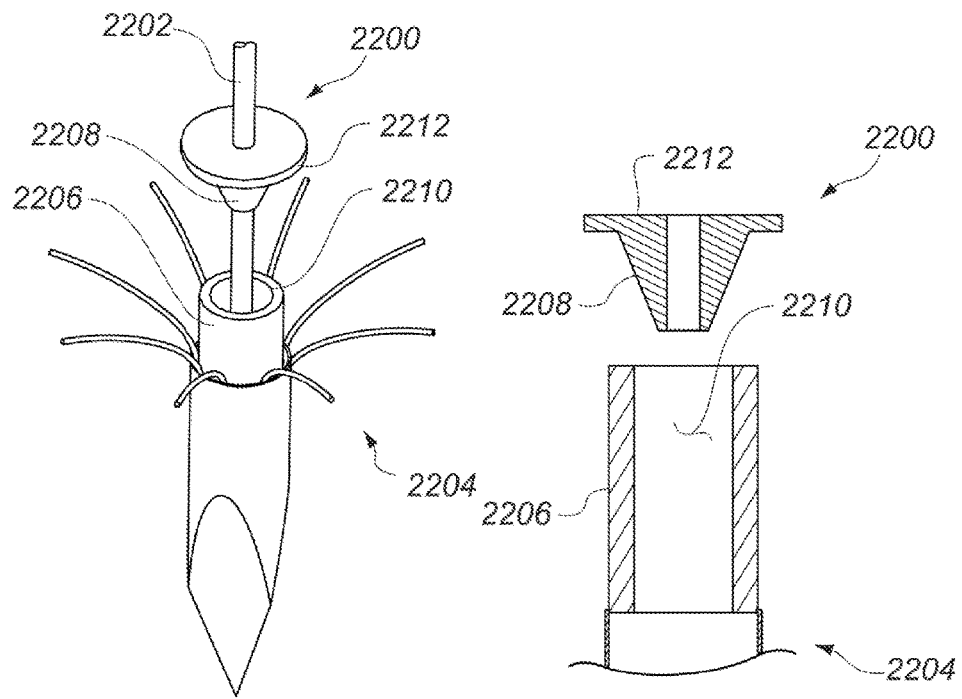
FIG. 22A is an isometric view of a fastener that fastens a guide line to a tissue anchor, according to another illustrated embodiment.
FIG. 22B is a cross-sectional view of the fastener, guide line and tissue anchor of FIG. 22A.

FIGS. 22A and 22B show a fastener 2200 that fastens a guide line 2202 to a tissue anchor 2204, according to another illustrated embodiment.

The fastener 2200 physically interacts with a fastening portion 2206 of the tissue anchor 2204. In particular, the fastener 2200 has a sloped outer surface or swaging surface 2208 that is received in a cavity 2210 of the fastening portion 2206 of the tissue anchor 2204. Engagement of the inner wall forming the cavity 2210 plastically deforms the fastener 2200, increasing the frictional force applied to the guide line 2202. Such can secure the fastener 2200 to the tissue anchor 2204 and secure the guide line 2202 to the fastener 2200. The fastener 2200 is a bidirectional fastener, resisting movement of the guide line 2202 in either direction once swaged. Such may be employed to secure the fastener against the implant member in its second configuration (not shown in FIG. 22A or 22B) to secure the implant member to the tissue anchors embedded in the tissue. While illustrated with the fastener 2200 having a sloped surface 2208, in some embodiments, the inside wall forming the cavity 2210 may be sloped to achieve a similar result. The fastener 2200 may include a peripheral flange 2212 to form a head. The size of the peripheral flange 2212 may be larger than the openings of the implant member that receive the guide lines 2202. The fastener 2200 may be comprised of a biocompatible material, for example a metal that does not react with bodily tissues or fluids.

Figure 22C:
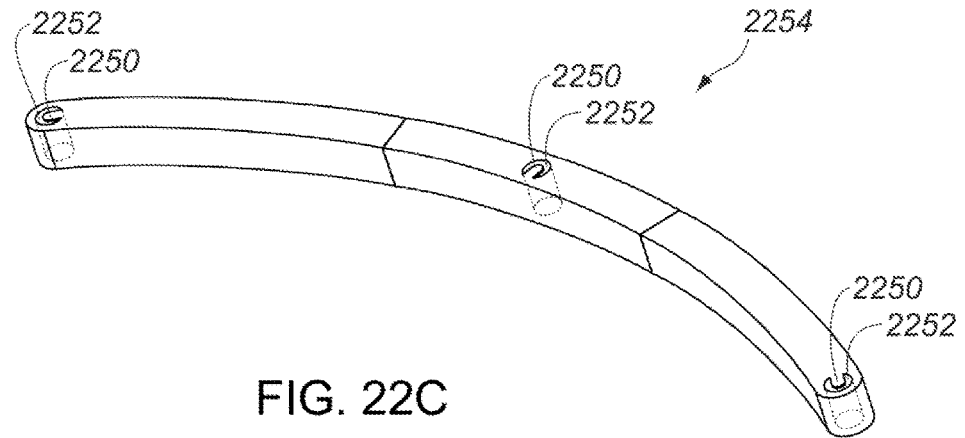
FIG. 22C is an isometric view of an implant member that has single piece, unitary part fasteners that fastens a guide line to a tissue anchor, according to another illustrated embodiment.

Fasteners other than fasteners 2100, 2200 generally described above may be employed in various example embodiments. While illustrated as separate from the implant member, the fasteners may be incorporated into the implant member. For example, the fasteners 2100, 2200 may be secured to the implant member. For instance, the fasteners 2100, 2200 may be secured in apertures or recesses of the implant member, for example via press fit, swaging, and/or adhesives, to become an integral part of the implant member. Alternatively, the fasteners 2100, 2200 may be formed as a unitary, single piece portion of the implant member. For instance, as illustrated in FIG. 22C, a fastener may take the form of a resilient member, such as a tab or pawl 2250, that extends into the guide line receiver 2252 of an implant member 2254, and which allows the guide line to easily advance in one direction but which resists retreat of the guide line in the opposite direction. In each of these examples, a passage through the fastener 2100, 2200, 2250 may serve as the guide line receiver.

Figure 24A:
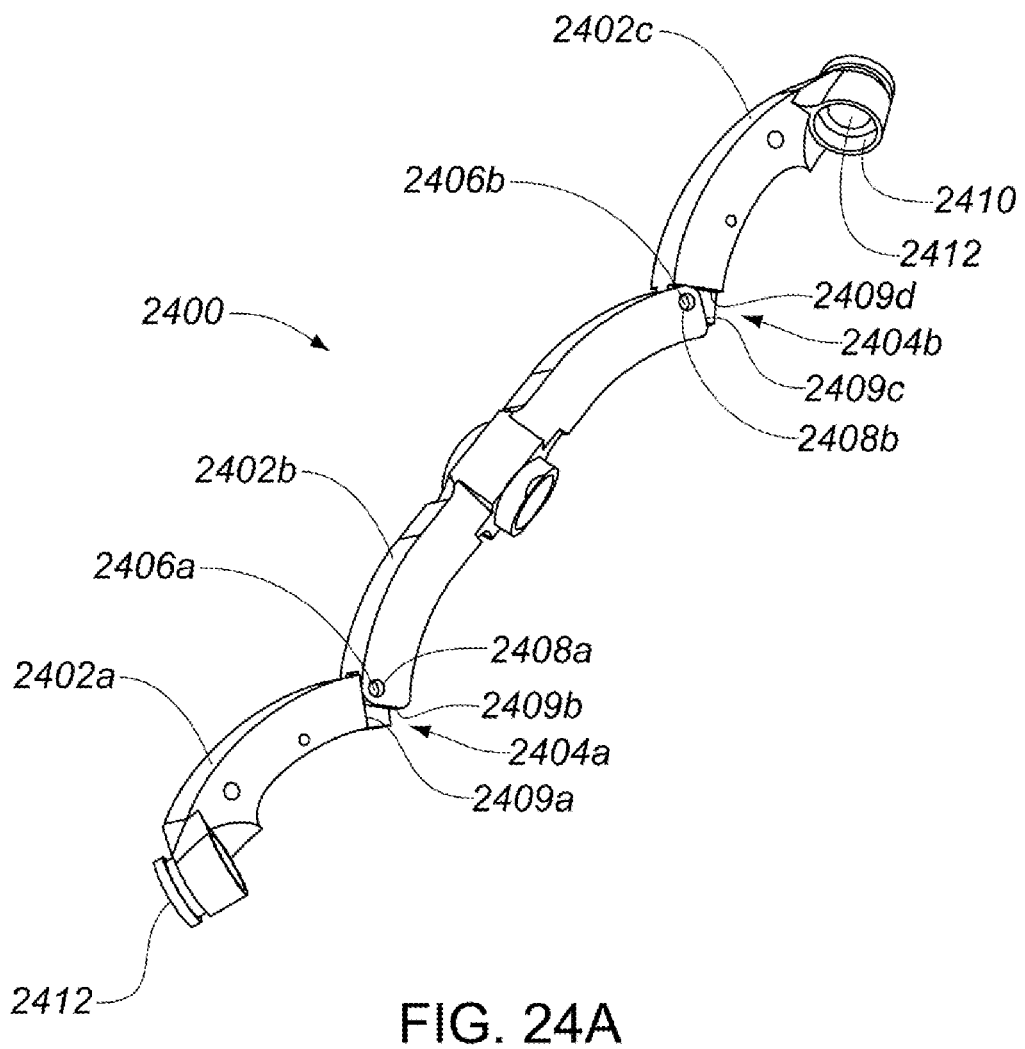
FIG. 24A is an isometric view of an implant member according to another illustrated embodiment, the implant member shown in a delivery configuration.
Figure 24B:
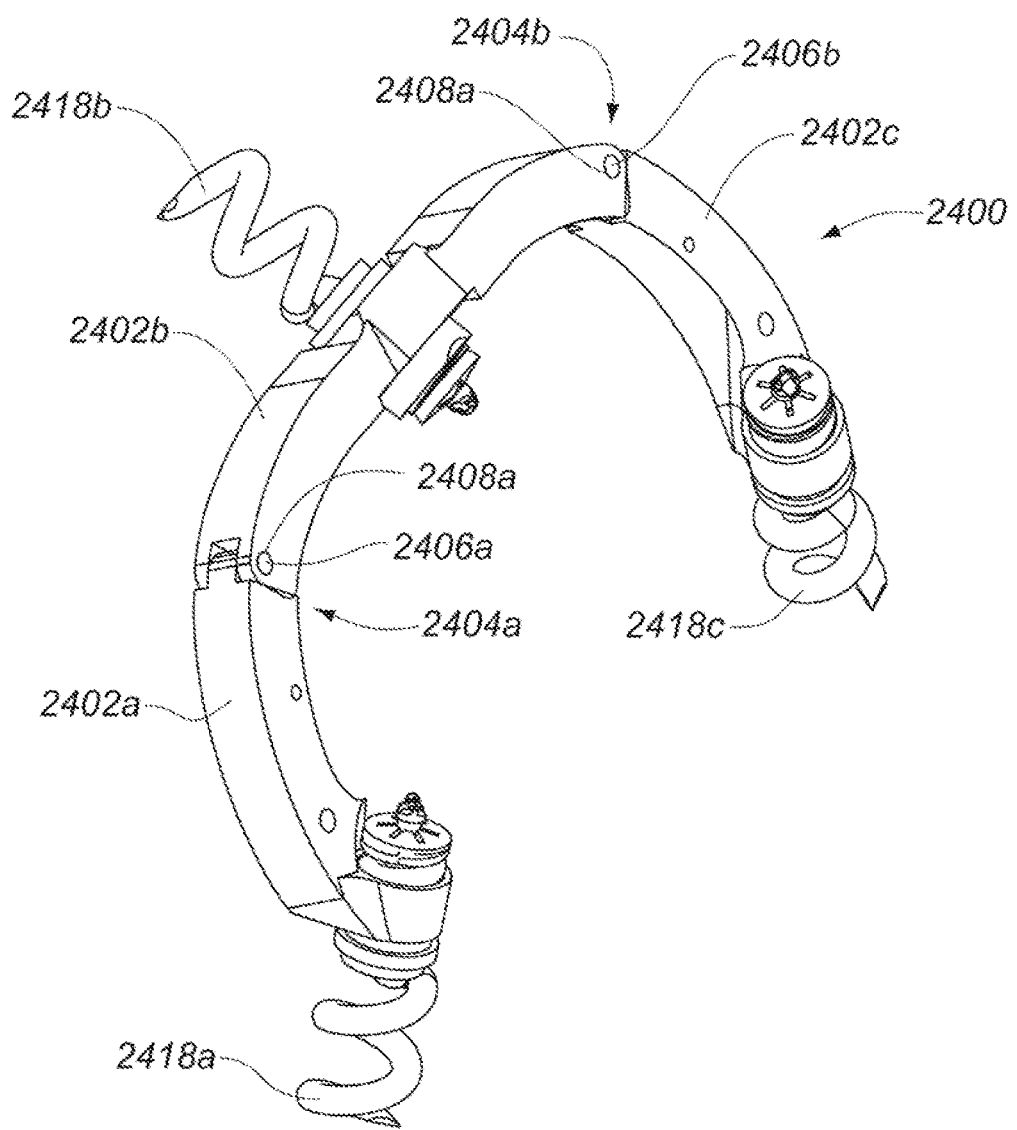
FIG. 24B is an isometric view of the implant member of FIG. 24A shown mated with a plurality of tissue anchors.

FIGS. 24A-24H show an implant member 2400, according to one illustrated embodiment. In particular, FIG. 24A shows the implant member 2400 in a first configuration that is representative of one of a delivery configuration, an unanchored configuration or an untensioned configuration, while FIG. 24B shows the implant member 2400 in a second configuration that is representative of one of an implantable configuration, a deployed configuration, an anchored configuration or a tensioned configuration.

The implant member 2400 is similar to previously described implant member 1900 and may be used to reshape, reconfigure and/or reinforce an orifice in bodily tissue. For example, the implant member 2400 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 2400 has a plurality of arcuate segments 2402*a*-2402*c* (collectively 2402). While three segments 2402 are illustrated, the implant member 2400 may include additional segments. The total number of segments 2402 may be based on the size of the valve with which the implant member 2400 will be used. The total number of segments 2402 may additionally or alternatively be based on a largest lateral dimension that may be accommodated by a given or desired catheter (i.e., diameter of catheter lumen). For instance, in a manner similar to that described for implant member 1900, employing a greater number of segments 2402 means that each segment may have a smaller height, while still achieving a desired lateral dimension or height of the overall implant member 2400 when in the second configuration.

The segments 2402 are physically coupled to one another, and in at least some configurations are articulated for movement with respect to one another, for example pivotal movement. The implant member 2400 includes a number of hinges 2404*a*, 2404*b* (collectively 2404) pivotally coupling neighboring ones of the segments 2402. Each hinge 2404 may include a hinge pin 2406*a*, 2406*b* (collectively 2406) received via throughholes 2408*a*, 2408*b* (collectively 2408) in the segments 2402. Each hinge pin 2406 should be fixedly received in the throughhole 2408 to ensure that the hinge pin 2406 does not become dislodged after implantation. The hinge pin 2406 may be swaged in the throughhole 2408, and may additionally or alternatively be fixed using other mechanisms. The locations of the hinge pins 2406 of the hinges 2404 may be offset from a longitudinal centerline (i.e., the arc that passes longitudinally through the geometric center between the longitudinal arcuate edges) of the respective one of the arcuate segments 2402. Alternatively, the hinge pins 2406 may lie along the longitudinal centerline.

The segments 2402 include stops 2409*a*-2409*d* (collectively 2409) proximate the hinges 2404. The stops 2409 on neighboring ones of the segments 2402 cooperatively interact by engaging one another to prevent the segments 2402 from being pivoted past a defined angle with respect to one another. The stops 2409 thus serve to restrain the segments 2402 from further articulation in one direction. While illustrated as simple complementary engagement surfaces, the stops may take other forms. For example, stops may take the form of a detent or other lock structure. Stops 2409 may lock the segments 2402 from moving along each of two opposing directions when the implant member is in the second configuration. Stops 2409 may also provide torsional stiffness to the hinges 2404. Stops 2409 may also impart a greater bending stiffness to a portion of the implant member 2400 in its second configuration than it has in its first configuration.

As illustrated in FIGS. 24A and 24B, the segments 2402 of the implant member 2400 may be moved with respect to one another into a first configuration, which in this illustrated embodiment is representative of a delivery configuration or unanchored configuration or untensioned configuration. In the first configuration, the implant member 2400 is sized and dimensioned to be deliverable via a catheter. In the first configuration, the implant member 2400 may have an elongated, scalloped, crenulated or serpentine profile, as best illustrated in FIG. 24A. A maximum longitudinal dimension in the first configuration is relatively long as compared to the maximum longitudinal dimension in the second configuration. As illustrated in FIGS. 24A and 24B, the segments 2402 of the implant member 2400 may be moved with respect to one another into the second configuration representative of an implantable or deployed or anchored or tensioned configuration. In the second configuration, the implant member 2400 has an arcuate shape or profile. The arcuate shape is sized and dimensioned to encompass at least part of an orifice. For example, the arcuate shape may be sized and dimensioned to overlie part of an annulus of a mitral valve of a heart. In the second configuration, the dimensions of the implant member 2400 are too large to be accommodated by a typical catheter sheath. In particular, a lateral dimension or height of the implant member 2400 is too large to be received by a lumen of the catheter sheath. Advantageously, the articulated segments 2402 of implant member 2400 allow implant member 2400 to be delivered percutaneously in a first configuration while assuming a structure in a second configuration that is sufficiently rigid to affect a shape of the tissue orifice in a desired manner. In this example embodiment, implant member 2400 is shown coupled with each helical tissue anchors 2418a, 2418b and 2418c (collectively tissue anchors 2418) which have been previously embedded into tissue (not shown).

In a manner similar to other described embodiments, forces or tension may be applied to the implant member 2400 at the guide line receivers 2410 (one called out in FIG. 24A), for instance via embedded helical tissue anchors and/or wires and/or sutures (not shown in FIGS. 24A and 24B). Such may tension the implant member 2400 into the second configuration (FIG. 24B), while the stops 2409 prevent the segments 2402 of implant member 2400 from articulating past the second configuration. Such results in implant member 2400 having a generally rigid structure in the second configuration.

In this illustrated embodiment, implant member 2400 has a plurality of tissue anchor receivers 2412 (two called out in FIG. 24A), each of the tissue anchor receivers 2412 configured to receive or mate with a respective one of the embedded helical tissue anchors 2418 when implant member is positioned in the second configuration. In this example embodiment, each of the guide line receivers 2410 is co-axially aligned with a respective one of the tissue anchor receivers, although other alignments may be employed in other example embodiments. As implant member 2400 travels along the guide lines extending from the embedded helical tissue anchors 2418, segments 2402 articulate about respective hinges 2404 to position the implant member in the second configuration. Tensile forces on the guide lines draw portions of the tissue into which the helical tissue anchors 2418 are embedded towards implant member 2400 as implant member 2400 transitions into the second configuration. Tensile forces on the guide lines move portions of the tissue into which respective ones of the helical tissue anchors 2418 are embedded into locations where each of the embedded helical tissue anchors 2418 is coupled with a respective one of the tissue anchor receivers 2412 when the implant member 2400 is in the second configuration. In this illustrated embodiment, various portions of the tissue are moved to desired locations and are maintained in these locations by the coupling of implant member 2400 to the embedded helical tissue anchors 2418 via tissue anchor receivers 2412. In this illustrated embodiment, the coupled embedded helical tissue anchors 2418 may cause portions of some of the segments 2402 to flex against associated stops 2408. In this illustrated embodiment, the coupled embedded helical tissue anchors 2418 tension implant member 2400 in the second configuration. The tension in the coupled implant member 2400 in the second configuration may be sufficient to reduce a pivoting movement of at least some of the segments 2402 about their associated hinges 2404 during the recipient's subsequent cardiac cycle.

Figure 24C:
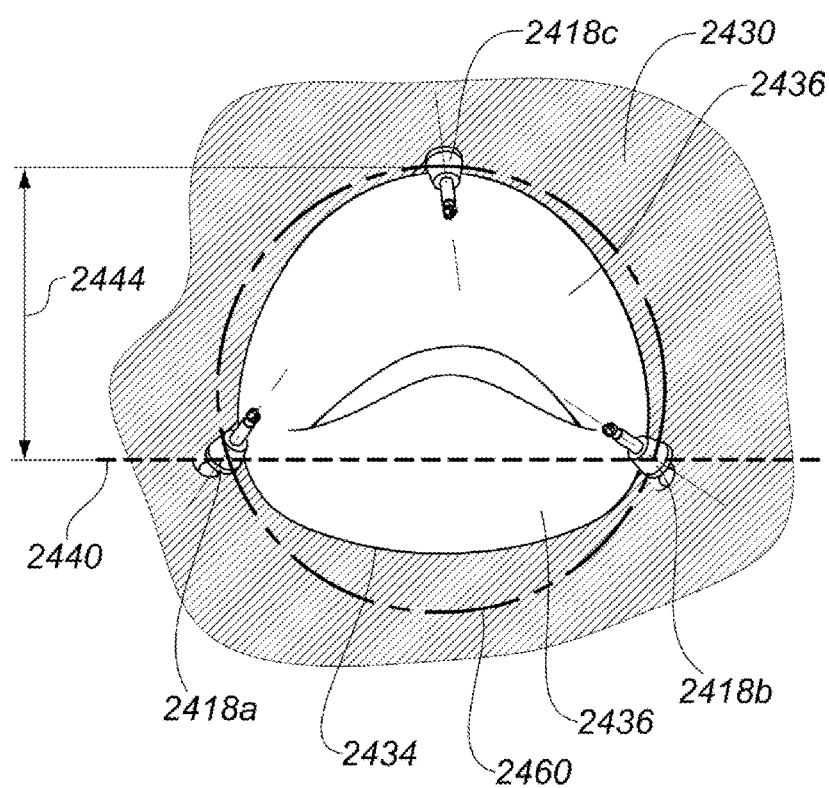
FIG. 24C shows a plurality of tissue anchors embedded in a tissue according to an illustrated embodiment.

The locations of the embedded tissue anchors 2418 and the locations of their respective tissue anchor receivers 2412 can be configured to alter a shape of a tissue valve or orifice in a desired manner. For example, FIG. 24C shows each of a first helical tissue anchor 2418a, a second helical tissue anchor 2418b and a third helical tissue anchor 2418c (collectively helical tissue anchors 2418) embedded into a respective location about a periphery of an orifice in a tissue 2430. In this example embodiment, a location of the embedded third tissue anchor 2418c is laterally offset by a first distance 2444 from a first axis 2440 (i.e., shown in broken lines) that extends between a location of the embedded first helical tissue anchor 2418a and a location of the embedded second helical tissue anchor 2418b. In this example embodiment, helical tissue anchors 2418 are embedded into tissue 2430 prior to a coupling with implant member 2400. In this example embodiment, the helical tissue anchors 2418 are embedded into tissue 2430 that forms part of a heart. Specifically, the helical tissue anchors 2418 are embedded about a mitral annulus 2434 within a left atrium. In this example embodiment, the location of each of the embedded helical tissue anchors 2418 is proximate to mitral annulus 2434. In this example embodiment, the location of each of the embedded helical tissue anchors 2418 is proximate to a longitudinal axis of the helical tissue anchor 2418. It is understood that the locations of the embedded helical tissue anchors 2418 can be specified relative to other datums in other example embodiments. In some example embodiments, each of the helical tissue anchors 2418 is transported sequentially through a catheter to its respective implantation location while in other example embodiments, two or more of the helical tissue anchors 2418 are transported as a group through a catheter to their respective implantation locations. In some example embodiments, each helical tissue anchor 2418 is implanted sequentially while in other example embodiments, two or more of the helical tissue anchors 2418 are implanted at substantially the same time or concurrently.

Figure 24D:
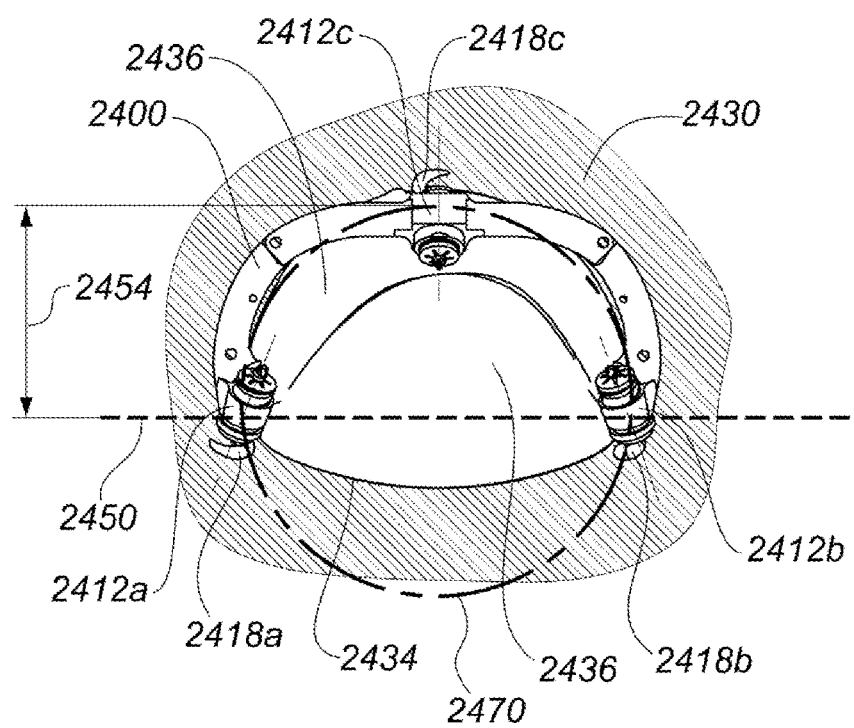
FIG. 24D shows an implant member coupled with the embedded tissue anchors of FIG. 24C.

FIG. 24D shows implant member 2400 coupled with the helical tissue anchors 2412 after they have been embedded into tissue 2430. Implant member 2400 is reconfigurable between the first configuration and the second configuration and is selected to include at least a first tissue anchor receiver 2412a corresponding to the first helical tissue anchor 2418a, a second tissue anchor receiver 2412b corresponding to the second helical tissue anchor 2418b, and a third tissue anchor receiver 2412c corresponding to the third helical tissue anchor 2418c. First tissue anchor receiver 2412a, second tissue anchor receiver 2412b and third tissue anchor receiver 2412c are collectively referred to as tissue anchor receivers 2412. As shown in FIG. 24D, implant member 2400 can be selected such that a location of the third tissue anchor receiver 2412c on the implant member 2400 in the second configuration is laterally offset by a second distance 2454 from a second axis 2450 (i.e., shown in broken lines) that extends between a location of the first tissue anchor receiver 2412a on the implant member 2400 and a location of the second tissue anchor receiver 2412b on the implant member 2400 such that the second distance 2454 is smaller than the first distance 2444. In this example embodiment, the location of each tissue anchor receiver 2412 is proximate to a longitudinal axis of the tissue anchor receiver 2412. It is understood that the locations of the tissue anchor receivers 2412 can be specified relative to other datums in other example embodiments.

As shown in FIG. 24D, a coupling between the tissue anchor receivers 2418 and the embedded helical tissue anchors 2418 will affect a shape of the mitral annulus 2434 which can be used to reposition mitral valve leaflets 2436 relative to one another in a desired way. A coupling between the tissue anchor receivers 2412 and the embedded helical tissue anchors 2418 will cause a portion of the tissue 2430 into which the third helical tissue anchor 2418c is embedded to move relative to another portion of the tissue 2430 in a desired way. Other portions of the tissue 2430 can be moved in a similar fashion based at least on the selection of an appropriately sized and dimensioned implant member 2400.

The relationship between the locations of the embedded helical tissue anchors 2418 and the locations of the tissue anchor receivers 2412 employed to alter a shape of mitral annulus 2434 can be illustrated in other ways. FIG. 24C shows that a circle 2460 (i.e., shown in broken line) can be dimensioned and sized to pass through the locations of the embedded helical tissue anchors 2418. In this example embodiment, a circumference of circle 2460 is greater than a circumference or perimeter of mitral annulus 2434. FIG. 24D shows that a circle 2470 (i.e., shown in broken line) can be dimensioned and sized to pass through the locations of the tissue anchor receivers 2412 when implant member 2440 is coupled with the embedded tissue anchors 2418. In this example embodiment, circle 2460 has a circumference that is greater than a circumference of circle 2470.

Figure 24E:
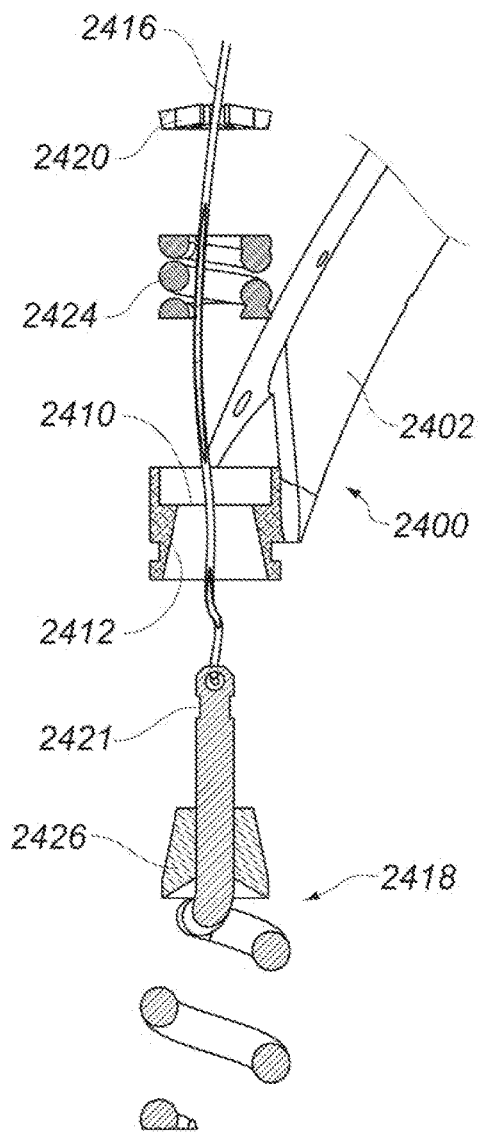
FIG. 24E is a sectional exploded view of a portion of the implant member of FIGS. 24A and 24B prior to a mating with an embedded tissue anchor.
Figure 24F:
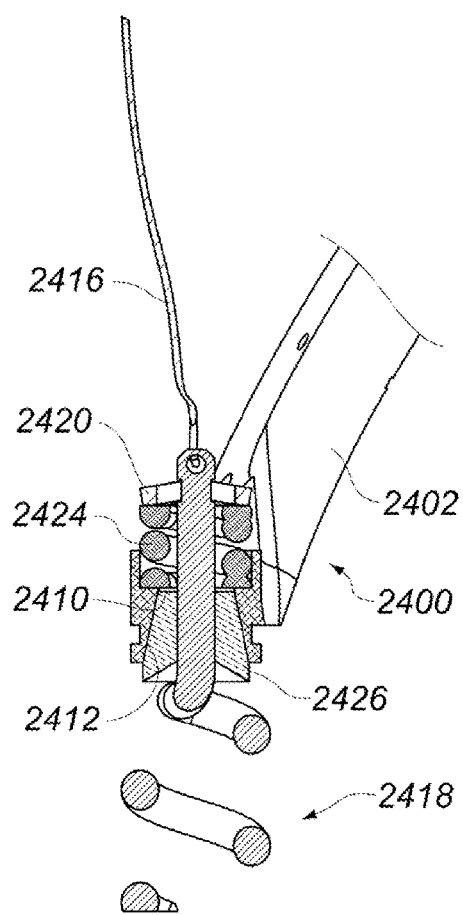
FIG. 24F is a sectional view of a portion of the implant member of FIGS. 24A and 24B mated with an embedded tissue anchor.
Figure 24G:
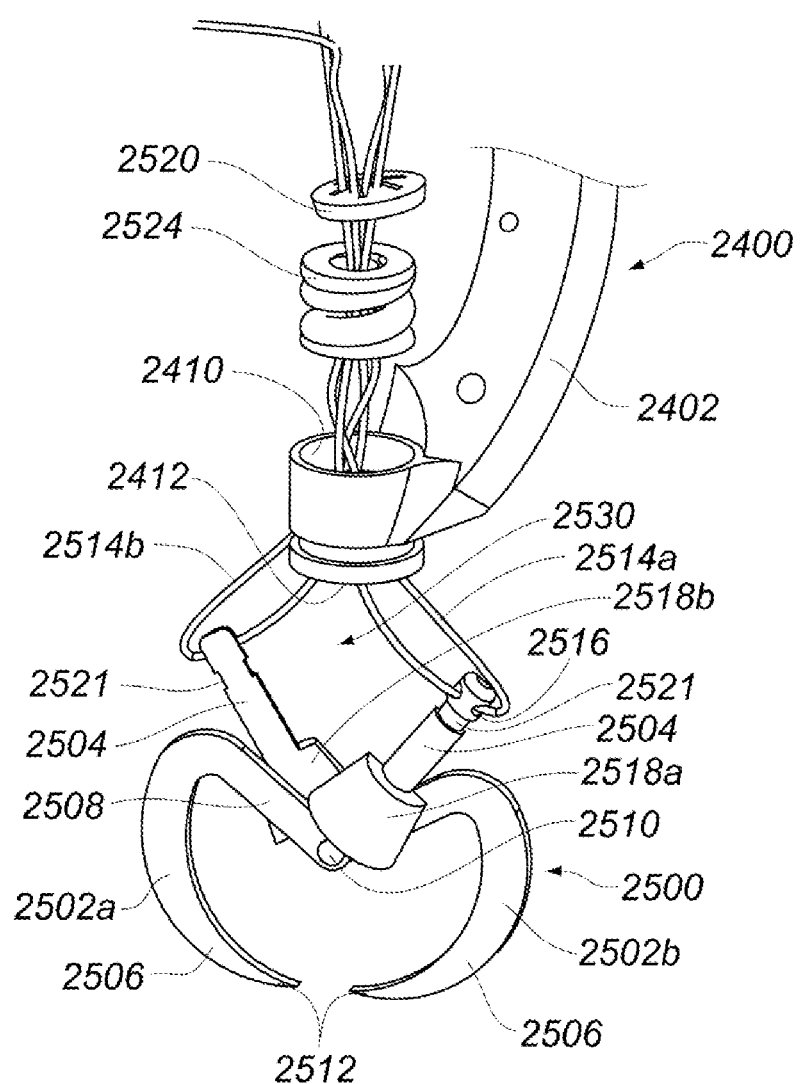
FIG. 24G is an exploded isometric view of a portion of the implant member of FIG. 24A and a grapple tissue anchor.
Figure 24H:
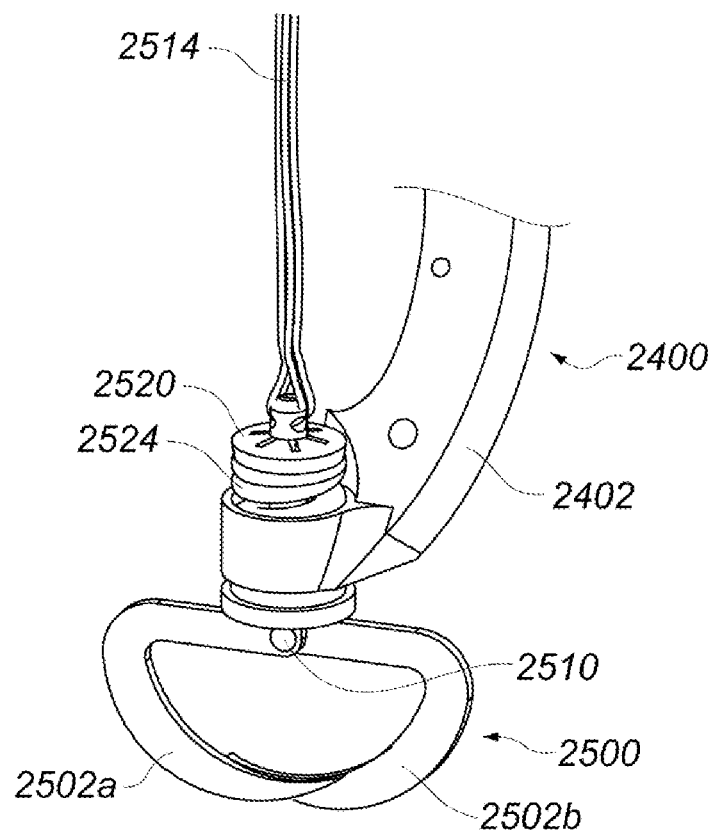
FIG. 24H is an isometric view of a portion of the implant member of FIG. 24A mated with a grapple tissue anchor.

FIGS. 24E and 24F respectively show a portion of a segment 2402 of implant member 2400 before and after a coupling with an embedded helical tissue anchor 2418. Tissue into which helical tissue anchor 2418 is embedded is not shown for clarity. In this illustrated embodiment, a guide line 2416 extends from embedded helical tissue anchor 2418 through the tissue anchor receiver 2412 and guide line receiver 2410 of segment 2402. Helical tissue anchor 2418 includes seat 2426 that is configured to mate or engage with tissue anchor receiver 2412. In this illustrated embodiment, seat 2426 and tissue anchor receiver 2412 include mating tapered surfaces. Seat 2426 and helical tissue anchor may be provided as a unitary structure. Alternatively, seat 2426 may be secured to helical tissue anchor 2418 by variety of methods including adhesives, crimping, and heat fitting, by way of non-limiting example. In this illustrated embodiment, fastener 2420 is provided via guide line 2416 to secure segment 2402 to embedded helical tissue anchor 2418. Unlike other fasteners employed in other described embodiments that secure an implant member to the tissue by coupling with a guide line (e.g., fasteners 2100, 2200), fastener 2420 couples directly with the embedded helical tissue anchor 2418 itself as shown in FIG. 24F. In this illustrated embodiment, fastener 2420 includes snap-ring features configured to engage with groove 2421 in embedded helical tissue anchor 2418, although other well known securement mechanisms can be employed in other example embodiments. Spring 2424 is also provided via guide line 2416 such that it is captured between fastener 2420 and segment 2402. Spring 2424 can provide various functions which can include by way of non-limiting example preloading segment 2402 against the embedded helical tissue anchor 2418 to reduce occurrences of the generation of potentially harmful wear particulates, or compensating for component manufacturing or assembly tolerances. Once implant member 2400 is secured to the embedded helical tissue anchor 2418, guide line 2416 can be decoupled from the embedded helical tissue anchor 2418. Decoupling can include cutting guide line 2416 or drawing guide line 2416 from an opening in embedded helical tissue anchor 2418 into which guide line 2416 is looped. It is noted that this aspect is not limited to helical tissue anchors such as helical tissue anchors 2418 and that other forms of tissue anchors may be employed. For example, FIGS. 24G and 24H respectively show a portion of a segment 2402 of implant member 2400 before and after a coupling with a grapple tissue anchor 2500 as per another example embodiment. Specifically, FIG. 24G shows an exploded isometric view of grapple tissue anchor 2500, the portion of segment 2402 and various other components while FIG. 24H shows an assembled isometric view into which grapple tissue anchor 2500 is secured to the portion of segment 2402 of implant member 2400. In this example embodiment, grapple tissue anchor 2500 is secured to implant member 2400 after grapple tissue anchor 2500 has been implanted or embedded into tissue. Tissue into which grapple tissue anchor 2500 is embedded is not shown for clarity.

Grapple tissue anchor 2500 includes at least two elongate members 2502a and 2502b (collectively elongated members 2502). Each of the elongated members 2502 includes a first end 2504, a second end 2506 and intermediate portion 2508 (only one called out in FIG. 24G) positioned along the elongate member 2502 between its first end 2504 and its second end 2506. Each of the second ends 2506 includes a tip 2512 shaped to penetrate the tissue. Each of the intermediate portions 2508 of the elongate members 2502 is pivotably coupled together by a pivot 2510. In this example embodiment, each of the elongated members 2502 includes an arcuate shaped portion. Specifically, in this example embodiment, each of the elongated members 2502 includes a portion between pivot member 2510 and the second end 2506 of the elongate member that extends along an arcuate path. In this example embodiment, each of the elongated members 2502 forms a prong.

Pivot member 2510 allows the elongated members 2502 to pivot with respect to one another to position the tips 2512 spaced relatively apart from one another at locations advantageous for penetrating the tissue. Upon further deployment of grapple tissue anchor 2500 into the tissue, the elongated members 2502 are pivoted relative to each other to cause tips 2502 to travel along a path through the tissue such that tips 2512 are positioned closer to one another than during their initial deployment into the tissue. This allows grapple tissue anchor 2500 to firmly anchor into the tissue. FIG. 24G shows the elongate members 2502 pivoted to a point where the opposed tips 2512 are spaced such that grapple tissue anchor 2500 is not fully deployed into the tissue (again, not shown). FIG. 24H shows the elongate members 2502 pivoted to position the opposed tips 2512 such that grapple tissue anchor 2500 is fully deployed into tissue (again not shown). Those skilled in the art will appreciate that other deployment configurations can be employed by other grapple tissue anchors employed by various embodiments. For example, each of the elongated members 2502 can be configured to follow a different path through tissue during the deployment of the grapple tissue anchor 2500 into tissue.

In some example embodiments, tips 2512 may, or may not overlap when grapple tissue anchor 2500 is fully deployed into tissue.

In this example embodiment, grapple tissue anchor 2500 is part of a tissue anchor system that includes at least one coupler 2530 that is physically coupled to at least one of the elongated member 2502, the at least one coupler 2530 being additionally configured to be received by implant member 2400 when the grapple tissue anchor 2500 is secured to implant member 2400. In this illustrated embodiment, a guide line 2514 extends from each elongated member 2502. As best shown in FIG. 24G, a guide line 2514a extends from elongate member 2502a and a guide line 2514b extends from elongate member 2502b. In this example embodiment, each guide line 2514 is sized to be received through an opening 2516 (only one called out in FIG. 24G). In this example embodiment, each of the guide lines 2514a and 2514b is looped through an associated one of the openings 2516 (e.g., eyelet). This allows each of the guide lines 2514 to be releasably coupled with an associated one of the elongated members 2502, the coupling being released by simply releasing an end of the guide line 2514 to allow it to be extracted through an associated one of the openings 2516.

In this example embodiment, guide lines 2514 are also each sized to be received through tissue anchor receiver 2412 and guide line receiver 2410 provided in segment 2402. In this example embodiment, guide lines 2514 are received through each of tissue anchor receiver 2412 and guide line receiver 2410 after grapple tissue anchor 2500 is embedded into tissue. In this particular embodiment, the at least one coupler 2530 includes a two component seat 2518 that is configured to mate or engage with tissue anchor receiver 2412 in a similar manner to seat 2426 employed by the embodiment illustrated in FIGS. 24E and 24F. Seat 2518 includes a first seat component 2518a coupled to elongated member 2502a and a second seat component 2518b coupled to elongate member 2502b. Each component of seat 2518 and an associated one of the elongated members 2502 can be provided in a unitary structure. Alternatively, each component of seat 2518 may be secured to an associated one of the elongated members 2502 by variety of methods including adhesives, crimping, and heat fitting, by way of non-limiting example. When grapple tissue anchor 2500 is deployed into tissue, seat 2518 is configured to mate or engage with tissue anchor receiver 2412 in this illustrated embodiment. In this illustrated embodiment, the seat components 2518a and 2518b include tapered surfaces configured to mate with a tapered surface provided by tissue anchor receiver 2412 in a manner similar to that employed by the embodiment illustrated in FIGS. 24E and 24F.

In this illustrated embodiment, fastener 2520 is provided via guide lines 2514 to secure segment 2402 to embedded grapple tissue anchor 2500. Unlike other fasteners employed in other described embodiments that secure an implant member to the tissue by coupling with a guide line (e.g., fasteners 2100, 2200), fastener 2520 couples directly with the embedded grapple tissue anchor 2500 itself as shown in FIG. 24H. In this illustrated embodiment, fastener 2520 includes snap-ring features configured to engage with a portion of groove 2521 provided in each of the elongated members 2502, when grapple tissue anchor 2500 is embedded into tissue. Spring 2524 is also provided via guide lines 2514 such that it is captured between fastener 2520 and segment 2402. Spring 2524 can provide various functions which can include by way of non-limiting example preloading segment 2402 against the embedded grapple tissue anchor 2500 to reduce occurrences of the generation of potentially harmful wear particulates, or compensating for component manufacturing or assembly tolerances. Once implant member 2400 is secured to the embedded grapple tissue anchor 2500, guide lines 2514 can be decoupled from the embedded grapple tissue anchor 2500.

The present embodiments are not limited to securing grapple tissue anchor 2500 to articulated implant members such as implant member 2400. Other example embodiments may employ other members or mechanisms to secure tissue anchors such as grapple tissue anchor 2500 to an implant member employed in an implant procedure. Without limitation, various couplers 2530 can be employed to couple a tissue anchor such as grapple tissue anchor 2500 to an implant member. By way of non limiting example, coupler 2530 can include a clamp configured to clamp a portion of the implant member. Coupler 2530 can include an extension sized to be received within an opening provided in an implant member. Coupler 2530 can include an expansion member configured to expand and grip one or more surfaces of an implant member. Coupler 2530 can include a contraction member configured to contract and grip one or more surfaces of an implant member. Coupler 2530 can include detent or a snap-action component.

Figure 25A:
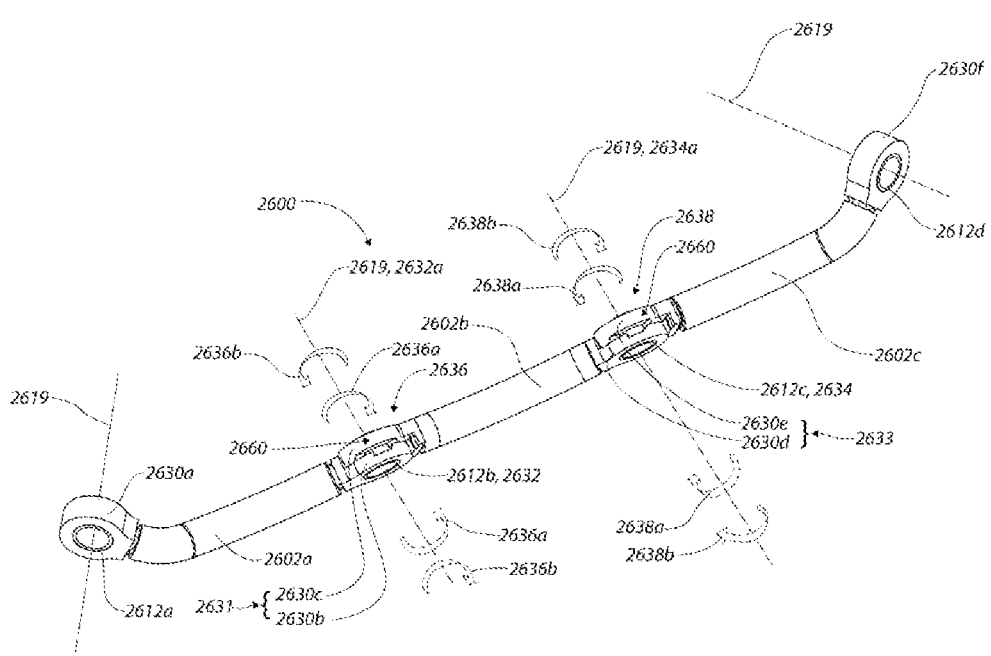
FIG. 25A is an isometric view of an implant member in a delivery configuration according to one illustrated embodiment.
Figure 25B:
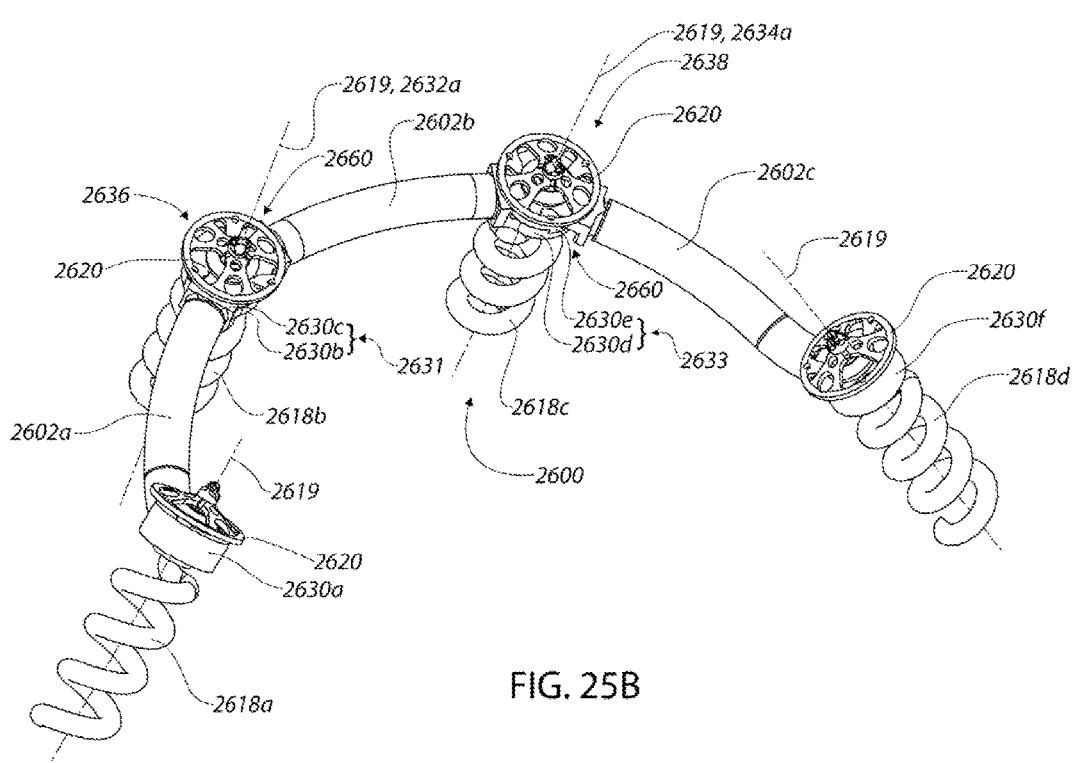
FIG. 25B is an isometric view of the implant member of FIG. 25A, the implant member shown in a deployed configuration physically coupled to a number of tissue anchors.

FIGS. 25A-25F show an implant member 2600, according to one example embodiment. In particular, FIG. 25A shows implant member 2600 in a first configuration that is representative of one of a delivery configuration, an unanchored configuration or an untensioned configuration, while FIG. 25B shows implant member 2600 in a second configuration that is representative of one of an implantable configuration, a deployed configuration, an anchored configuration or a tensioned configuration.

The implant member 2600 is similar to previously described implant member 2400 and may be used to reshape, reconfigure and/or reinforce an orifice in bodily tissue. For example, the implant member 2600 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 2600 has a plurality of segments 2602a-2602c (collectively 2602). While three segments 2602 are illustrated, the implant member 2600 may include a different number of segments. The total number of segments 2602 may be based on the size of the valve with which the implant member 2600 will be used. The total number of segments 2602 may additionally or alternatively be based on a largest lateral dimension that may be accommodated by a given or desired catheter (i.e., diameter of catheter lumen) or catheter sheath. For instance, in manner similar to that described for implant member 2400, employing a greater number of segments 2602 means that each segment may have a smaller height (e.g., height 1922), while still achieving a desired lateral dimension or height of the overall implant member 2600 when in the second configuration.

In this embodiment, segment 2602b includes an arcuate portion lying substantially in a single plane (not shown) as best seen in FIG. 25B. In this embodiment, each of segment 2602a and 2602c includes a plurality of arcuate portions. Each of the arcuate portions may lie substantially in a different one of a plurality of intersecting planes (not shown). Each of the segments 2602 can be formed by various techniques and from various materials. For example, suitable techniques can include controlled bending techniques which are employed to bend segment 2602b about a single bending axis and which are employed to bend each of segments 2602a and 2602c about each of a plurality of non-parallel bending axes. The use of non-parallel bending axes may provide numerous advantages including allowing implant member 2600 to better conform to a non-planar tissue surface when implanted. In this example embodiment, each of the segments 2602 is physically coupled to another of the segments 2602.

As illustrated in FIG. 25A, the segments 2602 of the implant member 2600 may be moved with respect to one another into the first configuration. In the first configuration, the implant member 2600 is sized and dimensioned to be deliverable via a catheter. In the first configuration, the implant member 2600 may have an elongated, scalloped, crenulated or serpentine profile. A maximum longitudinal dimension in the first configuration is relatively long as compared to the maximum longitudinal dimension in the second configuration. As illustrated in FIG. 25B, the segments 2602 of the implant member 2600 may be moved with respect to one another into the second configuration. In the second configuration, the implant member 2600 can have a substantially arcuate shape or profile. In this example embodiment, the arcuate shape is sized and dimensioned to encompass at least part of an orifice. For example, the arcuate shape may be sized and dimensioned to overlie part of an annulus of a mitral valve of a heart. In the second configuration, the dimensions of the implant member 2600 are too large to be accommodated by a typical catheter sheath. In particular, a lateral dimension or height of the implant member 2600 is too large to be received by a lumen of the catheter sheath. Advantageously, the segments 2602 of implant member 2600 allow implant member 2600 to be delivered percutaneously in a first configuration while assuming a structure in a second configuration that is sufficiently rigid to affect a shape of the tissue orifice in a desired manner.

As shown in FIG. 25B, each of a plurality of tissue anchors 2618a, 2618b, 2618c and 2618d (collectively tissue anchors 2618) are secured to implant member 2600. In some embodiments, various ones of the tissue anchors 2618 are secured to implant member 2600 when implant member 2600 is moved into the second configuration. In some embodiments, various ones of the tissue anchors 2618 are secured to implant member 2600 after implant member is delivered percutaneously to a bodily cavity. In this example embodiment, various ones of the tissue anchors 2618 are secured to implant member 2600 after the various ones of the tissue anchors 2618 have been at least partially embedded into tissue. For clarity of illustration, tissue is not shown in FIG. 25B. In this example embodiment each tissue anchor 2618 is a helical tissue anchor. It is noted that this embodiment is not limited to helical tissue anchors and that other types of tissue anchors may be employed. Other example embodiments may include barbed tissue anchors (e.g., multi-barbed tissue anchor 808) or grapple tissue anchors (e.g., grapple tissue anchor 2500) by way of non-limiting example.

Figure 25C:
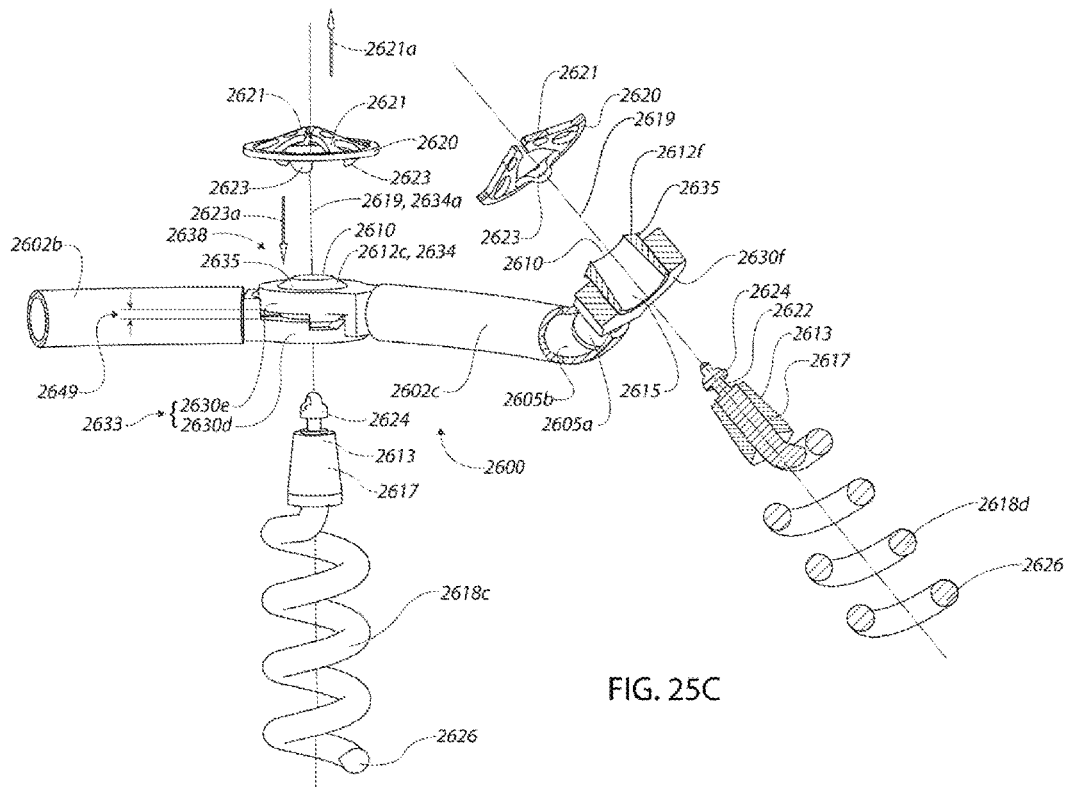
FIG. 25C is a partially sectioned view of the implant member of FIGS. 25A-25B, the implant member shown positioned between the delivery configuration and the deployed configuration, positioned to be physically coupled to the tissue anchors.
Figure 25D:
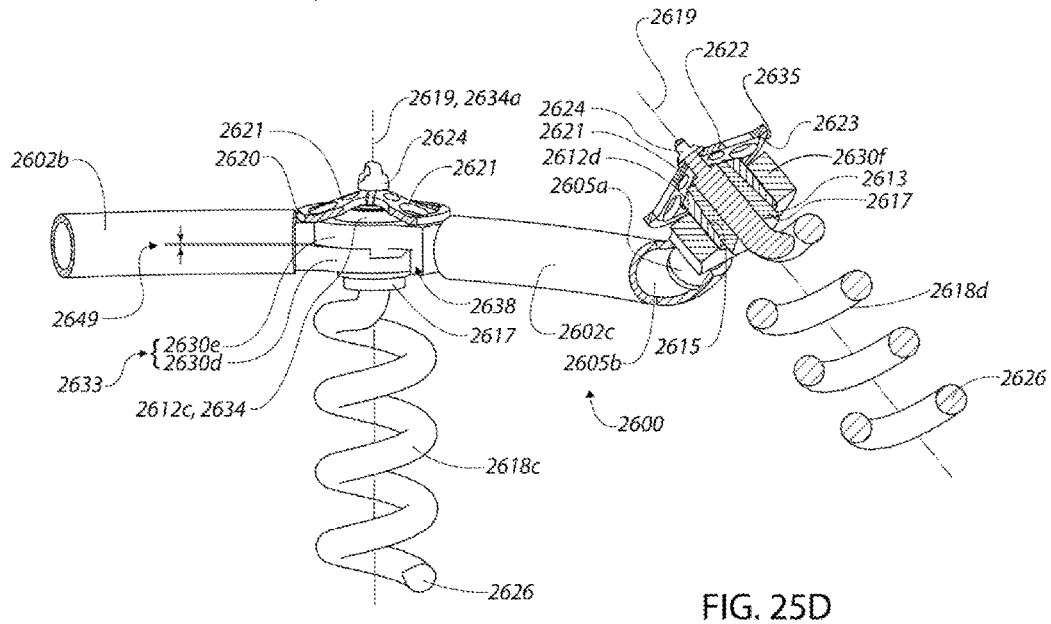
FIG. 25D is a partially sectioned view of the implant member of FIGS. 25A-25B, the implant member shown in the deployed configuration, physically coupled to the tissue anchors.

In this illustrated embodiment, implant member 2600 has a plurality of tissue anchor receivers 2612a, 2612b, 2612c and 2612d (collectively 2612) (best seen in FIG. 25A), each of the tissue anchor receivers 2612 configured to receive or mate with a respective one of the tissue anchors 2618 when the tissue anchors 2618 are secured to implant member 2600. FIG. 25C shows a partially sectioned exploded view of a portion of implant member 2600 positioned between the first configuration and the second configuration and prior to a securing of tissue anchors 2618c and 2618d to implant member 2600. FIG. 25D shows a partially sectioned view of implant member 2600 in the second configuration. FIG. 25D shows a partially sectioned view of implant member 2600 in which tissue anchors 2618c, 2618d are received by respective ones of tissue anchor receivers 2612c and 2612d and are secured to implant member 2600. In this embodiment, tissue anchors 2618a and 2618b (not shown in FIGS. 25C and 25D) have similar structures to that of tissue anchors 2618c and 2618d and are received by respective ones of tissue anchor receivers 2612a and 2612b (not shown in FIGS. 25C and 25D) which have similar structures to that of tissue anchor receivers 2612c and 2612d. Tissue anchors 2618 and/or tissue anchor receivers 2612 having different structures may be employed in other example embodiments.

Each tissue anchor 2618 includes a portion 2617 (two called out in each of FIGS. 25C and 25D) that is configured to mate or engage with a respective one of tissue anchor receivers 2612. Portion 2617 and the other portions of the tissue anchor 2618 may be provided as a unitary structure. Alternatively, portion 2617 may be a separate component. A separate portion 2617 may be secured to other portions of a tissue anchor 2618 by variety of methods including adhesives, crimping, and heat fitting, by way of non-limiting example.

In this embodiment, each of the tissue anchor receivers 2612 includes at least one alignment surface 2615 (one called out in each of FIGS. 25C and 25D) arranged to guide portion 2617 of an associated one of the tissue anchors 2618 to a position where the associated one of the tissue anchors 2618 is securable to implant member 2600. In this embodiment, each of the tissue anchor receivers 2612 includes at least one alignment surface 2615 arranged to guide portion 2617 of an associated one of the tissue anchors 2618 to a position where the portion 2617 is seated within the tissue anchor receiver 2612. In some example embodiments, each of the at least one alignment surfaces 2615 includes a curved surface portion. In some example embodiments, each of the at least one alignment surfaces 2615 includes a tapered, frustoconical or conical surface portion. In this illustrated embodiment, each portion 2617 and tissue anchor receiver 2612 includes tapered mating surfaces. In this example embodiment, each of the at least one alignment surfaces 2615 includes a tapered surface portion that is circumferentially arranged about a respective alignment axis 2619 (two called out in each of FIGS. 25C and 25D). In this example embodiment, as the respective portion 2617 of each tissue anchor 2618 is brought into engagement with the at least one alignment surface 2615 of an associated one of the tissue anchor receivers 2612, the at least one alignment surface 2615 engages a surface 2613 (two called out in FIG. 25C, one called out in FIG. 25D) of the portion 2617 and guides or orients portion 2617 with respect to the alignment axis 2619 so as to appropriately position portion 2617 for securement to the implant member 2600 by coupler 2620 (two called out in each of FIGS. 25C and 25D). In some example embodiments, other positional arrangements may be employed between the at least one alignment surface 2615 and a respective alignment axis 2619. In some example embodiments, the at least one alignment surface 2615 includes a plurality of surfaces arranged about a respective alignment axis 2619.

In this example embodiment, each of the at least one alignment surfaces 2615 is arranged to impede or restrain movement of the respective portion 2617 of an associated one of the tissue anchors 2618 along at least one direction that is perpendicular to the alignment axis 2619 associated with the at least one alignment surface 2615 when the associated one of the tissue anchors 2618 is secured to implant member 2600. In this example embodiment, each of the at least one alignment surfaces 2615 is arranged to impede or restrain movement of the respective portion 2617 of an associated one of the tissue anchors 2618 along at least one direction that is radially oriented to the alignment axis 2619 associated with the at least one alignment surface 2615 when the associated one of the tissue anchors 2618 is secured to implant member 2600. In this example embodiment, each of the at least one alignment surfaces 2615 is arranged to impede or restrain movement of the respective portion 2617 of an associated one of the tissue anchors 2618 along at least one direction that intersects the alignment axis 2619 associated with the at least one alignment surface 2615 when the associated one of the tissue anchors 2618 is secured to implant member 2600. Restraining movement along various directions perpendicular to, radial to, or intersecting an alignment axis 2619 corresponding to a coupled tissue anchor 2618 and tissue anchor receiver 2612 may provide numerous advantages including, by way of example, reducing potential movement between the coupled tissue anchor 2618 and tissue anchor receiver 2612 during the recipient's subsequent cardiac cycle which may lead to the formation of potentially harmful wear induced debris. In this example embodiment, each of the at least one alignment surfaces 2615 is arranged to impede or restrain movement of the respective portion 2617 of an associated one of the tissue anchors 2618 along a direction that is parallel to a direction that the alignment axis 2619 associated with the at least one alignment surface 2615 extends along when the associated one of the tissue anchors 2618 has been fully seated in a respective tissue anchor receiver 2612.

In this example embodiment, each alignment axis 2619 is oriented along a direction of relative movement required to break contact between the at least one alignment surface 2615 of a tissue anchor receiver 2612 and surface 2613 of portion 2617 of a tissue anchor 2618 that has been fully received in the tissue anchor receiver 2612. In this example embodiment, each alignment axis 2619 is oriented along a direction of relative movement required to unseat the portion 2617 of a tissue anchor 2618 that has been fully seated in a respective tissue anchor receiver 2612. In this example embodiment, once a tissue anchor 2618 is secured to the implant member 2600 with a respective one of couplers 2620, movement of the tissue anchor 2618 along at least one direction of a respective one of the alignment axes 2619 is impeded. In this example embodiment, once a tissue anchor 2618 is secured to a tissue anchor receiver 2612 of implant member 2600, the tissue anchor 2618 is impeded from moving along the alignment axis 2619 of the tissue anchor receiver 2612 to break contact with the at least one alignment surface 2615 of the tissue anchor receiver 2612.

In some embodiments, a biasing device (e.g., springs 2424, 2524) may be employed during the securing of a tissue anchor 2618 to implant member 2600. A biasing device may provide various functions which can include by way of non-limiting example preloading various segments 2602 against the tissue anchor 2618 to reduce occurrences of the generation of potentially harmful wear particulates, or compensating for component manufacturing or assembly tolerances. In this example embodiment, combined biasing and tissue anchor securement capabilities are provided by each of couplers 2620. In a manner similar to previously described fasteners 2420, 2520 each coupler 2620 includes various resilient first fingers 2621 (three called out in each of FIGS. 25C and 25D) arranged to snap into a channel 2622 (one called out in each of FIGS. 25C and 25D) provided in each tissue anchor 2618 to secure the tissue anchor 2618 to the implant member 2600. In this example embodiment, each coupler 2620 includes various resilient second fingers 2623 (three called out in FIG. 25C and one called out in FIG. 25D) arranged to provide a biasing force arranged to preload the respective portion 2617 of a tissue anchor 2618 against the at least one alignment surface 2615 of an associated one of the tissue anchor receivers 2612 when the tissue anchor 2618 is secured to the implant member 2600. In this example embodiment, each coupler 2620 biases respective portions of two coupled segments 2602 together when the tissue anchor 2618 is secured to the implant member 2600. As compared in FIGS. 25C and 25D, each coupler 2620 biases respective portions of two coupled segments 2602 together to reduce an axial separation 2649 therebetween in this example embodiment.

In this example embodiment, when a tissue anchor 2618 is secured to implant member 2600 by a coupler 2620, each of resilient the first and second fingers 2621 and 2623 extends along respective directions having opposing directional components 2621a, 2623a (one of each called out in FIG. 25C) that are each parallel with an extension direction of an associated one of the alignment axes 2619. Each channel 2622 is located on its respective tissue anchor 2618 to cause resilient second fingers 2623 to flex and provide a required biasing force when respective resilient first fingers 2621 are snapped into the channel 2622 to secure the tissue anchor 2618 to the implant member 2600. In this example embodiment, each coupler 2620 is arranged to engage a first portion 2624 (two called out in each of FIGS. 25C and 25D) of an associated tissue anchor 2618 to capture a portion of implant member 2600 between the coupler 2620 and a second portion 2626 (two called out in each of FIGS. 25C and 25D) of the tissue anchor 2618 when the tissue anchor 2618 is secured to the implant member. In this example embodiment, the respective second portion 2626 of each tissue anchor 2618 is embeddable into tissue. In this example embodiment, coupler 2620 is provided separately from implant member 2600. In some example embodiments, a portion of coupler 2620 and implant member 2600 are provided in a unitary structure. For example, a portion of coupler 2620 and a portion of a segment 2602 or housing 2630 may be provided in a unitary structure.

Other suitable couplers may be employed to secure a tissue anchor 2618 to implant member 2600 in other embodiments. By way of non-limiting example, a coupler 2620 can include a clamp configured to clamp a portion of implant member 2600 or tissue anchor 2618. Coupler 2620 can include an extension sized to be received within an opening provided in implant member 2600 or tissue anchor 2618. Coupler 2620 can include an expansion member configured to expand and grip one or more surfaces of implant member 2600 or tissue anchor 2618. Coupler 2620 can include a contraction member configured to contract and grip one or more surfaces of implant member 2600 or tissue anchor 2618. Coupler 2620 can include a threaded fastener (e.g., a nut) or a pin-like fastener.

In this example embodiment, one of a plurality of the guide line receivers 2610 (two called out in FIG. 25C) is provided in each of the tissue anchor receivers 2612. Each of the guide line receivers 2610 is sized and dimensioned to allow for the passage of a guide line (not shown in FIG. 25C) therethrough. In a manner similar to that described in previous embodiments, implant member 2600 may travel via guideline receivers 2610 along guide lines extending from tissue anchors 2618 that are embedded into tissue.

Segments 2602 may articulate with respect to one another to position the implant member 2600 in the second configuration during this movement.

In this example embodiment, coupler 2620 is also provided via a guide line (not shown) to secure tissue anchor 2618 to implant member 2600. Unlike other fasteners employed in other described embodiments that secure an implant member to the tissue by coupling with a guide line (e.g., fasteners 2100, 2200), each coupler 2620 couples directly with a tissue anchor 2618 itself as shown in FIGS. 25B and 25D. Once implant member 2600 is secured to the tissue anchor 2618, the guide line can be decoupled from the tissue anchor 2618. Decoupling can include cutting the guide line or drawing the guide line from an opening in tissue anchor 2618 through which guide line passes. In this example embodiment, each of the guide line receivers 2610 is co-axially aligned with the alignment axis 2619 of a respective one of the tissue anchor receivers 2612, although other alignments may be employed in other example embodiments. In some embodiments, one or more of the guide line receivers 2610 may be located in components other than the tissue anchor receivers 2612.

In this example embodiment, each tissue anchor receiver 2612 is provided as a separate component from the segments 2602. In some embodiments, one or more of the tissue anchor receivers 2612 is integrally provided with a segment 2602. In this example embodiment, each tissue anchor receiver 2612 is assembled into at least one of a plurality of housings 2630a, 2630b, 2630c, 2630d, 2630e and 2630f (collectively 2630) that is physically coupled to a respective one of the segments 2602 as shown in FIGS. 25A and 25B. An example coupling between segment 2602c and housing 2630f is shown in each of FIGS. 25C and 25D. In this embodiment, housing 2630f includes a male coupling element 2605a received in a female coupling element 2605b provided in a segment 2602c. In some embodiments, male coupling element 2605a may be provided by segment 2602c and female coupling element 2605b may be provided in housing 2630f. Male coupling element 2605a may be fixedly coupled to female coupling element 2605b by various techniques including, by way of non-limiting example, welding, crimping, and bonding. Various fixtures or keying elements may be employed to establish a desired orientation between a housing 2630 and a segment 2602. Other physical couplings between various other ones of the segments 2602 and housings 2630 can be established using similar or other techniques. In some example embodiments, a housing 2630 is integrally provided in a segment 2602. In some example embodiments, a tissue anchor receiver 2612 is integrally provided in a housing 2630.

In this example embodiment, each of tissue anchor receivers 2612a and 2612d is assembled into a single housing 2630 (i.e., a respective one of housings 2630a and 2630f). Each of the tissue anchor receivers 2612a and 2612d can be fixedly attached into a respective one of housings 2630a and 2630f by a variety of techniques including by way of non-limiting example, welding, crimping, and bonding. In this example embodiment, each of tissue anchor receivers 2612b and 2612c is assembled into a set of at least two of the housings (i.e., a respective one of a first set 2631 of housings 2630b and 2630c and a second set 2633 of housings 2630d and 2630e in this illustrated embodiment).

In this embodiment, various sets of the segments 2602 are provided with the segments 2602 in a given set physically coupled to one another in a manner that provides articulated movement with respect to one another, for example pivotal movement. In this embodiment, implant member 2600 includes a number of pivot joints 2636 and 2638. Pivot joint 2636 is provided to pivotally couple a first set of segments 2602 made up of segments 2602a and 2602b. In this example embodiment, each of the segments 2602a and 2602b is pivotable about a pivot axis 2632a (shown in FIG. 25A) associated with a pivot joint 2636 along a respective first rotational direction 2636a towards the other of the segments 2602a and 2602b and along a respective second rotational direction 2636b away from the other of the segments 2602a and 2602b as implant member 2600 is moved between the first configuration and the second configuration. Pivot joint 2638 is provided to pivotally couple a second set of segments 2602 made up of segments 2602b and 2602c. In this example embodiment, each of the segments 2602b and 2602c is pivotable about a pivot axis 2634a (shown in FIG. 25A) associated with a pivot joint 2638 along a respective first rotational direction 2638a towards the other of the segments 2602b and 2602c and along a respective second rotational direction 2638b away from the other of the segments 2602b and 2602c as implant member 2600 is moved between the first configuration and the second configuration. In this embodiment each of the sets of segments 2602 include a same or common segment (i.e., 2602b). Each of first rotational directions 2636a and 2638a is opposite to a respective one of second rotational directions 2636b and 2638b. Each of the first and second rotational directions 2636a and 2636b represented by continuous line arrows in FIG. 25A correspond to rotational movements of segment 2602a relative to segment 2602b. Each of the first and second rotational directions 2636a and 2636b represented by broken line arrows in FIG. 25A correspond to rotational movements of segment 2602b relative to segment 2602a. Each of the first and second rotational directions 2638a and 2638b represented by continuous line arrows in FIG. 25A correspond to rotational movements of segment 2602c relative to segment 2602b. Each of the first and second rotational directions 2638a and 2638b represented by broken line arrows in FIG. 25A correspond to rotational movements of segment 2602b relative to segment 2602c.

In this embodiment, each of the pivot joints 2636, 2638 includes a respective one of pivot members 2632 and 2634. In this example embodiment, each of pivot members 2632 and 2634 is a pivot pin sized to be received in an opening in various ones of the housings 2630. Each one of pivot members 2632 and 2634 includes a journal surface about which various ones of segments 2602 are guided to rotate or pivot about. In this example embodiment, each of the tissue anchor receivers 2612b and 2612c and a respective one of pivot members 2632 and 2634 forms a unitary structure. In other example embodiments, separate pivot members and tissue anchor receivers are employed. In this example embodiment, the respective alignment surface 2615 of each of the tissue anchor receivers 2612b and 2612c is positioned radially inboard from a journal surface of a respective one of pivot members 2632 and 2634.

Each of the pivot members 2632 and 2634 is preferably configured to axially capture the housings 2630 in a respective one of first set 2631 of housings 2630 (i.e., housings 2630b and 2630c) and second set 2633 of housings 2630 (i.e., housings 2630d and 2630e) to reduce occurrences where the pivot member 2632, 2634 or any of the housings 2630 in the respective set becomes dislodged after implantation. For example, each of the pivot members 2632 and 2634 may be fixedly coupled to one of the housings 2630 in a respective one of the first and second sets 2631, 2633 of housings by a number of various techniques including, but not limited to, welding, bonding, and swaging. Each of the pivot members 2632 and 2634 may include an obstruction or protruding element such as a flange to capture the other one of the housings 2630 in a respective one of the first and second sets 2631, 2633 of housings 2630. Alternatively, each of the pivot members 2632 and 2634 may employ a plurality of spaced-apart protruding elements arranged to capture each of the housings 2630 in a respective one of the first and the second sets 2631, 2633 of housings 2630 while allowing each of the housings 2630 to rotate with respect to the pivot member. In this example embodiment, each of pivot members 2632 and 2634 is welded to one of the housings 2630 in a respective one of the first and the second sets 2631, 2633 of housings 2630. Each of the pivot members 2632 and 2634 includes a flange 2635 (two called out in FIG. 25C) to capture the other housing 2630 in the respective one of the first and the second sets 2631, 2633 of housings 2630.

In various example embodiments, at least a first pivot joint employed by implant member 2600 is arranged such that a pivot axis associated with the first pivot joint intersects a surface of one of the tissue anchors 2618 when the tissue anchor is secured to implant member 2600. For example, as shown in FIG. 25D, the pivot axis 2634a associated with pivot joint 2638 intersects a surface of tissue anchor 2618c when tissue anchor 2618c is fully received in tissue anchor receiver 2612c. As shown in FIG. 25D, the pivot axis 2634a associated with pivot joint 2638 intersects a surface of tissue anchor 2618c when tissue anchor 2618c is secured to implant member 2600. In this example embodiment, the pivot axis 2632a associated with pivot joint 2636 (not shown in FIG. 25D) also intersects a surface of tissue anchor 2618b when tissue anchor 2618b is fully received in tissue anchor receiver 2612b or is secured to implant member 2600. In this example embodiment, pivot axis 2632a is parallel to pivot axis 2634a. In other example embodiments, pivot joints 2636 and 2638 may be arranged such that pivot axis 2632a is not parallel to pivot axis 2634a.

As shown in FIG. 25D, the pivot axis 2634a associated with pivot joint 2638 is substantially parallel to the alignment axis 2619 associated with tissue anchor receiver 2612c in this illustrated embodiment. In this example embodiment, pivot axis 2634a and the alignment axis 2619 associated with tissue anchor receiver 2612c are collinear axes.

In this example embodiment, the tissue anchor receivers 2612 and the pivot joints 2636, 2638 are arranged on implant member 2600 such that each of the pivot axes 2632a and 2634a are parallel to at least some, but not all of the alignment axes 2619 associated with the tissue anchor receivers 2612. For example, as shown in FIG. 25D, the pivot axis 2634a associated with pivot joint 2638 is substantially parallel to the alignment axis 2619 associated with tissue anchor receiver 2612c and is not parallel with the alignment axis 2619 associated with tissue anchor receiver 2612d. In this example embodiment, pivot joint 2638 forms part of an articulable or bendable portion of implant member 2600, the bendable portion arranged to pivotally couple at least one substantially rigid portion of implant member 2600 (i.e., a portion including segment 2602b) with at least another substantially rigid portion of implant member 2600 (i.e., a portion including segment 2602c and housing 2630f). In this example embodiment, at least a first one of the tissue anchor receivers 2612 (i.e., tissue anchor receiver 2612d) is located in one of the rigid portions while at least a second one of the tissue anchor receivers 2612 (i.e., tissue anchor receiver 2612c) is located in the bendable portion. Other forms of bendable portions may be employed in other example embodiments.

In some example embodiments, at least a first pivot joint employed by implant member 2600 is arranged such that a pivot axis associated with the first pivot joint intersects a minimum cylindrical volume that contains one of the tissue anchors 2618 when the tissue anchor is positioned at a location where the tissue anchor is secured to implant member 2600. FIG. 25F shows an exploded view of a portion of implant member 2600 in the second configuration. Specifically, FIG. 25F shows an exploded view of a positioning of pivot joint 2636 when tissue anchor 2618b is received by tissue anchor receiver 2612b and is secured to implant member 2600. An exploded view is used in FIG. 25F for clarity and it is understood that all the illustrated components are in secured engagement. In this example embodiment, the pivot axis 2632a associated with pivot joint 2636 intersects a minimum cylindrical volume 2670 (i.e., shown in broken lines) that contains tissue anchor 2618b when tissue anchor 2618b is positioned in secured engagement with implant member 2600. In this example embodiment, the minimum cylindrical volume 2670 is the smallest cylindrical volume that contains tissue anchor 2618b. In this example embodiment, minimum cylindrical volume 2670 is tangentially arranged with various extremities or peripheries of tissue anchor 2618b. In this example embodiment, each tissue anchor of at least one of the tissue anchors 2618 (e.g., tissue anchors 2618a and 2618d) is positioned such that a minimum cylindrical volume 2670 that contains the tissue anchor of the at least one of the tissue anchors 2618 is not intersected by each of the pivot axes 2632a and 2634a when the tissue anchors 2618 are secured to implant member 2600.

Figure 25E:
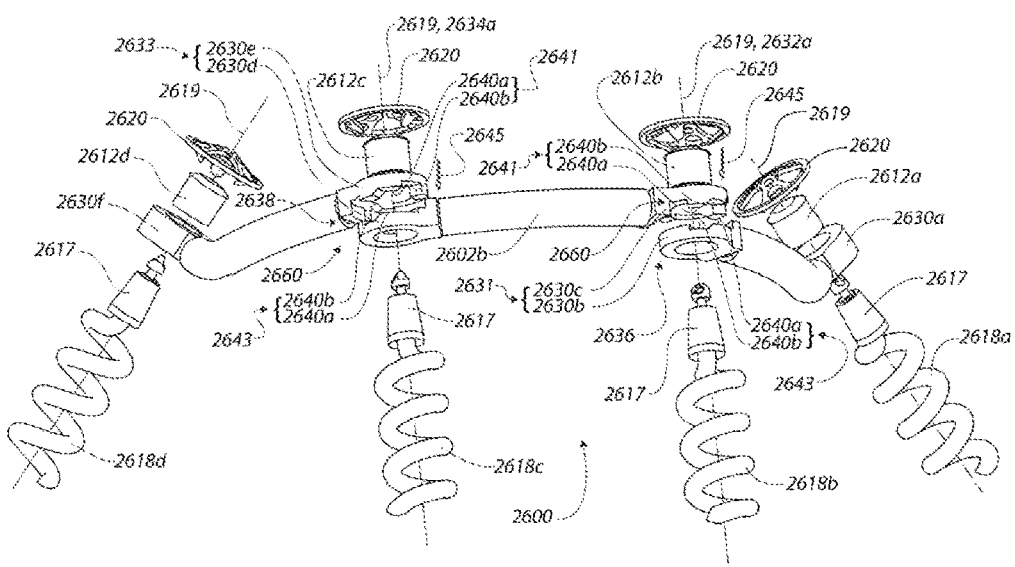
FIG. 25E is an exploded isometric view of the implant member of FIGS. 25A-25B, the implant member shown in the deployed configuration along with the tissue anchors.
Figure 25F:
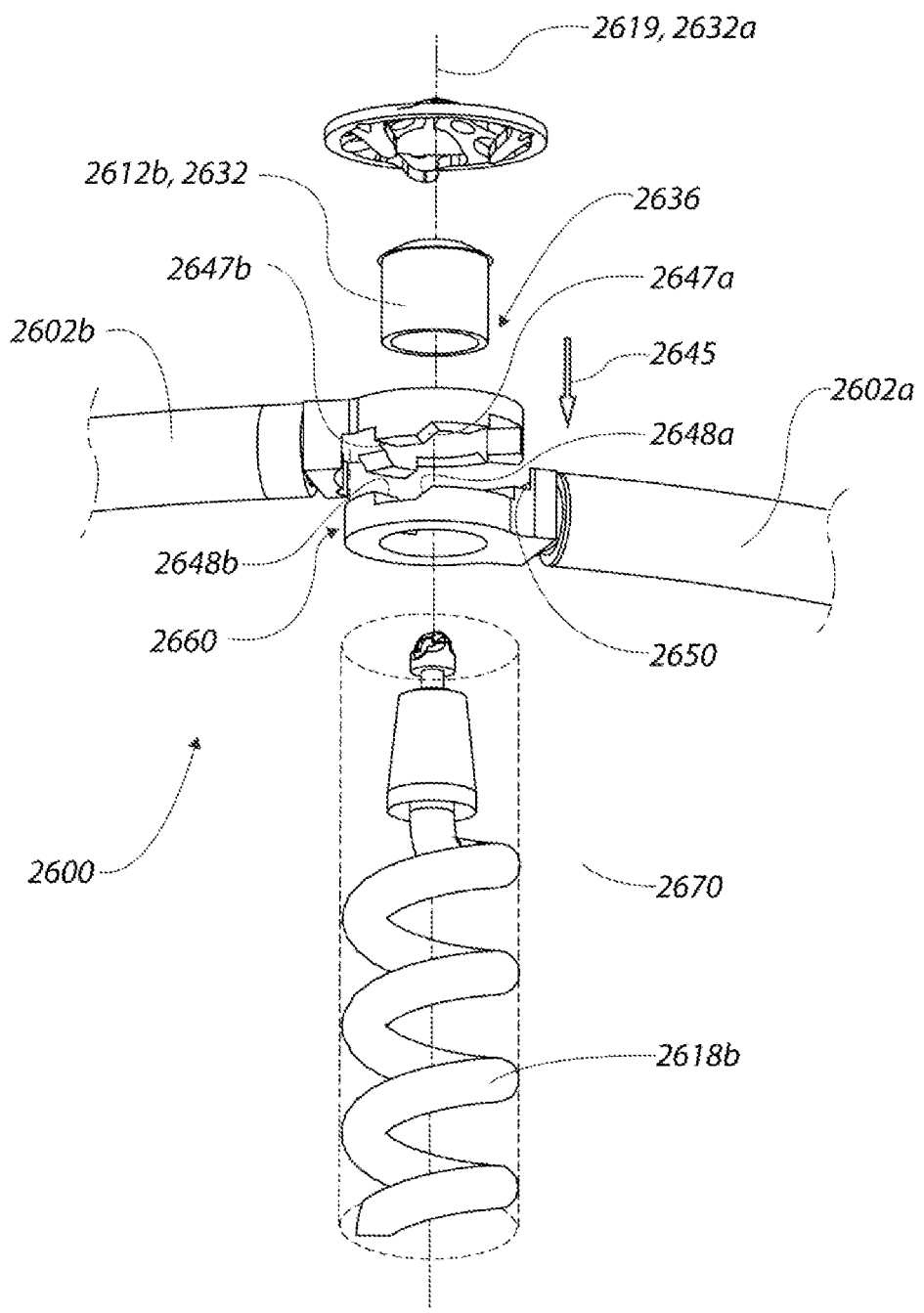
FIG. 25F is an exploded view of a portion of the implant member of FIGS. 25A-25B, the implant member shown in the deployed configuration along with the tissue anchors.

FIG. 25E shows an exploded isometric view of implant member 2600, tissue anchors 2618 and couplers 2620 in the second configuration (i.e., as viewed in a direction substantially opposite to that shown in FIG. 25B). As shown in FIG. 25E, each of the respective two housings 2630 in each of the first and the second sets 2631, 2633 of housings 2630 includes a respective set of interlockable elements. In this example embodiment, each of the interlockable elements takes the form of a projection 2640a or a recess 2640b (collectively referred to as interlockable elements 2640). Each of the projections 2640a provided in a first set 2641 of the interlockable elements 2640 associated with one of the housings 2630 in a respective one of the first and the second sets 2631, 2633 of housings 2630 is sized and dimensioned to be complementarily received by a respective one of the recesses 2640b provided in a second set 2643 of the interlockable elements 2640 associated with the other housing 2630 in the respective one of the first and the second sets 2631, 2633 of housings 2630. In this example embodiment, each first set 2641 of interlockable elements 2640 and each second set 2643 of interlockable elements 2640 includes plurality of projections 2640a and plurality of recesses 2640b. Specifically, in this example embodiment, each first set 2641 of interlockable elements 2640 and each second set 2643 of interlockable elements 2640 includes three (3) projections 2640a and three (3) recesses 2640b. Other embodiments may employ other numbers of projections 2640a and recesses 2640b.

In this example embodiment, each associated pair of the first and the second sets 2641, 2643 of interlockable elements 2640 forms part of respective holder 2660 that is activatable between a free configuration in which each segment 2602 in a set of pivotally coupled segments 2602 is arranged to rotate, turn or pivot (used interchangeably herein) towards and away from another segment 2602 in the set of the pivotally coupled segments 2602, and a fixed configuration in which the segment 2602 in the set of the pivotally coupled segments 2602 is impeded from rotating, turning or pivoting towards and away from another segment 2602 in the set of the pivotally coupled segments with a greater resistance than when the holder 2660 is in the free configuration.

In this example embodiment, each first set 2641 of interlockable elements 2640 and each second set 2643 of interlockable elements 2640 is integrally provided in a unitary structure with a respective one of the two housings 2630 in a respective one of the first and the second sets 2631, 2633 of housings 2630. In this example embodiment, the interlockable elements 2640 in each associated pair of the first and the second sets 2641, 2643 of interlockable elements 2640 are radially oriented about a respective one of pivot axes 2632a and 2634a. In this example embodiment, the interlockable elements 2640 in each associated pair of the first and the second sets 2641, 2643 of interlockable elements 2640 are circumferentially arranged about a respective one of pivot members 2632 and 2634. In this example embodiment, the interlockable elements 2640 in each associated pair of the first and the second sets 2641, 2643 of interlockable elements 2640 are radially oriented about a respective alignment axis 2619 of a respective one of tissue anchor receivers 2612b and 2612c. In some example embodiments, various ones of the projections 2640a and the recesses 2640b include various surfaces that extend radially towards a respective one of pivot axis 2632a and pivot axis 2634a. An exploded detailed view of the first and second sets 2641, 2643 associated with pivot joint 2636 is shown in FIG. 25F.

As shown in FIGS. 25A and 25C, when the implant member 2600 is not in the second configuration, each holder 2660 is in the free configuration and the various interlockable elements 2640 are not interlocked thereby allowing the opposing sets of projections 2640a to ride adjacently to one another as the implant member 2600 is moved between the first configuration and the second configuration. In this example embodiment, each of pivot members 2632 and 2634 is appropriately sized and dimensioned to allow for sufficient axial separation between the housings 2630 in a respective one of the first and the second sets 2631, 2633 of housings 2630 to allow end portions of opposing projections 2640a to ride adjacently to one another as the implant member 2600 is moved between the first configuration and the second configuration.

In this example embodiment, various ones of the segments 2602 may be rotated about respective ones of pivot axes 2632a and 2634a to a position where projections 2640a in each of the first sets 2641 of interlockable elements 2640 are rotationally aligned or approximately rotationally aligned with respective ones of the recesses 2640b in an associated one of the second sets 2643 of interlockable elements 2640. Further movement of the segments 2602 brings projections 2640a in each of the first sets 2641 of interlockable elements 2640 closer to respective ones of the recesses 2640b in an associated one of the second sets 2643 of interlockable elements 2640 to establish interlocked engagement therebetween and activate the holders 2660 into the fixed configuration. In this example embodiment, this movement is along a direction having a first directional component 2645 parallel to a direction that a respective one of pivot axes 2632a and 2634a extends along. As compared with FIG. 25D, an axial separation 2649 between the housings 2630d and 2630e of the second set 2633 shown in FIG. 25C decreases when the interlocked engagement is established between the interlockable elements 2640 associated with housings 2630d and 2630e. In this example embodiment, a interlocked engagement between an associated pair of the first and the second sets 2641, 2643 of interlockable elements 2640 is established when at least one segment 2602 in a set of pivotally coupled segments 2602 is moved along an associated one of pivot members 2632 and 2634 to reduce an axial distance between the pivotally coupled segments 2602.

In this example embodiment, the interlocked engagement between an associated pair of the first and the second sets 2641, 2643 of interlockable elements 2640 occurs at a single rotational positioning between the respective segments 2602 that rotationally manipulate the associated pair of the first and the second sets 2641, 2643 of interlockable elements 2640. In this example embodiment, the interlocked engagement between each associated pair of the first and the second sets 2641, 2643 of interlockable elements 2640 occurs when the segments 2602 are manipulated to position implant member 2600 in the second configuration. In this example embodiment, when the associated pair of the first and the second sets 2641, 2643 of interlockable elements 2640 of a holder 2660 is positioned in interlocked engagement, the holder 2660 is in the fixed configuration and impedes a segment 2602 in a set of pivotally coupled segments 2602 from pivoting towards and away from another segment 2602 in the set of the pivotally coupled segments with a greater resistance than when the holder 2660 is in the free configuration.

As best shown in FIG. 25F, each of the projections 2640a and recesses 2640b associated with pivot joint 2636 includes a truncated triangular shape as each is viewed along a respective direction extending radially towards pivot axis 2632a in this example embodiment. In some example embodiments, each of the projections 2640a and recesses 2640b has a trapezoidal shape as each is viewed along a respective direction extending radially towards an associated pivot axis. Each of the projections 2640a and recesses 2640b can include other shapes including, for example, arcuate and rectangular shapes in other example embodiments.

In various example embodiments, at least some of the projections 2640a in at least one set of an associated pair of the first and the second sets 2641, 2643 of interlockable elements 2640 are shaped for wedged engagement with at least some of the recesses 2640b in the other set of the associated pair of the first and the second sets 2641, 2643 of interlockable elements 2640. Wedged engagement can occur for example, when at least one projection 2640a in one set of an associated pair of the first and the second sets 2641, 2643 of interlockable elements 2640 is shaped to be wedged within a respective one of the recesses 2640b in the other set of the associated pair of the first and the second sets 2641, 2643 of interlockable elements 2640 when the various interlockable elements 2640 are positioned for interlocking engagement. In this example embodiment, each projection 2640a includes a respective pair of opposing and non-parallel surfaces 2647a and 2647b (collectively surfaces 2647) (only one of each called out in FIG. 25F) that are positioned to be wedged between two opposing surfaces 2648a and 2648b (collectively surfaces 2648) (only one of each called out in FIG. 25F) of a respective recess 2640b when the projection 2640a and the respective recess 2640b are moved relatively closer with respect to one another along a direction having a first directional component 2645 parallel to a direction extended along by pivot axis 2632a. In this example embodiment, the first surface 2647a is oriented with respect to the first directional component 2645 by a greater angular amount than the second surface 2647b. In this example embodiment, the second surface 2647b is oriented substantially parallel with respect to the first directional component 2645.

In this example embodiment, each recess 2640b includes a matching set of non-parallel surfaces 2648a and 2648b sized to provide the desired wedging action. Surfaces employing different orientations or shapes may be employed by recesses 2640b and/or projections 2640a in other example embodiments. In some example embodiments, the interlockable elements 2640 in associated first and second sets 2641, 2643 of interlockable elements 2640 are arranged such that a respective single surface of each of two more of the projections 2640a is brought into wedged engagement with a respective single surface of each of two or more of the recesses 2640b. In these example embodiments, the wedged engagement occurs between the combination of the two more of the projections 2640a and the combination of the two or more recesses 2640b unlike a wedged engagement created by the wedging of a single projection 2640a into a single recess 2640b. It is understood that other embodiments may employ holders 2660 that include mechanisms other than interlockable elements 2640 to impede a segment 2602 in a set of pivotally coupled segments 2602 from pivoting towards and away from another segment 2602 in the set of the pivotally coupled segments with a greater resistance when the holder is in the fixed configuration than when the holder 2660 is in the free configuration. For example, holders 2660 including selectively activatable friction members may be used in some embodiments.

In this example embodiment, when the interlockable elements 2640 are not positioned in interlocked engagement, various ones of the surfaces 2647a can be moved to engage a respective one of a plurality of surfaces 2650 (only one called out in FIG. 25F) to act as a stop that restrains various ones of the segments 2602 from being pivoted past a defined angle with respect to one another. In this example embodiment, the stops serve to restrain the segments 2602 from further articulation in one direction. In this example embodiment, when the implant member 2600 is in the first configuration (i.e., as shown in FIG. 25A) the stops constrain the segments 2604 to pivot along a single direction (i.e., along a respective one of first rotational directions 2636a, 2638a) suitable for moving the implant member 2600 into the second configuration (i.e., as shown in FIG. 25B). In this example embodiment, the stops restrain segments 2602 from pivoting back on themselves (i.e., along a respective one of second rotational directions 2636b, 2638b) when the implant member 2600 is in the first configuration. The employment of the stops can provide various advantages including for example, restraining segments 2602 from pivoting back on themselves to facilitate the percutaneous manipulation of the implant member 2600 from the first configuration to the second configuration within a bodily cavity.

In this example embodiment, various portions of the tissue (not shown in FIGS. 25A-25F) are moved to desired locations and are maintained in these locations by a physical coupling of implant member 2600 to the embedded tissue anchors 2618 via tissue anchor receivers 2612. In a manner similar to other described embodiments, implant member 2600 may be delivered via a number of guide lines (not shown) coupled to respective ones of tissue anchors 2618 that have been at least partially embedded into tissue about an orifice within a body. Forces or tension may be applied to the implant member 2600 through guide line receivers 2610, for instance via embedded tissue anchors 2618 and/or guide lines (not shown). As implant member 2600 travels along the guide lines extending from the embedded tissue anchors 2618, segments 2602 pivot about respective ones of pivot joints 2636, 2638 to position the implant member 2600 in the second configuration. The locations of the embedded tissue anchors 2618 can be determined in various manners including methods similar to those employed in relation to FIGS. 24C and 24D.

Tensile forces on the guide lines draw portions of the tissue into which the tissue anchors 2618 are embedded towards implant member 2600 as implant member 2600 transitions into the second configuration. Tensile forces on the guide lines move portions of the tissue into which respective ones of the tissue anchors 2618 are embedded into locations where each of the embedded tissue anchors 2618 is received by a respective one of the tissue anchor receivers 2612.

In this example embodiment, the holders 2660 are moved into the fixed configuration to allow the implant member 2600 in the second configuration to form a structure sufficiently rigid to affect a shape of an orifice in the tissue. In this example embodiment, the tissue coupled to implant member 2600 via the embedded tissue anchors 2618 tensions implant member 2600 in the second configuration.

In various example embodiments, when the implant member 2600 is positioned in the second configuration, the holders 2660 can be secured in the fixed configuration. In this example embodiment, once the implant member 2600 is positioned in the second configuration, the interlockable elements 2640 in each associated pair of the first and the second sets 2641, 2643 of interlockable elements 2640 are secured in interlocked engagement when a tissue anchor 2618 is received by a tissue anchor receiver 2612 surrounded by the associated pair of the first and the second sets 2641, 2643 of interlockable elements 2640 and the tissue anchor 2618 is secured to the implant member 2600 with a coupler 2620. In this example embodiment, coupler 2620 is arranged to provide a biasing force to maintain the interlockable elements 2640 in the associated pair of the first and the second sets 2641, 2643 of interlockable elements 2640 in interlocked engagement. In this example embodiment, each segment 2602 in each set of pivotally coupled segments 2602 is impeded from pivoting along a respective one of a first rotational directions 2636a, 2638a towards another segment 2602 in the set of pivotally coupled segments 2602 when the associated pair of the first and the second sets 2641, 2643 of interlockable elements 2640 are secured in interlocked engagement. In this example embodiment, each segment 2602 in each set of pivotally coupled segments 2602 is impeded from pivoting along a respective one of second rotational directions 2636b, 2638b away from another segment 2602 in the set of pivotally coupled segments 2602 when the associated pair of the first and the second sets 2641, 2643 of interlockable elements 2640 are secured in wedged engagement. A pivot joint can include some amount of radial and axial play which can lead to movement along various directions which may generate dangerous wear debris that enters the recipient's circulatory system and potentially increases the occurrence of strokes. In this example embodiment, the interlockable elements 2640 and coupler 2620 combine to reduce movements associated with each of the pivot joints 2636 and 2638.

This illustrated embodiment may provide enhancements over other described embodiments in which an implant member (e.g., implant members 2400, 2500) is secured to previously embedded tissue anchors under tension with various stops (e.g., stops 2409) serving to restrain the segments of the implant member from further articulation in one rotational direction. In particular, the use of holders 2660 allows implant member 2600 to be maintained in its second configuration if minor tissue forces that act to reduce tension on the implant member 2600 arise during or after the remodeling of the orifice.

It is noted that in this example embodiment an associated pair of the first and the second sets 2641, 2643 of interlockable elements 2640 of at least one of the holders 2660 may become interlocked when the implant member 2600 is in the midst of being positioned between the first configuration and the second configuration. That is, the associated pair of the first and the second sets 2641, 2643 of interlockable elements 2640 can become inadvertently interlocked within the bodily cavity prior to a positioning of the implant member 2600 at a desired location on a tissue surface having an orifice that is to be remodeled. Additionally or alternatively, situations may arise where implant member 2600 is positioned in the second configuration about an orifice on a tissue surface only to discover that the implant member 2600 is incorrectly sized to remodel the orifice. Since the interlockable elements 2640 are interlocked when the implant member 2600 is in the second configuration, the interlockable elements 2640 can require disengagement from one another before the implant member 2640 can be removed from the bodily cavity and replaced with an appropriately sized version. This can become especially difficult to do when percutaneous techniques are employed.

In this example embodiment, the first surface 2647a of each projection 2640a is oriented with respect to the first directional component 2645 by a sufficient angular amount to facilitate disengagement between first and the second sets 2641, 2643 of interlockable elements 2640 should an inadvertent engagement occur. In this example embodiment, the first surface 2647a of each projection 2640a is oriented with respect to the first directional component 2645 by an angular amount sufficient to axially separate a pair of interlocked first and second sets 2641, 2643 of interlockable elements 2640 under the application of a force to move an associated one of the segments 2602 along a respective one of second rotational directions 2636b, 2638b to disengage the interlockable elements 2640. The angular amount that the first surface 2647a of each projection 2640a is oriented with respect to the first directional component 2645 is however limited to withstand possible tissue forces that may act to move the implant member 2600 away from its second configuration when the implant member 2600 is secured to the tissue. It is noted that a biasing force applied by a biasing element (i.e., coupler 2620 in this embodiment) can also help to withstand possible tissue forces that may act to move the implant member 2600 away from its second configuration when the implant member 2600 is secured to the tissue. In this illustrated embodiment, the first surface 2647a of each projection 2640a is oriented with respect to the first directional component 2645 by approximately fifty (50) degrees.

In this example embodiment, each second surface 2647b is less steeply inclined with respect to the first directional component 2645 than a respective one of the first surfaces 2647a to provide implant member 2600 with the necessary rigidity to withstand the tissue tension forces when the implant member 2600 is secured to the tissue in the second configuration. Accordingly, in this example embodiment, a first one of two pivotally coupled segments 2602 is impeded with a first resistance from pivoting about an associated one of the pivots axes 2632a and 2634a along a first rotational direction (i.e., a respective one of first rotational directions 2636a and 2638a) towards a second one of the two pivotally coupled segments 2602 when an associated holder 2660 is in the fixed configuration, and the first one of two pivotally coupled segments 2602 is impeded with a second resistance from pivoting about an associated one of the pivots axes 2632a and 2634a along a second rotational direction (i.e., a respective one of second rotational directions 2636b and 2638b) away from the second one of the two pivotally coupled segments 2602 when the associated holder 2660 is in the fixed configuration, each of the first resistance and the second resistance being provided at least in part by the holder 2660 and a magnitude of the second resistance being less than a magnitude of the first resistance.

Figure 23A:
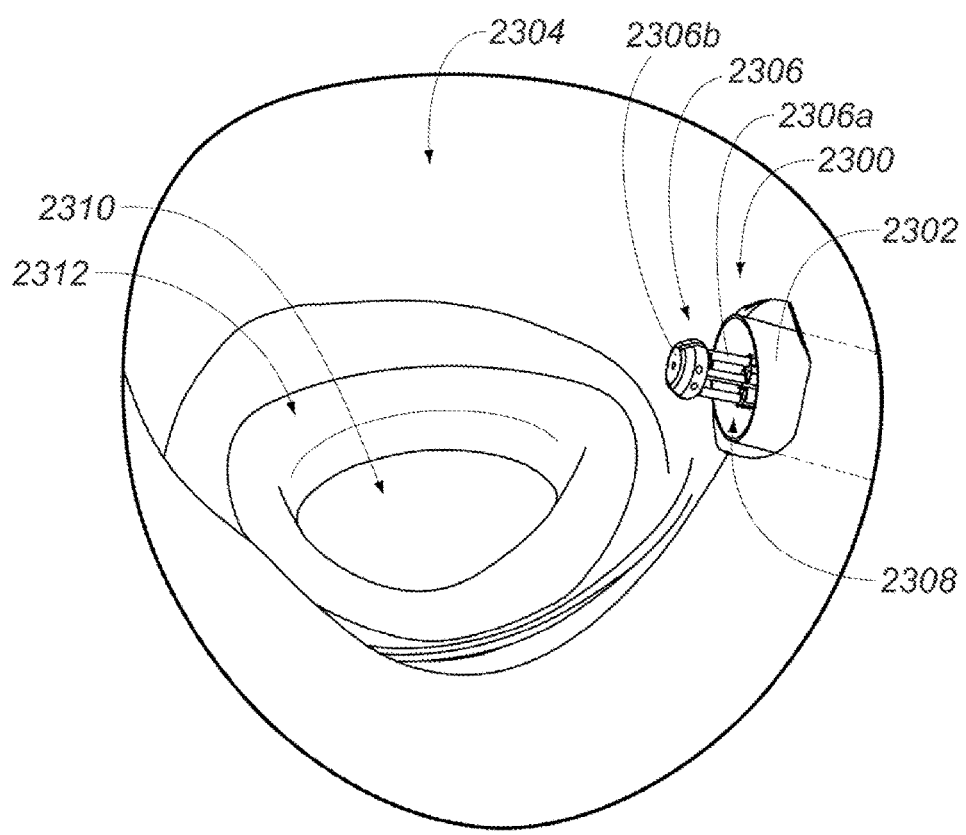
FIGS. 23A-23T are sequential schematic diagrams showing an implant procedure according to one illustrated embodiment, which includes placement of tissue anchors via an anchor guide frame at selected locations in an annulus surrounding a mitral valve of a left atrium of a heart and the securement of an implant member to the annulus via the tissue anchors.
Figure 23B:
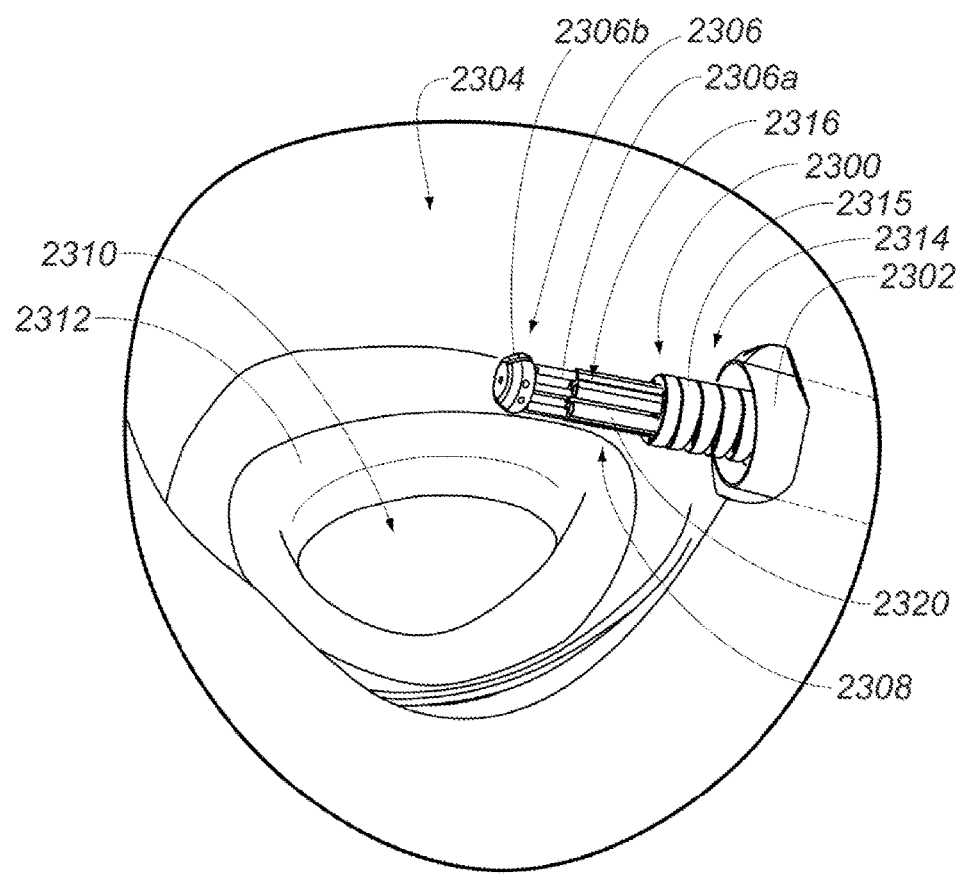
FIG. 23U is a schematic diagram showing an implant member in the form of an annuloplasty ring attached to an annulus of a mitral valve via tissue anchors, guide wires and fasteners, according to one illustrated embodiment.
Figure 23C:
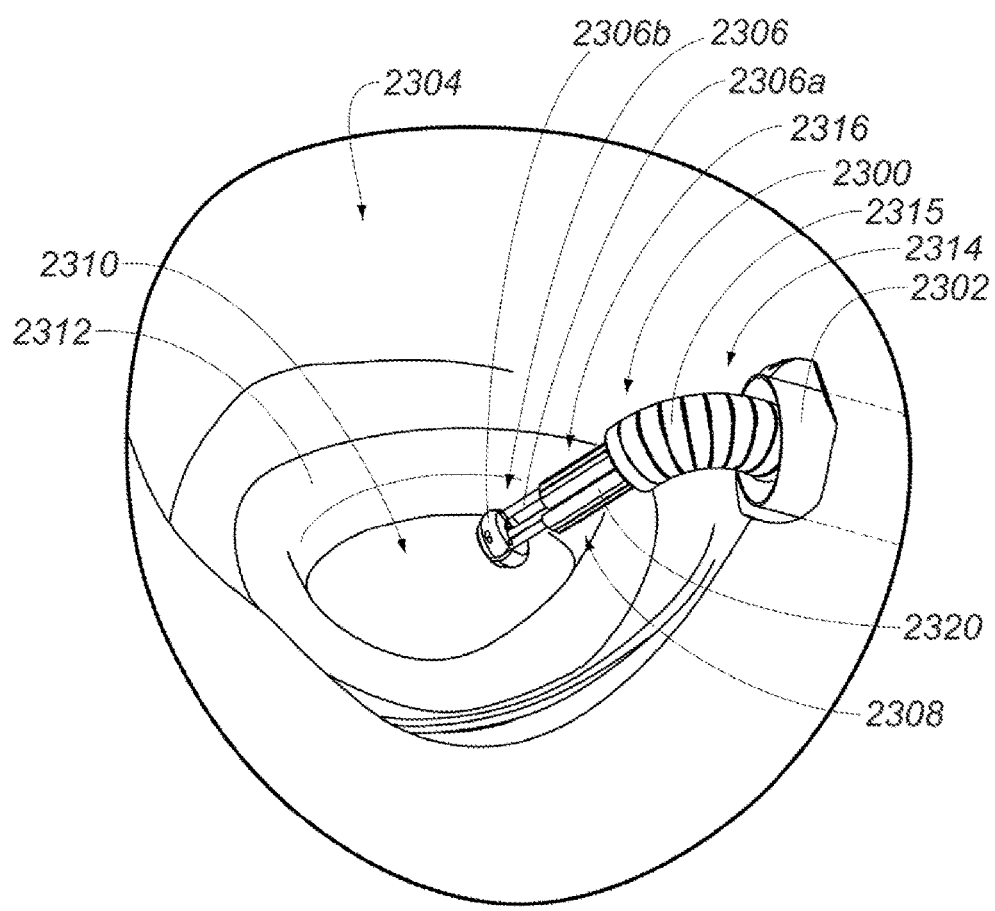
Figure 23D:
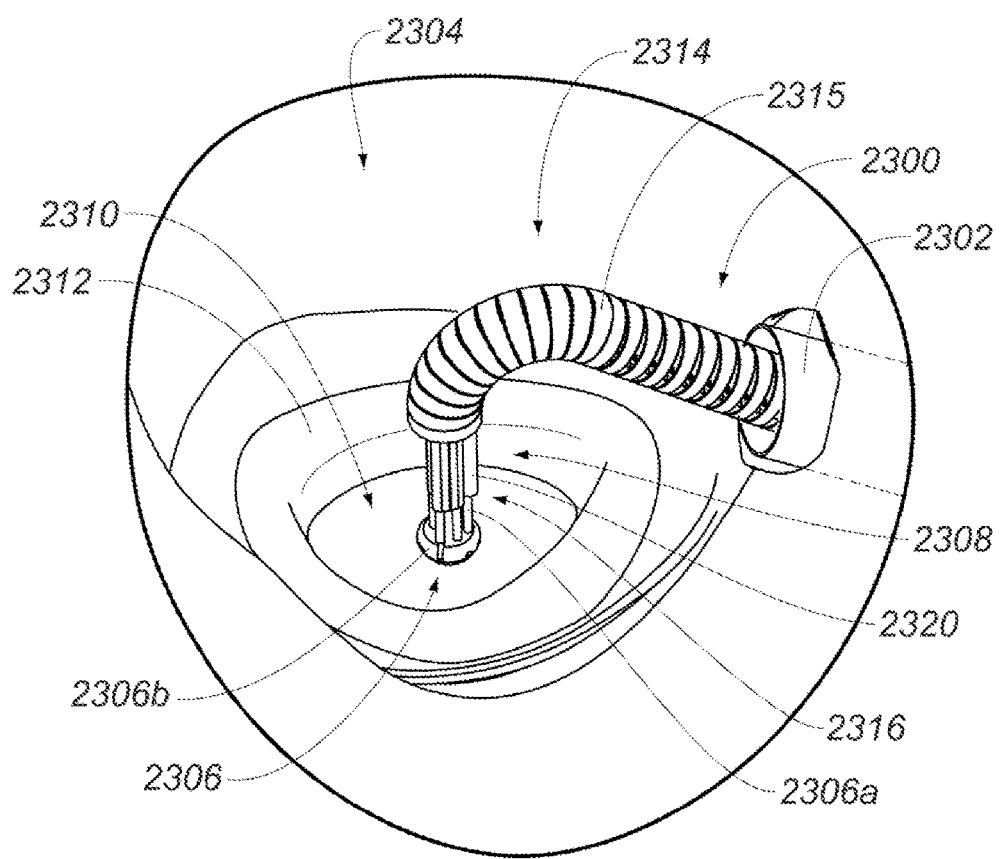
Figure 23E:
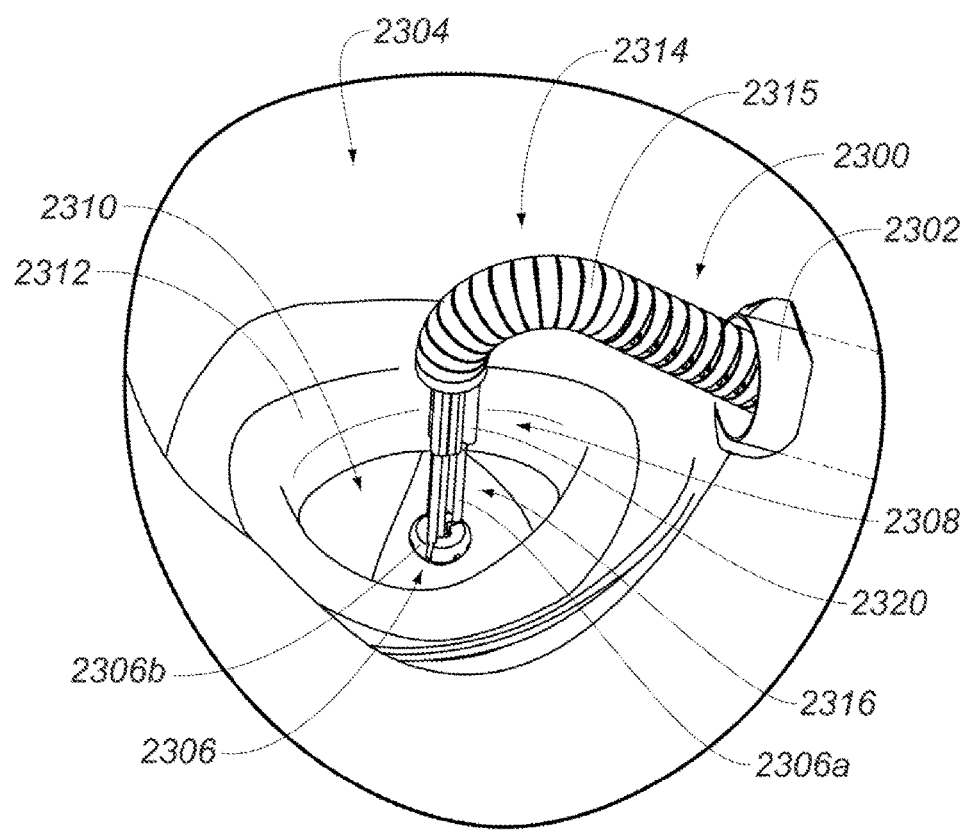
Figure 23F:
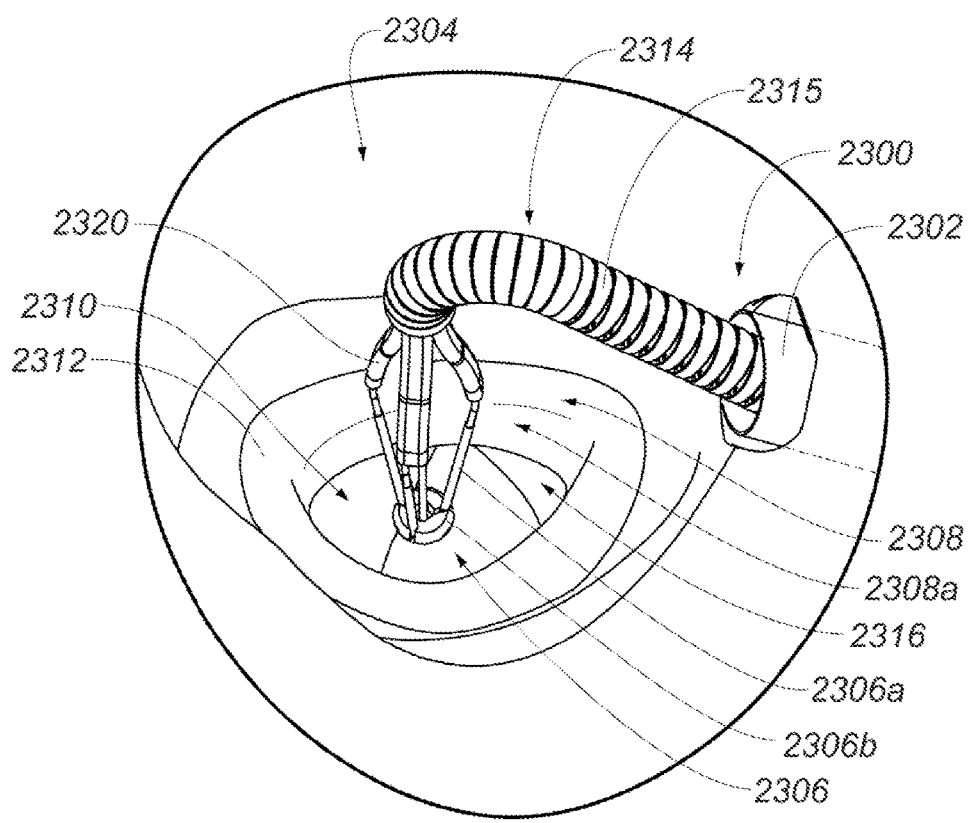
Figure 23G:
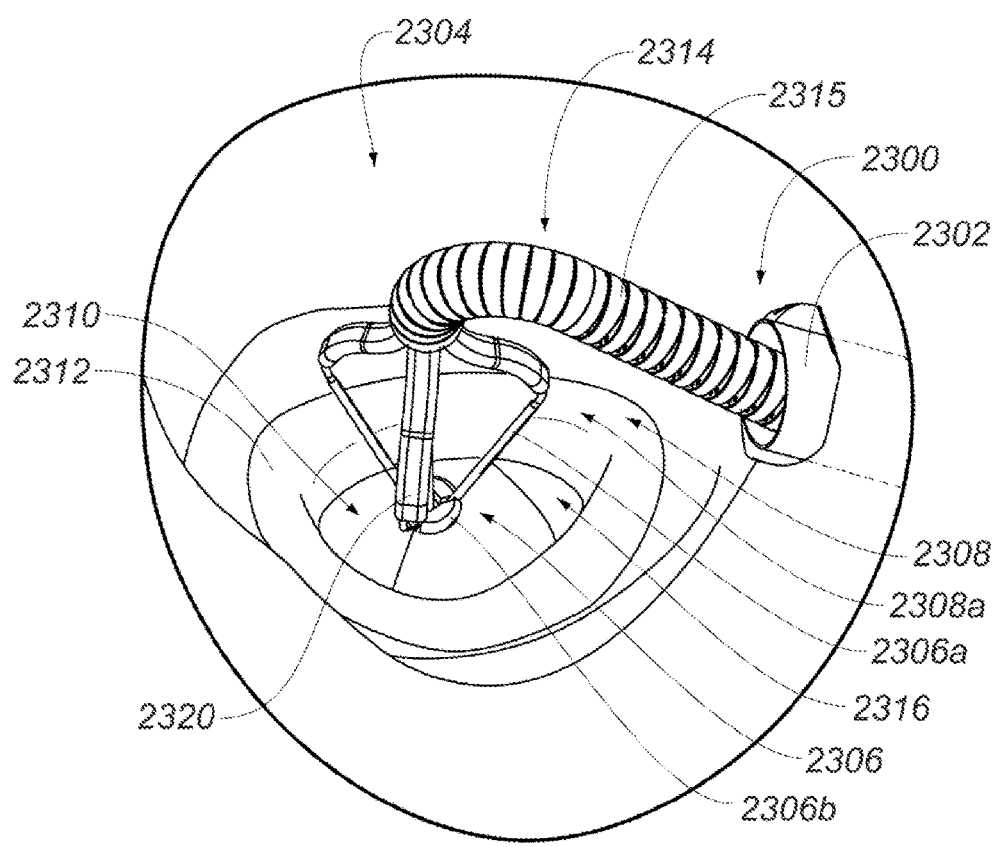
Figure 23H:
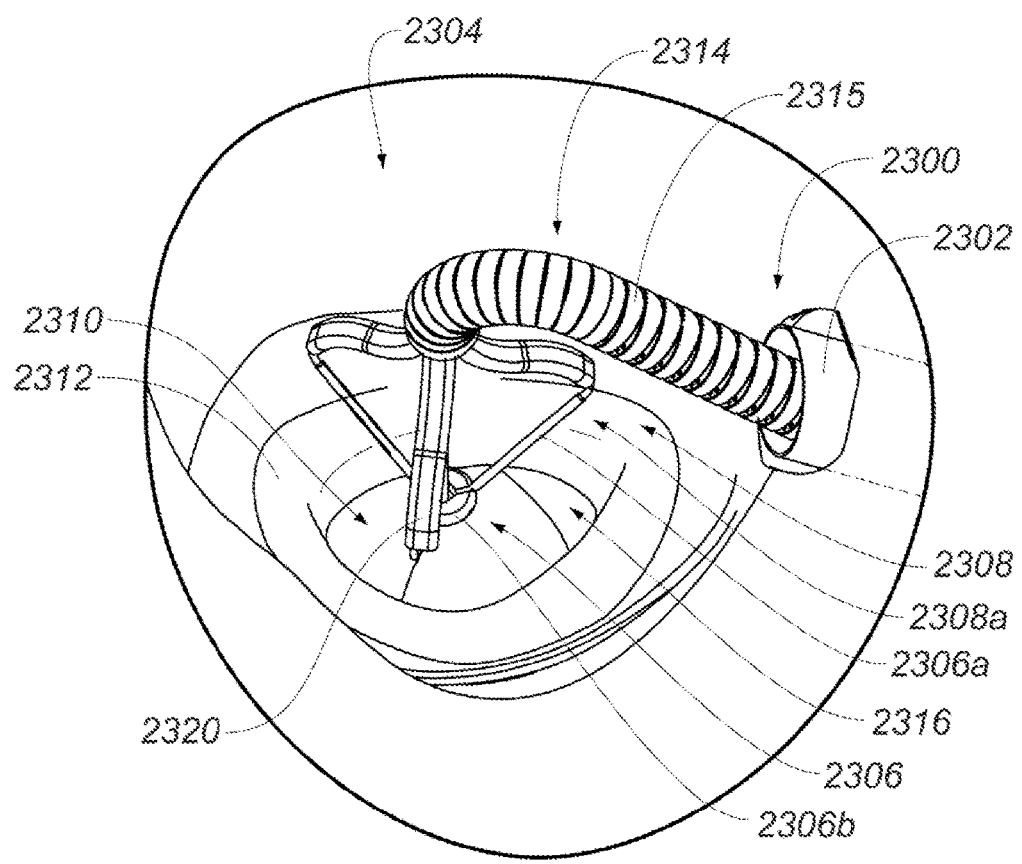
Figure 23I:
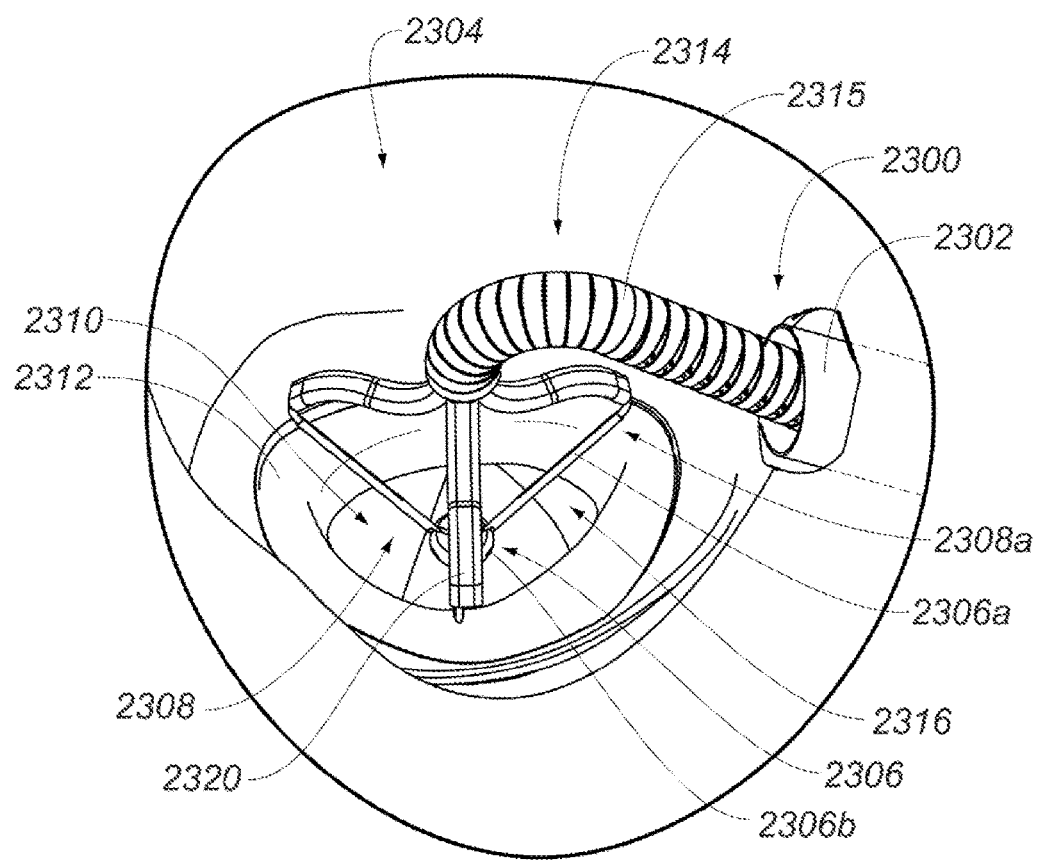
Figure 23J:
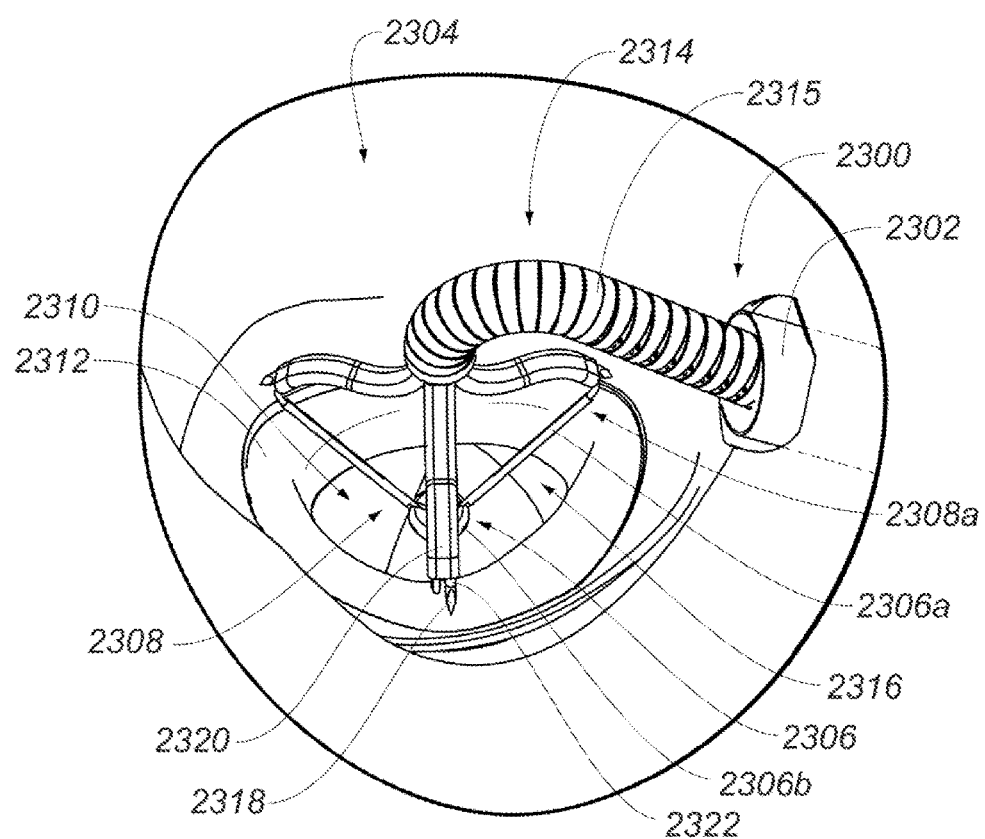
Figure 23K:
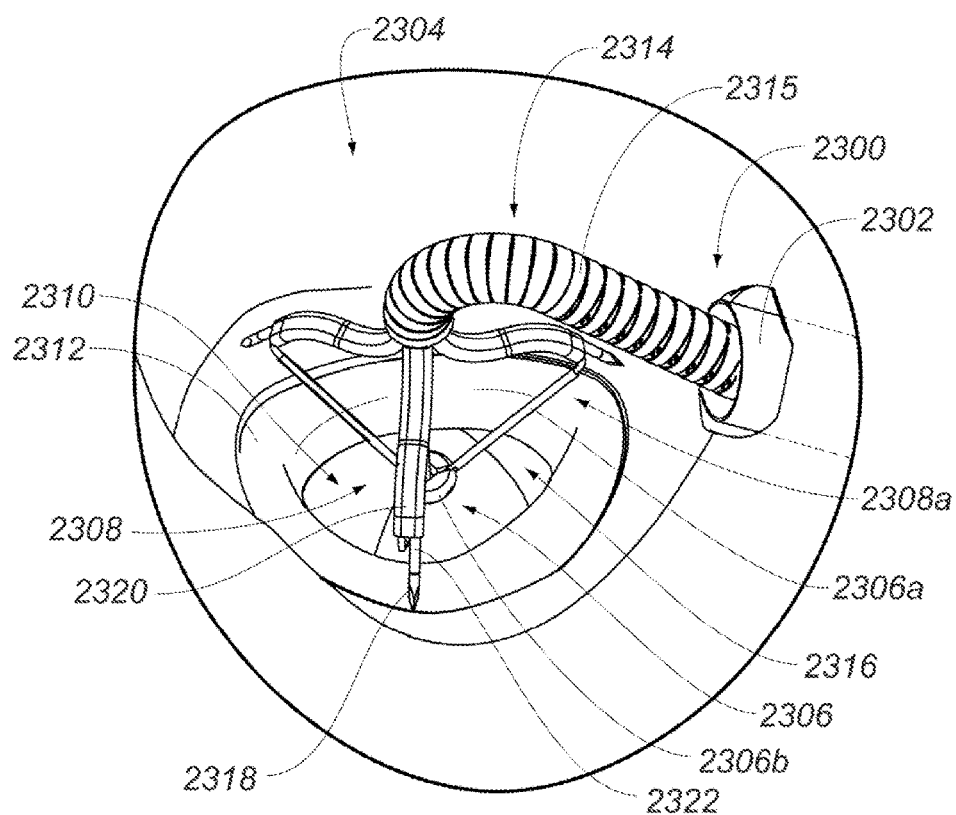
Figure 23L:
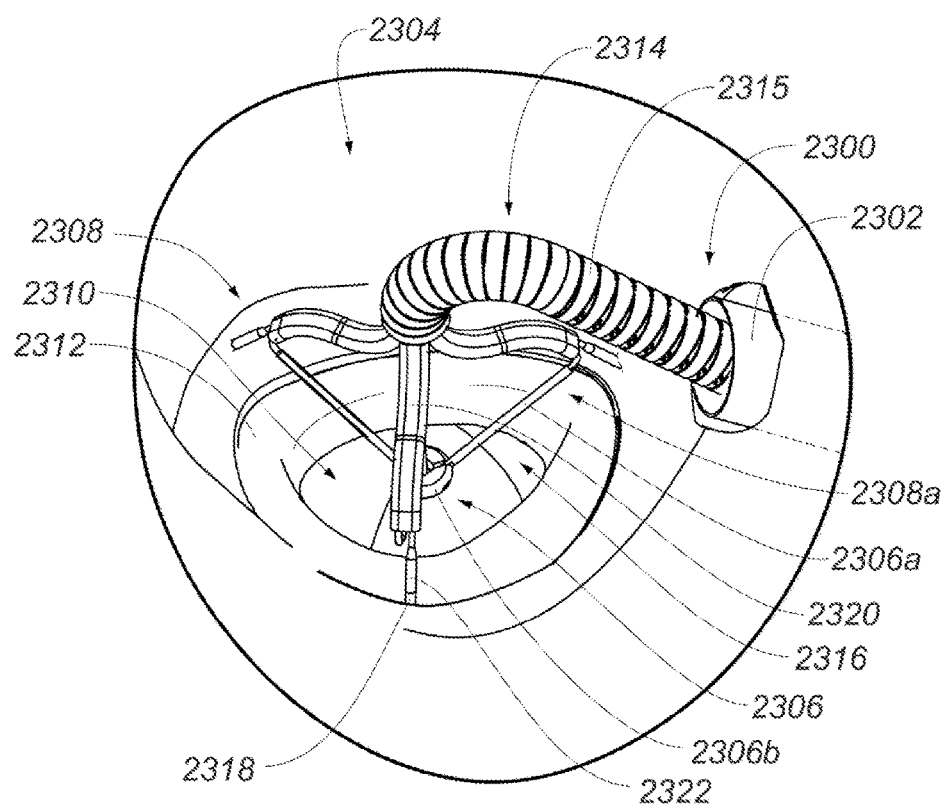
Figure 23M:
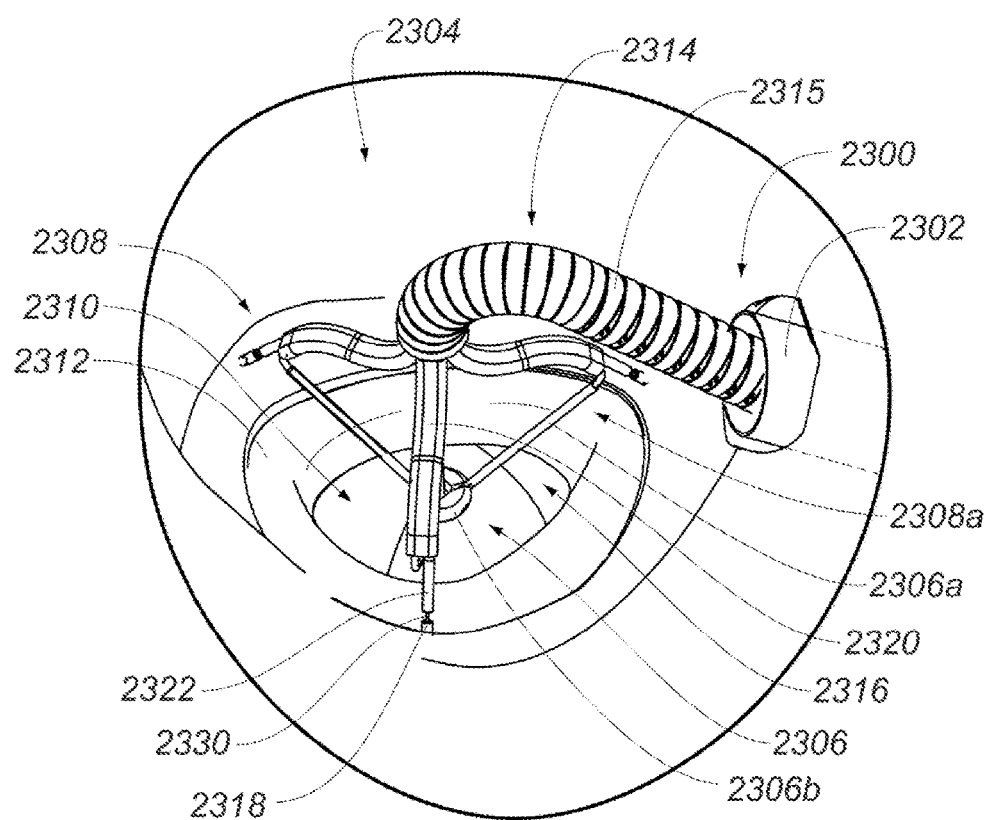
Figure 23N:
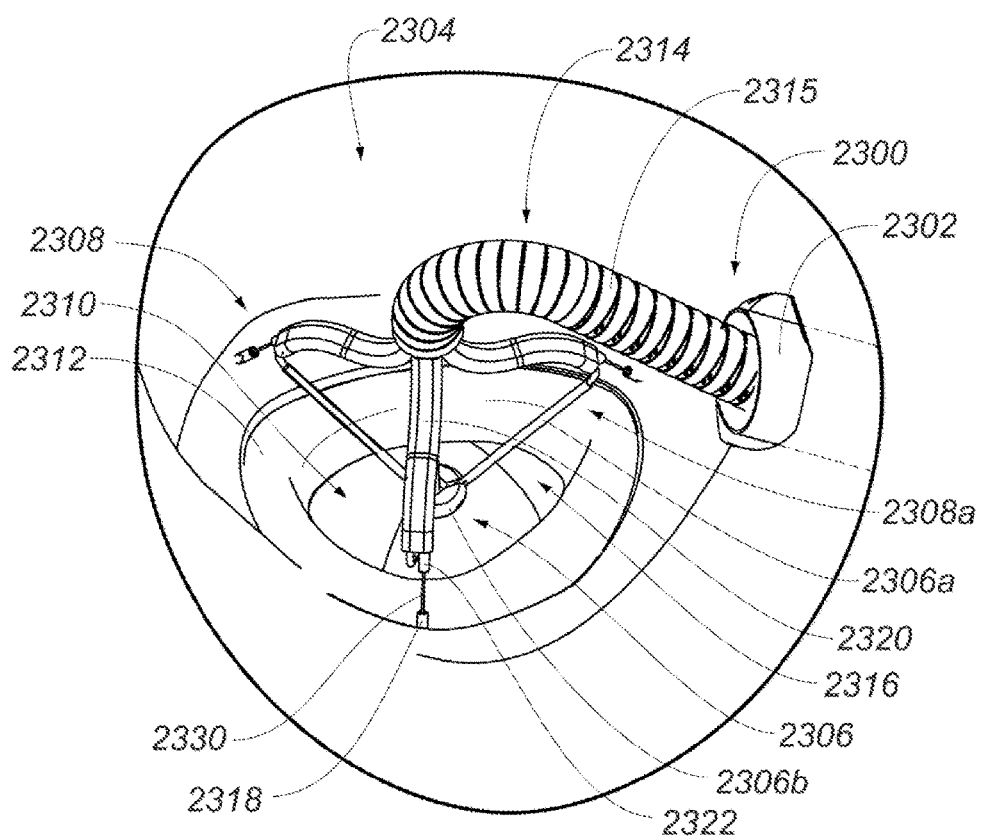
Figure 23O:
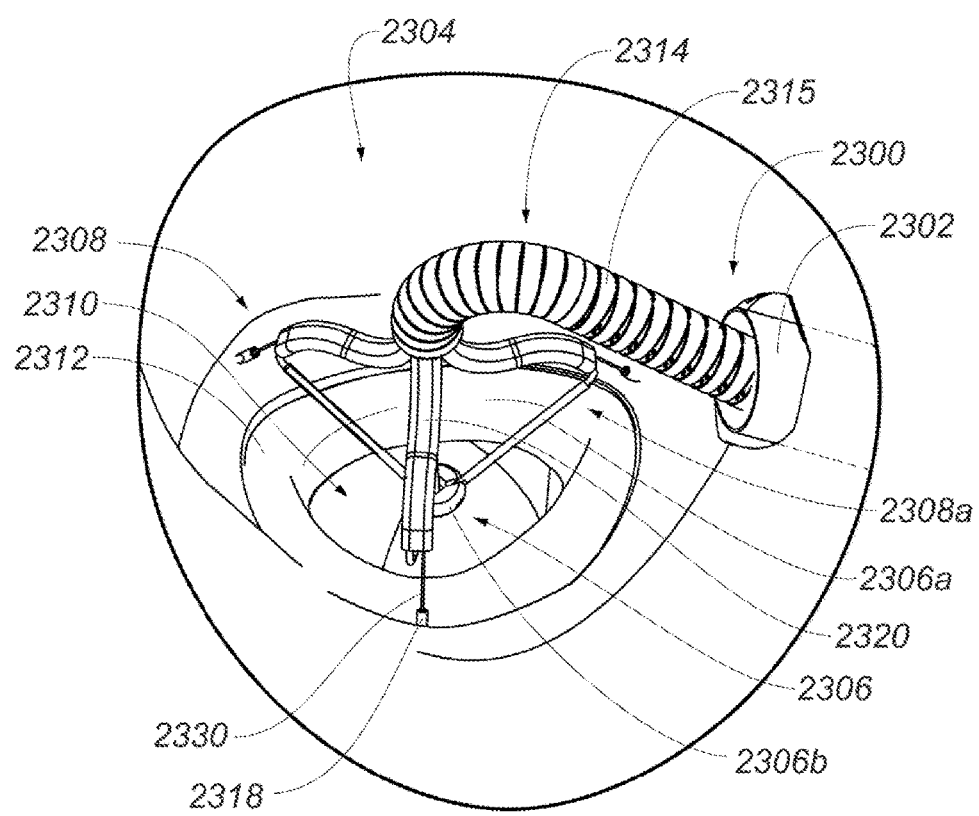
Figure 23P:
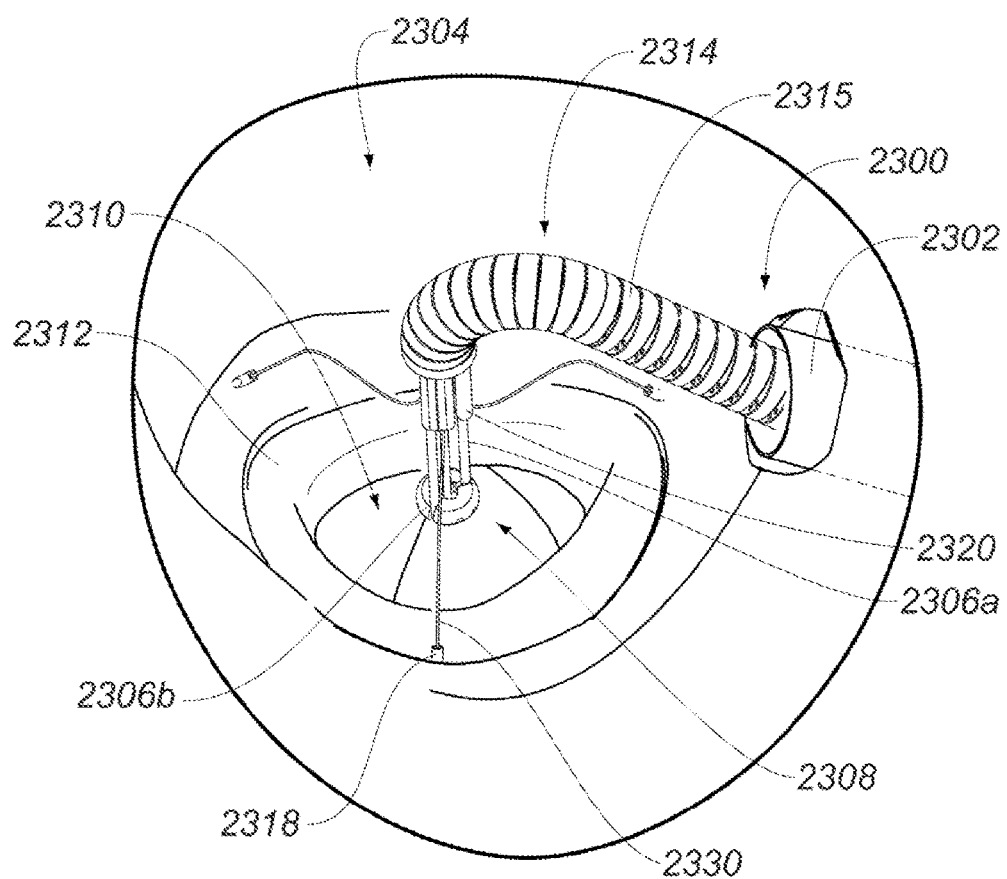
Figure 23Q:
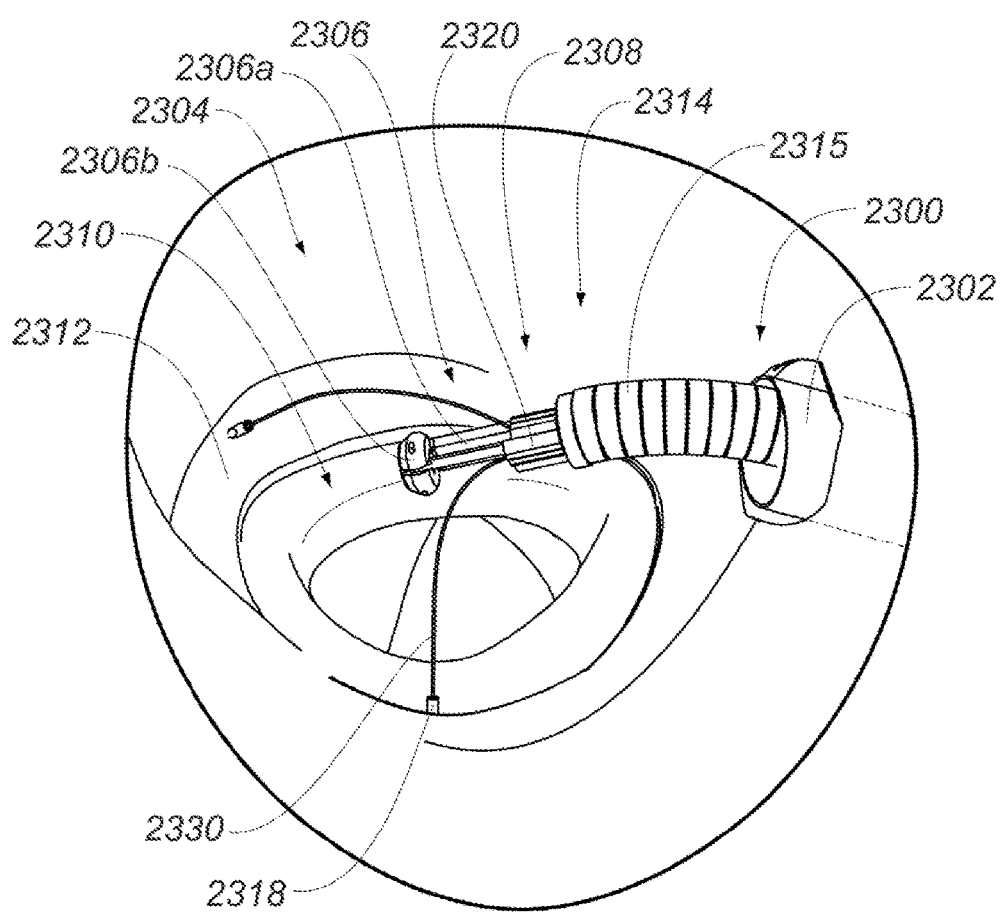
Figure 23R:
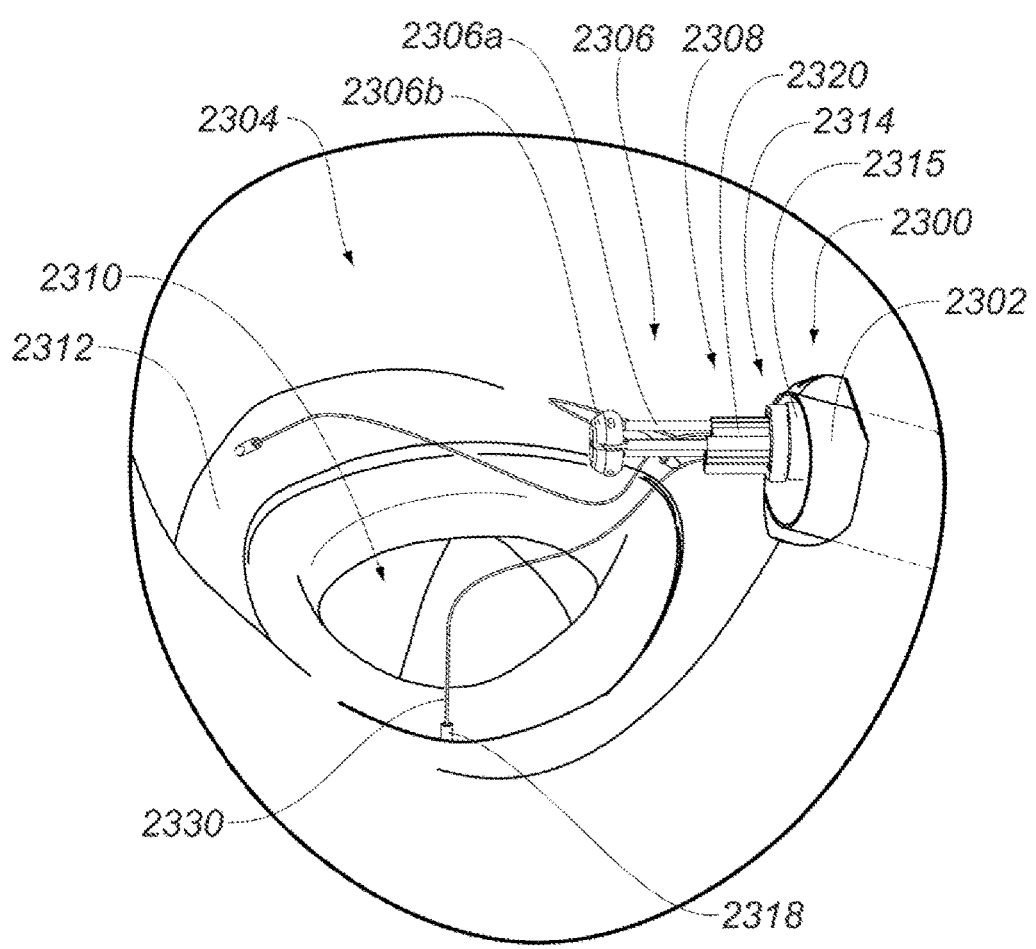
Figure 23S:
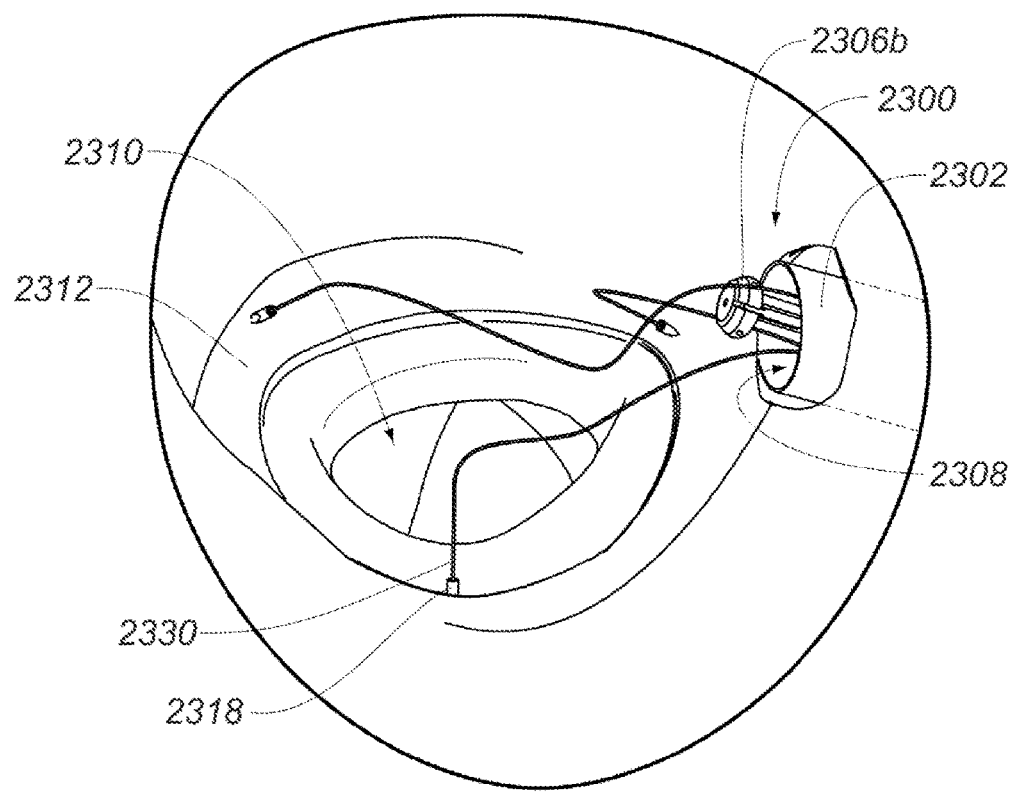
Figure 23T:
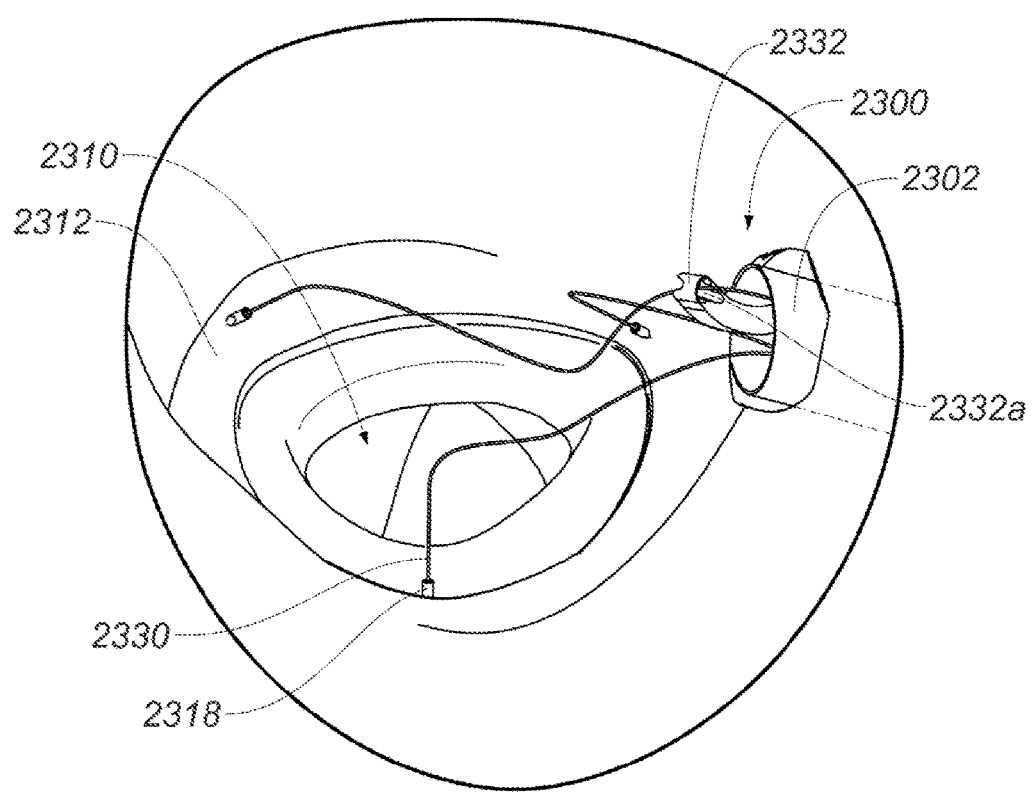

FIGS. 23A-23T sequentially show an implant procedure according to one illustrated embodiment. The implant procedure includes placement of tissue anchors via an anchor guide frame at selected locations in an annulus surrounding a mitral valve of a left atrium of a heart, and the securement of an implant member to the annulus via the embedded tissue anchors. Fluoroscopy, C T scanning, transesophageal echography (TEE) and/or other imaging or radiological techniques may be employed during all or part of the medical procedure, for example for guiding various catheters and/or locating the anchor guide frame for precisely placing or embedding the tissue anchors. For instance, TEE techniques may be employed to determine when to lock the implant member in position in the implantable configuration with the fasteners. Ultrasound imaging may be employed before the medical procedure, or as part of the medical procedure, to determine a size of the mitral valve. Such information may be employed in selecting an appropriately sized implant member or in adjusting a size of the implant member. In some instances, the implant member may also be selected based on the actual locations of the tissue anchors.

In particular, FIG. 23A shows a distal end 2300 of a cardiac catheter sheath 2302 advancing in a left atrium 2304 of a heart. The cardiac catheter sheath 2302 may, for example, enter the heart via the inferior vena cava (not shown) or the superior vena cava (not shown), then enter the left atrium via a hole formed in the septum (not shown) of the heart. The cardiac catheter sheath 2302 may be inserted using an introducer and guide wire, as is commonly known. A proximate end (not shown) of the cardiac catheter sheath 2302 is outside of the bodily or accessible from outside of the body.

An engagement or locating member 2306 of an anchor guide frame 2308 is visible, extending out of the distal end 2300 of the cardiac catheter sheath 2302. The engagement or locating member 2306 may have a number of arms 2306a (three illustrated, only one called out in FIGS. 23A-23T) and a hub 2306b. The hub 2306b may couple the arms 2306a. A mitral valve 2310 of the heart is also visible, including an annulus 2312, which is natural tissue that surrounds the mitral valve 2310. In use, the hub 2306b may be centered in the mitral valve 2310 in contact with the cusps or leaflets of the mitral valve 2310. The hub 2306b may take the form of an alignment member, for instance the alignment fin 1305 previously described with reference to FIG. 13.

FIG. 23B shows an anchoring catheter 2314 extending out of the cardiac catheter sheath 2302. The anchoring catheter 2314 carries the anchor guide frame 2308. The anchoring catheter 2314 has a steerable portion 2315, which may be selectively steered from a location outside the body. The steerable portion 2315 may include an articulated section. The steerable portion 2315 may be steered mechanically, for example using wires (not shown in FIGS. 23A-23T) that extend through the anchoring catheter 2314 and which are attached to opposing portions of the articulated section.

Alternatively, the steerable portion 2315 may be steered hydraulically, for example by controlling pressure in a number of lumens that extend through the anchoring catheter and which terminate in the articulated section. In addition to the engagement or locating member 2306, the anchor guide frame 2308 includes a number of anchor guides 2316 (three illustrated in FIGS. 23A-23T, only one called out) which guide tissue anchors 2318 (FIGS. 23J-23T) to selected locations on the annulus 2312. The anchor guides 2316 may each include a dual lumen outer tube 2320 (only one called out in FIGS. 23A-23T). One lumen may carry a respective one of the arms 2306a of the engagement or locating member 2306 for movement through the lumen. The other lumen may carry an inner or guide tube 2322, the tissue anchor 2318 and a guide line or guide wire 2330 (only one called out in FIGS. 23M-23T) for movement through the lumen. The inner or guide tube 2322 may be physically coupled to advance the tissue anchor 2318 through the lumen. Such a structure, and its use, were previously explained with reference to FIGS. 8C-8F.

FIG. 23C shows the anchoring catheter 2314 being steered to face the mitral valve 2310. FIG. 23D shows the anchoring catheter 2314 being advanced toward the mitral valve 2310.

FIG. 23E shows the engagement or locating member 2306 being extended from the anchoring catheter 2314 toward the mitral valve 2310. FIG. 23F shows the anchor guide frame 2308 beginning to open or expand, a slight bow in arms 2308a (only one called out in FIGS. 23F-23S) being visible in FIG. 23F. The anchor guide frame 2308 is opened once the engagement or locating member 2306 or hub 2306b is approximately in a desired position and orientation with respect to the mitral valve 2310. FIGS. 23G and 23H show the anchor guide frame 2308 opening or expanding further at successive intervals. FIG. 23I shows the anchor guide frame 2308 fully open or expanded. The anchor guide frame 2308 may move automatically into position because of the correspondence of the shape of the anchor guide frame 2308 with the anatomical structure of the valve. The anchor guide frame 2308 may be constructed so that the two rear most arms (as illustrated, one labeled 2306a and other one at the back of the figure) slide into the mitral commissures. Even if the anchor guide frame 2308 is deployed at the wrong angle, expanding the arms caused the anchor guide frame 2308 to rotate as the arms get pushed into the commissures. The mitral annulus is not perfectly round, and "corners" of the mitral annulus can advantageously be used to cause the anchor guide frame 2308 to automatically align with the mitral valve.

FIG. 23J shows the inner or guide tubes 2322 with tissue anchors 2318 beginning to protrude from the outer tubes 2320. FIGS. 23K and 23L show the inner or guide tubes 2322 with tissue anchors 2318 protruding further from the outer tubes 2320, at successive intervals, embedding the tissue anchors 2318 into the annulus 2312 of the mitral valve 2310. FIG. 23M shows the inner or guide tubes 2322 being withdrawn back into the outer tubes 2320, leaving the tissue anchors 2318 embedded in the tissue of the annulus 2312. The guide line or guide wire 2330 is first visible in FIG. 23M. As explained in reference to FIGS. 8C-8F, the guide line or guide wire 2330 may be pushed or held in place as the inner or guide tubes 2322 are withdrawn back into the outer tube 2320. FIG. 23N shows the inner or guide tubes 2322 almost fully withdrawn in the outer tube 2320, while FIG. 23O shows the inner or guide tubes 2322 fully withdrawn in the outer tube 2320.

FIG. 23P shows the anchor guide frame 2308 closing or collapsing. FIGS. 23Q and 23R shows the closed or collapsed anchor guide frame 2308 and anchoring catheter 2314 being positioned and oriented at successive intervals to be withdrawn into the cardiac catheter sheath 2302. FIG. 23S shows the anchoring catheter 2314 withdrawn into the cardiac catheter sheath 2302, leaving the tissue anchors 2318 and guide lines or guide wires 2330 behind in the left atrium 2304 of the heart. The anchoring catheter 2314 may then be removed, clearing the cardiac catheter sheath 2302 for the next catheter, used to deliver an implant member. After the anchoring catheter 2314 is withdrawn from the cardiac catheter sheath 2302, the guide lines or guide wires 2330 extend from the tissue anchors 2318 through the cardiac catheter sheath 2302 at least to the proximate end thereof. Such allows an implant member to be coupled to the guide lines or guide wires 2330.

FIG. 23T shows a portion of an implant member 2332 being advanced into the left atrium 2304 through the cardiac catheter sheath 2302. The implant member 2332 may take the form of an annuloplasty ring. As used herein and in the claims, a ring or annular structure may be an open structure (e.g., C-shaped) or a closed structure (e.g., O-shaped or D-shaped). The implant member 2332 has a number of guide line receivers 2332a (only one illustrated in FIG. 23T) that couple the implant member 2332 to a respective guide line or guide wire 2330. In the illustrated embodiment, the guide line receiver 2332a takes the form of a hole or aperture, sized to receive the guide line or guide wire 2330. Such allows the implant member 2332 to ride or otherwise advance along the guide lines or guide wires 2330 toward the tissue anchors 2318 embedded in the tissue around an orifice (e.g., mitral valve 2310). As previously explained in reference to FIGS. 5C and 5D, the implant member 2332 may include a relief (not illustrated in FIG. 23T) proximate the guide line receiver 2332a.

Figure 23U:
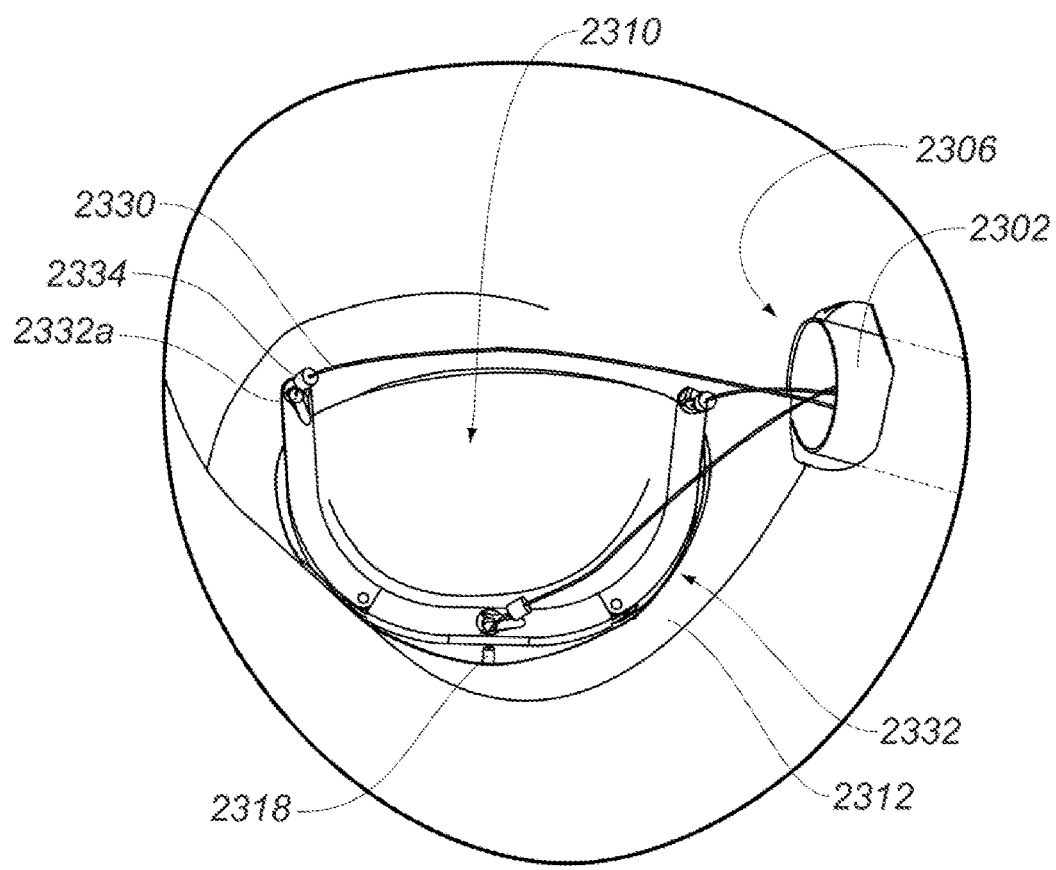

FIG. 23U shows the implant member 2332, guide lines or guide wires 2318 and fasteners 2334 (only one called out in FIG. 23U), according to one illustrated embodiment.

The implant member 2332 takes the form of an annuloplasty ring. Suitable segmented structures for the implant member 2332 have been previously described, for example in reference to FIGS. 19A-19D, 20A-20D, 24A-24H and 25A-25F although other implant member structures may be employed. The implant member 2332 is physically attached directly or coupled indirectly to the annulus 2312 of the mitral valve 2310. The implant member 2332 encompasses or surrounds a portion of the mitral valve 2310, for example angularly surrounding approximately half of the mitral valve 2310. In particular, the implant member 2332 is positioned and oriented to allow an anterior-posterior annular dimension of the mitral valve 2310 to be changed, for instance reduced. Such may cause the leaflets of the mitral valve 2310 to better coapt.

The implant member 2332 may ride or otherwise advance along the guide lines or guide wires 2318 to the locations on the annulus 2312 where the tissue anchors 2318 are embedded. A desired position and orientation is achieved due to the ability to precisely locate the tissue anchors 2318 using the anchor guide frame 2308. In particular, the engagement or locating member 2306 or hub 2306b and/or the anchor guides 2316 allows precise positioning and orientation of the embedding of the tissue anchors 1218, and hence the precise positioning and orientation of the implant member 2332.

In this example embodiment, fasteners 2334 are advanced along each of the guide lines or guide wires 2330 to secure the implant member 2332 to the annulus 2312. As previously described, the fasteners 2334 may take a variety of forms. For example, one-way clutch or cam mechanisms may allow the fasteners 2334 to advance in one direction along the guide lines or guide wires 2330 toward the tissue anchors 2318, but prevent or resist retreat of the fasteners 2334 along the guide lines or guide wires 2330 away from the tissue anchors 2318. After the fasteners 2334 are in place, excess portions of the guide lines or wires 2330 may be cut, broken or otherwise severed, and the excess portions removed from the body via the cardiac catheter sheath 2302. Various embodiments of suitable cutting or severing mechanisms have been described above. Alternatively, a mechanism that facilitates a twisting or flexing of the guide lines or guide wires 2330 may be employed. The guide lines or guide wires 2330 are typically very fine, and may be easily severed with appropriate twisting or rotation about a longitudinal axis thereof. A small tail piece of guide line or guide wire 2330 may be left exposed beyond the fastener 2334 to allow later access, for example to replace the implant member 2332. In other example embodiments, fasteners 2334 are employed to couple directly with the embedded tissue anchors 2318 to secure implant member 2332 to the annulus 2312. In some example embodiments implant member 2332 and fasteners 2334 are combined into a unitary structure.

The various embodiments described above can be combined to provide further embodiments. All of any U.S. patents, U.S. patent application publications, U.S. patent applications, foreign patents, foreign patent applications and non-patent publications referred to in this specification and/or listed in the Application Data Sheet, including U.S. provisional patent application Ser. No. 61/278,232, filed Oct. 1, 2009, and U.S. patent application Ser. No. 12/894,912, filed Sep. 30, 2010 are incorporated herein by reference, in their entirety. Aspects of the various embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. An implant kit, comprising:
a plurality of tissue anchors configured to be at least partially embedded into tissue at respective locations about an orifice within a body during an implant procedure; and
an implant member reconfigurable between a delivery configuration in which the implant member is manipulable to a size and dimension to be deliverable percutaneously to the tissue within the body, and a deployed configuration in which the implant member forms a structure sufficiently rigid to affect a shape of the orifice in the tissue, the implant member comprising:
a plurality of segments;
a number of pivot joints, each pivot joint comprising a respective pivot pin and a respective pivot axis, the pivot pin of each pivot joint arranged to pivotally couple each of the segments together in a respective one of a number of sets of two or more of the segments, at least one segment in each respective one of the number of sets of two or more of the segments pivoting about the respective pivot axis of the pivot joint when the implant member is moved between the delivery configuration and the deployed configuration; and
a plurality of tissue anchor receivers, each tissue anchor receiver comprising at least one alignment surface arranged to contact a portion of a respective one of the plurality of tissue anchors and align the portion of the respective one of the plurality of tissue anchors with respect to an alignment axis of the tissue anchor receiver when the respective one of the plurality of tissue anchors is secured to the implant member, the portion of the respective one of the plurality of tissue anchors impeded from moving along the alignment axis of the tissue anchor receiver to break contact with the at least one alignment surface of the tissue anchor receiver when the respective one of the plurality of tissue anchors is secured to the implant member, wherein the respective alignment axis of at least a first one of the plurality of tissue anchor receivers is non-parallel with the respective pivot axis of at least one of the number of pivot joints, and wherein the respective alignment axis of at least a second one of the plurality of tissue anchor receivers is substantially parallel to the respective pivot axis of the at least one of the number of pivot joints.

2. The implant kit of claim 1 wherein the respective at least one alignment surface of each tissue anchor receiver is arranged to impede the portion of the respective one of the plurality of tissue anchors from moving along a direction having a directional component perpendicular to the respective alignment axis of the tissue anchor receiver when the respective one of the plurality of tissue anchors is secured to the implant member.

3. The implant kit of claim 1 wherein at least one of the plurality of tissue anchors is configured to be embedded in the tissue when the respective portion of the at least one of the plurality of tissue anchors is aligned by the at least one alignment surface of a respective one of the plurality of tissue anchor receivers.

4. The implant kit of claim 1 wherein at least one of the plurality of tissue anchors is configured to be embedded in the tissue when the at least one of the plurality of tissue anchors is secured to the implant member.

5. The implant kit of claim 4, further comprising a number of implant guide lines, each of the number of implant guide lines physically coupled to the at least one of the plurality of tissue anchors when the at least one of the plurality of tissue anchors is configured to be embedded in the tissue to provide a physical path for the implant member to the at least one of the plurality of tissue anchors, the implant member moveable along the physical path to a position where the implant member is secured to the at least one of the plurality of tissue anchors.

6. The implant kit of claim 1 wherein the number of pivot joints comprises a plurality of pivot joints arranged such that the respective pivot axes of at least two of the plurality of pivot joints are parallel with respect to one another.

7. The implant kit of claim 1, further comprising a plurality of biasing devices, each of the biasing devices biasing the segments together in a respective one of the number of sets of two or more of the segments when the plurality of tissue anchors are secured to the implant member.

8. The implant kit of claim 1, further comprising a plurality of couplers, each coupler configured to engage a respective first portion of a respective one of the plurality of tissue anchors to capture a portion of the implant member between the coupler and a respective second portion of the respective one of the plurality of tissue anchors when the respective one of the plurality of tissue anchors is secured to the implant member, the respective second portion of each of the plurality of tissue anchors embeddable into the tissue.

9. The implant kit of claim 1, further comprising a number of holders, each holder activatable between a free configuration in which each segment in a respective one of the number of sets of two or more of the segments is arranged to pivot towards and away from another one of the segments in the respective one of the number of sets of two or more of the segments, and a fixed configuration in which the segment in the respective one of the number of sets of two or more of the segments is impeded from pivoting towards and away from the another one of the segments in the respective one of the number of sets of two or more of the segments with a greater resistance than when the holder is in the free configuration.

10. The implant kit of claim 9 wherein each holder comprises a respective plurality of interlockable elements which are brought into interlocked engagement when the implant member is moved into the deployed configuration.

11. The implant kit of claim 10 wherein each of the plurality of interlockable elements comprises a trapezoidal shaped projection or a trapezoidal shaped recess.

12. The implant kit of claim 1 wherein the respective alignment axis of at least the second one of the plurality of tissue anchor receivers is collinear with the respective pivot axis of the at least one of the number of pivot joints.

13. The implant kit of claim 1 wherein the respective at least one alignment surface of each tissue anchor receiver is arranged to impede the portion of the respective one of the plurality of tissue anchors from moving relative to the tissue anchor receiver along a direction having a directional component perpendicular to the respective alignment axis of the tissue anchor receiver when the respective one of the plurality of tissue anchors is secured to the implant member.

14. An implant kit, comprising:
a plurality of tissue anchors, each of the plurality of tissue anchors at least partially embeddable into tissue at a respective location about an orifice within a body during an implant procedure; and
an implant member reconfigurable between a delivery configuration in which the implant member is manipulable to a size and dimension to be deliverable percutaneously to the tissue within the body, and a deployed configuration in which the implant member forms a structure sufficiently rigid to affect a shape of the orifice in the tissue, the implant member comprising:
a plurality of segments;
a plurality of tissue anchor receivers, each tissue anchor receiver comprising at least one alignment surface arranged to contact a portion of a respective one of the plurality of tissue anchors and position the portion of the respective one of the plurality of tissue anchors at a location where the one of the plurality of tissue anchors is securable to the implant member; and
at least a first pivot joint comprising a first pivot member, the first pivot joint arranged to pivotally couple a first set of two or more of the segments together, at least some of the segments in the first set of two or more of the segments arranged to turn about the first pivot member when the implant member is moved between the delivery configuration and the deployed configuration, the first pivot member and a first one of the tissue anchor receivers provided in a unitary structure to which the first set of two or more of the segments is coupled.

15. The implant kit of claim 14 wherein the first pivot member is fixedly coupled to one of the segments in the first set of two or more of the segments.

16. The implant kit of claim 14 wherein at least one segment in the first set of two or more of the segments is slidably and pivotably coupled to the first pivot member, the at least one segment in the first set of two or more of the segments arranged to translate along, and turn about, the first pivot member when the implant member is moved between the delivery configuration and the deployed configuration.

17. The implant kit of claim 16 wherein the first pivot member comprises at least one obstruction positioned to capture the at least one segment in the first set of two or more of the segments on the first pivot member.

18. The implant kit of claim 14 wherein the respective at least one alignment surface of the first one of the tissue anchor receivers is radially spaced apart from a pivot axis of the first pivot joint by a different radial distance than a surface of the first pivot member contacted by the at least some of the segments in the first set of two or more of the segments.

19. The implant kit of claim 18 wherein the respective at least one alignment surface of the first one of the tissue anchor receivers comprises a tapered surface portion.

20. The implant kit of claim 14 wherein the implant member comprises a plurality of interlockable elements arranged about a pivot axis of the first pivot joint, a first set of the interlockable elements arranged to interlock with a second set of interlockable elements when the implant member is in the deployed configuration.

21. An implant kit, comprising:
a plurality of tissue anchors, each of the plurality of tissue anchors at least partially embeddable into tissue at a respective location about an orifice within a body during an implant procedure; and
an implant member reconfigurable between a delivery configuration in which the implant member is manipulable to a size and dimension to be deliverable percutaneously to the tissue within the body, and a deployed configuration in which the implant member forms a structure sufficiently rigid to affect a shape of the orifice in the tissue, the implant member comprising:
a plurality of rigid portions;
at least one bendable portion arranged to pivotally couple at least one of the rigid portions with at least another of the rigid portions; and
a plurality of tissue anchor receivers, each tissue anchor receiver comprising at least one alignment surface arranged to contact a portion of a respective one of the plurality of tissue anchors and position the portion of the respective one of the plurality of tissue anchors at a location where the one of the plurality of tissue anchors is securable to the implant member, at least a first one of the plurality of tissue anchor receivers located in one of the plurality of rigid portions and at least a second one of the plurality of tissue anchor receivers located in the at least one bendable portion.

22. The implant kit of claim 21 wherein the respective at least one alignment surface of each tissue anchor receiver is arranged to align the portion of the respective one of the plurality of tissue anchors with respect to an alignment axis of the tissue anchor receiver when the respective one of the plurality of tissue anchors is secured to the implant member, the portion of the respective one of the plurality of tissue anchors impeded from moving along the alignment axis of the tissue anchor receiver to break contact with the at least one alignment surface of the tissue anchor receiver when the respective one of the plurality of tissue anchors is secured to the implant member.

23. The implant kit of claim 22 wherein the at least one bendable portion is arranged to pivotally couple the at least one of the rigid portions with the at least another of the rigid portions about a pivot axis when the implant member is moved between the delivery configuration and the deployed configuration, wherein the respective alignment axis of at least the first one of the plurality of tissue anchor receivers located in the one of the plurality of rigid portions is non-parallel with the pivot axis, and wherein the respective alignment axis of at least the second one of the plurality of tissue anchor receivers located in the at least one bendable portion is substantially parallel to the pivot axis.

24. The implant kit of claim 23
wherein the pivot axis is a first pivot axis,
wherein at least the first one of the plurality of tissue anchor receivers is located in the one of the rigid portions and at least the second one of the plurality of tissue anchor receivers is located in the at least one bendable portion,
wherein the implant kit further comprises at least a second bendable portion arranged to pivotally couple at least the another of the rigid portions with at least a third rigid portion of the plurality of rigid portions about a second pivot axis when the implant member is moved between the delivery configuration and the deployed configuration, and
wherein the first pivot axis is parallel to the second pivot axis.

25. The implant kit of claim 23 wherein the respective alignment axis of at least the second one of the plurality of tissue anchor receivers is collinear with the respective pivot axis.

26. The implant kit of claim 22 wherein the respective at least one alignment surface of each tissue anchor receiver is arranged to impede the portion of the respective one of the plurality of tissue anchors from moving along a direction having a directional component perpendicular to the respective alignment axis of the tissue anchor receiver when the respective one of the plurality of tissue anchors is secured to the implant member.

27. The implant kit of claim 22 wherein the respective at least one alignment surface of each tissue anchor receiver is arranged to impede the portion of the respective one of the plurality of tissue anchors from moving relative to the respective one of the plurality of tissue anchors along a direction having a directional component perpendicular to the respective alignment axis of the tissue anchor receiver when the respective one of the plurality of tissue anchors is secured to the implant member.

28. The implant kit of claim 21 wherein at least one of the plurality of tissue anchors is configured to be embedded in the tissue when the respective portion of the at least one of the plurality of tissue anchors is aligned by the at least one alignment surface of a respective one of the plurality of tissue anchor receivers.

29. The implant kit of claim 21 wherein at least one of the plurality of tissue anchors is configured to be embedded in the tissue when the at least one of the plurality of tissue anchors is secured to the implant member.

30. The implant kit of claim 29, further comprising a number of implant guide lines, each of the number of implant guide lines physically coupled to the at least one of the plurality of tissue anchors when the at least one of the plurality of tissue anchors is configured to be embedded in the tissue to provide a physical path for the implant member to the at least one of the plurality of tissue anchors, the implant member moveable along the physical path to a position where the implant member is secured to the at least one of the plurality of tissue anchors.

31. The implant kit of claim 21, further comprising a plurality of biasing devices, each of the biasing devices biasing the rigid portions together in a respective one of a number of sets of two or more of the rigid portions of the plurality of rigid portions when the plurality of tissue anchors are secured to the implant member.

32. The implant kit of claim 21, further comprising a plurality of couplers, each coupler configured to engage a respective first portion of a respective one of the plurality of tissue anchors to capture a portion of the implant member between the coupler and a respective second portion of the respective one of the plurality of tissue anchors when the respective one of the plurality of tissue anchors is secured to the implant member, the respective second portion of each of the plurality of tissue anchors embeddable into the tissue.

33. The implant kit of claim 21, further comprising a number of holders, each holder activatable between a free configuration in which each rigid portion in a respective one of a number of sets of two or more of the rigid portions of the plurality of rigid portions is arranged to pivot towards and away from a second one of the rigid portions in the respective one of the number of sets of two or more of the rigid portions, and a fixed configuration in which the rigid portion in the respective one of the number of sets of two or more of the rigid portions is impeded from pivoting towards and away from the second one of the rigid portions in the respective one of the number of sets of two or more of the rigid portions with a greater resistance than when the holder is in the free configuration.

34. The implant kit of claim 33 wherein each holder comprises a respective plurality of interlockable elements which are brought into interlocked engagement when the implant member is moved into the deployed configuration.

35. The implant kit of claim 34 wherein each of the plurality of interlockable elements comprises a trapezoidal shaped projection or a trapezoidal shaped recess.

36. An implant kit, comprising:
a plurality of tissue anchors, each of the plurality of tissue anchors at least partially embeddable into tissue at a respective location about an orifice within a body during an implant procedure; and
an implant member reconfigurable between a delivery configuration in which the implant member is manipulable to a size and dimension to be deliverable percutaneously to the tissue within the body, and a deployed configuration in which the implant member forms a structure sufficiently rigid to affect a shape of the orifice in the tissue, the implant member comprising:
a plurality of segments;
a plurality of tissue anchor receivers, each tissue anchor receiver comprising at least one alignment surface arranged to contact a portion of a respective one of the plurality of tissue anchors and position the portion of the respective one of the plurality of tissue anchors at a location where the one of the plurality of tissue anchors is securable to the implant member; and at least a first pivot joint comprising a first pivot member, the first pivot joint arranged to pivotally couple a first set of two or more of the segments together, at least some of the segments in the first set of two or more of the segments arranged to turn about the first pivot member when the implant member is moved between the delivery configuration and the deployed configuration, the first pivot member and a first one of the tissue anchor receivers provided in a unitary structure, wherein at least one segment in the first set of two or more of the segments is slidably and pivotably coupled to the first pivot member, the at least one segment in the first set of two or more of the segments arranged to translate along, and turn about, the first pivot member when the implant member is moved between the delivery configuration and the deployed configuration.

* * * * *

UNITED STATES PATENT AND TRADEMARK OFFICE
CERTIFICATE OF CORRECTION

PATENT NO. : 10,058,318 B2  
APPLICATION NO. : 14/696853  
DATED : August 28, 2018  
INVENTOR(S) : Aleksandar Tegzes Page 1 of 1

It is certified that error appears in the above-identified patent and that said Letters Patent is hereby corrected as shown below:

On page 5, Item (56) References Cited, WO 2004/07679 A1 should read as WO 2004/047679 A1

Signed and Sealed this  
Sixth Day of November, 2018

Andrei Iancu  
*Director of the United States Patent and Trademark Office*